United States Patent [19]

Allen et al.

[11] Patent Number: 5,177,074

[45] Date of Patent: Jan. 5, 1993

[54] ANGIOTENSIN II ANTAGONISTS INCORPORATING A SUBSTITUTED THIOPHENE OR FURAN

[75] Inventors: Eric E. Allen, Somerset; Ralph A. Rivero, Tinton Falls; Nancy Kevin, Clifton, all of N.J.

[73] Assignee: Merck & Co., Inc., Rahway, N.J.

[21] Appl. No.: 846,151

[22] Filed: Mar. 11, 1992

Related U.S. Application Data

[63] Continuation-in-part of Ser. No. 675,371, Mar. 26, 1991, abandoned.

[51] Int. Cl.$^5$ .................. A61K 31/435; C07D 471/04
[52] U.S. Cl. ........................... 514/234.2; 514/234.5; 514/249; 514/261; 514/262; 514/265; 514/266; 514/303; 514/359; 514/382; 514/383; 514/394; 514/395; 544/118; 544/127; 544/139; 544/236; 544/264; 544/265; 544/266; 544/268; 544/269; 544/277; 544/350; 546/118; 548/252; 548/253; 548/254; 548/266.2; 548/304.7; 548/305.1; 548/306.1
[58] Field of Search ............... 544/118, 127, 139, 236, 544/264, 265, 266, 268, 269, 277, 350; 546/118; 548/254, 252, 253, 327, 266.2; 514/234.5, 249, 234.2, 261, 262, 265, 266, 303, 382, 383, 394, 395, 359

[56] References Cited

U.S. PATENT DOCUMENTS 4,880,804 11/1989 Carini et al. ................ 514/234.5

FOREIGN PATENT DOCUMENTS

| A58696/90 | 1/1991 | Australia . |
|---|---|---|
| 0253310 | 1/1988 | European Pat. Off. . |
| 0409332 | 1/1988 | European Pat. Off. . |
| 0260613 | 3/1988 | European Pat. Off. . |
| 0323841 | 7/1989 | European Pat. Off. . |
| 0324377 | 7/1989 | European Pat. Off. . |
| 0400974 | 5/1990 | European Pat. Off. . |
| 0392317 | 10/1990 | European Pat. Off. . |
| 0399731 | 11/1990 | European Pat. Off. . |
| 0399732 | 11/1990 | European Pat. Off. . |
| 0403158 | 12/1990 | European Pat. Off. . |
| 0403159 | 12/1990 | European Pat. Off. . |
| 0411766 | 2/1991 | European Pat. Off. . |
| 0412594 | 2/1991 | European Pat. Off. . |
| 0415886 | 3/1991 | European Pat. Off. . |
| 0419048 | 3/1991 | European Pat. Off. . |
| 0429257 | 5/1991 | European Pat. Off. . |
| 0430709 | 6/1991 | European Pat. Off. . |
| 0434249 | 6/1991 | European Pat. Off. . |
| 0468372 | 1/1992 | European Pat. Off. . |
| 0480204 | 4/1992 | European Pat. Off. . |

Primary Examiner—Bernard Dentz
Attorney, Agent, or Firm—Valerie J. Camara; William H. Nicholson; Joseph F. DiPrima

[57] ABSTRACT

There are disclosed substituted thiophene and furan derivatives of Formula I which are useful as angiotensin II antagonists.

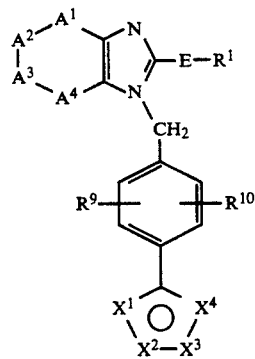

Formula I

15 Claims, No Drawings

ANGIOTENSIN II ANTAGONISTS INCORPORATING A SUBSTITUTED THIOPHENE OR FURAN

BACKGROUND OF THE INVENTION

The present application is a continuation in part of U.S. Ser. No. 07/675,371 filed on Mar. 26, 1991 now abandoned.

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio, *Clin. Exp. Hypertens.* A4, 27–46 (1982); D. H. P. Streeten and G. H. Anderson, Jr. —*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847 in European Patent Applications 028,834; 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in this application have been identified in any U.S. Patent, European Applications or articles. The substituted imidazoles, have been disclosed in patents to DuPont (EPO 253,310 and EPO 324,377) focusing on the design of Angiotensin II Antagonists. Substituted benzimidazole containing compounds useful as angiotensin II antagonists have been disclosed in U.S. Pat. No. 4,880,804 and European Patent Application 392,317. Substituted imidazopyridine containing compounds useful as angiotensin II antagonists have also been disclosed in European Patent Applications 399,731, 412,848 and 415,886 and U.S. Ser. No. 516,286 (filed May 4, 1990).

BRIEF DESCRIPTION OF THE INVENTION

The compounds of formula (I) are angiotensin II antagonists and are useful in the treatment of hypertension and congestive heart failure. Additionally, pharmaceutically acceptable compositions of these novel compounds, as the sole therapeutically active ingredient and in combination with diuretics and other antihypertensive agents, including beta-blockers, angiotensin converting enzyme inhibitors, calcium channel blockers or a combination thereof are disclosed. Further, methods of treating hypertension, congestive heart failure and elevated intraocular pressure are also described.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

DETAILED DESCRIPTION OF THE INVENTION

This invention relates to compounds having the formula:

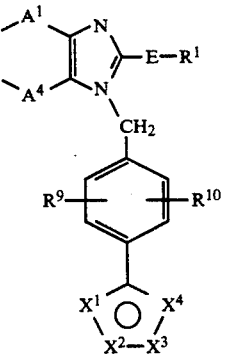

Formula I wherein:

$R^1$ is:

(a) $(C_1-C_6)$-alkyl, $(C_2-C_6)$-alkenyl or $(C_2-C_6)$-alkynyl each of which can be unsubstituted or substituted with a substituent selected from the group consisting of:
   i) aryl as defined below in $R^1$(b),
   ii) $(C_3-C_7)$-cycloalkyl,
   iii) Cl, Br, I, F,
   iv) OH,
   v) $NH_2$,
   vi) $NH(C_1-C_4)$-alkyl,
   vii) $N[((C_1-C_4)\text{-alkyl})]_2$,
   viii) $NHSO_2R^2$,
   ix) $CF_3$,
   x) $COOR^2$, or
   xi) $SO_2NHR^{2a}$;

(b) aryl, wherein aryl is defined as phenyl or naphthyl, unsubstituted or substituted with 1 or 2 substituents selected from the group consisting of:
   i) Cl, Br, I, F,
   ii) $(C_1-C_4)$-alkyl,
   iii) $(C_1-C_4)$-alkoxy,
   iv) $NO_2$,
   v) $CF_3$,
   vi) $SO_2NR^{2a}R^{2a}$,
   vii) $(C_1-C_4)$-alkylthio,
   viii) hydroxy,
   ix) amino,
   x) $(C_3-C_7)$-cycloalkyl, or
   xi) $(C_3-C_{10})$-alkenyl, (c) heteroaryl, wherein heteroaryl is defined as a 5- or 6-membered heteroaromatic moiety, which can contain one or two members selected from the group consisting of N, O, S and wherein the heteroaryl is unsubstituted, mono- or disubstituted with substituents selected from the group consisting of:
i) Cl, Br, I, F,
ii) OH,
iii) SH,
iv) $NO_2$,
v) $(C_1-C_4)$-alkyl,
vi) $(C_2-C_4)$-alkenyl,
vii) $(C_2-C_4)$-alkynyl,
viii) $(C_1-C_4)$-alkoxy, or
ix) $CF_3$, or
(d) polyfluoro-$(C_1-C_4)$-alkyl;
—$A^1$—$A^2$—$A^3$—$A^4$— represents:

(a) 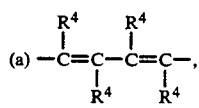

(b) 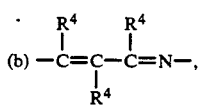

(c) 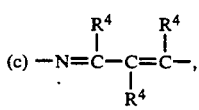

(d) 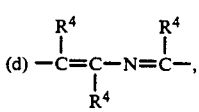

(e) 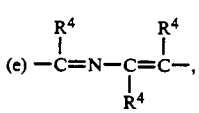

(f) 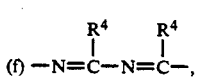

(g) 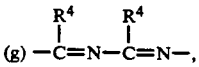

(h) 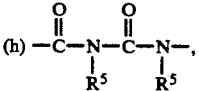

(i) 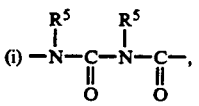

(j) 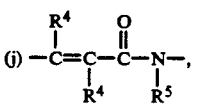

(k) 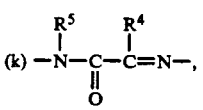

-continued (l) 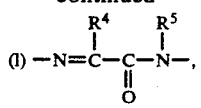

(m) 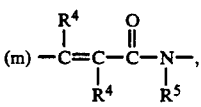

(n) 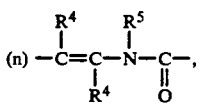

(o) 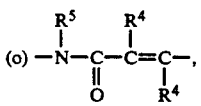

(p) 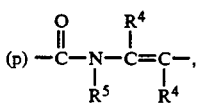

(q) 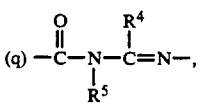

(r) 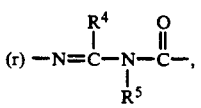

(s) 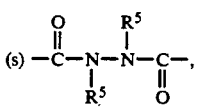

(t) 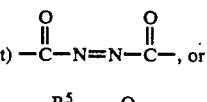, or (u) 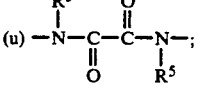

E is:
(a) a single bond,
(b) —$S(O)_n(CH_2)_s$—, or
(c) —O—;
n is 0 to 2;
s is 0 to 5;
$R^2$ is:
(a) H, or
(b) $(C_1-C_6)$-alkyl;
$R^{2a}$ is:
(a) $R^2$,
(b) $CH_2$-aryl, or
(c) aryl;
$R^4$ groups are independently:
(a) H,
(b) $(C_1-C_6)$-alkyl, $(C_2-C_6)$-alkenyl, or $(C_2-C_6)$-alkynyl, each of which is unsubstituted or substituted with:
i) OH,
ii) $(C_1-C_4)$-alkoxy,
iii) $CO_2R^2$, iv) OCOR$^2$,
v) CONHR$^2$,
vi) CON(R$^2$)$_2$,
vii) N(R$^2$)C(=O)R$^2$,
viii) NH$_2$,
ix) (C$_1$-C$_4$)-alkylamino,
x) di[(C$_1$-C$_4$)-alkyl]amino,
(c) —C(=O)-aryl,
(d) (C$_3$-C$_7$)-cycloalkyl,
(e) Cl, Br, I, F,
(f) —OH,
(g) —OR$^{21}$,
(h) —CF$_3$,
(i) —SH,
(j) —S(O)$_n$-(C$_1$-C$_4$)-alkyl,
(k) —CO$_2$R$^{2a}$,
(l) —SO$_3$H,
(m) —NR$^2$R$^{21}$,
(n) —NR$^2$C(=O)R$^{21}$,
(o) —NR$^2$COOR$^{21}$,
(p) —SO$_2$NHR$^{2a}$,
(q) —SO$_2$NR$^2$R$^{2a}$,
(r) —NO$_2$, or
(s) —NHSO$_2$-(C$_1$-C$_4$)-alkyl;

R$^5$ is:
(a) H, or
(b) (C$_1$-C$_6$)-alkyl or (C$_2$-C$_6$)-alkenyl, unsubstituted or substituted with:
i) hydroxy, or
ii) (C$_1$-C$_4$)-alkoxy;

—X$^1$—X$^2$—X$^3$—X$^4$— is:
(a) —Y—CR$^{11}$—CR$^{12}$—CZ—,
(b) —CR$^{11}$—Y—CR$^{12}$—CZ—,
(c) —CR$^{11}$—CR$^{12}$—Y—CZ—,
(d) —Y—CR$^{11}$—CZ—CR$^{12}$—,
(e) —CR$^{11}$—Y—CZ—CR$^{12}$—, or
(f) —CR$^{11}$—CR$^{12}$—CZ—Y—;

Y is: O, S, SO, or SO$_2$;

R$^9$ and R$^{10}$ are each independently:
(a) H,
(b) Cl, Br, I, F,
(c) NO$_2$,
(d) (C$_1$-C$_6$)-alkyl,
(e) (C$_1$-C$_6$)-acyloxy,
(f) (C$_3$-C$_6$)-cycloalkyl,
(g) (C$_1$-C$_6$)-alkoxy,
(h) NHSO$_2$R$^{2a}$,
(i) hydroxy-(C$_1$-C$_4$)-alkyl,
(j) (C$_1$-C$_4$)-alkyl-aryl,
(k) S(O)$_n$—(C$_1$-C$_4$)-alkyl,
(n) NR$^{2a}$R$^{2a}$,
(q) CF$_3$,
(r) SO$_2$NHR$^{2a}$,
(s) furyl, or
(t) aryl, wherein aryl is phenyl or naphthyl, unsubstituted or substituted with one or two substituents selected from the group consisting of: Cl, Br, I, F, (C$_1$-C$_4$)-alkyl, (C$_1$-C$_4$)-alkoxy, NO$_2$, CF$_3$, (C$_1$-C$_4$)-alkylthio, OH, NH$_2$, —NH[(C$_1$-C$_4$)-alkyl], —N[(C$_1$-C$_4$)-alkyl]$_2$, —CO$_2$H, or —CO$_2$—(C$_1$-C$_4$)-alkyl, or
(u) when R$^9$ and R$^{10}$ are bonded to adjacent carbon atoms, they can be joined to form an aryl ring;

R$^{11}$ and R$^{12}$ are independently:
(a) H,
(b) Cl, Br, I, F,
(c) NO$_2$,
(d) NH$_2$,
(e) NH[(C$_1$-C$_4$)-alkyl],
(f) N[(C$_1$-C$_4$)-alkyl]$_2$,
(g) SO$_2$NHR$^{2a}$,
(h) CF$_3$,
(i) (C$_1$-C$_7$)-alkyl,
(j) (C$_1$-C$_7$)-alkoxy,
(k) (C$_3$-C$_7$)-cycloalkyl,
(l) when R$^{11}$ and R$^{12}$ are bonded to adjacent carbon atoms, they can be joined to form an aryl ring,
(m) (CH$_2$)$_{n+1}$O(CH$_2$)$_s$CH$_3$,
(n) O(CH$_2$)$_{n+1}$O(CH$_2$)$_s$CH$_3$,
(o) (CH$_2$)N(R$^{2a}$)$_2$,
(p) (CH$_2$)$_n$N[CH$_2$CH$_2$]$_2$X,
(q) (CH$_2$)$_n$N[CH$_2$CH$_2$]$_2$CH$_2$,
(r) CH(OR$^{2a}$)[(C$_1$-C$_7$)-alkyl],
(s) CHO,
(t) CO$_2$R$^{2a}$,
(u) CH=CH—R$^{2a}$,
(v) CH$_2$CR$^{2a}$=C(R$^{2a}$)$_2$,
(w) (CH$_2$)$_n$NCOR$^{2a}$,
(x) (CH$_2$)$_n$aryl, or
(y) CH(R$^{2a}$)$_2$;

X is: O, S, or NR$^{2a}$;

Z is:
(a) —CO$_2$R$^{2a}$,
(b) —SO$_3$R$^{13}$,
(c) —NHSO$_2$CF$_3$,
(d) —PO(OR$^{13}$)$_2$,
(e) —SO$_2$NHR$^{2a}$,
(f) —CONHOR$^{13}$,
(g) —C(OH)(R$^{2a}$)PO(OR$^{13}$)$_2$,
(h) —CN,
(i) —SO$_2$NH-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: —OH, —SH, —(C$_1$-C$_4$)-alkyl, —(C$_1$-C$_4$)-alkoxy, —CF$_3$, Cl, Br, F, I, —NO$_2$, —CO$_2$H, —CO$_2$—(C$_1$-C$_4$)-alkyl, —NH$_2$, NH[(C$_1$-C$_4$)-alkyl] and —N[(C$_1$-C$_4$)-alkyl]$_2$,
(j) —CH$_2$SO$_2$NH-heteroaryl,
(k) —SO$_2$NH—CO—R$^{14}$,
(l) —CH$_2$SO$_2$NH—CO—R$^{14}$,
(m) —CONH—SO$_2$R$^{14}$,
(n) —CH$_2$CONH—SO$_2$R$^{14}$,
(o) —NHSO$_2$NHCO—R$^{14}$,
(p) —NHCONHSO$_2$—R$^{14}$,

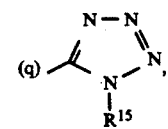

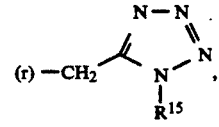

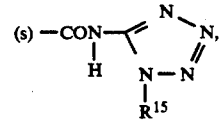

-continued (t) —CONHNHSO$_2$CF$_3$,

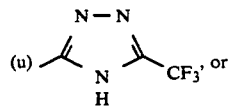

(u)

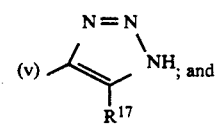

(v)

R$^{13}$ is H, or —CH(R$^4$)—O—C(O)R$^4$;
R$^{14}$ is
 (a) aryl,
 (b) heteroaryl,
 (c) (C$_3$-C$_7$)-cycloalkyl, or
 (d) (C$_1$-C$_7$)-alkyl, unsubstituted or substituted with a substituent selected from the group consisting of: aryl, heteroaryl, —OH, —SH, (C$_1$-C$_4$)-alkyl, —(C$_1$-C$_6$)-alkoxy, —S(C$_1$-C$_6$)-alkyl, (C$_3$-C$_7$)-cycloalkyl, —CF$_3$, Cl, Br, F, I, —NO$_2$, —CO$_2$H, CO$_2$—(C$_1$-C$_4$)-alkyl, —NH$_2$, —N[(C$_1$-C$_4$)-alkyl]$_2$, —PO$_3$H or PO(OH)(O—(C$_1$-C$_4$)-alkyl),
 (e) (C$_1$-C$_7$)-alkoxy,
 (f) O(CH$_2$)$_{n+1}$O(CH$_2$)$_s$CH$_3$,
 (g) (CH$_2$)$_{n+1}$O(CH$_2$)$_s$CH$_3$,
 (h) CH(R$^{2a}$)$_2$,
 (i) (C$_1$-C$_6$)-polyfluoroalkyl, or
 (j) —NH(C$_1$-C$_6$)-alkyl;
R$^{15}$ is:
 (a) H,
 (b) (C$_1$-C$_6$)-alkyl,
 (c) (C$_2$-C$_4$)-alkenyl,
 (d) (C$_1$-C$_4$)-alkoxy, or
 (e) benzyl, wherein the phenyl moiety is unsubstituted or substituted with a substituent selected from the group consisting of: —NO$_2$, —NH$_2$, —OH or —OCH$_3$;
R$^{17}$ is —CN, —NO$_2$, —CO$_2$R$^{2a}$, or —CF$_3$; and
R$^{21}$ is:
 (a) H, or
 (b) (C$_1$-C$_4$)-alkyl unsubstituted or substituted with:
  i) NH$_2$,
  ii) NH[(C$_1$-C$_4$)-alkyl],
  iii) N[(C$_1$-C$_4$)-alkyl]$_2$,
  iv) CO$_2$H,
  v) CO$_2$(C$_1$-C$_4$)-alkyl,
  vi) OH,
  vii) SO$_3$H,
  viii) SO$_2$NH$_2$, or
  ix) aryl;
 (c) aryl; with the proviso that when —A$^1$—A$^2$—A$^3$—A$^4$— is —C(Me)=CH—C(Me)=N, E is a single bond, R$^1$ is ethyl and —X$^1$—X$^2$—X$^3$—X$^4$— is —CH—CR$^{11}$—S—CZ—, R$^{11}$ is n-butyl or isobutyl, and Z is SO$_2$NHCOR$^{14}$, then R$^{14}$ cannot be O—n—C$_4$H$_9$ or CH$_2$O—n—C$_4$H$_9$.
or a pharmaceutically acceptable salt thereof.

The alkyl substitutents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The aryl substituent recited above represents phenyl or naphthyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

One embodiment of the invention is a compound of Formula I or its pharmaceutically acceptable salt wherein:
R$^1$ is:
 (a) (C$_1$-C$_6$)-alkyl, (C$_2$-C$_6$)-alkenyl or (C$_2$-C$_6$)-alkynyl each of which can be unsubstituted or substituted with a substituent selected from the group consisting of:
  i) aryl as defined below in R$^1$(b),
  ii) (C$_3$-C$_7$)-cycloalkyl,
  iii) Cl, Br, I, F,
  iv) OH,
  v) NH$_2$,
  vi) NH[(C$_1$-C$_4$)-alkyl],
  vii) N[((C$_1$-C$_4$)-alkyl)]$_2$,
  viii) NHSO$_2$R$^2$,
  ix) CF$_3$,
  x) COOR$^2$, or
  xi) SO$_2$NHR$^{2a}$;
 (b) aryl, wherein aryl is defined as phenyl or naphthyl, unsubstituted or substituted with 1 or 2 substituents selected from the group consisting of:
  i) Cl, Br, I, F,
  ii) (C$_1$-C$_4$)-alkyl,
  iii) (C$_1$-C$_4$)-alkoxy,
  iv) NO$_2$
  v) CF$_3$,
  vi) SO$_2$NR$^{2a}$R$^{2a}$,
  vii) (C$_1$-C$_4$)-alkylthio,
  viii) hydroxy,
  ix) amino,
  x) (C$_3$-C$_7$)-cycloalkyl, or
  xi) (C$_3$-C$_{10}$)-alkenyl;
 (c) polyfluoro-(C$_1$-C$_4$)-alkyl;
—A$^1$—A$^2$—A$^3$—A$^4$— is:

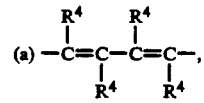

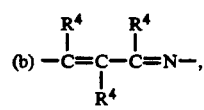

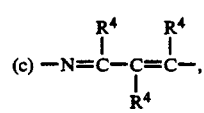

-continued

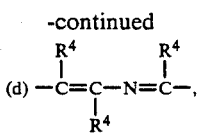
(d)

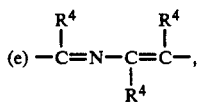
(e)

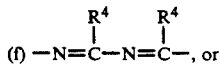
(f) , or

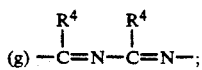
(g) ;

$R^2$ is:
(a) H, or
(b) $(C_1-C_6)$-alkyl;

$R^{2a}$ is:
(a) $R^2$,
(b) $CH_2$-aryl, or
(c) aryl;

$R^4$ groups are independently:
(a) H,
(b) $(C_1-C_6)$-alkyl, $(C_2-C_6)$-alkenyl, or $(C_2-C_6)$-alkynyl, each of which is unsubstituted or substituted with:
  i) OH,
  ii) $(C_1-C_4)$-alkoxy,
  iii) $CO_2R^2$,
  iv) $OCOR^2$,
  v) $CONHR^2$,
  vi) $CON(R^2)_2$,
  vii) $N(R^2)C(=O)R^2$,
  viii) $NH_2$,
  ix) $(C_1-C_4)$-alkylamino,
  x) di[$(C_1-C_4)$-alkyl]amino,
(c) $(C_3-C_7)$-cycloalkyl,
(d) Cl, Br, I, F,
(e) —$OR^{21}$,
(f) —$CF_3$,
(g) —$S(O)_n$-$(C_1-C_4)$-alkyl,
(h) —$CO_2R^{2a}$,
(i) —$NR^2R^{21}$,
(j) —$NR^2C(=O)R^{21}$,
(k) —$NR^2COOR^{21}$,
(l) —$SO_2NHR^{2a}$,
(m) —$SO_2NR^2R^{2a}$, or
(s) —$NHSO_2$-$(C_1-C_4)$-alkyl;

$R^5$ is:
(a) H, or
(b) $(C_1-C_6)$-alkyl or $(C_2-C_6)$-alkenyl, unsubstituted or substituted with:
  i) hydroxy, or
  ii) $(C_1-C_4)$-alkoxy;

$R^{5a}$ is:
(a) $R^5$, or
(b) $(C_1-C_4)$-acyl;

—$X^1$—$X^2$—$X^3$—$X^4$— is:
(a) —Y—$CR^{11}$—$CR^{12}$—CZ—,
(b) —$CR^{11}$—Y—$CR^{12}$—CZ—,
(c) —$CR^{11}$—$CR^{12}$—Y—CZ—,
(d) —Y—$CR^{11}$—CZ—$CR^{12}$—,
(e) —$CR^{11}$—Y—CZ—$CR^{12}$—, or
(f) —$CR^{11}$—$CR^{12}$—CZ—Y—;

Y is: O, or S;

$R^9$ and $R^{10}$ are each independently:
(a) H,
(b) Cl, Br, I, F,
(c) $(C_1-C_6)$-alkyl,
(d) $(C_3-C_6)$-cycloalkyl,
(e) $(C_1-C_6)$-alkoxy,
(f) —$NHSO_2R^{2a}$,
(g) $S(O)_n$-$(C_1-C_4)$-alkyl,
(h) $NR^{2a}R^{2a}$,
(i) $CF_3$,
(j) —$SO_2NHR^{2a}$,
(k) when $R^9$ and $R^{10}$ are bonded to adjacent carbon atoms, they can be joined to form an aryl ring;

$R^{11}$ and $R^{12}$ are independently:
(a) H,
(b) Cl, Br, I, F,
(c) $NO_2$,
(d) $NH_2$,
(e) $NH[(C_1-C_4)$-alkyl],
(f) $N[(C_1-C_4)$-alkyl]$_2$,
(g) $SO_2NHR^{2a}$,
(h) $CF_3$,
(i) $(C_1-C_6)$-alkyl,
(j) $(C_1-C_6)$-alkoxy,
(k) $(C_3-C_7)$-cycloalkyl,
(l) when $R^{11}$ and $R^{12}$ are bonded to adjacent carbon atoms, they can be joined to form an aryl ring,
(m) $O(CH_2)_{n+1}O(CH_2)_sCH_3$,
(n) $(CH_2)_{n+1}O(CH_2)_sCH_3$,
(o) $(CH_2)N(R^{2a})_2$,
(p) $(CH_2)_nN[CH_2CH_2]^2X$,
(q) $(CH_2)_nN[CH_2CH_2]_2CH_2$,
(r) $CH(OR^{2a})[(C_1-C_7)$-alkyl],
(s) CHO,
(t) $CO_2R^{2a}$,
(u) $CH=CHR^{2a}$,
(v) $CH_2CR^{2a}=C(R^{2a})_2$,
(w) $(CH_2)_nNCOR^{2a}$,
(x) $(CH_2)_n$-aryl, or
(y) $CH(R^{2a})_2$;

Z is:
(a) —$CO_2R^{2a}$,
(b) —$NHSO_2CF_3$,
(c) —$SO_2NHR^{2a}$,
(d) —CN,
(e) —$SO_2NH$-heteroaryl, wherein heteroaryl is an unsubstituted, monosubstituted or disubstituted five or six membered aromatic ring which can optionally contain from 1 to 3 heteroatoms selected from the group consisting of O, N or S and wherein the substituents are members selected from the group consisting of —OH, —SH, -$(C_1-C_4)$-alkyl, -$(C_1-C_4)$-alkoxy, —$CF_3$, Cl, Br, F, I, —$NO_2$, —$CO_2H$, —$CO_2$-$(C_1-C_4)$-alkyl, —$NH_2$, $NH[(C_1-C_4)$-alkyl] and —$N[(C_1-C_4)$-alkyl]$_2$,
(f) -1H-tetrazol-5-yl,
(g) —$CH_2$-1H-tetrazol-5-yl,
(h) —CONH-1H-tetrazol-5-yl, or
(i) —$SO_2NHCOR^{14}$;

$R^{21}$:
(a) H, or
(b) $(C_1-C_4)$-alkyl unsubstituted or substituted with:
  i) $NH_2$,
  ii) $NH[(C_1-C_4)$-alkyl],
  iii) $N[(C_1-C_4)$-alkyl]$_2$,
  iv) $CO_2H$,
  v) $CO_2(C_1-C_4)$-alkyl, vi) OH,
vii) SO$_3$H,
viii) SO$_2$NH$_2$, or
ix) aryl;
(c) aryl.

Another embodiment of the invention is a compound of Formula I or its pharmaceutically acceptable salt wherein:

R$^1$ is:
(a) (C$_1$-C$_6$)-alkyl or (C$_2$-C$_6$)-alkenyl each of which can be unsubstituted or substituted with a substituent selected from the group consisting of:
i) (C$_3$-C$_7$)-cycloalkyl,
ii) Cl, Br, I, F,
iii) OH,
iv) NH$_2$,
v) NH[(C$_1$-C$_4$)-alkyl],
vi) N[((C$_1$-C$_4$)-alkyl)]$_2$,
vii) CF$_3$, or
viii) COOR$^2$;

—A$^1$—A$^2$—A$^3$—A$^4$— is:

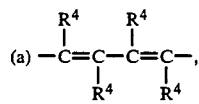
(a)

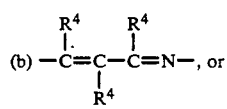
(b), or

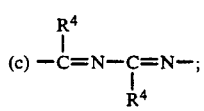
(c)

R$^2$ is:
(a) H, or
(b) (C$_1$-C$_6$)-alkyl;

R$^{2a}$ is:
(a) R$^2$,
(b) CH$_2$-aryl, or
(c) aryl;

R$^4$ groups are independently:
(a) H,
(b) (C$_1$-C$_4$)-alkyl, (C$_2$-C$_6$)-alkenyl, or (C$_2$-C$_4$)-alkynyl, each of which is unsubstituted or substituted with:
i) OH,
ii) (C$_1$-C$_4$)-alkoxy,
iii) CO$_2$R$^2$,
iv) OCOR$^2$,
v) CONHR$^2$,
vi) CON(R$^2$)$_2$,
vii) N(R$^2$)C(=O)R$^2$,
viii) NH$_2$,
ix) (C$_1$-C$_4$)-alkylamino,
x) di[(C$_1$-C$_4$)-alkyl]amino,
(c) (C$_3$-C$_7$)-cycloalkyl,
(d) Cl, Br, I, F,
(e) —OR$^{21}$,
(f) —CF$_3$,
(g) —S(O)$_n$-(C$_1$-C$_4$)-alkyl,
(h) —CO$_2$R$^{2a}$,
(i) —NR$^2$R$^{21}$,
(j) —NR$^2$C(=O)R$^{21}$,
(k) —NR$^2$COOR$^{21}$,
(l) —SO$_2$NHR$^{2a}$,
(m) —SO$_2$NR$^2$R$^{2a}$, or
(n) —NHSO$_2$—(C$_1$-C$_4$)-alkyl;

R$^5$ is:
(a) H, or
(b) (C$_1$-C$_6$)-alkyl or (C$_2$-C$_6$)-alkenyl, unsubstituted or substituted with:
i) hydroxy, or
ii) (C$_1$-C$_4$)-alkoxy;

R$^{5a}$ is
(a) R$^5$, or
(b) (C$_1$-C$_4$)-acyl;

—X$^1$—X$^2$—X$^3$—X$^4$— is:
(a) —Y—CR$^{11}$—CR$^{12}$—CZ—,
(b) —CR$^{11}$—Y—CR$^{12}$—CZ—,
(c) —CR$^{11}$—CR$^{12}$—Y—CZ—,
(d) —Y—CR$^{11}$—CZ—CR$^{12}$—,
(e) —CR$^{11}$—Y—CZ—CR$^{12}$—, or
(f) —CR$^{11}$—CR$^{12}$—CZ—Y—;

Y is: O or S;

n is: 0 to 2;

R$^{11}$ and R$^{12}$ are independently:
(a) H,
(b) Cl, Br, I, F,
(c) NH$_2$,
(d) NH[(C$_1$-C$_4$)-alkyl],
(e) N[(C$_1$-C$_4$)-alkyl]$_2$
(f) SO$_2$NHR$^{2a}$,
(g) CF$_3$,
(h) (C$_1$-C$_6$)-alkyl,
(i) (C$_1$-C$_6$)-alkoxy,
(j) (C$_3$-C$_7$)-cycloalkyl,
(k) when R$^{11}$ and R$^{12}$ are bonded to adjacent carbon atoms, they can joined to form a phenyl ring,
(l) (CH$_2$)$_n$[CH$_2$CH$_2$]$_2$X, or
(m) (C$_1$-C$_4$)-alkyl-aryl;

Z is:
(a) —CO$_2$R$^{2a}$,
(b) —NHSO$_2$CF$_3$,
(c) —SO$_2$NHR$^{14}$,
(d) -1H-tetrazol-5-yl,
(e) —SO$_2$NHCOR$^{14}$, or
(f) —NHSO$_2$R$^{14}$;

R$^{21}$ is:
(a) H, or
(b) (C$_1$-C$_4$)-alkyl unsubstituted or substituted with:
i) NH$_2$,
ii) NH[(C$_1$-C$_4$)-alkyl],
iii) N[(C$_1$-C$_4$)-alkyl]$_2$,
iv) CO$_2$H,
v) CO$_2$(C$_1$-C$_4$)-alkyl,
vi) OH,
vii) SO$_3$H,
viii) SO$_2$NH$_2$, or
ix) aryl;
(c) aryl.

TABLE I

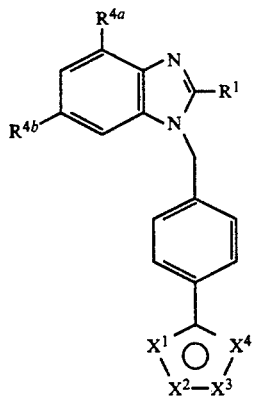

| # | $R^1$ | $R^{4a}$ | $R^{4b}$ | $-X^1-X^2-X^3-X^4-$ | $R^{12}$ | Z |
|---|---|---|---|---|---|---|
| 1 | n-propyl | H | H | —CH—S—CH—CZ— | | 1H-tetrazol-5-yl |
| 2 | n-butyl | H | H | —CH—S—CH—CZ— | | 1H-tetrazol-5-yl |
| 3 | n-propyl | H | H | —CH—S—C(Br)—CZ— | | 1H-tetrazol-5-yl |
| 4 | n-butyl | H | H | —CH—S—C(Br)—CZ— | | 1H-tetrazol-5-yl |
| 5 | n-butyl | H | H | —CH—CH—O—CZ— | | 1H-tetrazol-5-yl |
| 6 | n-propyl | H | H | —CH—CH—O—CZ— | | 1H-tetrazol-5-yl |
| 7 | n-propyl | H | H | —CH—S—CH—CZ— | | $SO_2NHCOPh$ |
| 8 | n-butyl | H | H | —CH—S—CH—CZ— | | $CO_2H$ |
| 9 | ethyl | H | H | —CH—S—CH—CZ— | | 1H-tetrazol-5-yl |
| 10 | ethyl | H | H | —CH—S—CH—CZ— | | $SO_2NHCOPh$ |
| 11 | n-propyl | H | H | —CH—CH—S—CZ— | | 1H-tetrazol-5-yl |
| 12 | n-butyl | H | H | —CH—CH—S—CZ— | | 1H-tetrazol-5-yl |
| 13 | n-butyl | $CH_3$ | H | —CH—S—CH—CZ— | | $SO_2NHCOPh$ |
| 14 | n-butyl | $CH_3$ | $CH_3$ | —CH—S—CH—CZ— | | $SO_2NHCOPh$ |
| 15 | ethyl | $CH_3$ | H | —CH—S—CH—CZ— | | $SO_2NHCOPh$ |
| 16 | n-propyl | H | H | —CH—CH—S—CZ— | | $SO_2NHCOPh$ |
| 17 | n-butyl | H | H | —CH—CH—S—CZ— | | $SO_2NHCOPh$ |
| 18 | ethyl | $CH_3$ | $CO_2H$ | —CH—S—CH—CZ— | | $SO_2NHCOPh$ |
| 19 | n-propyl | H | H | —S—CH—CH—CZ— | | $SO_2NHCOPh$ |
| 20 | n-butyl | H | H | —S—CH—CH—CZ— | | $SO_2NHCOPh$ |
| 21 | ethyl | $CH_3$ | $CH_3$ | —CH—S—C($SO_2NHCOPh$)CZ— | | $SO_2NHCOPh$ |
| 22 | ethyl | $CH_3$ | $CH_3$ | —CH—S—CH—CZ— | | 1H-tetrazol-5-yl |
| 23 | ethyl | $CH_3$ | $CH_3$ | benzo-fused —C—C—S—CZ— | | 1H-tetrazol-5-yl |
| 24 | ethyl | $CH_3$ | $CO_2H$ | benzo-fused —C—C—S—CZ— | | $SO_2NHCOPh$ |
| 25 | n-propyl | H | H | benzo-fused —C—C—S—CZ— | | $SO_2NHCOPh$ |
| 26 | n-butyl | H | H | benzo-fused —C—C—S—CZ— | | $SO_2NHCOPh$ |
| 27 | n-butyl | Me | H | —CH—$CR^{12}$—S—CZ— | nPr | 1H-tetrazol-5-yl |
| 28 | n-butyl | Me | H | —CH—$CR^{12}$—S—CZ— | iBu | 1H-tetrazol-5-yl |
| 29 | n-butyl | Me | H | —CH—$CR^{12}$—S—CZ— | nPr | $SO_2NHCOPh$ |
| 30 | n-butyl | Me | H | —CH—$CR^{12}$—S—CZ— | iBu | $SO_2NHCOPh$ |
| 31 | n-butyl | Me | H | —CH—$CR^{12}$—S—CZ— | nPn | $SO_2NHCOPh$ |
| 32 | ethyl | Me | H | —CH—$CR^{12}$—S—CZ— | nPr | 1H-tetrazol-5-yl |
| 33 | ethyl | Me | H | —CH—$CR^{12}$—S—CZ— | iBu | 1H-tetrazol-5-yl |
| 34 | ethyl | Me | H | —CH—$CR^{12}$—S—CZ— | nPn | 1H-tetrazol-5-yl |
| 35 | ethyl | Me | H | —CH—$CR^{12}$—S—CZ— | Bn | 1H-tetrazol-5-yl |
| 36 | ethyl | Me | H | —CH—$CR^{12}$—S—CZ— | nPr | $SO_2NHCOPh$ |
| 37 | ethyl | Me | H | —CH—$CR^{12}$—S—CZ— | iBu | $SO_2NHCOPh$ |
| 38 | ethyl | Me | H | —CH—$CR^{12}$—S—CZ— | nPn | $SO_2NHCOPh$ |
| 39 | ethyl | Me | H | —CH—$CR^{12}$—S—CZ— | Bn | $SO_2NHCOPh$ |
| 40 | n-butyl | Me | Me | —CH—$CR^{12}$—S—CZ— | nPr | 1H-tetrazol-5-yl |
| 41 | n-butyl | Me | Me | —CH—$CR^{12}$—S—CZ— | nBu | 1H-tetrazol-5-yl |

TABLE I-continued

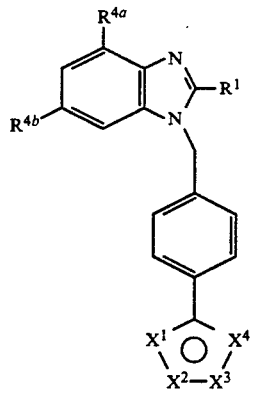

| # | $R^1$ | $R^{4a}$ | $R^{4b}$ | $-X^1-X^2-X^3-X^4-$ | $R^{12}$ | Z |
|---|---|---|---|---|---|---|
| 42 | n-butyl | Me | Me | $-CH-CR^{12}-S-CZ-$ | iBu | 1H-tetrazol-5-yl |
| 43 | n-butyl | Me | Me | $-CH-CR^{12}-S-CZ-$ | nPn | 1H-tetrazol-5-yl |
| 44 | n-butyl | Me | Me | $-CH-CR^{12}-S-CZ-$ | nPr | $SO_2NHCOPh$ |
| 45 | n-butyl | Me | Me | $-CH-CR^{12}-S-CZ-$ | iBu | $SO_2NHCOPh$ |
| 46 | n-butyl | Me | Me | $-CH-CR^{12}-S-CZ-$ | nPn | $SO_2NHCOPh$ |
| 47 | ethyl | Me | Me | $-CH-CR^{12}-S-CZ-$ | nPr | 1H-tetrazol-5-yl |
| 48 | ethyl | Me | Me | $-CH-CR^{12}-S-CZ-$ | iBu | 1H-tetrazol-5-yl |
| 49 | ethyl | Me | Me | $-CH-CR^{12}-S-CZ-$ | nPn | 1H-tetrazol-5-yl |
| 50 | ethyl | Me | Me | $-CH-CR^{12}-S-CZ-$ | Me | $SO_2NHCOPh$ |
| 51 | ethyl | Me | Me | $-CH-CR^{12}-S-CZ-$ | Et | $SO_2NHCOPh$ |
| 52 | ethyl | Me | Me | $-CH-CR^{12}-S-CZ-$ | nPr | $SO_2NHCOPh$ |
| 53 | ethyl | Me | Me | $-CH-CR^{12}-S-CZ-$ | nBu | $SO_2NHCOPh$ |
| 54 | ethyl | Me | Me | $-CH-CR^{12}-S-CZ-$ | iBu | $SO_2NHCOPh$ |
| 55 | ethyl | Me | Me | $-CH-CR^{12}-S-CZ-$ | nPn | $SO_2NHCOPh$ |
| 56 | ethyl | Me | Me | $-CH-CR^{12}-S-CZ-$ | Bn | $SO_2NHCOPh$ |
| 57 | ethyl | Me | Me | $-CH-CR^{12}-S-CZ-$ | $CH_2N(CH_2CH_2)_2O$ | $SO_2NHCOPh$ |
| 58 | ethyl | Me | Me | $-CH-CR^{12}-S-CZ-$ | $CH_2N(CH_2CH_2)_2O$ | $SO_2NHCOCH(Ph)_2$ |
| 59 | n-butyl | Me | $CON(ME)_2$ | $-CH-CR^{12}-S-CZ-$ | nPr | 1H-tetrazol-5-yl |
| 60 | n-butyl | Me | $CON(ME)_2$ | $-CH-CR^{12}-S-CZ-$ | iBu | 1H-tetrazol-5-yl |
| 61 | n-butyl | Me | $CON(ME)_2$ | $-CH-CR^{12}-S-CZ-$ | nPr | $SO_2NHCOPh$ |
| 62 | ethyl | Me | $CON(ME)_2$ | $-CH-CR^{12}-S-CZ-$ | nPr | 1H-tetrazol-5-yl |
| 63 | ethyl | Me | $CON(ME)_2$ | $-CH-CR^{12}-S-CZ-$ | nBu | 1H-tetrazol-5-yl |
| 64 | ethyl | Me | $CON(ME)_2$ | $-CH-CR^{12}-S-CZ-$ | iBu | 1H-tetrazol-5-yl |
| 65 | ethyl | Me | $CON(ME)_2$ | $-CH-CR^{12}-S-CZ-$ | nPn | 1H-tetrazol-5-yl |
| 66 | ethyl | Me | $CON(ME)_2$ | $-CH-CR^{12}-S-CZ-$ | nBu | $SO_2NHCOPh$ |
| 67 | ethyl | Me | $CON(ME)_2$ | $-CH-CR^{12}-S-CZ-$ | iBu | $SO_2NHCOPh$ |
| 68 | ethyl | Me | $CON(ME)_2$ | $-CH-CR^{12}-S-CZ-$ | Bn | $SO_2NHCOPh$ |
| 69 | n-butyl | Me | $CH_2OH$ | $-CH-CR^{12}-S-CZ-$ | nPr | 1H-tetrazol-5-yl |
| 70 | n-butyl | Me | $CH_2OH$ | $-CH-CR^{12}-S-CZ-$ | iBu | 1H-tetrazol-5-yl |
| 71 | n-butyl | Me | $CH_2OH$ | $-CH-CR^{12}-S-CZ-$ | nPr | $SO_2NHCOPh$ |
| 72 | n-butyl | Me | $CH_2OH$ | $-CH-CR^{12}-S-CZ-$ | nPn | $SO_2NHCOPh$ |
| 73 | ethyl | Me | $CH_2OH$ | $-CH-CR^{12}-S-CZ-$ | nBu | 1H-tetrazol-5-yl |
| 74 | ethyl | Me | $CH_2OH$ | $-CH-CR^{12}-S-CZ-$ | iBu | 1H-tetrazol-5-yl |
| 75 | ethyl | Me | $CH_2OH$ | $-CH-CR^{12}-S-CZ-$ | nPn | 1H-tetrazol-5-yl |
| 76 | ethyl | Me | Me | $-CH-CR^{12}-S-CZ-$ | nPr | $SO_2NHCO(CH_2)_2OMe$ |
| 77 | ethyl | Me | $CH_2OH$ | $-CH-CR^{12}-S-CZ-$ | nBu | $SO_2NHCOPh$ |
| 78 | ethyl | Me | $CH_2OH$ | $-CH-CR^{12}-S-CZ-$ | iBu | $SO_2NHCOPh$ |
| 79 | ethyl | Me | $CH_2OH$ | $-CH-CR^{12}-S-CZ-$ | nPn | $SO_2NHCOPh$ |
| 80 | ethyl | Me | $CO_2H$ | $-CH-CR^{12}-S-CZ-$ | nPr | $SO_2NHCOPh$ |
| 81 | propyl | Me | $CO_2H$ | $-CH-CR^{12}-S-CZ-$ | nPr | $SO_2NHCOPh$ |
| 82 | propyl | Me | $CO_2H$ | $-CH-CR^{12}-S-CZ-$ | iBu | $SO_2NHCOPh$ |
| 83 | propyl | Me | $CO_2H$ | $-CH-CR^{12}-S-CZ-$ | nPn | $SO_2NHCOPh$ |
| 84 | ethyl | Me | Me | $-CH-CR^{12}-S-CZ-$ | Me | $SO_2NHCOCH_2Ph$ |
| 85 | ethyl | Me | Me | $-CH-CR^{12}-S-CZ-$ | Me | $SO_2NHCOCH(Ph)_2$ |
| 86 | ethyl | Me | Me | $-CH-CR^{12}-S-CZ-$ | Et | $SO_2NHCOCH(Ph)_2$ |
| 87 | ethyl | Me | Me | $-CH-CR^{12}-S-CZ-$ | Et | $SO_2NHCOCH_2OEt$ |
| 88 | ethyl | Me | Me | $-CH-CR^{12}-S-CZ-$ | nBu | $SO_2NHCOCH_2OEt$ |
| 89 | propyl | Me | $CO_2H$ | $-CH-CR^{12}-S-CZ-$ | nPn | $SO_2NHCOCH_2OBu$ |
| 90 | ethyl | Me | Me | $-CH-CR^{12}-S-CZ-$ | nPr | $SO_2NHCOOCH_2CH(Me)_3$ |
| 92 | ethyl | Me | Me | $-CH-CR^{12}-S-CZ-$ | nPr | $SO_2NHCOCH_2OBu$ |
| 92 | ethyl | Me | Me | $-CH-CR^{12}-S-CZ-$ | nPr | $SO_2NHCOCH_2OEt$ |
| 93 | ethyl | Me | Me | $-CH-CR^{12}-S-CZ-$ | nPr | $SO_2NHCO(CH_2)_2CycPentyl$ |
| 94 | ethyl | Me | $CH_2OH$ | $-CH-CR^{12}-S-CZ-$ | nPr | $SO_2NHCOCH_2OEt$ |
| 95 | ethyl | Me | $CH_2OH$ | $-CH-CR^{12}-S-CZ-$ | iBu | $SO_2NHCOCH_2OBu$ |
| 96 | ethyl | Me | $CO_2H$ | $-CH-CR^{12}-S-CZ-$ | iBu | $SO_2NHCOCH_2OBu$ |
| 97 | ethyl | Me | Me | $-CH-CR^{12}-S-CZ-$ | iBu | $SO_2NHCOCH_2OBu$ |
| 98 | ethyl | Me | Me | $-CH-CR^{12}-S-CZ-$ | iBu | $SO_2NHCOCH_2OEt$ |
| 99 | ethyl | Me | Me | $-CH-CR^{12}-S-CZ-$ | nPn | $SO_2NHCOCH_2OEt$ |
| 100 | ethyl | Me | Me | $-CH-CR^{12}-S-CZ-$ | nPn | $SO_2NHCOCH_2OBu$ |
| 101 | ethyl | Me | Me | $-CH-CR^{12}-S-CZ-$ | nPn | $SO_2NHCO_2-$N-methylpyrrole |
| 102 | ethyl | Me | Me | $-CH-CR^{12}-S-CZ-$ | nPr | $SO_2NHCO_2-$N-methylpyrrole |

TABLE I-continued

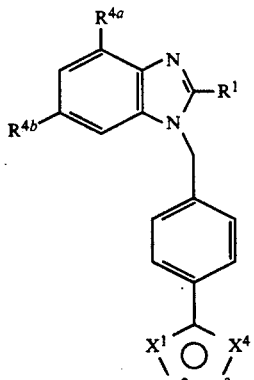

| # | R¹ | R⁴ᵃ | R⁴ᵇ | —X¹—X²—X³—X⁴— | R¹² | Z |
|---|---|---|---|---|---|---|
| 3 | n-propyl | CH₃ | CH₃ | —CH—S—CH—CZ— | | SO₂NHCOPh |
| 4 | n-propyl | CH₃ | CO₂H | —CH—S—CH—CZ— | | SO₂NHCOPh |
| 5 | ethyl | CH₃ | CH₃ | —CH—S—CH—CZ— | | 1H-tetrazol-5-yl |
| 6 | ethyl | CH₃ | CO₂H | —CH—S—CH—CZ— | | 1H-tetrazol-5-yl |
| 7 | ethyl | CH₃ | CH₃ | —CH—C(Si(CH₃)₃)—S—CZ— | | SO₂NHCOPh |
| 8 | n-propyl | CH₃ | CH₃ | 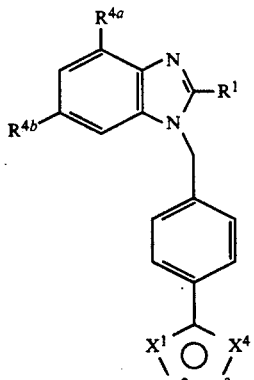 | | SO₂NHCOPh |
| 9 | ethyl | CH₃ | CH₃ | 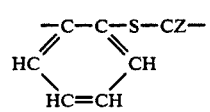 | | SO₂NHCOPh |
| 10 | ethyl | CH₃ | CH₃ | —CH—CH—S—CZ— | | SO₂NHCOPh |
| 11 | ethyl | CH₃ | CO₂H | —CH—CH—S—CZ— | | SO₂NHCOPh |
| 12 | ethyl | CH₃ | CH₃ | —S—CH—CH—CZ— | | 1H-tetrazol-5-yl |
| 13 | ethyl | CH₃ | CO₂H | —S—CH—CH—CZ— | | 1H-tetrazol-5-yl |
| 14 | ethyl | CH₃ | CH₃ | —S—CH—CH—CZ— | | SO₂NHCOPh |
| 15 | ethyl | CH₃ | CO₂H | —S—CH—CH—CZ— | | SO₂NHCOPh |
| 16 | ethyl | CH₃ | CH₃ | —CH—S—C(SO₂NHCOPh)—CZ— | | H |
| 17 | n-propyl | CH₃ | Cl | —CH—S—CH—CZ— | | 1H-tetrazol-5-yl |
| 18 | n-propyl | CH₃ | N(CH₃)₂ | —CH—S—CH—CZ— | | 1H-tetrazol-5-yl |
| 19 | n-propyl | CH₃ | Cl | —CH—S—C(Br)—CZ— | | 1H-tetrazol-5-yl |
| 20 | n-propyl | CH₃ | N(CH₃)₂ | —CH—S—C(Br)—CZ— | | 1H-tetrazol-5-yl |
| 21 | n-propyl | CH₃ | Cl | —CH—CH—S—CZ— | | 1H-tetrazol-5-yl |
| 22 | n-propyl | CH₃ | N(CH₃)₂ | —CH—CH—S—CZ— | | 1H-tetrazol-5-yl |
| 23 | n-propyl | CH₃ | Cl | —CH—CH—O—CZ— | | 1H-tetrazol-5-yl |
| 24 | n-propyl | CH₃ | N(CH₃)₂ | —CH—CH—O—CZ— | | 1H-tetrazol-5-yl |
| 25 | n-propyl | CH₃ | Cl | 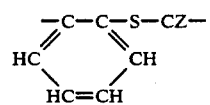 | | SO₂NHCOPh |
| 26 | n-propyl | CH₃ | N(CH₃)₂ | 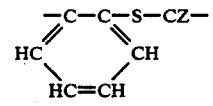 | | SO₂NHCOPh |
| 27 | n-propyl | CH₃ | Cl | —CH—CH—S—CZ— | | SO₂NHCOPh |
| 28 | n-propyl | CH₃ | N(CH₃)₂ | —CH—CH—S—CZ— | | SO₂NHCOPh |
| 29 | n-propyl | CH₃ | Cl | —S—CH—CH—CZ— | | SO₂NHCOPh |
| 30 | n-propyl | CH₃ | N(CH₃)₂ | —S—CH—CH—CZ— | | SO₂NHCOPh |
| 31 | n-butyl | Me | H | —CH—CR¹²—S—CZ— | nPr | 1H-tetrazol-5-yl |
| 32 | n-butyl | Me | H | —CH—CR¹²—S—CZ— | iBu | 1H-tetrazol-5-yl |
| 33 | n-butyl | Me | H | —CH—CR¹²—S—CZ— | nPr | SO₂NHCOPh |
| 34 | n-butyl | Me | H | —CH—CR¹²—S—CZ— | iBu | SO₂NHCOPh |
| 35 | n-butyl | Me | H | —CH—CR12—S—CZ— | nPn | SO₂NHCOPh |
| 36 | ethyl | Me | H | —CH—CR12—S—CZ— | nPr | 1H-tetrazol-5-yl |
| 37 | ethyl | Me | H | —CH—CR12—S—CZ— | iBu | 1H-tetrazol-5-yl |
| 38 | ethyl | Me | H | —CH—CR12—S—CZ— | nPn | 1H-tetrazol-5-yl |
| 39 | ethyl | Me | H | —CH—CR12—S—CZ— | Bn | 1H-tetrazol-5-yl |
| 40 | ethyl | Me | H | —CH—CR12—S—CZ— | nPr | SO₂NHCOPh |
| 41 | ethyl | Me | H | —CH—CR12—S—CZ— | iBu | SO₂NHCOPh |
| 42 | ethyl | Me | H | —CH—CR12—S—CZ— | nPn | SO₂NHCOPh |

TABLE I-continued

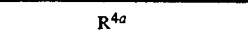

| # | $R^1$ | $R^{4a}$ | $R^{4b}$ | $-X^1-X^2-X^3-X^4-$ | $R^{12}$ | Z |
|---|---|---|---|---|---|---|
| 43 | ethyl | Me | H | $-CH-CR^{12}-S-CZ-$ | Bn | $SO_2NHCOPh$ |
| 44 | n-butyl | Me | Me | $-CH-CR^{12}-S-CZ-$ | nPr | 1H-tetrazol-5-yl |
| 45 | n-butyl | Me | Me | $-CH-CR^{12}-S-CZ-$ | nBu | 1H-tetrazol-5-yl |
| 46 | n-butyl | Me | Me | $-CH-CR^{12}-S-CZ-$ | iBu | 1H-tetrazol-5-yl |
| 47 | n-butyl | Me | Me | $-CH-CR^{12}-S-CZ-$ | nPn | 1H-tetrazol-5-yl |
| 48 | n-butyl | Me | Me | $-CH-CR^{12}-S-CZ-$ | nPr | $SO_2NHCOPh$ |
| 49 | n-butyl | Me | Me | $-CH-CR^{12}-S-CZ-$ | iBu | $SO_2NHCOPh$ |
| 50 | n-butyl | Me | Me | $-CH-CR^{12}-S-CZ-$ | nPn | $SO_2NHCOPh$ |
| 51 | ethyl | Me | Me | $-CH-CR^{12}-S-CZ-$ | nPr | 1H-tetrazol-5-yl |
| 52 | ethyl | Me | Me | $-CH-CR^{12}-S-CZ-$ | iBu | 1H-tetrazol-5-yl |
| 53 | ethyl | Me | Me | $-CH-CR^{12}-S-CZ-$ | nPn | 1H-tetrazol-5-yl |
| 54 | ethyl | Me | Me | $-CH-CR^{12}-S-CZ-$ | Me | $SO_2NHCOPh$ |
| 55 | ethyl | Me | Me | $-CH-CR^{12}-S-CZ-$ | Et | $SO_2NHCOPh$ |
| 56 | ethyl | Me | Me | $-CH-CR^{12}-S-CZ-$ | nPr | $SO_2NHCOPh$ |
| 57 | ethyl | Me | Me | $-CH-CR^{12}-S-CZ-$ | nBu | $SO_2NHCOPh$ |
| 58 | ethyl | Me | Me | $-CH-CR^{12}-S-CZ-$ | iBu | $SO_2NHCOPh$ |
| 59 | ethyl | Me | Me | $-CH-CR^{12}-S-CZ-$ | nPn | $SO_2NHCOPh$ |
| 60 | ethyl | Me | Me | $-CH-CR^{12}-S-CZ-$ | Bn | $SO_2NHCOPh$ |
| 61 | ethyl | Me | Me | $-CH-CR^{12}-S-CZ-$ | $CH_2N(CH_2CH_2)_2O$ | $SO_2NHCOPh$ |
| 62 | ethyl | Me | Me | $-CH-CR^{12}-S-CZ-$ | $CH_2N(CH_2CH_2)_2O$ | $SO_2NHCOCH(Ph)_2$ |
| 63 | n-butyl | Me | $CON(Me)_2$ | $-CH-CR^{12}-S-CZ-$ | nPr | 1H-tetrazol-5-yl |
| 64 | n-butyl | Me | $CON(Me)_2$ | $-CH-CR^{12}-S-CZ-$ | iBu | 1H-tetrazol-5-yl |
| 65 | n-butyl | Me | $CON(Me)_2$ | $-CH-CR^{12}-S-CZ-$ | nPr | $SO_2NHCOPh$ |
| 66 | ethyl | Me | $CON(Me)_2$ | $-CH-CR^{12}-S-CZ-$ | nPr | 1H-tetrazol-5-yl |
| 67 | ethyl | Me | $CON(Me)_2$ | $-CH-CR^{12}-S-CZ-$ | nBu | 1H-tetrazol-5-yl |
| 68 | ethyl | Me | $CON(Me)_2$ | $-CH-CR^{12}-S-CZ-$ | iBu | 1H-tetrazol-5-yl |
| 69 | ethyl | Me | $CON(Me)_2$ | $-CH-CR^{12}-S-CZ-$ | nPn | 1H-tetrazol-5-yl |
| 70 | ethyl | Me | $CON(Me)_2$ | $-CH-CR^{12}-S-CZ-$ | nBu | $SO_2NHCOPh$ |
| 71 | ethyl | Me | $CON(Me)_2$ | $-CH-CR^{12}-S-CZ-$ | iBu | $SO_2NHCOPh$ |
| 72 | ethyl | Me | $CON(Me)_2$ | $-CH-CR^{12}-S-CZ-$ | Bn | $SO_2NHCOPh$ |
| 73 | n-butyl | Me | $CH_2OH$ | $-CH-CR^{12}-S-CZ-$ | nPr | 1H-tetrazol-5-yl |
| 74 | n-butyl | Me | $CH_2OH$ | $-CH-CR^{12}-S-CZ-$ | iBu | 1H-tetrazol-5-yl |
| 75 | n-butyl | Me | $CH_2OH$ | $-CH-CR^{12}-S-CZ-$ | nPr | $SO_2NHCOPh$ |
| 76 | n-butyl | Me | $CH_2OH$ | $-CH-CR^{12}-S-CZ-$ | nPn | $SO_2NHCOPh$ |
| 77 | ethyl | Me | $CH_2OH$ | $-CH-CR^{12}-S-CZ-$ | nBu | 1H-tetrazol-5-yl |
| 78 | ethyl | Me | $CH_2OH$ | $-CH-CR^{12}-S-CZ-$ | iBu | 1H-tetrazol-5-yl |
| 79 | ethyl | Me | $CH_2OH$ | $-CH-CR^{12}-S-CZ-$ | nPn | 1H-tetrazol-5-yl |
| 80 | ethyl | Me | Me | $-CH-CR^{12}-S-CZ-$ | nPr | $SO_2NHCO(CH_2)_2OMe$ |
| 81 | ethyl | Me | $CH_2OH$ | $-CH-CR^{12}-S-CZ-$ | nBu | $SO_2NHCOPh$ |
| 82 | ethyl | Me | $CH_2OH$ | $-CH-CR^{12}-S-CZ-$ | iBu | $SO_2NHCOPh$ |
| 83 | ethyl | Me | $CH_2OH$ | $-CH-CR^{12}-S-CZ-$ | nPn | $SO_2NHCOPh$ |
| 84 | ethyl | Me | $CO_2H$ | $-CH-CR^{12}-S-CZ-$ | nPr | $SO_2NHCOPh$ |
| 85 | propyl | Me | $CO_2H$ | $-CH-CR^{12}-S-CZ-$ | nPr | $SO_2NHCOPh$ |
| 86 | propyl | Me | $CO_2H$ | $-CH-CR^{12}-S-CZ-$ | iBu | $SO_2NHCOPh$ |
| 87 | propyl | Me | $CO_2H$ | $-CH-CR^{12}-S-CZ-$ | nPn | $SO_2NHCOPh$ |
| 88 | ethyl | Me | Me | $-CH-CR^{12}-S-CZ-$ | Me | $SO_2NHCOCH_2Ph$ |
| 89 | ethyl | Me | Me | $-CH-CR^{12}-S-CZ-$ | Me | $SO_2NHCOCH(Ph)_2$ |
| 90 | ethyl | Me | Me | $-CH-CR^{12}-S-CZ-$ | Et | $SO_2NHCOCH(Ph)_2$ |
| 91 | ethyl | Me | Me | $-CH-CR^{12}-S-CZ-$ | Et | $SO_2NHCOCH_2OEt$ |
| 92 | ethyl | Me | Me | $-CH-CR^{12}-S-CZ-$ | nBu | $SO_2NHCOCH_2OEt$ |
| 93 | propyl | Me | $CO_2H$ | $-CH-CR^{12}-S-CZ-$ | nPn | $SO_2NHCOCH_2OBu$ |
| 94 | ethyl | Me | Me | $-CH-CR^{12}-S-CZ-$ | nPr | $SO_2NHCOOCH_2CH(Me)_3$ |
| 95 | ethyl | Me | Me | $-CH-CR^{12}-S-CZ-$ | nPr | $SO_2NHCOCH_2OBu$ |
| 96 | ethyl | Me | Me | $-CH-CR^{12}-S-CZ-$ | nPr | $SO_2NHCOCH_2OEt$ |
| 97 | ethyl | Me | Me | $-CH-CR^{12}-S-CZ-$ | nPr | $SO_2NHCO(CH_2)_2CycPentyl$ |
| 98 | ethyl | Me | $CH_2OH$ | $-CH-CR^{12}-S-CZ-$ | nPr | $SO_2NHCOCH_2OEt$ |
| 99 | ethyl | Me | $CH_2OH$ | $-CH-CR^{12}-S-CZ-$ | iBu | $SO_2NHCOCH_2OBu$ |
| 100 | ethyl | Me | $CO_2H$ | $-CH-CR^{12}-S-CZ-$ | iBu | $SO_2NHCOCH_2OBu$ |
| 101 | ethyl | Me | Me | $-CH-CR^{12}-S-CZ-$ | iBu | $SO_2NHCOCH_2OBu$ |
| 102 | ethyl | Me | Me | $-CH-CR^{12}-S-CZ-$ | iBu | $SO_2NHCOCH_2OEt$ |
| 103 | ethyl | Me | Me | $-CH-CR^{12}-S-CZ-$ | nPn | $SO_2NHCOCH_2OEt$ |

TABLE I-continued

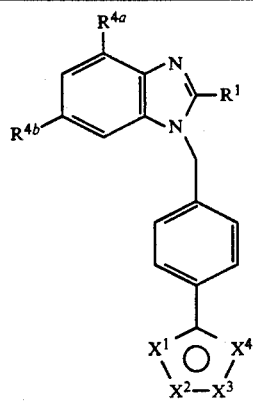

| # | R¹ | R⁴ᵃ | R⁴ᵇ | —X¹—X²—X³—X⁴— | R¹² | Z |
|---|---|---|---|---|---|---|
| 104 | ethyl | Me | Me | —CH—CR¹²—S—CZ— | nPn | $SO_2NHCOCH_2OBu$ |
| 105 | ethyl | Me | Me | —CH—CR¹²—S—CZ— | nPn | $SO_2NHCO_2$—N-methylpyrrole |
| 106 | ethyl | Me | Me | —CH—CR¹²—S—CZ— | nPr | $SO_2NHCO_2$—N-methylpyrrole |
| 107 | ethyl | Me | Me | —CH—CR¹²—S—CZ— | nPr | $SO_2NHCOOCH_2CH(Me)_2$ |
| 108 | ethyl | Me | Me | —CH—CR¹²—S—CZ— | iBu | $SO_2NHCOO(CH_2)_2OMe$ |
| 109 | ethyl | Me | Me | —CH—CR¹²—S—CZ— | nPr | $SO_2NHCOO(CH_2)_2OMe$ |
| 110 | ethyl | Me | Me | —CH—CR¹²—S—CZ— | nBu | $SO_2NHCOO(CH_2)_2OMe$ |
| 111 | ethyl | Me | Me | —CH—CR¹²—S—CZ— | nBu | $SO_2NHCO(CH_2)_5NHBoc$ |
| 112 | ethyl | Me | Me | —CH—CR¹²—S—CZ— | nBu | $SO_2NHCO(CH_2)_5NH_2$ |
| 113 | ethyl | Me | Me | —CH—CR¹²—S—CZ— | iBu | $SO_2NHCO(CH_2)_5NHBoc$ |
| 114 | ethyl | Me | Me | —CH—CR¹²—S—CZ— | iBu | $SO_2NHCO(CH_2)_5NH_2$ |
| 115 | ethyl | Me | Me | —CH—CR¹²—S—CZ— | nPn | $SO_2NHCO(CH_2)_5NHBoc$ |
| 116 | ethyl | Me | Me | —CH—CR¹²—S—CZ— | nPn | $SO_2NHCO(CH_2)_5NH_2$ |
| 117 | ethyl | Me | Me | —CH—CR¹²—S—CZ— | nPn | $SO_2NHCO(CH_2)_4CH_3$ |
| 118 | ethyl | Me | Me | —CH—CR¹²—S—CZ— | nPr | $SO_2NHCO(CH_2)_4CH_3$ |
| 119 | ethyl | Me | Me | —CH—CR¹²—S—CZ— | nBu | $SO_2NHCO(CH_2)_4CH_3$ |
| 120 | ethyl | Me | Me | —CH—CR¹²—S—CZ— | iBu | $SO_2NHCO(CH_2)_4CH_3$ |
| 121 | ethyl | Me | Me | —CH—CR¹²—S—CZ— | nPr | $SO_2NHCOcyPr$ |
| 122 | ethyl | Me | Me | —CH—CR¹²—S—CZ— | Bn | $SO_2NHCOcyPr$ |
| 123 | ethyl | Me | Me | —CH—CR¹²—S—CZ— | iBu | $SO_2NHCOO(CH_2)_2OMe$ |
| 124 | ethyl | Me | CON(Me)₂ | —CH—CR¹²—S—CZ— | iBu | $SO_2NHCOcyPr$ |
| 125 | ethyl | Me | Me | —CH—CR¹²—S—CZ— | nPr | $SO_2NHCOOBu$ |
| 126 | ethyl | Me | Me | —CH—CR¹²—S—CZ— | iBu | $SO_2NHCOOBu$ |
| 127 | ethyl | Me | Me | —CH—CR¹²—S—CZ— | iBu | $SO_2NHCOOBu$ |
| 128 | ethyl | Me | CO₂H | —CH—CR¹²—S—CZ— | nPr | $SO_2NHCOOBu$ |
| 129 | ethyl | Me | Me | —CH—CR¹²—S—CZ— | nPn | $SO_2NHCOOBu$ |
| 130 | ethyl | Me | CO₂H | —CH—CR¹²—S—CZ— | nPr | $SO_2NHCOOBu$ |
| 131 | ethyl | Me | Me | —CH—CR¹²—S—CZ— | iBu | $SO_2NHCOCH(Ph)_2$ |
| 132 | ethyl | Me | Me | —CH—CR¹²—S—CZ— | nPr | $SO_2NHCOCH(Ph)_2$ |
| 133 | ethyl | Me | CON(Me)₂ | —CH—CR¹²—S—CZ— | iBu | $SO_2NHCOCH(Ph)_2$ |
| 134 | ethyl | Me | Me | —CH—CR¹²—S—CZ— | nPr | $SO_2NHCOCH_2OEt$ |

TABLE III

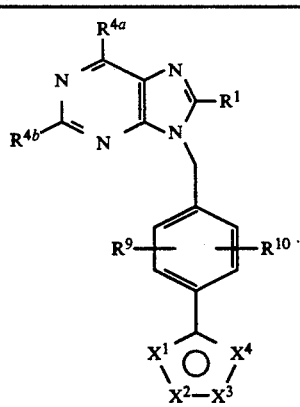

| # | R¹ | R⁴ᵃ | R⁴ᵇ | —X¹—X²—X³—X⁴— | R¹² | Z |
|---|---|---|---|---|---|---|
| 1 | n-butyl | H | H | —CH—S—CH—CZ— | | 1H-tetrazol-5-yl |
| 2 | ethyl | CH₃ | CO₂CH₃ | —CH—S—CH—CZ— | | 1H-tetrazol-5-yl |
| 3 | ethyl | CH₃ | CO₂H | —CH—S—CH—CZ— | | 1H-tetrazol-5-yl |
| 4 | n-propyl | CH₃ | CO₂CH₃ | —CH—S—CH—CZ— | | 1H-tetrazol-5-yl |
| 5 | propyl | CH₃ | CO₂H | —CH—S—CH—CZ— | | 1H-tetrazol-5-yl |

TABLE III-continued

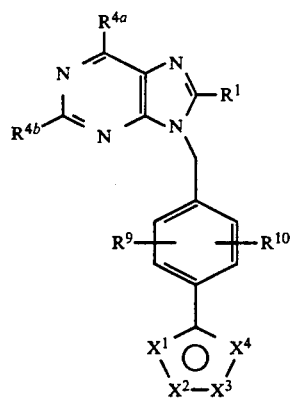

| # | $R^1$ | $R^{4a}$ | $R^{4b}$ | $-X^1-X^2-X^3-X^4-$ | $R^{12}$ | Z |
|---|---|---|---|---|---|---|
| 6 | n-butyl | $CH_3$ | $CH_3$ | $-CH-S-CH-CZ-$ | | $SO_2NHCOPh$ |
| 7 | n-propyl | H | $CH_3$ | $-CH-S-CH-CZ-$ | | 1H-tetrazol-5-yl |
| 8 | ethyl | $CH_3$ | $CH_3$ | $-CH-S-CH-CZ-$ | | $SO_2NHCOPh$ |
| 9 | ethyl | $CH_3$ | $CH_3$ | $-CH-S-CH-CZ-$ | | 1H-tetrazol-5-yl |
| 10 | ethyl | $CH_3$ | $CH_3$ | $-CH-S-C(SO_2NHCOPh)-CZ-$ | | 1H-tetrazol-5-yl |
| 11 | ethyl | $CH_3$ | $CH_3$ | $-S-CH-CH-CZ-$ | | $SO_2NHCOPh$ |
| 12 | ethyl | $CH_3$ | $CH_3$ | $-CH-CH-S-CZ-$ | | $SO_2NHCOPh$ |
| 13 | ethyl | $CH_3$ | $CO_2H$ | $-CH-CH-S-CZ-$ | | $SO_2NHCOPh$ |
| 14 | ethyl | $CH_3$ | $CH_3$ | $-CH-CH-S-CZ-$ | | 1H-tetrazol-5-yl |
| 15 | n-propyl | $CH_3$ | H | $-CH-CH-S-CZ-$ | | 1H-tetrazol-5-yl |
| 16 | ethyl | $CH_3$ | $CO_2H$ | $-CH-S-CH-CZ-$ | | 1H-tetrazol-5-yl |
| 17 | ethyl | $CH_3$ | $CH_3$ | $-CH-S-C(Br)-CZ-$ | | 1H-tetrazol-5-yl |
| 18 | propyl | $CH_3$ | H | $-CH-S-C(Br)-CZ-$ | | 1H-tetrazol-5-yl |
| 19 | ethyl | $CH_3$ | $CO_2CH_3$ | $-CH-S-C(Br)-CZ-$ | | 1H-tetrazol-5-yl |
| 20 | propyl | $CH_3$ | $CO_2CH_3$ | $-CH-S-C(Br)-CZ-$ | | 1H-tetrazol-5-yl |
| 103 | ethyl | Me | Me | $-CH-CR^{12}-S-CZ-$ | nPr | $SO_2NHCOOCH_2CH(Me)_2$ |
| 104 | ethyl | Me | Me | $-CH-CR^{12}-S-CZ-$ | iBu | $SO_2NHCOO(CH_2)_2OMe$ |
| 105 | ethyl | Me | Me | $-CH-CR^{12}-S-CZ-$ | nPr | $SO_2NHCOO(CH_2)_2OMe$ |
| 106 | ethyl | Me | Me | $-CH-CR^{12}-S-CZ-$ | nBu | $SO_2NHCOO(CH_2)_2OMe$ |
| 107 | ethyl | Me | Me | $-CH-CR^{12}-S-CZ-$ | nBu | $SO_2NHCO(CH_2)_5NHBoc$ |
| 108 | ethyl | Me | Me | $-CH-CR^{12}-S-CZ-$ | nBu | $SO_2NHCO(CH_2)_5NH_2$ |
| 109 | ethyl | Me | Me | $-CH-CR^{12}-S-CZ-$ | iBu | $SO_2NHCO(CH_2)_5NHBoc$ |
| 110 | ethyl | Me | Me | $-CH-CR^{12}-S-CZ-$ | iBu | $SO_2NHCO(CH_2)_5NH_2$ |
| 111 | ethyl | Me | Me | $-CH-CR^{12}-S-CZ-$ | nPn | $SO_2NHCO(CH_2)_5NHBoc$ |
| 112 | ethyl | Me | Me | $-CH-CR^{12}-S-CZ-$ | nPn | $SO_2NHCO(CH_2)_5NH_2$ |
| 113 | ethyl | Me | Me | $-CH-CR^{12}-S-CZ-$ | nPn | $SO_2NHCO(CH_2)_4CH_3$ |
| 114 | ethyl | Me | Me | $-CH-CR^{12}-S-CZ-$ | nPr | $SO_2NHCO(CH_2)_4CH_3$ |
| 115 | ethyl | Me | Me | $-CH-CR^{12}-S-CZ-$ | nBu | $SO_2NHCO(CH_2)_4CH_3$ |
| 116 | ethyl | Me | Me | $-CH-CR^{12}-S-CZ-$ | iBu | $SO_2NHCO(CH_2)_4CH_3$ |
| 117 | ethyl | Me | Me | $-CH-CR^{12}-S-CZ-$ | nPr | $SO_2NHCOcyPr$ |
| 118 | ethyl | Me | Me | $-CH-CR^{12}-S-CZ-$ | Bn | $SO_2NHCOcyPr$ |
| 119 | ethyl | Me | Me | $-CH-CR^{12}-S-CZ-$ | iBu | $SO_2NHCOO(CH_2)_2OMe$ |
| 120 | ethyl | Me | $CON(Me)_2$ | $-CH-CR^{12}-S-CZ-$ | iBu | $SO_2NHCOcyPr$ |
| 121 | ethyl | Me | Me | $-CH-CR^{12}-S-CZ-$ | nPr | $SO_2NHCOOBu$ |
| 122 | ethyl | Me | Me | $-CH-CR^{12}-S-CZ-$ | iBu | $SO_2NHCOOBu$ |
| 123 | ethyl | Me | Me | $-CH-CR^{12}-S-CZ-$ | iBu | $SO_2NHCOOBu$ |
| 124 | ethyl | Me | $CO_2H$ | $-CH-CR^{12}-S-CZ-$ | nPr | $SO_2NHCOOBu$ |
| 125 | ethyl | Me | Me | $-CH-CR^{12}-S-CZ-$ | nPr | $SO_2NHCOOBu$ |
| 126 | ethyl | Me | $CO_2H$ | $-CH-CR^{12}-S-CZ-$ | nPn | $SO_2NHCOOBu$ |
| 127 | ethyl | Me | Me | $-CH-CR^{12}-S-CZ-$ | iBu | $SO_2NHCOCH(Ph)_2$ |
| 128 | ethyl | Me | Me | $-CH-CR^{12}-S-CZ-$ | nPr | $SO_2NHCOCH(Ph)_2$ |
| 129 | ethyl | Me | $CON(Me)_2$ | $-CH-CR^{12}-S-CZ-$ | iBu | $SO_2NHCOCH(Ph)_2$ |
| 130 | ethyl | Me | Me | $-CH-CR^{12}-S-CZ-$ | nPr | $SO_2NHCOCH_2OEt$ |

TABLE II

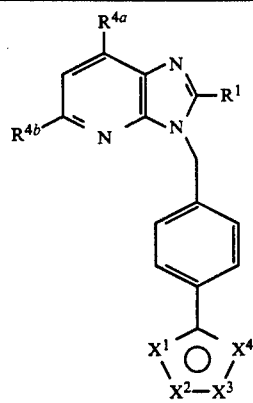

| # | R¹ | R⁴ᵃ | R⁴ᵇ | —X¹—X²—X³—X⁴— | R¹² | Z |
|---|---|---|---|---|---|---|
| 1 | n-butyl | H | H | —CH—S—CH—CZ— | | 1H-tetrazol-5-yl |
| 2 | n-butyl | H | H | —CH—S—CH—CZ— | | SO₂NHCOPh |
| 21 | ethyl | CH₃ | CO₂H | —CH—S—C(Br)—CZ— | | 1H-tetrazol-5-yl |
| 22 | propyl | CH₃ | CO₂H | —CH—S—C(Br)—CZ— | | 1H-tetrazol-5-yl |
| 23 | ethyl | CH₃ | CO₂CH₃ | —CH—CH—S—CZ— | | 1H-tetrazol-5-yl |
| 24 | propyl | CH₃ | CO₂CH₃ | —CH—CH—S—CZ— | | 1H-tetrazol-5-yl |
| 25 | ethyl | CH₃ | CO₂H | —CH—CH—S—CZ— | | 1H-tetrazol-5-yl |
| 26 | n-propyl | CH₃ | CO₂H | —CH—CH—S—CZ— | | 1H-tetrazol-5-yl |
| 27 | ethyl | CH₃ | CH₃ | —CH—CH—O—CZ— | | 1H-tetrazol-5-yl |
| 28 | n-propyl | CH₃ | H | —CH—CH—O—CZ— | | 1H-tetrazol-5-yl |
| 29 | ethyl | CH₃ | CO₂CH₃ | —CH—CH—O—CZ— | | 1H-tetrazol-5-yl |
| 30 | n-propyl | CH₃ | CO₂CH₃ | —CH—CH—O—CZ— | | 1H-tetrazol-5-yl |
| 31 | ethyl | CH₃ | CO₂H | —CH—CH—O—CZ— | | 1H-tetrazol-5-yl |
| 32 | n-propyl | CH₃ | CO₂H | —CH—CH—O—CZ— | | 1H-tetrazol-5-yl |
| 33 | ethyl | CH₃ | CH₃ | —CH—S—CH—CZ— | | 1H-tetrazol-5-yl |
| 34 | ethyl | CH₃ | CH₃ | —CH—S—CH—CZ— | | SO₂NHCOCF₃ |
| 35 | ethyl | CH₃ | CH₃ | —CH—S—CH—CZ— | | CO₂H |
| 36 | ethyl | CH₃ | CH₃ | —CH—S—C(SO₂NHCOCF₃)—CZ— | | H |
| 37 | ethyl | CH₃ | CH₃ | —CH—S—C(SO₂NHCOPh)—CZ— | | H |
| 38 | ethyl | CH₃ | CH₃ | —CH—S—C(SO₂NHCO-4-pyr)—CZ— | | H |
| 39 | n-propyl | CH₃ | H | —S—CH—CH—CZ— | | SO₂NHCOPh |
| 40 | ethyl | CH₃ | CO₂CH₃ | —S—CH—CH—CZ— | | SO₂NHCOPh |
| 41 | ethyl | CH₃ | CO₂H | —S—CH—CH—CZ— | | SO₂NHCOPh |
| 42 | ethyl | CH₃ | CH₃ | —C=C—S—CZ— with HC=CH—CH=CH fused | | SO₂NHCOPh |
| 43 | n-propyl | CH₃ | H | —C=C—S—CZ— with HC=CH—CH=CH fused | | SO₂NHCOPh |
| 44 | ethyl | CH₃ | CO₂CH₃ | —C=C—S—CZ— with HC=CH—CH=CH fused | | SO₂NHCOPh |
| 45 | n-propyl | CH₃ | CO₂CH₃ | —C=C—S—CZ— with HC=CH—CH=CH fused | | SO₂NHCOPh |
| 46 | ethyl | CH₃ | CO₂H | —C=C—S—CZ— with HC=CH—CH=CH fused | | SO₂NHCOPh |
| 47 | n-propyl | CH₃ | CO₂H | —C=C—S—CZ— with HC=CH—CH=CH fused | | SO₂NHCOPh |
| 48 | n-propyl | CH₃ | H | —CH—CH—S—CZ— | | SO₂NHCOPh |
| 49 | ethyl | CH₃ | CO₂CH₃ | —CH—CH—S—CZ— | | SO₂NHCOPh |

TABLE II-continued

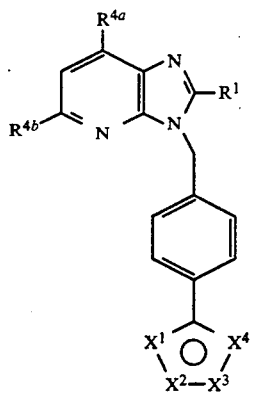

| # | R$^1$ | R$^{4a}$ | R$^{4b}$ | —X$^1$—X$^2$—X$^3$—X$^4$— | R$^{12}$ | Z |
|---|---|---|---|---|---|---|
| 50 | n-propyl | CH$_3$ | CO$_2$CH$_3$ | —CH—CH—S—CZ— |  | SO$_2$NHCOPh |
| 51 | n-propyl | CH$_3$ | CO$_2$CH$_3$ | —CH—CH—S—CZ— |  | SO$_2$NHCOPh |
| 52 | n-propyl | CH$_3$ | CO$_2$CH$_3$ | —S—CH—CH—CZ— |  | SO$_2$NHCOPh |
| 53 | n-propyl | CH$_3$ | CO$_2$H | —S—CH—CH—CZ— |  | SO$_2$NHCOPh |
| 54 | n-butyl | Me | H | —CH—CR$^{12}$—S—CZ— | nPr | 1H-tetrazol-5-yl |
| 55 | n-butyl | Me | H | —CH—CR$^{12}$—S—CZ— | iBu | 1H-tetrazol-5-yl |
| 56 | n-butyl | Me | H | —CH—CR$^{12}$—S—CZ— | nPr | SO$_2$NHCOPh |
| 57 | n-butyl | Me | H | —CH—CR$^{12}$—S—CZ— | iBu | SO$_2$NHCOPh |
| 58 | n-butyl | Me | H | —CH—CR$^{12}$—S—CZ— | nPn | SO$_2$NHCO(Ph)$_2$ |
| 59 | ethyl | Me | H | —CH—CR$^{12}$—S—CZ— | nPr | 1H-tetrazol-5-yl |
| 60 | ethyl | Me | H | —CH—CR$^{12}$—S—CZ— | iBu | 1H-tetrazol-5-yl |
| 61 | ethyl | Me | H | —CH—CR$^{12}$—S—CZ— | nPn | 1H-tetrazol-5-yl |
| 62 | ethyl | Me | H | —CH—CR$^{12}$—S—CZ— | Bn | 1H-tetrazol-5-yl |
| 63 | ethyl | Me | H | —CH—CR$^{12}$—S—CZ— | nPr | SO$_2$NHCOPh |
| 64 | ethyl | Me | H | —CH—CR$^{12}$—S—CZ— | iBu | SO$_2$NHCOPh |
| 65 | ethyl | Me | H | —CH—CR$^{12}$—S—CZ— | nPn | SO$_2$NHCOPh |
| 66 | ethyl | Me | H | —CH—CR$^{12}$—S—CZ— | Bn | SO$_2$NHCOPh |
| 67 | n-butyl | Me | Me | —CH—CR$^{12}$—S—CZ— | nPr | 1H-tetrazol-5-yl |
| 68 | n-butyl | Me | Me | —CH—CR$^{12}$—S—CZ— | nBu | 1H-tetrazol-5-yl |
| 69 | n-butyl | Me | Me | —CH—CR$^{12}$—S—CZ— | iBu | 1H-tetrazol-5-yl |
| 70 | n-butyl | Me | Me | —CH—CR$^{12}$—S—CZ— | nPn | 1H-tetrazol-5-yl |
| 71 | n-butyl | Me | Me | —CH—CR$^{12}$—S—CZ— | nPr | SO$_2$NHCOPh |
| 72 | n-butyl | Me | Me | —CH—CR$^{12}$—S—CZ— | iBu | SO$_2$NHCOPh |
| 73 | n-butyl | Me | Me | —CH—CR$^{12}$—S—CZ— | nPn | SO$_2$NHCOPh |
| 74 | ethyl | Me | Me | —CH—CR$^{12}$—S—CZ— | nPr | 1H-tetrazol-5-yl |
| 75 | ethyl | Me | Me | —CH—CR$^{12}$—S—CZ— | iBu | 1H-tetrazol-5-yl |
| 76 | ethyl | Me | Me | —CH—CR$^{12}$—S—CZ— | nPn | 1H-tetrazol-5-yl |
| 77 | ethyl | Me | Me | —CH—CR$^{12}$—S—CZ— | Me | SO$_2$NHCOPh |
| 78 | ethyl | Me | Me | —CH—CR$^{12}$—S—CZ— | Et | SO$_2$NHCOPh |
| 79 | ethyl | Me | Me | —CH—CR$^{12}$—S—CZ— | nPr | SO$_2$NHCOPh |
| 80 | ethyl | Me | Me | —CH—CR$^{12}$—S—CZ— | nBu | SO$_2$NHCOPh |
| 81 | ethyl | Me | Me | —CH—CR$^{12}$—S—CZ— | iBu | SO$_2$NHCOPh |
| 82 | ethyl | Me | Me | —CH—CR$^{12}$—S—CZ— | nPn | SO$_2$NHCOPh |
| 83 | ethyl | Me | Me | —CH—CR$^{12}$—S—CZ— | Bn | SO$_2$NHCOPh |
| 84 | ethyl | Me | Me | —CH—CR$^{12}$—S—CZ— | CH$_2$N(CH$_2$CH$_2$)$_2$O | SO$_2$NHCOCH$_2$Ph |
| 85 | ethyl | Me | Me | —CH—CR$^{12}$—S—CZ— | CH$_2$N(CH$_2$CH$_2$)$_2$O | SO$_2$NHCOCH(Ph)$_2$ |
| 86 | n-butyl | Me | CON(Me)$_2$ | —CH—CR$^{12}$—S—CZ— | nPr | 1H-tetrazol-5-yl |
| 87 | n-butyl | Me | CON(Me)$_2$ | —CH—CR$^{12}$—S—CZ— | iBu | 1H-tetrazol-5-yl |
| 88 | n-butyl | Me | CON(Me)$_2$ | —CH—CR$^{12}$—S—CZ— | nPr | SO$_2$NHCOPh |
| 89 | ethyl | Me | CON(Me)$_2$ | —CH—CR$^{12}$—S—CZ— | nPr | 1H-tetrazol-5-yl |
| 90 | ethyl | Me | CON(Me)$_2$ | —CH—CR$^{12}$—S—CZ— | nBu | 1H-tetrazol-5-yl |
| 91 | ethyl | Me | CON(Me)$_2$ | —CH—CR$^{12}$—S—CZ— | iBu | 1H-tetrazol-5-yl |
| 92 | ethyl | Me | CON(Me)$_2$ | —CH—CR$^{12}$—S—CZ— | nPn | 1H-tetrazol-5-yl |
| 93 | ethyl | Me | CON(Me)$_2$ | —CH—CR$^{12}$—S—CZ— | nBu | SO$_2$NHCOPh |
| 94 | ethyl | Me | CON(Me)$_2$ | —CH—CR$^{12}$—S—CZ— | iBu | SO$_2$NHCOPh |
| 95 | ethyl | Me | CON(Me)$_2$ | —CH—CR$^{12}$—S—CZ— | Bn | SO$_2$NHCOPh |
| 96 | n-butyl | Me | CH$_2$OH | —CH—CR$^{12}$—S—CZ— | nPr | 1H-tetrazol-5-yl |
| 97 | n-butyl | Me | CH$_2$OH | —CH—CR$^{12}$—S—CZ— | iBu | 1H-tetrazol-5-yl |
| 98 | n-butyl | Me | CH$_2$OH | —CH—CR$^{12}$—S—CZ— | nPr | SO$_2$NHCOPh |
| 99 | n-butyl | Me | CH$_2$OH | —CH—CR$^{12}$—S—CZ— | nPr | SO$_2$NHCOPh |
| 100 | ethyl | Me | CH$_2$OH | —CH—CR$^{12}$—S—CZ— | nBu | 1H-tetrazol-5-yl |
| 101 | ethyl | Me | CH$_2$OH | —CH—CR$^{12}$—S—CZ— | iBu | 1H-tetrazol-5-yl |
| 102 | ethyl | Me | CH$_2$OH | —CH—CR$^{12}$—S—CZ— | nPn | 1H-tetrazol-5-yl |
| 103 | ethyl | Me | Me | —CH—CR$^{12}$—S—CZ— | nPr | SO$_2$NHCO(CH$_2$)$_2$OMe |
| 104 | ethyl | Me | CH$_2$OH | —CH—CR$^{12}$—S—CZ— | nBu | SO$_2$NHCOPh |
| 105 | ethyl | Me | CH$_2$OH | —CH—CR$^{12}$—S—CZ— | iBu | SO$_2$NHCOPh |
| 106 | ethyl | Me | CH$_2$OH | —CH—CR$^{12}$—S—CZ— | nPn | SO$_2$NHCOPh |
| 107 | ethyl | Me | CO$_2$H | —CH—CR$^{12}$—S—CZ— | nPr | SO$_2$NHCOPh |
| 108 | propyl | Me | CO$_2$H | —CH—CR$^{12}$—S—CZ— | nPr | SO$_2$NHCOPh |
| 109 | propyl | Me | CO$_2$H | —CH—CR$^{12}$—S—CZ— | iBu | SO$_2$NHCOPh |
| 110 | propyl | Me | CO$_2$H | —CH—CR$^{12}$—S—CZ— | nPn | SO$_2$NHCOPh |

TABLE II-continued

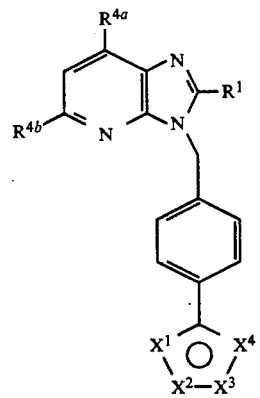

| # | R[1] | R[4a] | R[4b] | —X[1]—X[2]—X[3]—X[4]— | R[12] | Z |
|---|---|---|---|---|---|---|
| 111 | ethyl | Me | Me | —CH—CR[12]—S—CZ— | Me | $SO_2NHCOCH_2Ph$ |
| 112 | ethyl | Me | Me | —CH—CR[12]—S—CZ— | Me | $SO_2NHCOCH(Ph)_2$ |
| 113 | ethyl | Me | Me | —CH—CR[12]—S—CZ— | Et | $SO_2NHCOCH(Ph)_2$ |
| 114 | ethyl | Me | Me | —CH—CR[12]—S—CZ— | Et | $SO_2NHCOCH_2OEt$ |
| 115 | ethyl | Me | Me | —CH—CR[12]—S—CZ— | nBu | $SO_2NHCOCH_2OEt$ |
| 116 | propyl | Me | $CO_2H$ | —CH—CR[12]—S—CZ— | nPn | $SO_2NHCOCH_2OBu$ |
| 117 | ethyl | Me | Me | —CH—CR[12]—S—CZ— | nPr | $SO_2NHCOOCH_2CH(Me)_2$ |
| 118 | ethyl | Me | Me | —CH—CR[12]—S—CZ— | nPr | $SO_2NHCOCH_2OBu$ |
| 119 | ethyl | Me | Me | —CH—CR[12]—S—CZ— | nPr | $SO_2NHCOCH_2OEt$ |
| 120 | ethyl | Me | Me | —CH—CR[12]—S—CZ— | nPr | $SO_2NHCO(CH_2)_2CycPen$ |
| 121 | ethyl | Me | $CH_2OH$ | —CH—CR[12]—S—CZ— | nPr | $SO_2NHCOCH_2OEt$ |
| 121 | ethyl | Me | $CH_2OH$ | —CH—CR[12]—S—CZ— | iBu | $SO_2NHCOCH_2OBu$ |
| 122 | ethyl | Me | $CO_2H$ | —CH—CR[12]—S—CZ— | iBu | $SO_2NHCOCH_2OBu$ |
| 123 | ethyl | Me | Me | —CH—CR[12]—S—CZ— | iBu | $SO_2NHCOCH_2OBu$ |
| 124 | ethyl | Me | Me | —CH—CR[12]—S—CZ— | iBu | $SO_2NHCOCH_2OEt$ |
| 125 | ethyl | Me | Me | —CH—CR[12]—S—CZ— | nPn | $SO_2NHCOCH_2OEt$ |
| 126 | ethyl | Me | Me | —CH—CR[12]—S—CZ— | nPn | $SO_2NHCOCH_2OBu$ |
| 127 | ethyl | Me | Me | —CH—CR[12]—S—CZ— | nPn | $SO_2NHCO_2$—N-methylpyrrole |
| 128 | ethyl | Me | Me | —CH—CR[12]—S—CZ— | nPr | $SO_2NHCO_2$—N-methylpyrrole |
| 129 | ethyl | Me | Me | —CH—CR[12]—S—CZ— | nPr | $SO_2NHCOOCH_2CH(Me)_2$ |
| 130 | ethyl | Me | Me | —CH—CR[12]—S—CZ— | iBu | $SO_2NHCOO(CH_2)_2OMe$ |
| 131 | ethyl | Me | Me | —CH—CR[12]—S—CZ— | nPr | $SO_2NHCOO(CH_2)_2OMe$ |
| 132 | ethyl | Me | Me | —CH—CR[12]—S—CZ— | nBu | $SO_2NHCOO(CH_2)_2OMe$ |
| 133 | ethyl | Me | Me | —CH—CR[12]—S—CZ— | nBu | $SO_2NHCO(CH_2)_5NHBoc$ |
| 134 | ethyl | Me | Me | —CH—CR[12]—S—CZ— | nBu | $SO_2NHCO(CH_2)_5NH_2$ |
| 135 | ethyl | Me | Me | —CH—CR[12]—S—CZ— | iBu | $SO_2NHCO(CH_2)_5NHBoc$ |
| 136 | ethyl | Me | Me | —CH—CR[12]—S—CZ— | iBu | $SO_2NHCO(CH_2)_5NH_2$ |
| 137 | ethyl | Me | Me | —CH—CR[12]—S—CZ— | nPn | $SO_2NHCO(CH_2)_5NHBoc$ |
| 138 | ethyl | Me | Me | —CH—CR[12]—S—CZ— | nPn | $SO_2NHCO(CH_2)_5NH_2$ |
| 139 | ethyl | Me | Me | —CH—CR[12]—S—CZ— | nPn | $SO_2NHCO(CH_2)_4CH_3$ |
| 140 | ethyl | Me | Me | —CH—CR[12]—S—CZ— | nPr | $SO_2NHCO(CH_2)_4CH_3$ |
| 141 | ethyl | Me | Me | —CH—CR[12]—S—CZ— | nBu | $SO_2NHCO(CH_2)_4CH_3$ |
| 142 | ethyl | Me | Me | —CH—CR[12]—S—CZ— | iBu | $SO_2NHCO(CH_2)_4CH_3$ |
| 143 | ethyl | Me | Me | —CH—CR[12]—S—CZ— | nPr | $SO_2NHCOcyPr$ |
| 144 | ethyl | Me | Me | —CH—CR[12]—S—CZ— | Bn | $SO_2NHCOcyPr$ |
| 145 | ethyl | Me | Me | —CH—CR[12]—S—CZ— | iBu | $SO_2NHCOO(CH_2)_2OMe$ |
| 146 | ethyl | Me | $CON(Me)_2$ | —CH—CR[12]—S—CZ— | iBu | $SO_2NHCOcyPr$ |
| 147 | ethyl | Me | Me | —CH—CR[12]—S—CZ— | nPr | $SO_2NHCOOBu$ |
| 148 | ethyl | Me | Me | —CH—CR[12]—S—CZ— | iBu | $SO_2NHCOOBu$ |
| 149 | ethyl | Me | Me | —CH—CR[12]—S—CZ— | iBu | $SO_2NHCOOBu$ |
| 150 | ethyl | Me | Me | —CH—CR[12]—S—CZ— | nPr | $SO_2NHCOOBu$ |
| 151 | ethyl | Me | Me | —CH—CR[12]—S—CZ— | nPn | $SO_2NHCOOBu$ |
| 152 | ethyl | Me | $CO_2H$ | —CH—CR[12]—S—CZ— | nPn | $SO_2NHCOOBu$ |
| 153 | ethyl | Me | Me | —CH—CR[12]—S—CZ— | iBu | $SO_2NHCOCH(Ph)_2$ |
| 154 | ethyl | Me | Me | —CH—CR[12]—S—CZ— | nPr | $SO_2NHCOCH(Ph)_2$ |
| 155 | ethyl | Me | $CON(Me)_2$ | —CH—CR[12]—S—CZ— | iBu | $SO_2NHCOCH(Ph)_2$ |
| 156 | ethyl | Me | Me | —CH—CR[12]—S—CZ— | nPr | $SO_2NHCOCH_2OEt$ |

DETAILED DESCRIPTION OF THE INVENTION

General Methods for Preparation of Compounds of General Formula I

The methods described in PART I AND PART II below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component and a substituted benzyl substitutent which is attached to the heterocyclic component at a nitrogen atom. Thus, two generally applicable approaches to antagonists of formula I are these:

1. A heterocycle, designated above with Formula is prepared as described in PART I below. Then the heterocycle is alkylated at a nitrogen atom with a substituted benzyl halide or pseudohalide giving an alkylated hetrocycle in the Schemes below, this alkylating agent is often designated as "AR—CH$_2$Q" where Q is a halide (—Cl,Br,I) or pseudohalide (—OMs, OTs, OTf). In some cases, alkylation may take place at more than one nitrogen atom of the heterocycle, and in these cases, separation by fractional crystallization or by chromotographic methods may be necessary for isolation of the desired product. In some cases, the alkylation step produces a fully-assembled antagonist of Formula I, except that functional groups in the alkylating agent or in the heterocycle may be present in protected form and require deprotection steps to be carried out to complete the synthesis. In other cases, the alkylation is carried out with a substituted benzylic halide or pseudohalide ("Ar—CH$_2$Q"), but here the alkylation step is followed by subsequent steps which are required to assemble the substituted benzyl element of the antagonist of Formula I. The alkylation steps and subsequent steps used to prepare antagonists of Formula I, are described in PART II below.

The compounds of this invention, their pharmaceutically acceptable salts and their prodrug forms are included within the scope of this invention. Abbreviations used in the schemes and examples are listed in Table IV.

TABLE IV

| Reagents | |
|---|---|
| NBS | N-bromosuccinimide |
| AIBN | Azo(bis) isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |
| FMOC-Cl | 9-Fluorenylmethyloxycarbonyl chloride |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | OSO$_2$CF$_3$ |
| Ph | phenyl |
| FAB-MS | Fast atom bombardment mass spectroscopy |
| NOE | Nuclear Overhauser Effect |
| SiO$_2$ | silica gel |
| trityl | triphenylmethyl |

PART I: Preparation of the heterocyclic component

Benzimidazoles

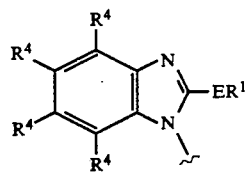

The compounds of Formula I wherein (—A$^1$—A$^2$—A$^3$—A$^4$—) is defined by (a) in the specification of the invention can be synthesized using the reactions and techniques described herein below. The reactions are performed in a solvent appropriate to the reagents and materials employed and suitable for the transformation being effected. It is understood by those skilled in the art of organic synthesis that the functionality present on the benzimidazole and other parts of the structure should be consistent with the chemical transformations proposed. Depending upon the reactions and techniques employed, this may involve changing the order of synthetic steps, use of required protecting groups followed by deprotection, and activation of the benzylic position of the alkylating agents used to enable alkylation at the nitrogen on the imidazole part of benzimidazoles.

SCHEME I-1

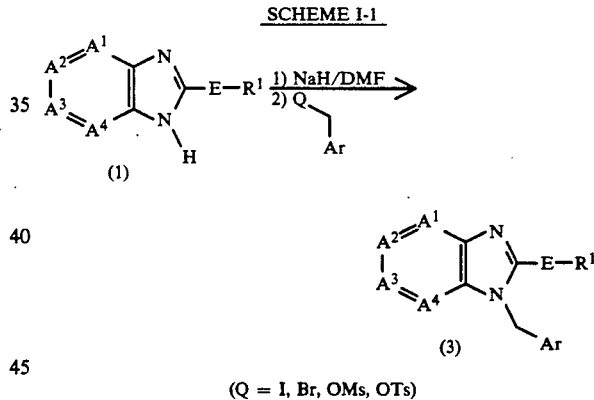

(Q = I, Br, OMs, OTs)

As shown in Scheme I-1, compounds of Formula (3) can be prepared by carrying out direct alkylation of alkali-metal salt of benzimidazole (1), wherein A$^1$—A$^2$—A$^3$—A$^4$=CR$^4$—CR$^4$—CR$^4$—CR$^4$, (preparation of benzimidazoles are described in Schemes I-2 to I-5) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with metal alkoxide such as sodium or potassium methoxide, ethoxide or t-butoxide in an appropriate alcohol such as methanol, ethanol or t-butanol as the solvent. The alkylation is generally carried-out by dissolving the metal salt of benzimidazole in a dipolar aprotic solvent such as DMF or dimethylsulfoxide (DMSO) and reacting it with the alkylating agent at 20° C. to reflux temperature of the solvent for 1–24 hours.

If substituents on the benzene ring result in an unsymmetrical benzimidazole, the alkylation may produce a mixture of two regioisomers as products. These regioisomers possess distinct physico-chemical and biological properties and in most cases can be separated and purified by using conventional separation techniques such as chromatography (flash column chromatography, medium-pressure liquid chromatography, high pressure liquid chromatography (HPLC) and/or crystallization. In those cases where separation of regioisomers is difficult by conventional techniques, the mixture can be transformed into suitable derivatives that can be separated by usual separation methods. The structural assignments of the isomers can be made using proton NMR, Nuclear Overhauser Effect (NOE) experiments or X-ray crystallography.

pounds, Vol. 40, part I, pp. 1–286 (1981) and references cited therein]. Several alternative routes to obtain benzimidazoles are outlined in Scheme I-2. The most widely used starting material, o-phenylenediamines (11), can be readily prepared from the corresponding o-nitroaniline (10) using standard reductive procedures such as metal-acid reduction or catalytic reduction. The substituted or unsubstituted (11) can then be treated with an appropriate imidate hydrochloride (12) to form corresponding benzimidazoles (13). Alternatively, the reaction of carboxylic acids (14) with o-phenylenediamines in the presence of polyphosphoric acid (PPA) is also effective in producing benzimidazoles (15). Benzimidazoles (17) can

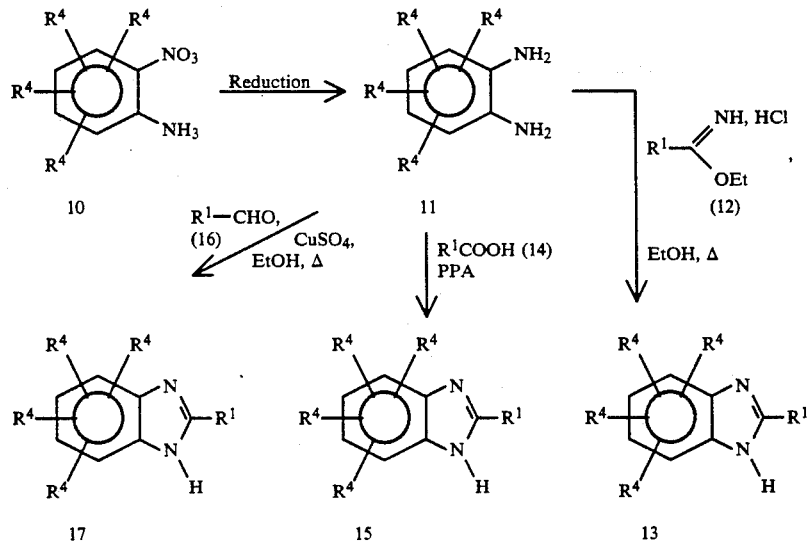

SCHEME I-2

The starting benzimidazoles can be readily prepared by any of the standard procedures described in the literature [P. N. Preston, *Chemistry of Heterocyclic Compounds*, Vol. 40, part I, pp. 1–286 (1981) and references cited therein].

also be prepared from o-phenylenediamines and aldehyde (16) using cupric salt as an oxidant [R. Weidenhagen, *Chem. Ber.*, 69, 2263 (1936)].

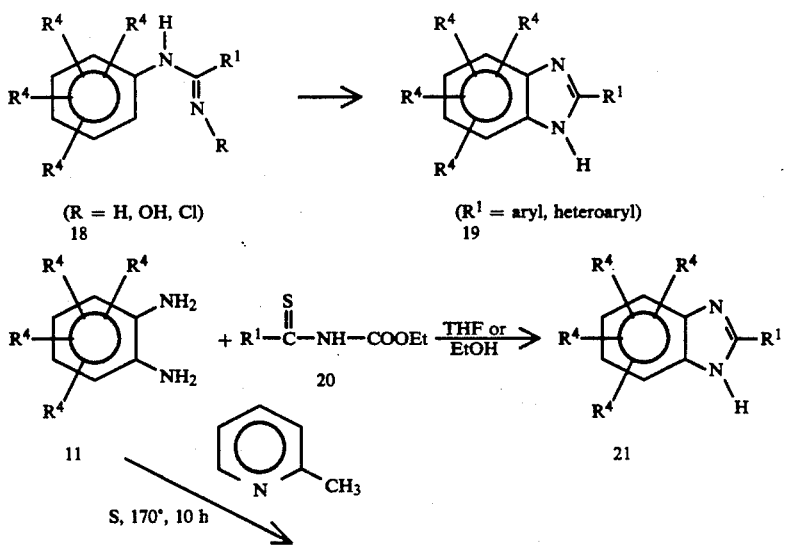

SCHEME I-3

SCHEME I-3 -continued

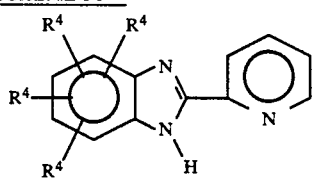

22

Although some benzimidazoles having aryl and heteroaryl groups at the 2 position can be prepared using the methods described in Scheme I-2, Scheme I-3 outlines methods which are more suitable for the synthesis of this class of compounds. N'-aryl-N-hydroxyamidines (18; R=OH) are cyclized under mild conditions using benzenesulfonyl chloride in pyridine or triethylamine to give 19 in good yield [M. W. Partridge and H. A. Turner, *J. Chem. Soc.*, 2086 (1958)]. Parent amidines (18; R=H) can also be oxidized with sodium hypochlorite under basic conditions to form 19 [V. J. Grenda, R. E. Jones, G. Gal and M. Sletzinger, *J. Org. Chem.*, 30, 259, (1965)].

Alternatively, as shown in Reaction Scheme I-3, o-phenylenediamines (11) can be reacted with N-ethoxycarbonylthioamides (20) to give 2-substituted benzimidazoles (21) in excellent yields. This method avoids the use of acidic catalysts. The reagents (20) are easily obtained in one step from ethoxycarbonyl isothiocyanate and simple aromatic or heterocyclic compounds or alkylmagnesium halides [B. George and E. P. Papadopoulos., *J. Org. Chem.*, 41, 3233(1976); E. P. Papadopoulos., *J. Org. Chem.*, 41, 962(1976)]. Heterocyclic compounds containing reactive methyl groups (e.g., 2-picoline) can also be reacted with o-phenylenediamines in the presence of sulfur at elevated temperatures to give 2-heteroaryl benzimidazoles (22).

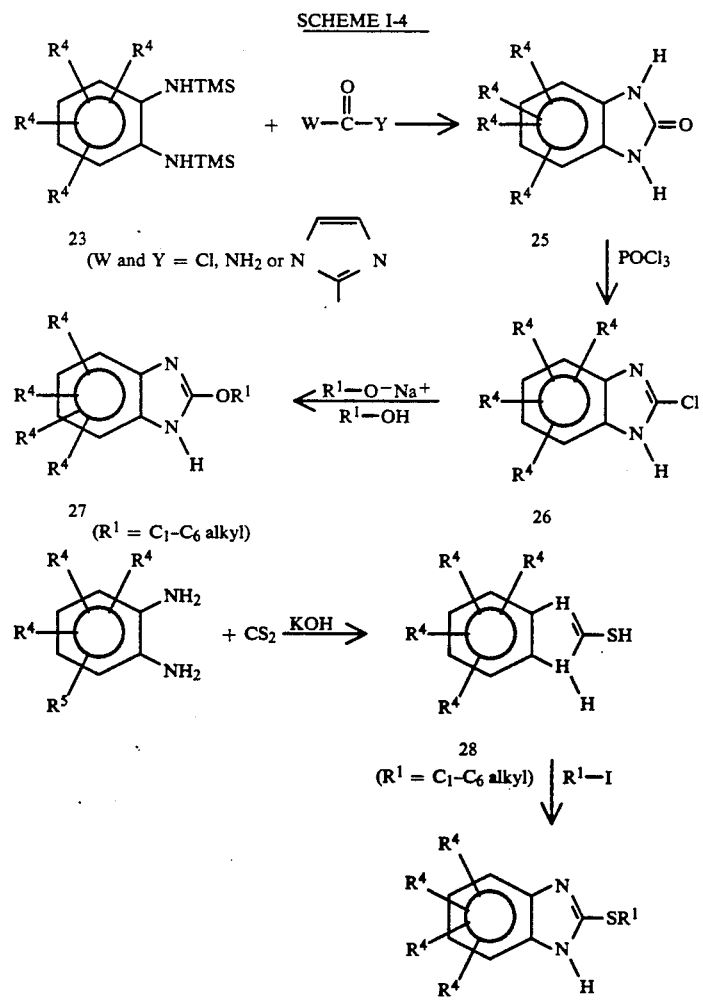

As outlined in Scheme I-4, benzimidazoles containing 2-alkoxy and thioalkyl substituents (27 and 29) can be prepared from the corresponding benzimidazolones (25) or benzimidazolethiones (28). Benzimidazolones are conveniently prepared from o-phenylenediamines and phosgene or urea [K. Hofmann, "Imidazole and its Derivatives, Part 1," Wiley-Interscience, New York, 1953, pp. 285-291]. Carbonate esters, diethylpyrocarbonate, N,N-carbonyldiimidazole and N,N-diethylcarbamyl chloride may also be used in this reaction. The reaction of phosgene is apparently facilitated by the use of N,N'-bis-trimethylsilyl (TMS) derivative (23) instead of the parent diamine [L. Birkhofer, H. P. Kuhlthau, and A. Ritter, Chem. Ber., 93, 2810 (1960)].

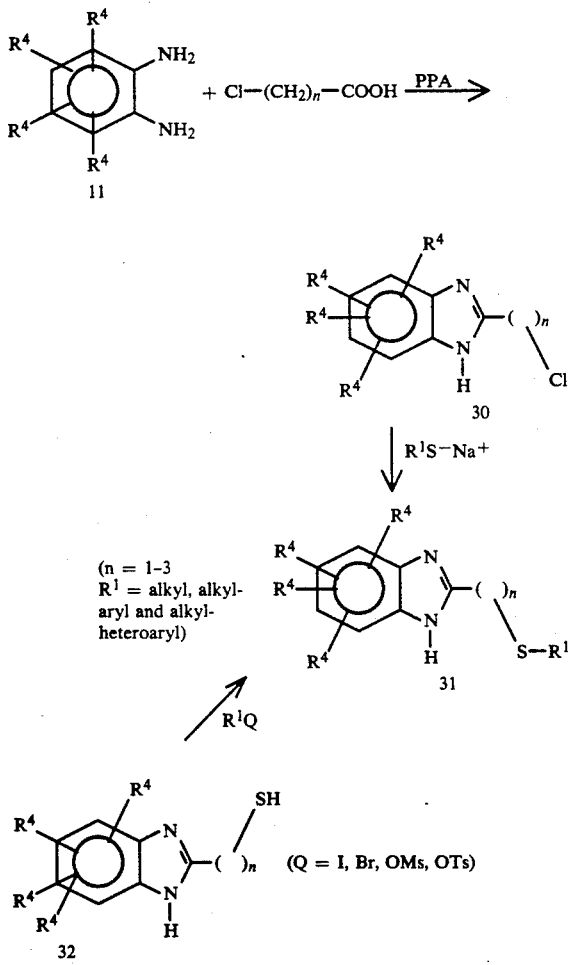

As described in Scheme I-5, 2-alkylthioalkyl substituted benzimidazoles (31) can be prepared from the reaction of RS-M (where M is sodium, potassium or lithium) with 2-chloroalkyl benzimidazoles (30). 2-Chloroalkyl benzimidazoles (30) can be conveniently prepared from the diamines and the chloroalkyl carboxylic acids using PPA [W. Knobloch, Chem. Ber., 91, 2557 (1958)]. Alternatively, compound 31 can also be prepared from the readily available 2-thioalkyl derivative (32) [E. S. Milner, S. Snyder, and M. M. Joullie, J. Chem. Soc., 4151 (1964)].

IMIDAZO-6-FUSED HETEROCYCLES

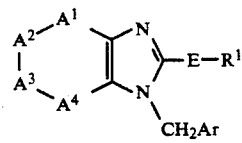

The compounds of Formula I, wherein —$A^1$—$A^2$—$A^3$—$A^4$— are defined by (b) to (u) in the Specification can be synthesized using the reactions and techniques described herein below. The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

As shown in Scheme I-1, compounds of Formula I can be prepared by carrying-out direct alkylation of alkali-metal salts of heterocycles (1) (preparation of the imidazo-6-fused heterocycles are described in Reaction Schemes I-6 thru I-9) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried-out by dissolving the metal salt of the heterocycle in a dipolar aprotic solvent such as DMF or dimethylsulfoxide (DMSO) and reacting it with the alkylating agent at 20° C. to reflux temperature of the solvent for 1-24 hours.

If substituents and/or the hetero atom positions in the six membered ring are not symmetrically disposed, the alkylation on the imidazole nitrogen(s) generally produces a mixture of two regioisomers as products arising from $N^1$ and $N^3$ alkylation. These regioisomers possess distinct physico-chemical and biological properties and in most cases can be separated and purified by using conventional separation techniques such as chromatography (flash column chromatography, medium-pressure liquid chromatography, high performance liquid chromatography) and/or crystallization. In those cases where separation of regioisomers is difficult by conventional techniques, the mixture can be transformed into suitable derivatives that can be separated by the above separation methods. The structural assignments of the isomers can be made using Nuclear Overhauser Effect (NOE), $^1H$-$^{13}C$ coupled NMR experiments or X-ray crystallography.

When there is potential for alkylation of the 6-membered heterocyclic ring, this can be avoided by the use of suitable protecting groups.

The heterocycles of type (1) can be prepared by any of the standard procedures described in the literature [J. A. Montgomery and J. A. Secrist III in "Comprehensive Heterocyclic Chemistry," Vol. 5, A. R. Katritsky and C. W. Rees Eds., Pergamon Press 1984; pp 567-597 and 631-656 and references cited therein]. As shown in Scheme I-6, the most widely used starting materials are six member heterocyclic vicinal diamines (9). Fused imidazoles (10) can be prepared by condensation of (9) with an appropriate carboxylic acid, nitrile, imidate ester, or orthoester, either neat, or in a solvent appropriate and compatible with the starting materials and reagents, such as polyphosphoric acid, ethanol, methanol, hydrocarbon solvents, and with a catalytic amount of acid if required. Oxidation of an imine formed by reaction of diamine (9) with an appropriate aldehyde using oxidants such as Cu (II), nitrobenzene, or 2,3-dichloro-5,6-dicyano-1,4-benzoquinone (DDQ) also affords heterocycles (10). Aminoamides (11, W=H) or diamides (11, W=R$^6$CO) can be converted to fused imidazoles (10) by heating neat, or at an elevated temperature in a solvent such as xylene under acidic or neutral conditions.

Halogenation of the imidazo[4,5-b]pyridine ring at the 6-position can be accomplished using Br$_2$, or N-bromosuccinimide. Halogenation of the 7-position can be accomplished by reaction of the corresponding imidazopyridine-4-oxide (prepared by reaction of the imidazopyridine with peracids such as m-chloroperbenzoic acid) with POCl$_3$. When the 7-position is substituted other than hydrogen halogenation at the 5-position of the 4(N)-oxide precursor occurs on treatment with POCl$_3$. Chlorides may be substituted by bromides or iodides by treatment with either HBr or HI, respectively, in a solvent such as HOAc.

2-Alkyl-imidazo[4,5-b]pyridines can be substituted at the 5, 6, or 7 positions by displacement of a halogen at that position by nucleophiles such as cyanide (followed by hydrolysis to obtain carboxylic acids), amines, copper alkoxides, trialkylphosphites, and thiolates. Also, substitution of the halogens, in particular bromides or iodides, can be accomplished by reaction with a coupling partner such as alkylzinc or arylzinc halides, or monoalkylarylphosphonites in the presence of an appropriate metal catalyst such as nickel, palladium, ruthenium, or platinum. In cases where the displacement of a halogen is sluggish or otherwise complicated due to an acidic proton, the imidazopyridine may be protected at the 1, 3, or 4 positions by benzyl or other arylmethyl groups.

7-Methyl-2-propylimidazo[4,5-b]pyridine-5-carboxylic acid or the 2-ethyl analog is prepared from 7-methyl-2-propylimidazo[4,5-b]pyridine or the 2-ethyl analog by treatment with m-chloroperoxybenzoic acid to obtain the N-oxide which is then treated with POCl$_3$ to give 5-chloro-7-methyl-2-propylimidazo-[4,5-b]pyridine or 2-ethyl analog. The chloride is then exchanged for a bromide by reaction of 5-chloro-7-methyl-2-propylimidazo[4,5-b]pyridine or the 2-ethyl analog with HBr in acetic acid. The resulting 5-bromo-7-methyl-2-propylimidazo[4,5-b]pyridine or 2-ethyl analog is treated with NaH in DMF followed by benzyl bromide to obtain 3-benzyl-5-bromo-7-methyl-2-propylimidazo[4,5-b]pyridine or its corresponding 2-ethyl analog which is in turn treated with CuCN in hot pyridine to obtain 3-benzyl-5-cyano-7-methyl-2-propylimidazo[4,5-b]pyridine or the corresponding 2-ethyl analog. The cyano compound is hydrolyzed to 3-benzyl-7-methyl-2-propylimidazo[4,5-b]pyridine-5-carboxylic acid or the corresponding 2-ethyl analog by treatment with H$_2$SO$_4$—H$_2$O. This acid is esterified by reaction with MeOH—HCl. The benzyl group is removed by hydrogenation at 1 atm. in MeOH-HCl solution using Pd(OH)$_2$ as catalyst. This compound can be alkylated as described earlier and the product methyl ester is converted to the carboxylic acid by treatment with hydroxide.

As shown in Scheme I-7, methods of preparing heterocycles of types (12 and 13) involve treatment of diamines (9) with reagents such as urea, phosgene, potassium cyanate, alkyl chloroformates, dialkylcarbonate, or carbon disulfide in the presence of bases such as potassium hydroxide or potassium carbonate. Amino acids (14) or (15) can be converted to (13) via Curtius or Hoffman rearrangement on suitable derivatives such as acyl azides, hydroxyamides, or N-haloamides. Bicyclic compounds of type (16, E=sulfur or oxygen) are formed from 12 by reaction under neutral or basic conditions with alkyl halides, alkylmesylates, alkyltosylates, trialkyloxonium salts, or with an appropriate diazoalkane. Compounds of type (16; B=oxygen or sulfur) are prepared by displacement reactions using alkoxides or alkyl mecaptides with chloro intermediates as indicated.

Diamines of type 9 can be prepared by a wide variety of methods such as hydrolysis of bis-amides or amino amides, reduction of dinitro or aminonitro or hydrazino amides, or azido groups, displacement of heteroaromatic halides or alkoxy or thio or alkylthio or hydroxy or alkyl sulfonyl groups with ammonia or amines, or rearrangement of acyl azides or amides or acids (Curtius, Hoffman, or Schmidt rearrangements). [A. S. Tomcufcik, L. N. Starker in "Heterocyclic Compounds, Pyridine and its Derivatives" Pt 3, E. Klingsberg Ed., Wiley Interscience, 1962, pp 59–62, and references cited there in; T. Nakagome in "Heterocyclic Compounds, Pyridazines" Vol. 28, R. N. Castle, Ed., Wiley Interscience, 1973, pp 597–601, and references cited therein; "Heterocyclic Compounds, The Pyrimidines" Vol. 16, D. J. Brown Ed., Wiley Interscience 1985, pp 299–325; E. Schipper, and A. R. Day *J. Am. Chem. Soc.* (1952) 74, 350; "Comprehensive Heterocyclic Chemistry," Vol. 5, A. R. Katritsky and C. W. Rees Eds., Pergamon Press 1984; pp 567–597 and 631–656 and references cited therein].

SCHEME I-6

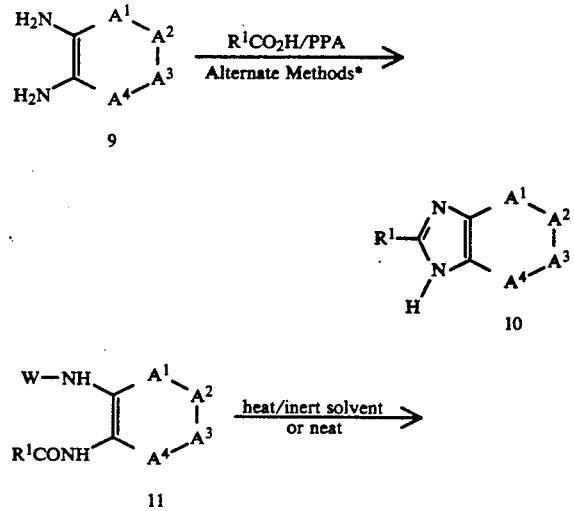

-continued
SCHEME I-6

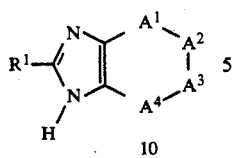
10

*Alternate reagents and reaction conditions:

R¹—CN, PPA
R¹—C(=NHHCl)—(OC₂H₅), C₂H₅OH, Δ
R¹C(OCH₃)₃, toluene, H⁺, Δ
R¹CHO, C₂H₅OH, Cu(OCH₃)₂

SCHEME I-7

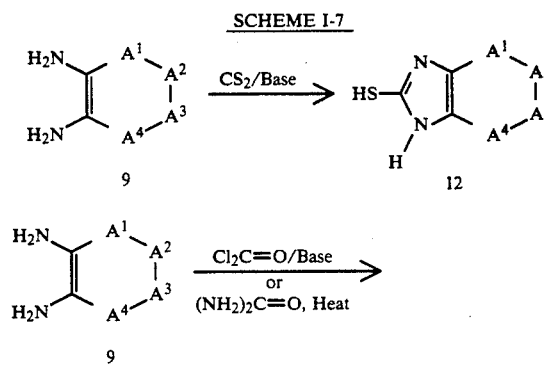

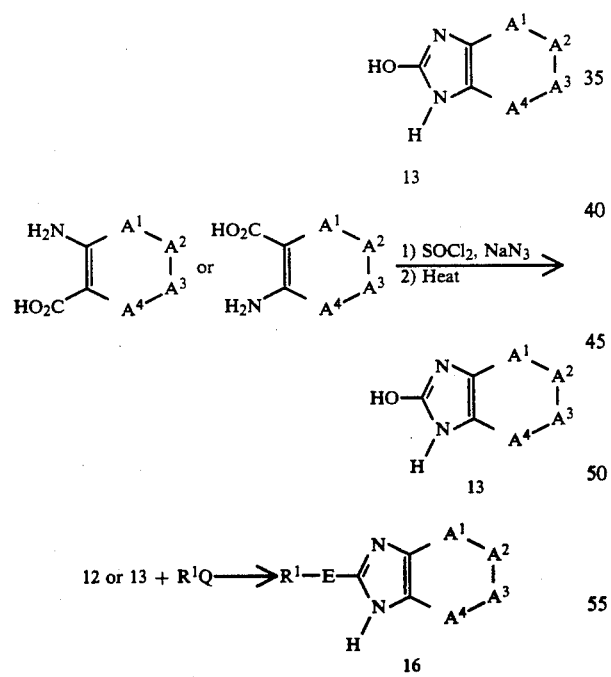

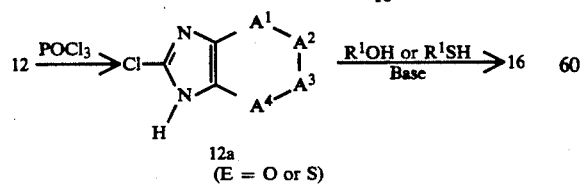
12a
(E = O or S)

In cases wherein heterocycles of type 10 or 16 are not easily prepared from their corresponding diamines, or when these diamines cannot be prepared then alternative routes, involving fusion of the six member heterocycle onto an appropriately substituted imidazole, are used. Two of these routes are illustrated in Scheme I-8. For example, imidazo[4,5-d][1,2,3]triazines (18) are preferentially prepared by treatment of amino carboxamido imidazoles (17) with sodium nitrite in aqueous acid. Precursor imidazoles (17) are prepared by degradation of an appropriately substituted xanthine or by condensation of an appropriate imidate ester with aminocyanoacetamide. Imidazo[4,5-b]pyridazines (20) can be prepared from imidazodicarboxylate esters (19) by treatment with hydrazine. Oxidation of (20) gives pyridazindiones (21). The oxygen(s) in (20) or (21) can be converted to other functionalities such as halides or thiones, which are themselves precursors for the synthesis of more elaborate systems ["Comprehensive Heterocyclic Chemistry," Vol. 5, A. R. Katritsky and C. W. Rees Eds., Pergamon Press 1984; pp 567–597 and 631–656 and references cited therein].

SCHEME I-8

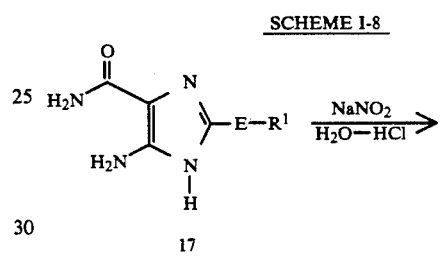
17

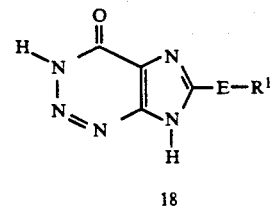
18

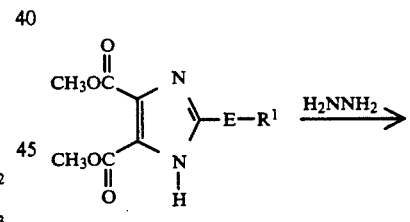
19

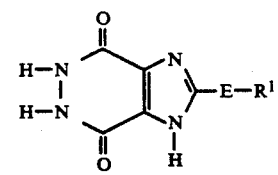
20

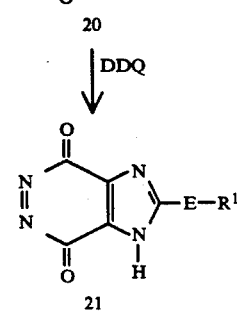
21

Moreover as shown in Scheme I-9 aminoimidazole esters and amides are versatile intermediates for the preparation of purines. This scheme also illustrates the synthesis of the 6-membered heterocyclic ring after the alkylating agent 2 has been reacted with a suitably substituted imidazole to afford 22 or 24.

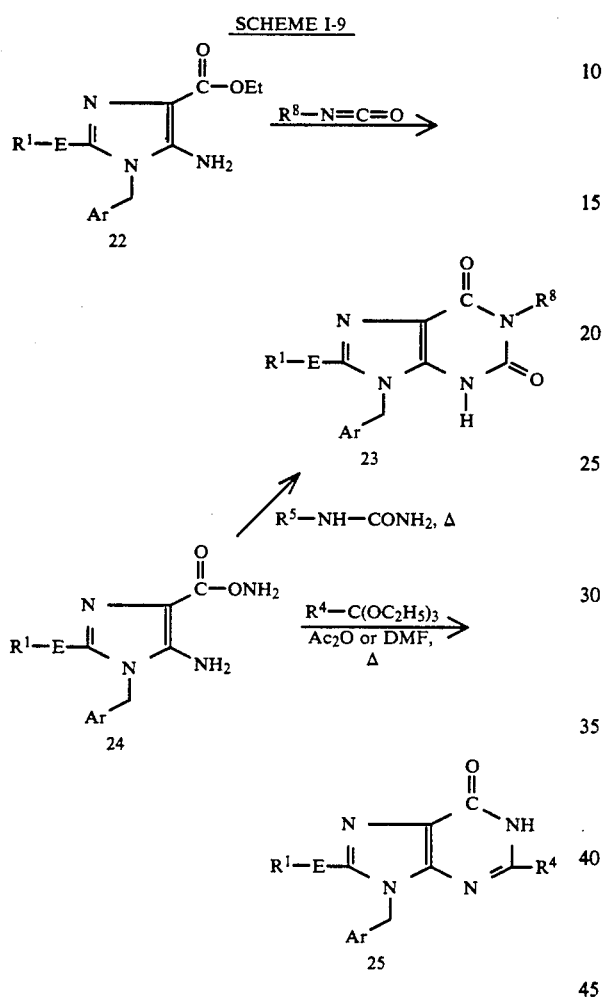

The preparation of reduced forms of heterocycles can be achieved by catalytic reduction, or by synthesis from a suitable imidazole precursor. For example, histidine and derivatives thereof react with formaldehyde to afford partially saturated imidazo[4,5-c]pyridines [cf. Neuberger, A. Biochem. J., (1944), 38, 309].

PART II: Preparation of substituted methylphenylthiophenes and furan derivatives and alkylation with the 6-fused imidazoles described in Part I The desired bromomethylphenyl thiophene necessary for the construction of 3,4-disubstituted thiophenes of formula I, where $X^1$—$X^2$—$X^3$—$X^4$=—CH—S—CH—CZ— and Z=tetrazolyl are prepared as illustrated in scheme II-1. Palladium (O) catalyzed coupling of p-tolyltrimethyltin with 3,4-dibromothiophene in refluxing toluene or DMF at 70°-80° C. for 12 to 24 hours provides 3-bromo-4-tolylthiophene. This bromide could be displaced with cyanide using copper (I) cyanide in hot quinoline. The nitrile is converted to the trityl protected tetrazole in a three step procedure using trimethyltin azide in refluxing toluene followed by treatment with acid and finally protection with triphenylmethyl chloride in the presence of triethyl amine using $CH_2Cl_2$ or $CHCl_3$ as solvent. The protected tetrazole compound can be treated with N-bromosuccinimide in refluxing carbontetrachloride in the presence of a catalytic amount of AIBN or benzoylperoxide to provide the necessary bromomethylphenyl thiophenes. Substitution in the 2-position of the thiophene ring can be accomplished by reaction with nBuLi or tBuLi followed by quenching with an appropriate electrophile. Again reaction with N-bromosuccinamide, as before, provides the required bromomethylphenyl thiophenes.

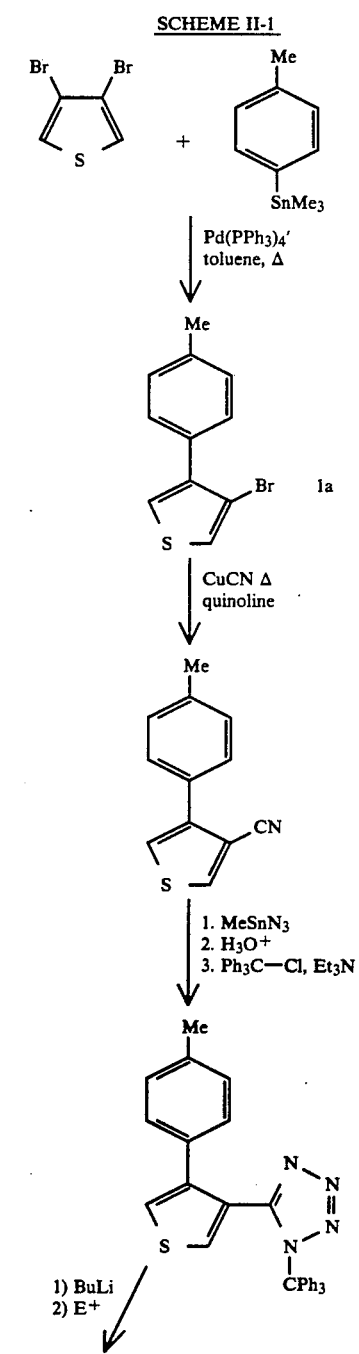

-continued
SCHEME II-1

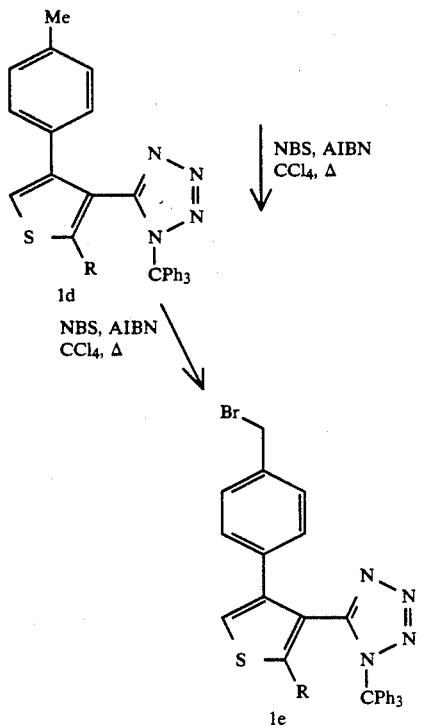

NBS, AIBN
CCl4, Δ

The desired bromomethylphenyl thiophene necessary for the construction of 3,4-disubstituted thiophenes of Formula I, where $X^1-X^2-X^3-X^4=-CH-S-CH-CZ-$ and $Z=SO_2NHCOR^7$, are prepared as illustrated in scheme II-2. Sequential dianion formation of 2a with nBuLi or tBuLi in THF at $-20°$ C., followed by quenching with TMSCl provides 2b. Treatment with strong base such as nBuLi, LDA or tBuLi, followed by quenching with Br2 affords the bromo thiophene derivative 2c. Palladium catalyzed cross-coupling of 2c with p-tolyltrimethyltin using PdCl2(PPh3)2 in hot DMF or Pd(PPh3)4 in hot toluene provides 2d. Biaryl compound 2d can be treated with N-bromosuccinimide in refluxing carbontetrachloride or benzene in the presence of a catalytic amount of AIBN or benzoylperoxide to provide the necessary bromomethylphenyl thiophenes.

SCHEME II-2

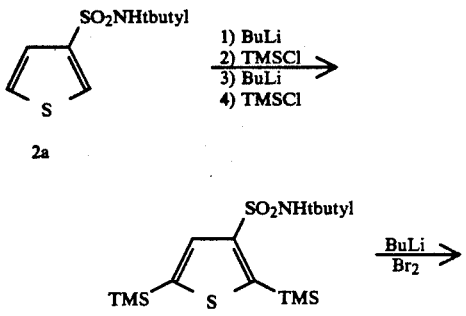

-continued
SCHEME II-2

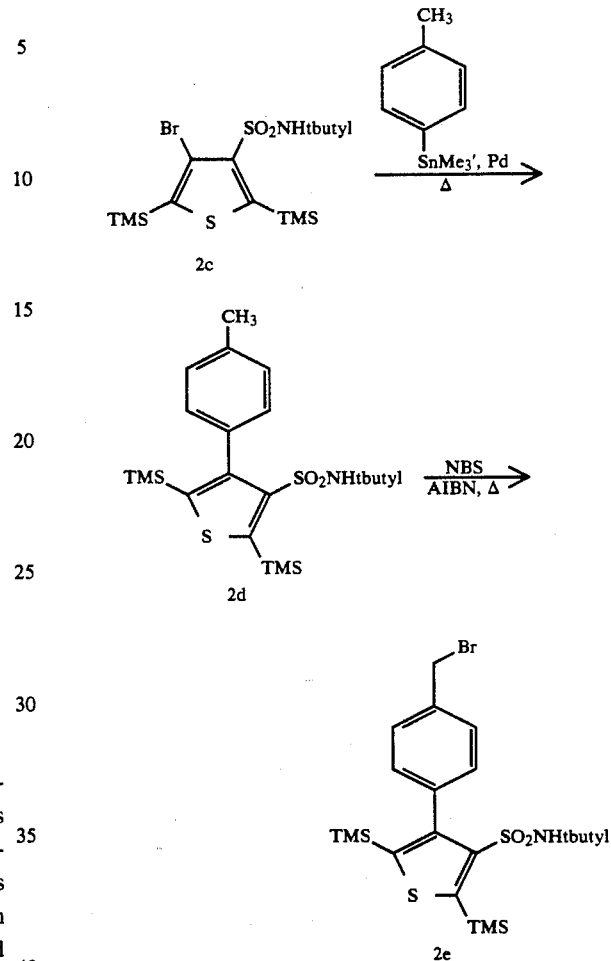

The desired methanesulfonyloxymethylphenyl thiophenes and furans necessary for the construction of 2,3-disubstituted thiophenes and furans (Y=O or S) or formula I, where $X^1-X^2-X^3-X^4=-CH-CH-S-CZ-$ and Z=tetrazolyl, are prepared as illustrated in scheme II-3. 2-Cyanothiophene and 2-cyanofuran are converted to their respective protected tetrazoles by reaction with trimethyltin azide in refluxing toluene followed by treatment with dilute mineral acid and finally protection with triphenylmethyl chloride in the presence of triethyl amine in a chlorinated solvent. Reaction of the heterocycle with a strong base such as nBuLi followed by quenching with trimethylsilyl chloride fixes a trimethyl silyl group in the 5-position. Again reaction with a strong base (tBuLi, nBuLi or LDA), this time, followed by quenching with trimethyltin chloride provides the protected tetrazolylaryltrimethyltin derivative. Palladium catalyzed cross coupling with methyl p-iodobenzoate in refluxing toluene or hot DMF for several hours is followed by lithium aluminum hydride reduction and conversion of the subsequent alcohol to the mesylate with methanesulfonyl chloride and triethyl amine.

SCHEME II-3

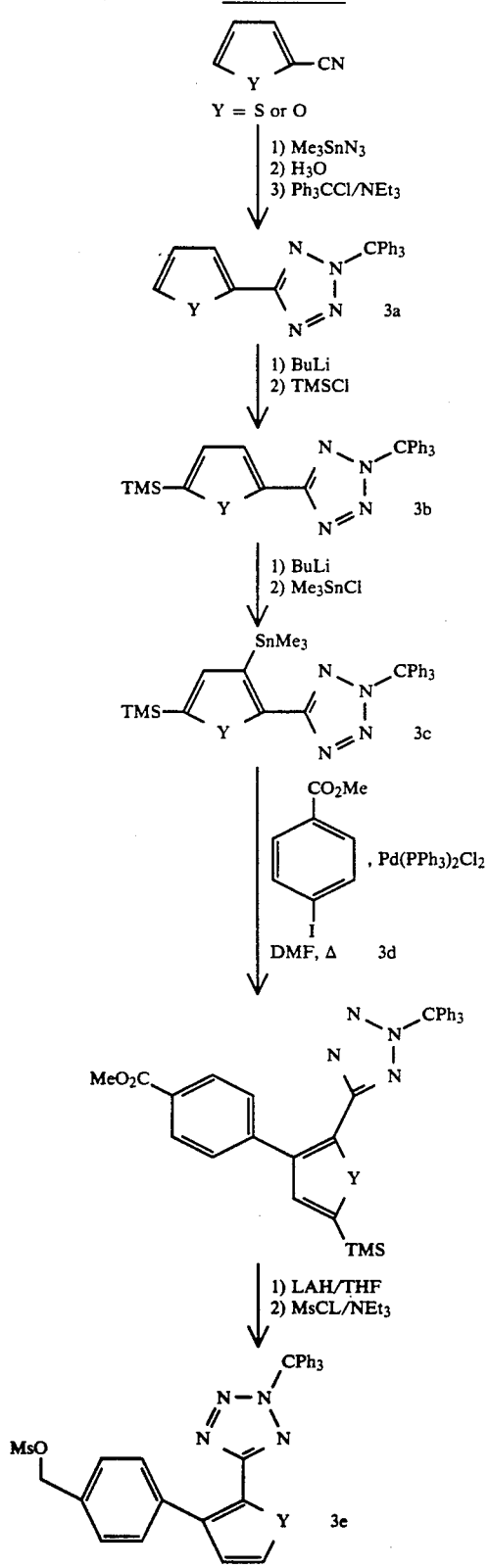

The desired bromomethylphenyl thiophenes and furans necessary for the construction of 2,3-disubstituted thiophenes and furans (Y=O or S) of formula I, where $X^1-X^2-X^3-X^4=-CR^{11}-CR^{12}-S-CZ-$ and $Z=SO_2NHCOR^7$ and $R^{11}=R^{12}=H$, are prepared as illustrated in scheme II-4. Palladium(O) catalyzed coupling of p-tolyltrimethyltin with a 3-bromothiophene or furan derivative in refluxing toluene provides the 3-tolylthiophene or 3-bromothiophene or furan. If the 5-position of the furan or thiophene is unsubstituted it is protected as was carried out in scheme II-3 with a trimethylsilyl group. Reaction with a strong base such as nBuLi, generating the anion at the 2-position, is followed by successive quenching with $SO_2(g)$ followed by N-chlorosuccinamide. The resultant sulfonyl chloride is reacted with tbutyl amine in $CH_2Cl_2$ and is followed by benzylic bromination with N-bromosuccinimide utilizing AIBN or benzoylperoxide as a radical intiator to afford the desired bromomethylphenyl thiophenes and bromomethylphenyl furans.

SCHEME II-4

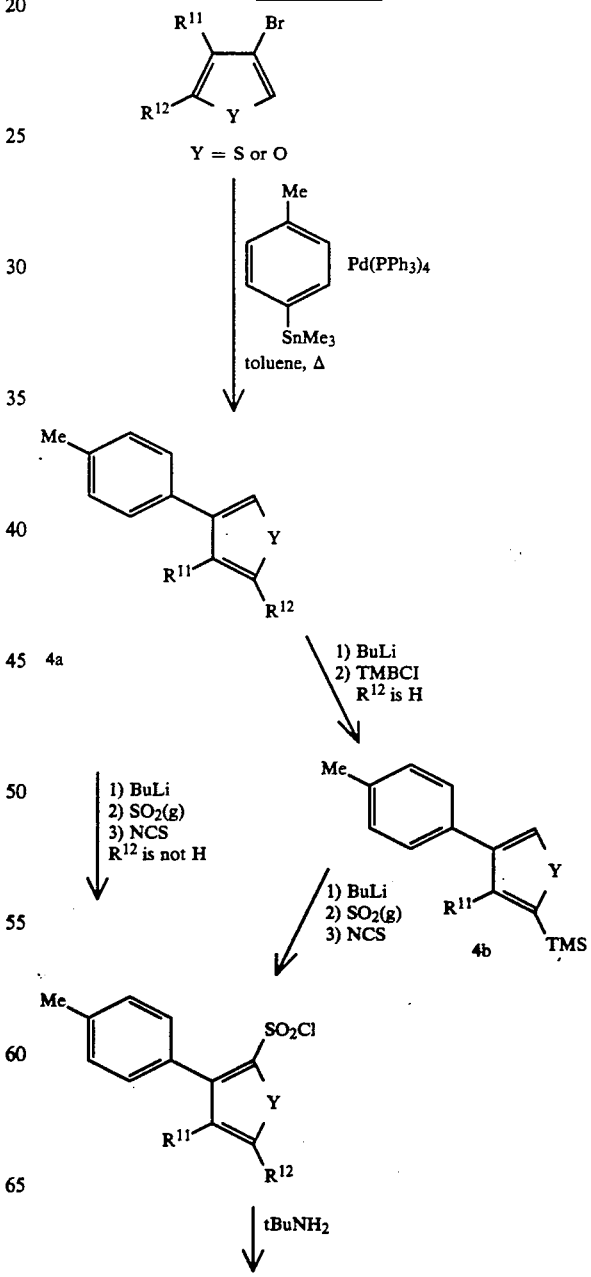

-continued
SCHEME II-4

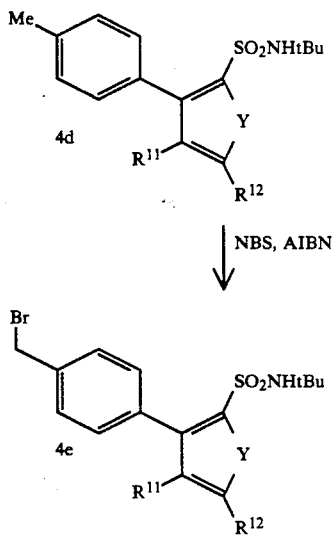

An alternative synthesis for the desired 3-(4-bromomethylphenyl) thiophenes and furans necessary for the construction of 2,3-disubstituted thiophenes and furans of the 2,3-disubstituted thiophenes and furans (Y=O or S) of formula I, where $X^1$—$X^2$—$X^3$—$X^4$ =—$CR^{11}$—$CR^{12}$—S—CZ— and Z=$SO_2NHCOR^7$ and $R^{11}$=$R^{12}$=H, is illustrated in scheme II-5. 2-Thiophenesulfonyl chloride and 2-furansulfonyl chloride are converted to their respective tbutyl sulfonamides by reaction with tbutylamine in $CH_2Cl_2$. The dianion is generated with two equivalents of a strong base such as nBuLi or tBuLi; this is followed by quenching with TMSCl, addition of another equivalent of strong base and finally quenching with $Br_2$. These bromo derivatives are coupled with p-tolyltrimethyl tin in the presence of a catalytic amount of palladium (0) in refluxing toluene or hot DMF. Benzylic bromination using N-bromosuccinimide provides the desired bromomethylphenyl thiophenes and bromomethylphenyl furans.

SCHEME II-5

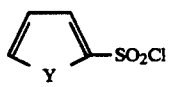

Y = S or O

1) $H_2NtBu$
2) 2 equiv BuLi
3) TMS Cl
4) 2 equiv BuLi
5) $Br_2$

-continued
SCHEME II-5

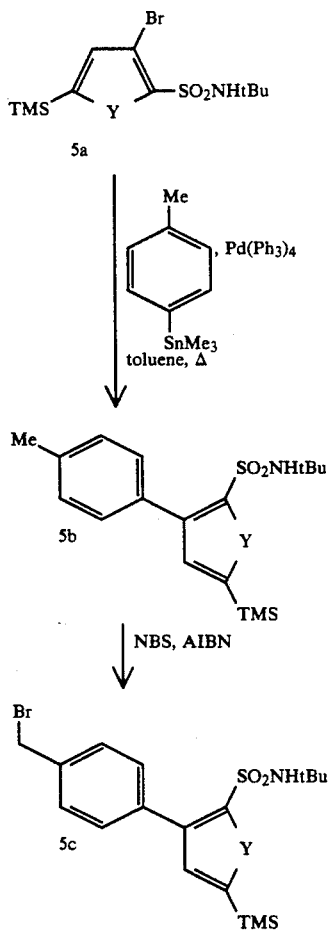

The desired methanesulfonyloxymethylphenyl thiophenes and furans necessary for the construction of 2,3-disubstituted thiophenes and furans (Y=O or S) of formula I, where $X^1$—$X^2$—$X^3$—$X^4$=—S—CH—CH—CZ— and Z=tetrazolyl, are prepared as illustrated in scheme II-6. 3-Cyanothiophene and 3-cyanofuran are converted to their respective protected tetrazole derivatives by reaction with trimethyltin azide in refluxing toluene followed by treatment with dilute mineral acid and finally protection with triphenylmethyl chloride in the presence of triethyl amine. Generation of the anion at the 2-position, using a strong base such as nBuLi, followed by quenching with trimethyltin chloride provides the desired protected tetrazolylaryltrimethyltin derivative. Palladium catalyzed cross coupling with methyl p-iodobenzoate using $Pd(PPh_3)_2Cl_2$ or $Pd(PPh_3)_4$ in refluxing toluene or hot DMF followed by lithium aluminum hydride reduction and treatment of the resultant alcohol with methanesulfonyl chloride and triethyl amine provides the desired methanesulfonyloxymethylphenyl thiophenes and methanesulfonyloxymethylphenyl furans.

SCHEME II-6

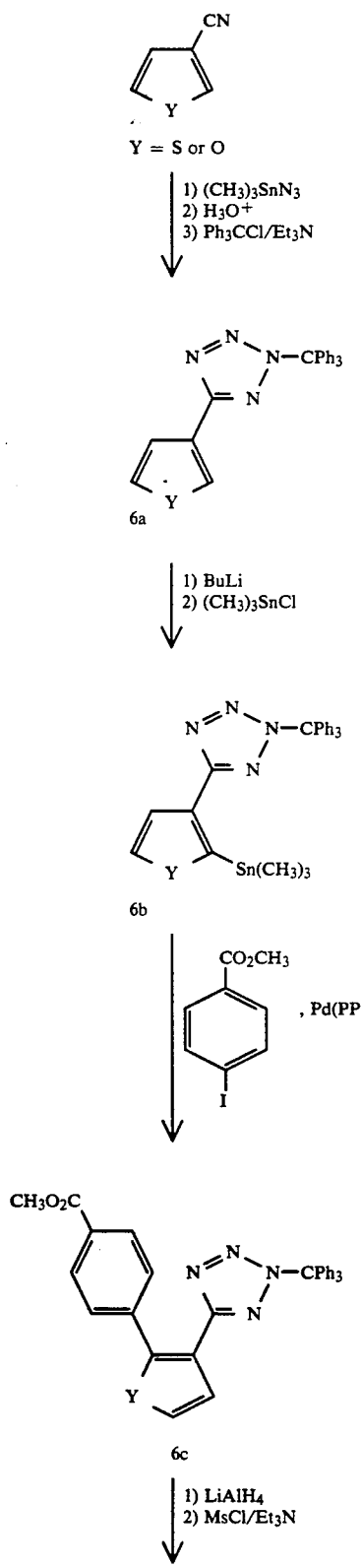

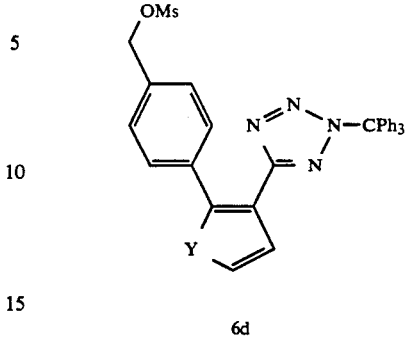

6d

The desired bromomethylphenyl thiophenes and furans necessary for the construction of 2,3-disubstituted thiophenes and furans (Y=O or S) or formula I, where $X^1-X^2-X^3-X^4=-S-CH-CH-CZ-$ and $Z=SO_2NHCOR^7$, are prepared are illustrated in scheme II-7. 2,5-Dibromothiophene or 2,5-dibromofuran can be chlorosulfonylated with chlorosulfonic acid to provide sulfonyl chloride 7a. Reaction with tbutylamine, followed by reduction with zinc in acetic acid affords 7c. Dianion generation, using a strong base (nBuLi or tBuLi), followed by quenching with $Br_2$, provides bromo compound 7d. Palladium catalyzed coupling of p-tolytrimethytin with the newly prepared arylbromide in hot DMF or refluxing toluene provides biaryl compound 7e. Treatment of 7e with N-bromosuccinimide in the presence of a catalytic amount of AIBN or benzoylperoxide in refluxing carbontetrachloride or benzene provides the desired bromomethylphenyl thiophenes and bromomethylphenyl furans.

SCHEME II-7

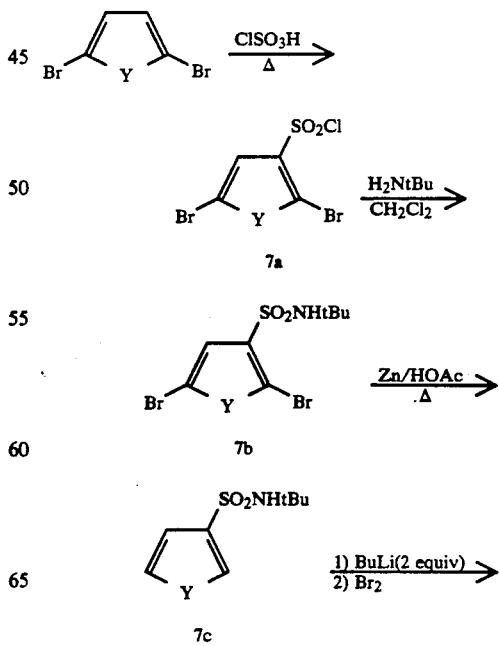

53

-continued
SCHEME II-7

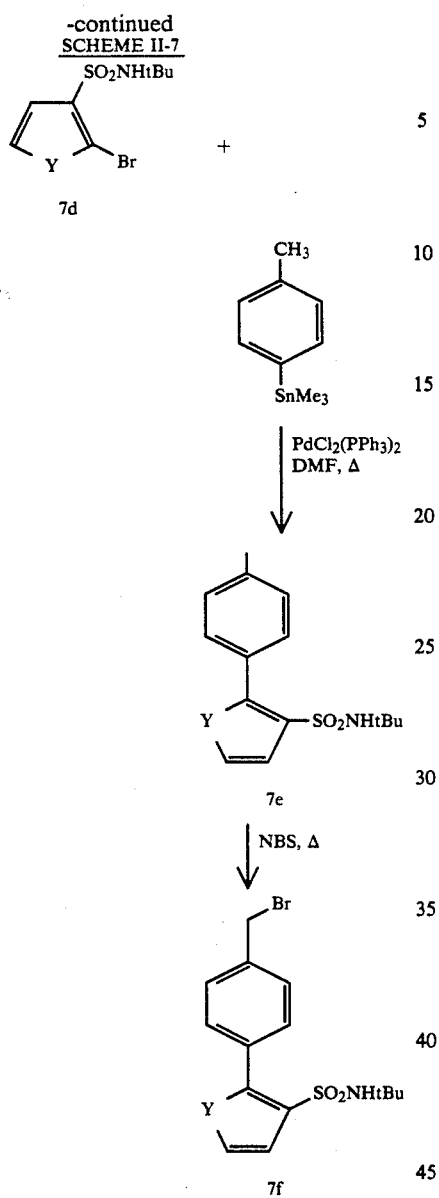

The desired antagonists of formula I (Z=tetrazolyl) are prepared, as illustrated in scheme II-8, by deprotonation of the desired heterocycle, for example 5,7-dimethyl-2-ethyl-[4,5-b]imidazopyridine, with sodium hydride in dimethylformamide to generate the sodium salt, 8a. Alkylation of the sodium salt with a derivative containing a good leaving group such as the bromomethyl derivative or the methanesulfonyl derivative, is followed by deprotection to provide the free tetrazole.

The desired antagonists of formula I (Z=SO$_2$NH-COR$^7$) are prepared, as illustrated in scheme II-9, by deprotonation of the desired heterocycle, for example 2-ethyl-5,7-dimethyl[4,5-b]imidazopyridine, with sodium hydride in dimethylformamide to generate the sodium salt. Alkylation of the sodium salt with the bromomethyl derivative or the methanesulfonyl derivative followed by deprotection with trifluoroacetic acid and coupling with an activated acid derivative completes the synthesis of the sulfonamide containing thiophene antagonists.

The desired antagonist of formula I, where X$^1$—X$^2$—X$^3$—X$^4$=—CR$^{11}$—CR$^{12}$—S—CZ—, Z=SO$_2$NH-

54

COR$^7$, R$^{11}$ and R$^{12}$ are joined to form an aryl ring, and R$^7$=Ph, is prepared as illustrated in scheme II-10 by deprotonation of the desired heterocycle 5,7-dimethyl-2-ethylimidazo[4,5-b]pyridine, with sodium hydride in dimethyl formamide to generate the sodium salt. Alkylation of the sodium salt with the benzothiophene derivative, compound 4e, which is prepared using the chemistry illustrated in scheme II-4, affords 10A. As in scheme II-9, deprotection with TFA is followed by coupling to an activated acid derivative to complete the synthesis.

SCHEME II-8

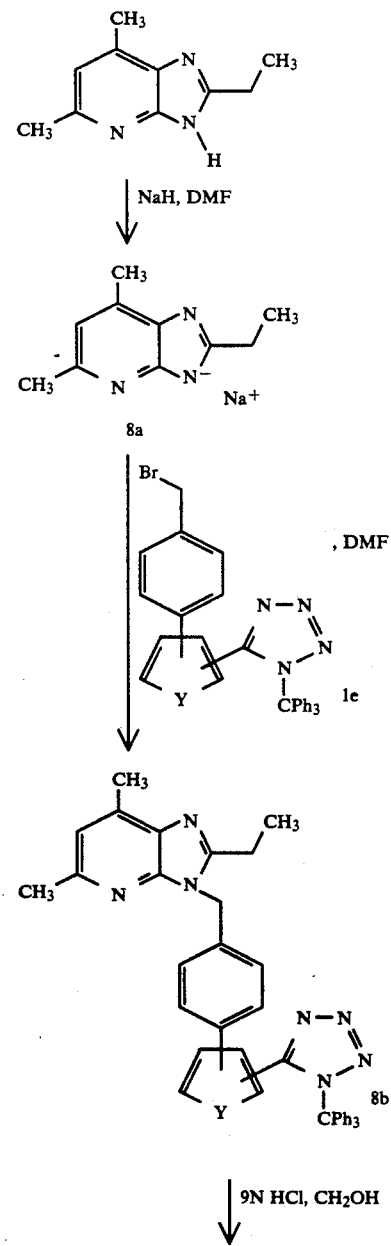

-continued
SCHEME II-8
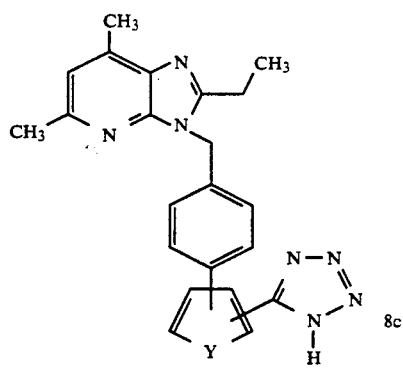
8c
SCHEME II-9
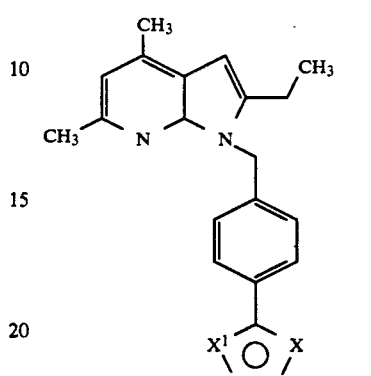
9d
Z = SO$_2$NHt Bu
SCHEME II-9
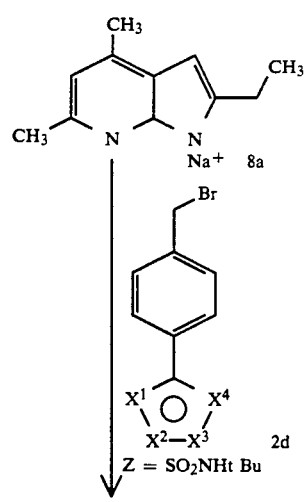
2d
Z = SO$_2$NHt Bu
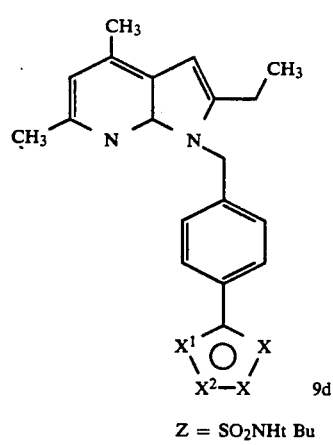
9d
Z = SO$_2$NHt Bu
1) TFA/anisole
2) R$^7$COCl/pyridine
SCHEME II-10
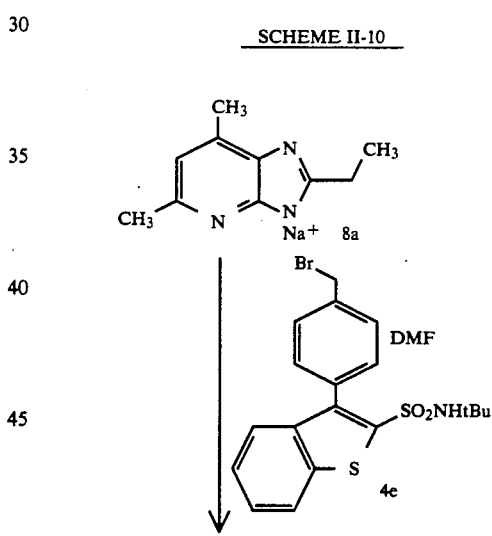
4e
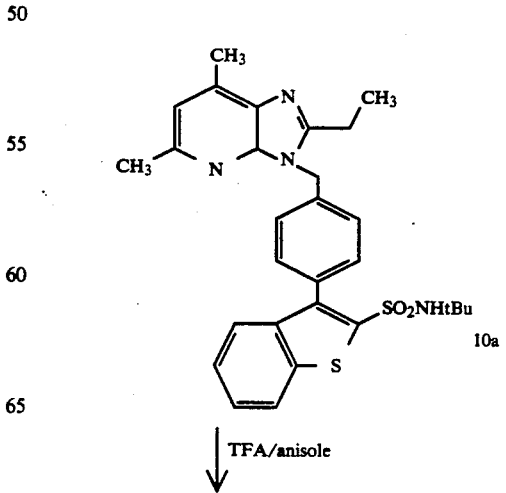
10a
TFA/anisole

-continued
SCHEME II-10

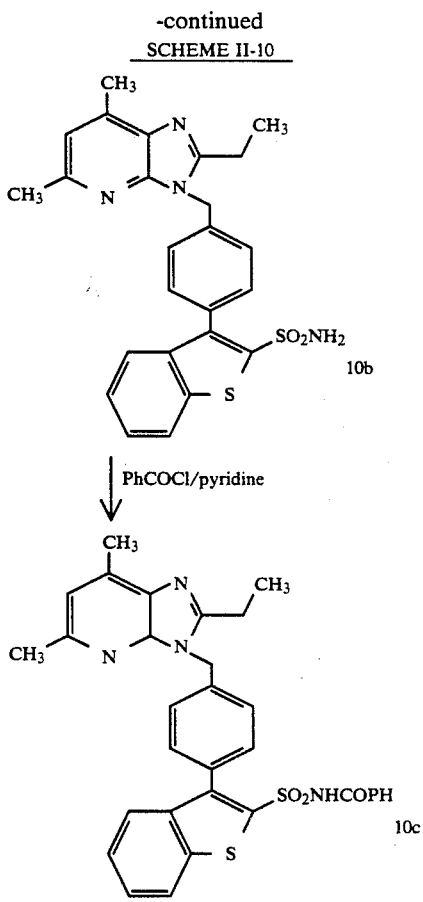

An alternative synthesis for the bromomethylphenyl thiophenes necessary for the construction of substituted thiophenes of formula I, where $X^1-X^2-X^3-X^4 = -CH=C(R^{12})-S-CZ=$ and $Z=SO_2NHCOR^{14}$ is illustrated in scheme II-11. Alkylthiophene 11a is cleanly prepared by alkylation of the dianion of 2-(tbutylsulfonamido)thiophene, generated with two equivalents of BuLi or LDA, with an appropriate alkylhalide ($R^{12}X$). A second dianion generation, followed by quenching first with triisopropylborate, then with 2N HCl, affords the boronic acid derivative 11b. Palladium catalyzed coupling of the 11b with 4-bromobenzyl alcohol provides 11c. The benzyl alcohol is then cleanly converted to the corresponding bromide (11d) with $PBr_3$ or $CBr_4/PPh_3$.

This benzyl bromide is used in place of compound 2d in scheme II-9 to complete the synthesis of the antagonist.

Scheme II-12 illustrates a more convergent approach to the synthesis of substituted thiophenes of formula I, where $X^1-X^2-X^3-X^4 = =CH=C(R^{12})-S-CZ=$ and $Z=SO_2NHCOR^{14}$. Palladium catalyzed coupling of boronic acid 11b with a 4-bromobenzyl derivative, such as 12a, provides a nearly complete antagonist. Completion of the antagonist from 12b is illustrated in scheme II-9.

SCHEME II-11

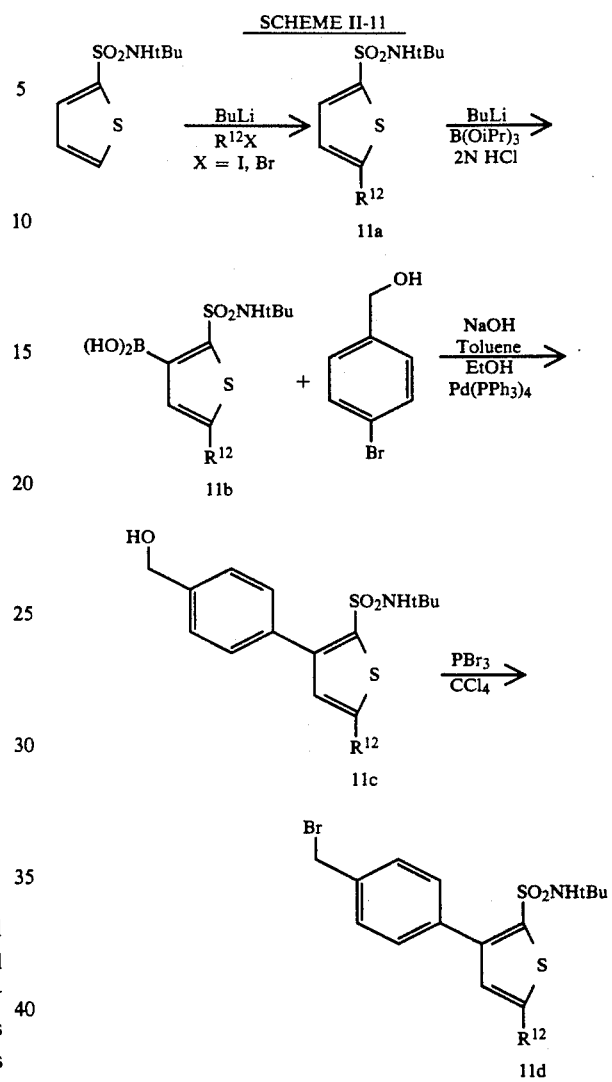

SCHEME II-12

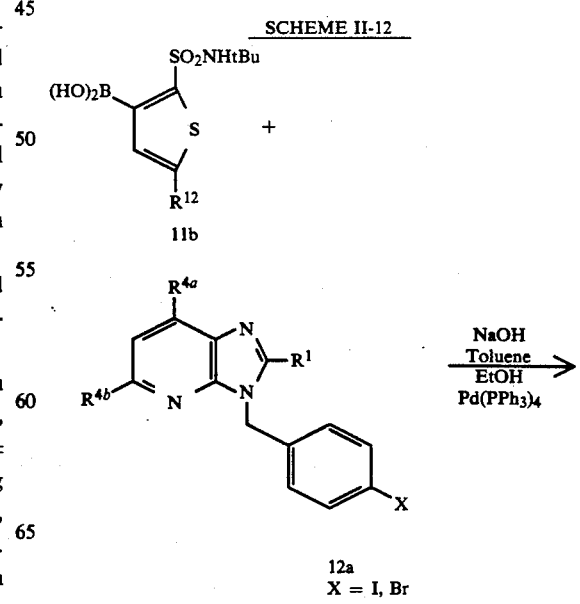

12a
X = I, Br

-continued
SCHEME II-12

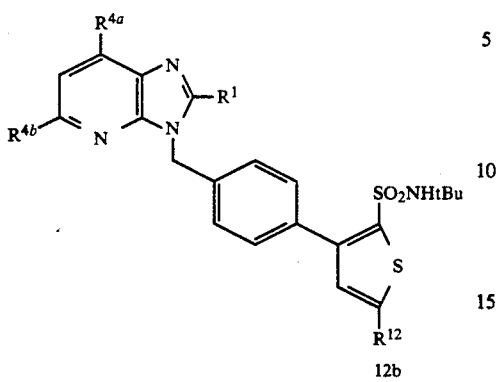

12b

An alternative synthesis for the bromomethylphenyl thiophenes necessary for the construction of substituted thiophenes of formula I, where $X^1—X^2—X^3—X^4 = —CH=C(R^{12})—S—CZ=$ and $Z$=tetrazolyl is illustrated in scheme II-13. Alkylthiophene 13a is prepared by alkylaltion of the 2-(triphenylmentyltetrazolyl)-thiophene with an appropriate alkylhalide ($R^{12}X$). Directed metalation with BuLi, is followed by quenching with triisopropylborate. The borate ester is gently hydrolyzed with dilute acetic acid to afford the boronic acid derivative 13b. Palladium catalyzed coupling of 13b with 4-bromobenzyl alcohol provides 13c. The benzyl alcohol is then cleanly converted to the corresponding bromide (13d) with $PBr_3$ or $CBr_4/PPh_3$.

This benzyl bromide is used in place of compound 2d in scheme II-9 to complete the synthesis of the antagonist.

Scheme II-14 illustrates a more convergent approach to the synthesis of substituted thiophenes of formula I, where $X^1—X^2—X^3—X^4 = —CH=C(R^{12})—S—CZ=$ and $Z$=tetrazolyl. Palladium catalyzed coupling of boronic acid 13b with a 4-bromobenzyl derivative, such as 12a, provides a nearly complete antagonist. Completion of the antagonist from 14b is illustrated in scheme II-9.

SCHEME II-13

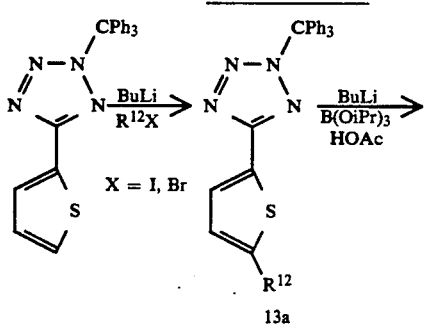

-continued
SCHEME II-13

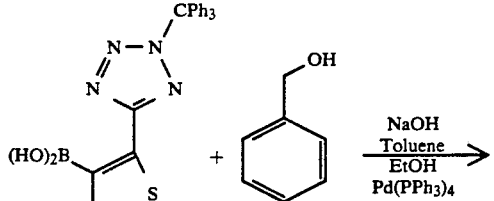
13b

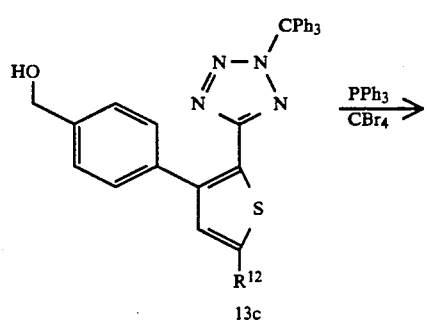
13c

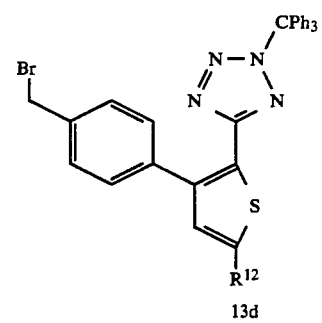
13d

SCHEME II-14

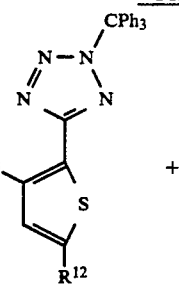
13b

+

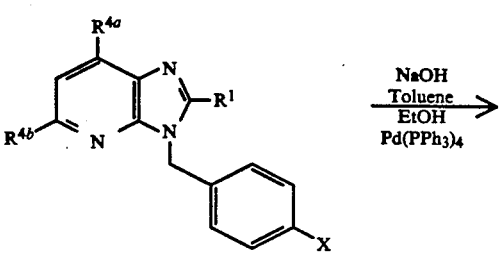

12a
X = I, Br

-continued
SCHEME II-14

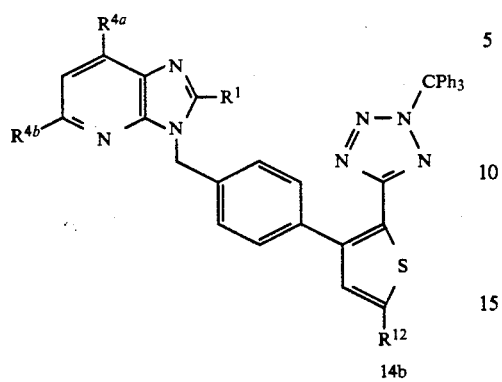
14b

Compounds of formula I, where $X^1$—$X^2$—$X^3$—$X^4$ =—CH=C($R^{12}$)—S—CZ=, Z=$SO_2NHCOR^{14}$ and $R^{12}$=$CH_2NR^{2a}R^{2a}$ best prepared as illustrated in scheme II-15. Palladium catalyzed coupling of boronic acid 11b ($R^{12}$=TMS) with 4-bromotoluene provides 15a. Fluoride mediated removal of the trimethylsilyl group is cleanly accomplished using nBu$_4$F in THF. Dianion formation of 15b followed by quenching with a formylating agent, such as DMF, provides the formyl derivative after acid work-up. Benzylic bromination is followed by coupling to the sodium salt of a heterocyle such as an imidazopyridine, to afford 15e. Reductive amination of the aldehyde is then followed by the usual reactions to complete the synthesis of the antagonist.

Alternatively, bromomethyl derivative 16e (scheme II-16) can be prepared and coupled to a heterocycle using previously described synthetic methods. NBS bromination of 2-methyl-5-(tbutylsulfinamido)thiophene provides bromomethyl derivative 16a. The bromomethyl derivative is then reacted with excess amine (HN$R^{2a}R^{2a}$), such as morpholine, to afford 16b. Reaction of 16b with two equivalents of a strong base, such as LDA or nBuLi, is followed by addition of bromine to provide 16c. Palladium catalyzed coupling of 16c with 4-(t-butyldimethylsilyloxymethyl)-phenyltrimethyltin provides compound 16d. Silyl removal followed by conversion to the corresponding bromide affords 16e.

SCHEME II-15

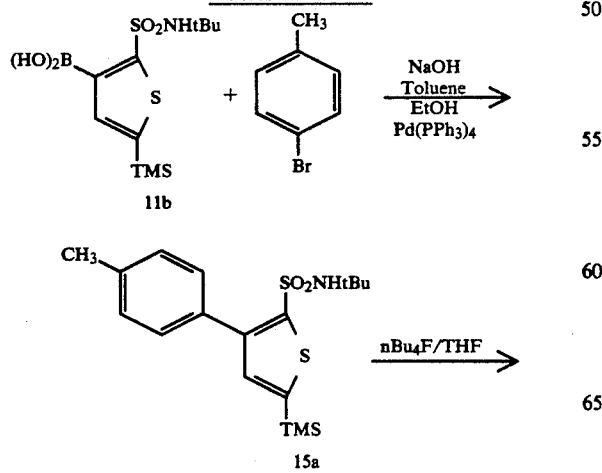

-continued
SCHEME II-15

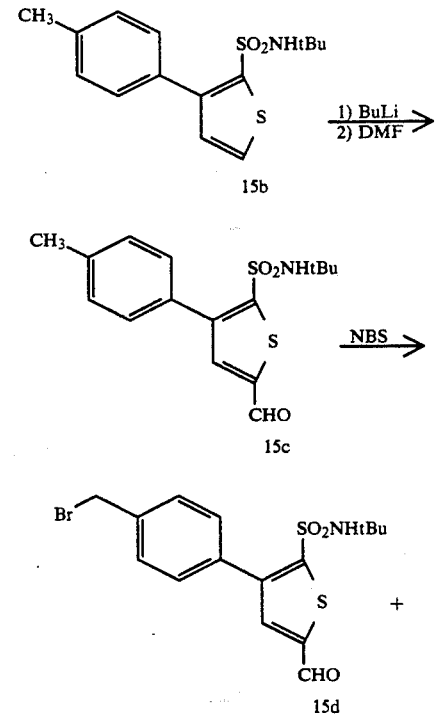

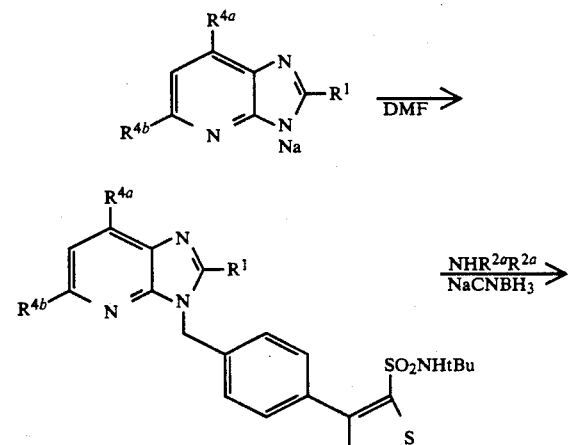

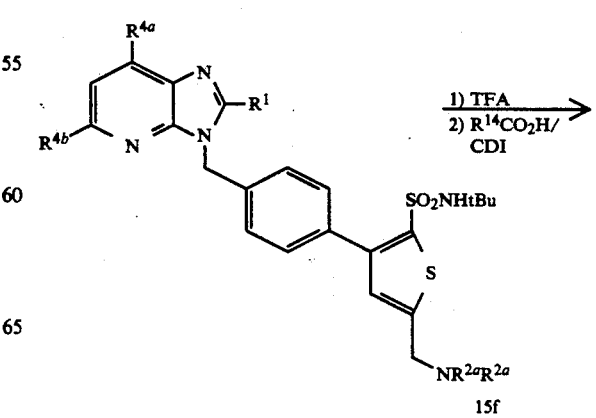

-continued
SCHEME II-15

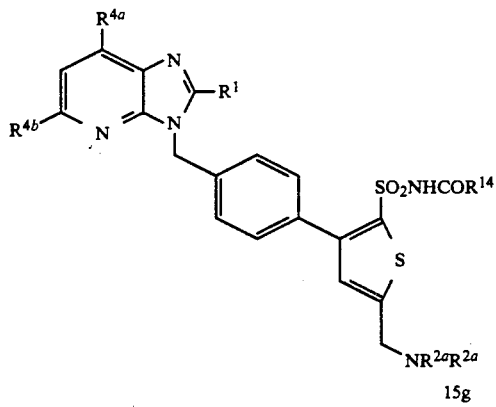
15g

SCHEME II-16

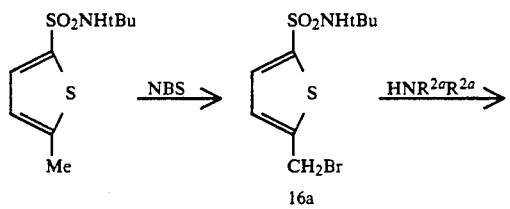
16a

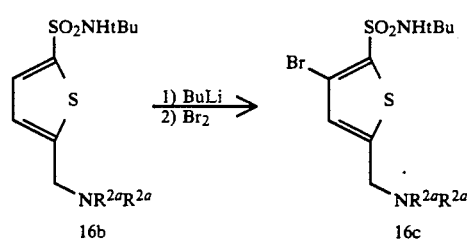
16b    16c

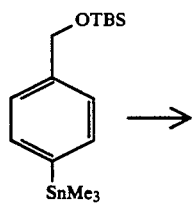

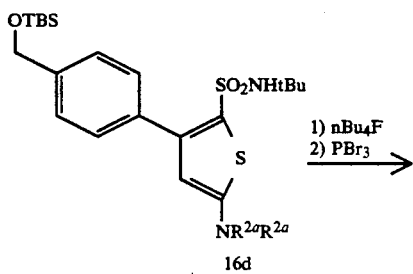
16d

-continued
SCHEME II-16

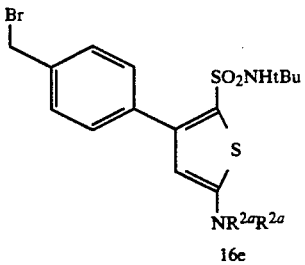
16e

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluensulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 mL) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/mL Bacitration and the suspension was used for 100 assay tubes. Samples tested for screening were done in duplicate. To the membrane preparation (0.25 mL) there was added $^{125}$I-Sar$^1$Ile$^8$-angiotensin II [obtained from New England Nuclear] (10 mL: 20,000 cpm) with or without the test sample and the mixture was incubated at 37° C. for 90 minutes. The mixture was then diluted with ice-cold 50 mM Tris-0.9% NaCl, pH 7.4 (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [Na$_2$HPO$_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used.) To the membrane preparation (0.5 mL) there was added 3H-angiotensin II (50 mM) (10 mL) with or without the test sample and the mixture was incubated at 37° C. for 1 hour. The mixture was then diluted with Tris buffer (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration (IC$_{50}$) of potential AII antagonist which gives 50% displacement of the total specifically bound $^3$H-angiotensin II was presented as a measure of the efficacy of such compounds as AII antagonists.

The potential antihypertensive effects of the compounds described in the present invention may be evaluated using the methodology described below: Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate−60 strokes per minute, volume−1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30 minute intervals and the increase in the diastolic blood pressure was recorded before and after drug or vehicle administration.

Using the methodology described above, representative compounds of the invention were evaluated and found to exhibit an activity of at least IC$_{50}$<50 mM thereby demonstrating and confirming the utility of the compounds of the invention as effective AII antagonists.

Receptor assay using rat brain membrane preparation

Membranes from rat brain (thalamus, hypothamus and midbrain) were prepared by homogenization in 50 mM Tris HCl (pH 7.4), and centrifuged at 50,000×g. The resulting pellets were washed twice in 100 mM NaCl, 5 mM Na$_2$.EDTA, 10 mM Na$_2$HPO$_4$ (pH 7.4) and 0.1 mM PMSF by resuspension and centrifugation. For binding assays, the pellets were resuspended in 160 volumes of binding assay buffer (100 mM NaCl, 10 mM Na$_2$HPO$_4$, 5 mM Na$_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$, Ile$^8$-angiotensin II (1 μM) (for nonspecific binding) or test compounds (for displacement) and 10 μl of [$^{125}$I]Sar$^1$,Ile$^8$-angiotensin II (23–46 pM) were added to duplicate tubes. The receptor membrane preparation (500 μl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters was counted using a gamma counter.

Thus, the compounds of the invention are useful in treating hypertension. They are also of value in the management of acute and chronic congestive heart failure, in the treatment of secondary hyperaldosteronism, primary and secondary pulmonary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like.

Pharmaceutical formulations prepared to treat intraocular pressure would typically contain about 0.1% to 15% by weight, and preferably 0.5% to 2.0% by weight of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg per patient per day which can be administered in single or multiple doses. Preferably, the dosage range will be about 2.5 to 250 mg per patient per day; more preferably about 2.5 to 75 mg per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflunisal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg), chlorothiazide (125-2000 mg), ethacrynic acid (15-200 mg), amiloride (5-20 mg), furosemide (5-80 mg), propranolol (20-480 mg), timolol maleate (5-60 mg), methyldopa (65-2000 mg), felodipine (5-60 mg), nifedipine (5-60 mg), and nitrendipine (5-60 mg). In addition, triple drug combinations of hydrochlorothiazide (15-200 mg) plus miloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced stereotypy model. A clinically useful antipyschotic drug that is used as a positive control in this assay is haloperidol. The assay method is based upon the observation that stimulation of the dopaminergic system in rats produces stereotyped motor behavior. There is a strong correlation between the effectiveness or classical neuroleptic drugs to block apomorphine-induced stereotype and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular adminstration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptyl-physostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers such as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered nor construed as limiting the invention set forth in the claims appended hereto.

EXAMPLE 1

5,7-Dimethyl-2-ethyl-3-[[4-[3-(1H-tetrazol-5-yl)-4thienyl]phenyl]methyl]imidazo[4,5-b]pyridine
(Compound 9 of Table VII)

Step A: Preparation of 2-nitramino-4,6-dimethylpyridine

2-Amino-4,6-dimethylpyridine (10.0 g, 81.8 mmol) was added portion-wise to 65 mL of $H_2SO_4$ (conc. d=1.84) which was stirred (mechanical) at 0° C. After complete addition, the mixture was warmed to room temperature until the mixture became homogeneous. The solution was then cooled to −10° C. and a precooled (0° C.) mixture of conc $HNO_3$ (11.5 mL, d=1.40) and $H_2SO_4$ (8.2 mL, d=1.84) was added at such a rate as not to raise the internal reaction temperature above −9° C. Ten minutes after the addition was complete this cooled (−10° C.) mixture was poured onto 400 g of crushed ice. The resulting slurry was neutralized by the addition of conc $NH_4OH$ (to pH 5.5) while cooling (ice bath). The solid was isolated by filtration, and dried at room temperature to give 13.3 g of the title compound as a white solid.

Step B: Preparation of 2-amino-3-nitro-4,6-dimethylpyridine

To 75 mL of stirred conc $H_2SO_4$ cooled to −5° C. (ice-salt bath) was added 4,6-dimethyl-2-nitraminopyridine (13.2 g, 79 mmol) portion-wise at such a rate as to maintain the internal temperature below −3° C. The mixture was warmed to 0° C. until homogeneous (30 minutes) at which time tlc ($SiO_2$, 1:1 EtOAc/hexanes on a $NH_4OH$ neutralized aliquot) indicated that the rearrangement was complete. The mixture was poured onto 400 g of crushed ice and the pH was adjusted to 5.5 by the addition of conc $NH_4OH$. The resulting yellow slurry was cooled to 0° C., filtered, washed with cold water (50 mL), and dried at room temperature to give 10.32 g of a mixture of the title compound and the 5-nitro isomer in a 55:45 ratio (determined by $^1H$ NMR). This mixture was used directly in the next step.

Step C: Preparation of 5,7-dimethyl-2-ethylimidazo[4,5-b]pyridine

To a mixture of 8.44 g of a 55:45 mixture of 2-amino-3-nitro-4,6-dimethylpyridine and 2-amino-5-nitro-4,6-dimethylpyrdine in MeOH (1.2 L) was added 10% Pd/C (2.4 g). The reaction vessel was evacuated then purged with $H_2$ at 1 atm. and stirred vigorously for 18 h. Filtration through a celite pad, and concentration gave 6.65 g of a mixture of 2,3-diamino-4,6-dimethylpyridine and 2,5-diamino-4,6-dimethylpyridine as a dark solid. To 5.40 g (39.4 mmol) of this mixture was added propionic acid (8.80 mL, 118 mmol) followed by polyphosphoric acid (100 mL). This stirred mixture was heated to 90° C. for 3 h then to 100° C. for 1 hour. The inside walls of the flask were scraped with a spatula to assist dissolution of the solids. After the reaction was complete, the warm mixture was poured onto 300 g of ice and the mixture was made basic with $NH_4OH$. The mixture was extracted (4×50 mL $CH_2Cl_2$), dried ($K_2CO_3$) and concentrated to give a mixture or the title compound and 4,6-dimethyl-2,5-bis(propionamido)pyridine. Purification ($SiO_2$, 5% MeOH/EtOAc) gave 1.66 g of the title compound as the slower eluting component.

$^1H$ NMR ($CD_3OD$, 300 MHz, ppm): δ6.95 (s, 1H), 2.92 (q, J=7.8 Hz, 2H), 2.54 (apparent s, 6H), 1.40 (t, J=7.8 Hz, 3H).

Step D: Preparation of 3-bromo-4-(4-methylphenyl)thiophene (scheme II-1, compound 1a)

Through a solution of p-tolyltrimethyltin (3.17 g, 12.4 mmol) in dry toluene (8 mL) was bubbled $N_2$ for 5 min to degas the solution. To this was added 3,4-dibromothiophene (2.31 g, 9.56 mmol) and a catalytic amount of $Pd(PPh_3)_4$ (552 mg, 5 mol %). The reaction mixture was brought to reflux (120° C.) and left overnight. The reaction was cooled to rt and the toluene and replaced by EtOAc. The insoluable salts were removed by filtration through a plug of celite. The product was purified by flash chromatography on a silica column eluting with hexane to afford 1.09 g (45%) of the titled compound as a clear, colorless oil.

$^1H$ NMR (300 MHz, $CDCl_3$) δ2.39 (s, 3H), 7.21–7.26 (m, 4H), 7.33 (d, 1H), 7.38 (d, 1H);

FAB mass spectrum, m/e 252/254 (m+, calcd for $C_{11}H_9SBr$, 253).

Step E: Preparation of 3-cyano-4-(4-methylphenyl)thiophene (scheme II-1, compound 1b)

To a solution of the product of example 1, Step D (329 mg, 1.30 mmol) in quinoline (3 mL) was added CuCN (233 mg, 2.60 mmol) and the solution heated to reflux (235° C.) overnight. The reaction was cooled and $Et_2O$ was added. The solution was washed with 9N HCl and brine, dried over anhydrous $MgSO_4$, and filtered. The product was purified by flash chromatography on a silica column using Hex/EtOAc (35:1) to afford 174 mg (67%) of the titled compound as a light yellow solid.

$^1H$ NMR (200 MHz, $CDCl_3$) δ2.42 (s, 3H), 7.28 (d, 2H), 7.36 (d, 1H), 7.53 (d, 2H), 8.04 (d, 1H); FAB mass spectrum, m/e 199 (m+, calcd for $C_{12}H_9SN$, 199).

Step F: Preparation of 3-N-triphenylmethyltetrazolyl-4-(4-methylphenyl)thiophene (scheme II-1, compound 1c)

To a solution of the product of example 1, Step E (174 mg, 0.873 mmol) in dry toluene (7 ml) was added $Me_3SnN_3$ (1.07 g, 5.22 mmol) and the solution brought to reflux (130° C.). A white solid that is product precipitates. The reaction was left overnight. There was still starting material present and another 363 mg of $Me_3SnN_3$ was added. After an additional 5 hours the reaction was cooled to RT. To the reaction was added $CH_2Cl_2$ and the reaction was washed with 2N HCl and water, dried over $MgSO_4$ and filtered. The volume was reduced and $NEt_3$ (244 μl, 1.75 mmol) and $Ph_3CCl$ (219 mg, 0.787 mmol) were added. After 2 hours $Et_2O$/EtOAc was added to the reaction and the solution was washed with 10% citric acid, 1N NaOH and water, dried over $MgSO_4$ and filtered. The titled compound was isolated in 94% yield, Rf=0.33 (10:1 hex/EtOAc).

$^1H$ NMR (300 MHz, $CDCl_3$) δ2.31 (s, 3H), 6.95 (d, 8H), 7.09 (d, 2H), 7.21–7.34 (m, 10H), 8.00 (d, 1H); FAB mass spectrum, m/e 485 (m+1, calcd for $C_{31}H_{24}SN_4$, 485).

Step G: Preparation of 3-N-triphenylmethyltetrazolyl-4-(4-bromomethyl-phenyl)thiophene (scheme II-1 compound 1e, R=H)

To a solution of the product of example 1, Step F (329 mg, 0.680 mmol) in dry CCl₄ (3mL) was added NBS (133 mg, 0.749 mmol) and a catalytic amount of AIBN. The mixture was heated to reflux (100° C.). After 2 h the reaction was cooled to rt and the insoluable succinimide removed by filtration. The solvent was replaced by EtOAc and washed with 1N NaOH and brine, dried over MgSO₄ and filtered. The solvent was removed to afford 428 mg (100%) of the crude product as a yellow foam. RF=0.32 (10:1/Hex:EtOAc).

Step H: Preparation of 5,7-dimethyl-2-ethyl-3-[4-(4(3-N-triphenylmethyltetrazol-5-yl)thienyl)phenyl]methylimidazo[4,5-b]pyridine To a solution of 5,7-dimethyl-2-ethylimidazopyridine from Step C (88 mg, 0.503 mmol) in dry DMF (2 mL) under N₂ was added NaH, 80% in oil dispersion, (24 mg, 0.81 mmol). The mixture was allowed to stir for 30 min. To this was added a solution of the product of example 1, Step G (214 mg crude) in dry DMF (1 ml). After 5 h the reaction was quenched with sat'd NH₄Cl solution (10 drops). The solvent was replaced by CH₂Cl₂ and the reaction mixture filtered. The product was purified by flash chromatography on a silica column using Hex/EtOAc (2:1). Rf=0.24 (1:1/Hex:EtOAc).

$^1$H NMR (300 MHz, CDCl₃) δ1.23 (t, 3H), 2.57 (s, 3H), 2.64 (s, 3H), 2.67 (q, 2H), 5.38 (s, 2H), 6.83-7.30 (m, 21H), 8.02 (d, 1H).

Step I: Preparation of 5,7-Dimethyl(2-ethyl-3-[[4-[3-(1H-tetrazol-5-yl)-4-thienyl]phenyl]methyl]imidazo[4.5-b]pyridine To a solution of the product of example 1, Step H in MeOH (10 ml) was added 9N HCl (10 drops). After 30 min the solvent was removed and the product triturated from Et₂O to afford 74 mg (47% Steps H through I) of the titled compound as a white solid.

$^1$H NMR (300 MHz, CD₃OD) δ1.42 (t, 3H), 2.72 (s, 3H), 2.73 (s, 3H), 3.32 (q, 2H), 5.82 (s, 2H), 7.27 (d, 2H), 7.38 (d, 2H), 7.44 (s, 1H), 7.68 (d, 1H), 8.09 (d, 1H);

FAB mass spectrum, m/e 416 (m+1, calcd for C₂₂H₂₁SN₇, 416).

EXAMPLE 2

7-Methyl-2-propyl-3-[[4-[3-(1H-tetrazol-5-yl)-4thienyl]-phenyl]methyl]imidazo[4,5-b]pyridine (Compound 7 of Table VII)

Step A: Preparation of 2-nitramino-4,6-dimethylpyridine

2-Amino-4,6-dimethylpyridine (10.0 g, 81.8 mmol) was added portion-wise to 65 mL of H₂SO₄ (conc. d=1.84) which was stirred (mechanical) at 0° C. After complete addition, the mixture was warmed to room temperature until the mixture became homogeneous. The solution was then cooled to −10° C. and a pre-cooled (0° C.) mixture of conc HNO₃ (11.5 mL, d=1.40) and H₂SO₄ (8.2 mL, d=1.84) was added at such a rate as not to raise the internal reaction temperature above −9° C. Ten minutes after the addition was complete this cooled (−10° C.) mixture was poured onto 400 g of crushed ice. The resulting slurry was neutralized by the addition of conc NH₄OH (to pH 5.5) while cooling (ice bath). The solid was isolated by filtration, and dried at room temperature to give 13.3 g of the title compound as a white solid.

Step B: Preparation of 2-amino-3-nitro-4,6-dimethylpyridine

To 75 mL of stirred conc H₂SO₄ cooled to −5° C. (ice-salt bath) was added 4,6-dimethyl-2-nitraminopyridine (13.2 g, 79 mmol) portion-wise at such a rate as to maintain the internal temperature below −3° C. The mixture was warmed to 0° C. until homogeneous (30 minutes) at which time tlc (SiO₂, 1:1 EtOAc/hexanes on a NH₄OH neutralized aliquot) indicated that the rearrangement was complete. The mixture was poured onto 400 g of crushed ice and the pH was adjusted to 5.5 by the addition of conc NH₄OH. The resulting yellow slurry was cooled to 0° C., filtered, washed with cold water (50 mL), and dried at room temperature to give 10.32 g of a mixture of the title compound and the 5-nitro isomer in a 55:45 ratio (determined by $^1$H NMR). This mixture was used directly in the next step.

Step C: Preparation of 7-Methyl-2-propyl-3-[[4-[3-(1H-tetrazol-5-yl)-4-thienyl]phenyl]methyl]imidazol[4,5-b]pyridine Following the procedures of Example 1, Steps D through I and replacing 5,7-dimethyl-2-ethylimidazo[4,5-b]pyridine with the product of Step B in Step H of Example 1, the title compound can be prepared.

EXAMPLE 3

5-Carbomethoxy-2-ethyl-7-methyl-3-[[4-[3-(1H-tetrazol-5-yl)-4-thienyl]phenyl]methyl]imidazo[4,5-b]pyridine Compound 2 of Table VII)

Step A: Preparation of 2-ethyl-7-methylimidazo[4,5-b]pyridine-4-oxide

A solution of 28 g (174 mmol) of 2-ethyl-7-methylimidazo[4,5-b]pyridine prepared according to Example 2, Steps A and B, but substituting propionic acid in place of butyric acid in Step B (described in European Patent Application #400,974, May 12, 1990) and m-chloroperbenzoic acid (80-90%, 44.6 g) in CHCl₃ (300 mL) was heated at reflux for 0.5 hours. The mixture was concentrated and purified (SiO₂, 100% CH₂Cl₂ gradient to 30% CH₂Cl₂/MeOH) to give 29.8 g of the title compound as a solid.

$^1$H NMR (300 MHz, CD₃OD, ppm): δ8.13 (d, 1H, J=6 Hz), 7.13 (d, 1H, J=6 Hz), 3.01 (q, 2H, J=7.5 Hz), 2.60 (s, 3H), 1.46 (t, 3H, J=7.5 Hz).

Step B: Preparation of 5-chloro-2-ethyl-7-methylimidazo[4,5-b]pyridine

A mixture of 29.75 g (0.168 mmol) of the product of Step A, CHCl₃ (25 mL) and POCl₃ (160 mL) was heated to 80° C. for 1 hour. After pouring over ice, the mixture was neutralized by careful addition of NH₄OH and extracted with EtOAc. Concentration gave 23.8 g of the title compound as a solid.

$^1$H NMR (250 MHz, CDCl₃, ppm): δ7.07 (s, 1H), 3.10 (q, 2H, J=7.5 Hz), 2.67 (s, 3H), 1.48 (t, 3H, J=7.5 Hz).

Step C: Preparation of 5-bromo-2-ethyl-7-methylimidazo[4,5-b]pyridine

A mixture of 22.2 g (0.113 mol) of the product of Step B in 30% HBr-HOAc was heated to 100° C. for 19 hours. The mixture was poured onto ice, neutralized with NH₄OH, extracted (5×EtOAc), and the organic layers were concentrated to give 15 g (1st crop) of the title compound as a solid after crystallization from EtOAc.

¹H NMR (300 MHz, CDCl₃, ppm): δ7.22 (s, 1H) 3.13 (q, 2H, J=7.5 Hz), 2.66 (s, 3H), 1.47 (t, 3H, J=7.5 Hz).

Step D: Preparation of 3-benzyl-5-bromo-2-ethyl-7-methylimidazo[4,5-b]pyridine To a solution of 10 g (39 mmol) of the product of Step C in DMF (70 mL) at rt was added NaH (1.3 g of an 80% oil dispersion, 43 mmol). After 20 minutes benzyl bromide (5.15 mL, 43 mmol) was added and the reaction was stirred for 16 hours. The mixture was poured onto 500 g of ice and the solid residue was filtered, washed with water and air dried to give 13 g of the title compound.

¹H NMR (300 MHz, CDCl₃, ppm): δ7.33-7.22 (m, 3H), 7.19 (s, 1H), 7.11-7.07 (m, 2H), 5.42 (s, 2H), 2.76 (q, 2H, J=7.5 Hz), 2.63 (s, 3H), 1.29 (t, 3H, J=7.5 Hz).

Step E: Preparation of 3-benzyl-5-cyano-2-ethyl-7-methylimidazo[4,5-b]pyridine A mixture of 620 mg (1.8 mmol) of the product of Step D and CuCN (806 mg, 9.0 mmol) was heated in pyridine (4 mL) at reflux for 10 hours under nitrogen. The reaction was cooled, then water (50 mL), KCN (1.17 g), and EtOAc (20 mL) were added and the mixture was heated to 50° C. for 5 min. Cooling and extraction with EtOAc (2×50 mL) gave 467 mg of the title compound as a tan solid.

¹H NMR (400 MHz, CDCl₃, ppm): δ7.40 (s, 1H), 7.35-7.20 (m, 3H), 7.18-7.07 (m, 2H), 5.44 (s, 2H), 2.83 (q, 2H, J=7.5 Hz), 2.67 (s, 3H), 1.32 (t, 3H, J=7.5 Hz).

Step F: Preparation of methyl 3-benzyl-2-ethyl-7-methylimidazo[4,5-b]pyridine-5-carboxylate A solution of 440 mg (1.59 mmol) of the product of Step E in H₂SO₄ (4 mL) and H₂O (4 mL) was heated to 80° C. for 8 hours. The reaction was cooled, MeOH (150 mL) was added, then conc NH₄OH was added until the mixture turned basic. The white solid (NH₄)₂SO₄ was filtered and washed with MeOH. The water and MeOH were removed in vacuo and the residue was taken up in MeOH and then filtered to remove any remaining (NH₄)₂SO₄. After concentrating, and removal of water from the residue by evaporation from toluene, anhydrous 3% HCl-MeOH (50 mL) was added and the mixture was stirred overnight at rt. Filtration, concentration, and extraction from 5% aqueous Na₂CO₃ with CH₂Cl₂ gave 750 mg of the crude title compound as a solid.

¹H NMR (300 MHz, CDCl₃, ppm): δ7.93 (s, 1H) 7.38-7.29 (m, 3H), 7.12-7.03 (m, 2H), 5.53 (s, 2H), 3.96 (s, 3H), 2.78 (q, 2H, J=7.5 Hz), 2.70 (s, 3H), 1.29 (t, 3H, J=7.5 Hz).

Step G: Preparation of methyl 2-ethyl-7-methylimidazo[4,5-b]pyridine-5-carboxylate A mixture of 750 mg of the crude product of Step F in MeOH (30 mL), concentrated aqueous HCl (1 mL), and 100 mg of moist Pearlman's catalyst were shaken under 1 atm. H₂ for 24 hours. The reaction was incomplete so 100 mg more of the catalyst was added and the reaction was shaken as described above for an additional 24 hours. Filtration, concentration, and extraction from dilute NH₄OH with EtOAc followed by drying (Na₂SO₄), concentration, and purification (SiO₂, 5% MeOH/EtOAc) gave 250 mg of the title compound as a solid.

¹H NMR (400 MHz, CDCl₃, ppm): δ7.90 (s, 1H), 4.00 (s, 3H), 3.10 (q, 2H, J=7.5 Hz), 2.71 (s, 3H), 1.38 (t, 3H, J=7.5 Hz).

Step H: Preparation of 5-Carbomethoxy-2-ethyl-7-methyl-3-[[4-[3-(1H-tetrazol-5-yl)-4-thienyl]phenyl]methyl]imidazo[4,5-b]pyridine Following the procedures of Example 1, Steps D-I replacing 5,7-dimethyl-2-ethylimidazo[4,5-b]pyridine with the product of Step G, in Step H of Example 1, the title compound can be prepared.

EXAMPLE 4

5-Carbomethoxy-7-methyl-2-propyl-3-[[4-(3-(1H-tetrazol-5-yl)-4-thienyl]phenyl]methyl]imidazo[4,5-b]pyridine (Compound 4 of Table VII)

Following the procedures of Example 3 but substituting 7-methyl-2-propylimidazo[4,5-b]pyridine in place of 2-ethyl-7-methylimidazo[4,5-b]pyridine, in Step A of Example 3, the title compound can be prepared.

EXAMPLE 5

5-Carboxy-2-ethyl-7-methyl-3-[[4-[3-(1H-tetrazol-5-yl)-4-thienyl]phenyl]methyl]imidazo[4,5-b]pyridine (Compound 3 of Table VII)

Following the procedures of Example 3 and in the final step hydrolysis of the ester, the title compound can be prepared.

EXAMPLE 6

5-Carboxy-7-methyl-2-propyl-3-[[4-[3-(1H-tetrazol-5-yl)-4-thienyl]phenyl]methyl]imidazo[4,5-b]pyridine (Compound 5 of Table VII)

Following the procedures of Example 4 and in the final step hydrolysis of the ester, the title compound can be prepared.

EXAMPLE 7

2-Propyl-1-[[4-[3-(1H-tetrazol-5-yl)-4-thienyl]phenyl]methyl]benzimidazole (Compound 1 of Table V)

Step A: Preparation of 2-Propylbenzimidazole

To a solution of o-phenylenediamine [obtained from the corresponding dihydrochloride (1.0 g, 5.52 mmols)] in methanol (30 ml) was added Cu(OAc)₂ (3.64 g, 18.2 mmols) as an aqueous solution (60 ml). After stirring for 10-15 min at room temperature, butyraldehyde (0.80 g, 11.1 mmols) was added and the mixture was heated at 100° C. for 4 h. Additional butyraldehyde (0.2 g) was added, and the mixture was stirred at room temperature overnight. The reaction was filtered and the residue was dissolved in methanol (40 ml). To this solution H₂S gas was bubbled for about 10 min followed by a stream of nitrogen. CuS was filtered-off, and the filtrate was evaporated in vacuo. The crude product was then purified by flash chromatography using ethyl acetate-hexane (3:1) to give the desired product (0.14 g, 16%). NMR(CD₃OD): δ1.0(t, J=7 Hz, 3H), 1.88(m, 2H), 2.86(t, J=7 Hz, 2H), 7.2(m, 2H), 7.5(m, 2H); FAB-MS: m/e 161(M+H).

Step B: Preparation of 2-Propyl-1-[[4-[3-(1H-tetrazol-5-yl)-4-thienyl]phenyl]methyl]benzimidazole Following the procedures of Example 1, Steps D through I and replacing 5,7-dimethyl-2-ethylimidazo[4,5-b]pyridine with the product of Step A, in Step H of Example 1, the title compound can be prepared.

EXAMPLE 8

2-Butyl-1-[[4-[3-(1H-tetrazol-5-yl)-4-thienyl]phenyl]methyl]benzimidazole (Compound 2 of Table V)

Step A: Preparation of 2-Butylbenzimidazole

To a solution of o-phenylenediamine (0.171 g, 1.58 mmol) in absolute ethanol (8 ml), ethyl valerylimidate (0.313 g, 1.9 mmol) was added, and the mixture was refluxed overnight. The reaction was cooled to room temperature and concentrated in vacuo. The residue was partitioned between ethyl acetate and saturated $NaHCO_3$. The organic phase was separated and the aqueous layer was extracted with ethyl acetate (3×20 ml). The organic layers were combined and washed with brine, dried ($MgSO_4$), and then concentrated in vacuo. The crude product, thus obtained, was purified by medium pressure liquid chromatography (MPLC) on silica-gel using ethyl acetate-hexane (1:1) to give cream colored crystalline solid (0.19 g, 69%). NMR ($CDCl_3$): δ0.92 (t, J=7 Hz, 3H), 1.42(m, 2H), 1.86(m, 2H), 2.95(t, J=7Hz, 2H), 7.22(m, 2H), 7.58(m, 2H); FAB-MS: m/e 174 (M+H).

Step B: Preparation of 2-Butyl-1-[[4-[3-(1H-tetrazol-5-yl)-4-thienyl]phenyl]methyl]benzimidazole Following the procedures of Example 1, Steps D-I and replacing 5,7-dimethyl-2-ethylimidazo[4,5-b]pyridine with the product of Step A, in Step H of Example 1, the title compound can be prepared.

EXAMPLE 9

2-Chloro-6-methyl-8-propyl-9-[[4-[3-(1H-tetrazol-5-yl)-4-thienyl]phenyl]methyl]purine (Compound 17 of Table VI)

Step A: Preparation of 2-Chloro-6-methyl-8-propyl purine

A mixture of 2-Chloro-4,5-diamino-6-methylpyrimidine (0.80 g, 5.04 mmol), trimethylorthobutyrate (1.2 ml, 7.6 mmol) and p-TsOH (0.08 g) in 2-methoxyethanol (24 ml) was heated in an oil bath at 140° C. for 24 hours. The product was isolated as described in Step 2 of Example 12 and purified by flash chromatography using EtOAc-hexane (1:1) to give the crystalline titled compound (0.5 g, 47%). NMR(CDCl3): δ1.03 (t, J=8 Hz, 3H), 1.9 (q, 2H), 2.82 (s, 3H), 3.0 (t, J=8 Hz, 2H). FAB-MS: m/e 211 and 213 (M+H). Analysis calculated for $C_9H^{11}N_4Cl$: C, 51.31; H, 5.26; N, 26.60. Found: C, 51.43; H, 5.50, N, 26.81.

Step B: Preparation of 2-Chloro-6-methyl-8-propyl-9-[[4-[3-(1H-tetrazol-5-yl)-4-thienyl]phenyl]methyl]purine Following the procedures of Example 1, Steps D-I and replacing 5,7-dimethyl-2-ethylimidazo[4,5-b]pyridine with the product of Step A, in Step H of Example 1, the title compound can be prepared.

EXAMPLE 10

2-Dimethylamino-6-methyl-8-propyl-9-[[4-[3-(1H-tetrazol-5-yl)-4-thienyl]phenyl]methyl]purine (Compound 18 of Table VI)

Step A: Preparation of 2-Dimethylamino-6-methyl-8-propylpurine

To a solution of 2-Chloro-6-methyl-8-propylpurine (from Step 1 of Example 32) (0.1 g, 0.47 mmol) in ethanol (2 ml) was added condensed dimethylamine (1 ml) at 0° C. The mixture was then placed in a steel-bomb and heated at 110° C. for 7 hours. The reactions was cooled and the mixture was concentrated in vacuo. The residue was partitioned between $CHCl_3$ and water, and the organic was separated and dried over $MgSO_4$. The crude product obtained after removal of the solvent was purified by flash-chromatography on silica-gel using 5% MeOH in $CHCl_3$ giving the titled compound as an amorphous solid (0.065 g, 64%). NMR ($CDCl_3$): δ1.01 (t, J=8 Hz, 3H), 1.8 (q, J=8 Hz, 2H), 2.65 (s, 3H), 2.8 (t, J=8 Hz, 2H), 3.2 (s, 6H). FAB-MS: m/e 220 (M+H).

Step B: Preparation of 2-Dimethylamino-6-methyl-8-propyl-9-[[4-[3-(1H-tetrazol-5-yl)-4-thienyl]phenyl]methyl]purine Following the procedures of Example 1, Steps D-I and replacing 5,7-dimethyl-2-ethylimidazo[4,5-b]pyridine with the product of Step A, in Step H of Example 1, the title compound can be prepared.

EXAMPLE 11

5,7-Dimethyl-2-ethyl-3-[[4-[2-bromo-3-[1H-tetrazol-5-yl)-4-thienyl]phenyl]methyl]imidazo[4,5-b]pyridine (Compound 17 of Table VII)

Step A: Preparation of 2-bromo-3-(N-triphenylmethyltetrazol-5-yl)-4-(4-methylphenyl)thiophene (scheme II-1, compound 1d R=Br).

To a solution of the product of Example 1, Step F (101 mg, 0.208 mmol) in dry THF (2 ml) cooled to −78° C. with a dry ice/acetone bath under $N_2$ was added a 1.7M tBuLi solution (0.190 ml, 0.323 mmol). The reaction turned slowly from orange to red then the color dissipated. Another 0.190 ml of tBuLi was added to the reaction. As soon as the red color persisted $Br_2$ (0.40 ml, 0.42 mmol) was added. The product was purified by flash chromatography on a silica column using Hex-/EtOAc (35:1). Removal of the solvent afforded 60 mg (51%) of the crude titled product. Rf=0.48 (10:1 Hex-/EtOAc).

Step B: Preparation of 2-bromo-3-N-triphenylmethyltetrazol-5-yl-4-(4-bromomethylphenyl)thiophene (scheme II-1, compound 1e, R=Br).

To a solution of the product of Step A (22 mg crude) in dry $CCl_4$ (3 mL) was added NBS (7 mg, 0.0448 mmol) and a catalytic amount of AIBN. The reaction was brought to reflux (100° C.). After 2 h the reaction was cooled to rt and the insoluable succinimide was removed by filtration. The solvent was replaced by $Et_2O$/EtOAc and washed with 1N NaOH and brine, dried over $MgSO_4$ and filtered. Removal of the solvent afforded 43 mg (100%) of the crude titled compound. Rf=0.66 (3:1/Hex:EtOAc).

Step C: Preparation of 5,7-dimethyl-2-ethyl-3-[4-(4-(2-bromo-3-N-triphenyl-methyltetrazol-5-yl)thienyl)phenyl]methylimidazo]4,5-b]pyridine To a solution of 5,7-dimethyl-2-ethylimidazopyridine from Example 1, Step C, (9 mg, 0.0514 mmol) in dry DMF (1 ml) under $N_2$ was added 80% NaH in oil (6 mg, 0.2 mmol). The reaction was allowed to stir for 30 min. To this was added a solution of the product of Step B (43 mg crude) in dry DMF (2 ml). After an hour the reaction was quenched with sat'd $NH_4Cl$ solution. The DMF was replaced by EtOAc and the insoluable salts removed by filtration. The product was purified by flash chromatography on a silica column using Hex-/EtOAc (2:1). Removal of the solvent afforded 5 mg (23% for steps A through C) of the crude titled compound. Rf=0.20 (1:1/Hex:EtOAc).

Step D: Preparation of 5,7-dimethyl-2-ethyl-3-[4-(3-(2-bromo-3-tetrazol-5-yl)thienyl)phenyl]methylimidazo[4,5-b]pyridine To a solution of the product of Step C (5 mg, crude) in MeOH (1 ml) was added 9N HCl (2 drops). After 30 min the solvent was removed in vacuo and the product was purified by flash chromatography on a silica column eluting with $CHCl_3$:MeOH:$NH_4OH$ (50:10:1). Removal of the solvent afforded 3 mg (24% for steps A through D) of the titled product. Rf=0.31(40:10:1/$CHCl_3$:MeOH:$NH_4OH$).

$^1H$ NMR (300 MHz, $CD_3OD$) δ1.27 (t, 3H), 2.60 (s, 3H), 2.64 (s, 3H), 2.85 (q, 2H), 5.53 (s, 2H), 7.00 (d, 2H), 7.05 (s, 1H), 7.09 (d, 2H), 7.59 (s, 1H).

EXAMPLE 12

7-Methyl-2-propyl-3-[[4-[2-bromo-3-(1H-tetrazol-5-yl)-4-thienyl]phenyl]methyl]imidazo[4,5-b]pyridine (Compound 18 of Table VII)

Following the procedures of Example 11, Steps A through D and replacing 5,7-dimethyl-2-ethylimidazo[4,5-b]pyridine with 7-methyl-2-propylimidazo[4,5-b]pyridine the product of Example 2, Step B, the titled compound can be prepared.

EXAMPLE 13

5-Carbomethoxy-2-ethyl-7-methyl-3-[[4-[2-bromo-3-(1H-tetrazol-5-yl)-4-thienyl]phenyl]methyl]imidazo[4,5-b]pyridine (Compound 19 of Table VII)

Following the procedures of Example 11, Steps A through D and replacing 5,7-dimethyl-2-ethylimidazo[4,5-b]pyridine with 2-ethyl-7-methylimidazo[4,5-b]pyridine the product of Example 3, Step G, the titled compound can be prepared.

EXAMPLE 14

5-Carbomethoxy-7-methyl-2-propyl-3-[[4-[2-bromo-3-(1H-tetrazol-5-yl)-4-thienyl]phenyl]methyl]imidazo[4,5-b]pyridine (Compound 20 of Table VII)

Following the procedures of Example 11, Steps A through D and replacing 5,7-dimethyl-2-ethylimidazo[4,5-b]pyridine with 7-methyl-2-propylimidazo[4,5-b]pyridine the titled compound can be prepared.

EXAMPLE 15

5-Carboxy-2-ethyl-7-methyl-3-[[4-[2-bromo-3-(1H-tetrazol-5-yl)-4-thienyl]phenyl]methyl]imidazo[4,5-b]pyridine (Compound 21 of Table VII)

Following the procedures of Example 13, Steps A through D and subsequent hydrolysis of the ester in the final step, the titled compound can be prepared.

EXAMPLE 16

5-Carboxy-7-methyl-2-propyl-3-[[4-[2-bromo-3-(1H-tetrazol-5-yl)-4-thienyl]phenyl]methyl]imidazo[4,5-b]pyridine (Compound 22 of Table VII)

Following the procedures of Example 14, Steps A through D and subsequent hydrolysis of the ester in the final step, the titled compound can be prepared.

EXAMPLE 17

2-Propyl-1-[[4-[2-bromo-3-(1H-tetrazol-5-yl)-4-thienyl]phenyl]methyl]benzimidazole (Compound 3 of Table V)

Following the procedures of Example 11, Steps A through D replacing the heterocycle of Step D with 2-propylbenzimidazole from Step A of Example 7, the titled compound can be prepared.

EXAMPLE 18

2-Butyl-1-[[4-[2-bromo-3-(1H-tetrazol-5-yl)-4-thienyl]phenyl]methyl]benzimidazole (Compound 4 of Table V)

Following the procedures of Example 11, Steps A through D replacing the heterocycle of Step D with 2-butylbenzimidazole from Step A of Example 8, the titled compound can be prepared.

EXAMPLE 19

2-Chloro-6-methyl-8-propyl-9-[[4-[2-bromo-3-(1H-tetrazol-5-yl)-4-thienyl]phenyl]methyl]purine (Compound 19 of Table VI)

Following the procedures of Example 11, Steps A through D and replacing 5,7-dimethyl-2-ethylimidazo[4,5-b]pyridine with 2-chloro-6-methyl-8-propylpurine the product of Example 9, Step A, the titled compound can be prepared.

EXAMPLE 20

2-Dimethylamino-6-methyl-8-propyl-9-[[4-[2-bromo-3-(1H-tetrazol-5-yl)-4-thienyl]phenyl]methyl]purine (Compound 20 of Table VI)

Following the procedures of Example 11, Steps A through D and replacing 5,7-dimethyl-2-ethylimidazo[4,5-b]pyridine with 2-dimethylamino-6-methyl-8-propylpurine, the product of Example 10, Step A, the titled compound can be prepared.

EXAMPLE 21

5,7-Dimethyl-2-ethyl-3-[[4-[2-(1H-tetrazol-5-yl)-3-thienyl]phenyl]methyl]imidazo[4,5-b]pyridine (Compound 14 of Table VII)

Step A: Preparation of 2-[(N-triphenylmethyltetrazol-5-yl]thiophene.(scheme II-3, compound 3a,Y=S)

To a solution of 2-cyanothiophene (1.4 g; 12.8 mmol) in dry toluene (10 ml) was added $Me_3SnN_3$ (2.8 g; 13.65 mmol). The mixture was stirred at reflux under N₂ for 12 hours. The reaction was cooled to room temperature diluted with CH₂Cl₂ and washed with 2N HCl soln and H₂O. The organic was dried over anhydrous MgSO₄ and concentrated in vacuo. The residue, containing the free tetrazole, was dissolved in CH₂Cl₂ (10 mL) and Ph₃CCl (3.2 g; 0.9 equiv.) and NEt₃ (3.6 mL) were added. After 20 minutes the mixture was diluted with Et₂O/EtOAc and washed with 1N NaOH, 10% citric acid and brine. The organic was dried over anhydrous MgSO₄ and concentrated in vacuo. The product was purified by recrystallization from hexanes. The titled compound was isolated in 80% yield, Rf=0.33 (10:1 hex/EtOAc). ¹H NMR (200 MHz, CDCl₃) δ7.12–7.21 (comp, 8H), 7.28–7.40 (comp, 8H), 7.42 (dd, 1H), 7.79 (dd, 1H).

Step B: Preparation of 2-trimethylsilyl-5-(N-triphenylmethyltetrazol-5-yl)thiophene (scheme II-3, compound 3b, Y=S)

A solution of the product of Step A (1.00 g, 2.54 mmol) in dry THF (10 ml) under N₂ was cooled to −20° C. with a dry ice/acetone bath. To this was added 1.6M nBuLi solution (2.38 ml, 3.81 mmol) by syringe. The reaction mixture turned orange then red and cloudy. The reaction was warmed to −10° C. and stirred for 45 min. The reaction was then cooled to −50° C. and TMSCl (0.322 mL, 2.54 mmol) was added by syringe. The reaction was warmed to 0° C. and quenched with sat'd NH₄Cl solution (5 drops). The solvent was replaced by Et₂O/EtOAc and washed with water and brine, dried over MgSO₄ and filtered. The product was purified by flash chromatography on a silica column eluting with Hex/EtOAc (40:1). Removal of the solvent afford 849 mg (72%) of the titled product as a slightly orange solid. Rf=0.40 (15:1/Hex:EtOAc). ¹H NMR (400 MHz, CDCl₃) δ0.32 (s, 9H), 7.13–7.15 (m, 5H), 7.22 (d, 1H), 7.31–7.33 (m, 10H), 7.82 (d, 1H).

Step C: Preparation of 2-trimethylsilyl-4-trimethyltin-5-(N-triphenylmethyltetrazol-5-yl)thiophene (scheme II-3, compound 3c, Y=S.)

A solution of the product of Step B (752 mg, 1.61 mmol) in dry THF (6 mL) under N₂ was cooled to −20° C. with a dry ice/acetone bath. To this was added a 1.6M nBuLi solution (1.53 ml, 2.45 mmol) by syringe. The reaction turned red. As the reaction was warmed to −10° C., the color began to return to orange indicating quenching. The reaction was cooled again to −20° C. and another 1.53 ml of the nBuLi solution was added. The solution turned dark red. The reaction was warmed to −10° C. and allowed to stir at this temperature for 45 min. The reaction was cooled to −60° C. and a solution of Me₃SnCl (844 mg, 4.24 mmol) in dry THF (2 ml) was added by cannula. The reaction was warmed to rt and quenched with sat'd NH₄Cl solution. To the flask was added Et₂O/EtOAc and the solution washed with 1N NaOH and brine, dried over MgSO₄ and filtered. The product was purified by flash chromatography on a silica column eluting with Hex/EtOAc (50:1). Removal of the solvent afford 879 mg (87%) of the titled compound as a white solid. Rf=0.54 (10:1/Hex:EtOAc). ¹H NMR (200 MHz, CDCl₃) δ0.13 (s, 9H), 0.35 (s, 9H),.7.12–7.35 (m, 16H).

Step D: Preparation of 2-trimethylsilyl-4-(4-(1-methoxycarbonyl)phenyl)-5-(N-triphenylmethyltetrazol-5-yl)thiophene (scheme II-3, compound 3d, Y=S).

To a concentrated solution of the product of Step C (194 mg, 0.308 mmol) in dry DMF (1.5 ml) was added p-iodomethylbenzoate (153 mg, 0.583 mmol) and Pd(PPh₃)₂Cl₂ (22 mg, 10 mol %). The reaction was heated at 75° C. for several hrs. Because some trityl had been removed by the heat, NEt₃ (0.0645 mL, 0.463 mmol) and Ph₃CCl (59 mg, 0.21 mmol) were added. The DMF was replaced by EtOAc and the product was purified by flash chromatography on a silica column eluting with Hex/EtOAc (15:1). Removal of the solvent afforded 116 mg of the titled compound as a white solid. Rf=0.32 (10:1/Hex:EtOAc). Step E: Preparation of mesylate 3e (scheme II-3, compound 3e, Y=S).

To a solution of the product of step D (116 mg crude) in dry THF (2 ml) under N₂ and cooled to 0° C. was added an LAH solution (0.580 ml, 0.580 mmol) by syringe. When the gas evolution subsided, about 5 min, the ice bath was removed and the reaction warmed to RT. To the reaction was added Et₂O then 1 drop water, 1 drop 5.0N NaOH, and 1 drop water. The insoluable salts precipitated. MgSO₄ was added and the solids were removed by filtration. Removal of the solvent afforded 142 mg (100% 2 steps) of the crude primary alcohol. Rf=0.41 (2:1/Hex:EtOA C). The primary alcohol (142 mg crude) was dissolved in dry CH₂Cl₂ (1.5 mL) under N₂ and was cooled to 0° C. To this solution was added NEt₃ (0.0595 mL, 0.429 mmol), CH₃SO₂Cl (0.030 mL, 0.388 mmol), and a catalytic amount of 4-dimethylaminopyridine (2 mg, 9 mol %). The reaction was kept at 0° C. After an hour the reaction was warmed to rt and Et₂O/EtOAc was added to the reaction. The solution was washed with 10% citric acid, 1N NaOH and brine, dried over MgSO₄, and filtered. Removal of the solvent afforded 113 mg (90% for steps D through E) of the crude titled compound. Rf=0.42 (2:1/Hex:EtOAc). The mesylate was used crude without further purification.

Step F: Preparation of 5,7-dimethyl-2-ethyl-3-[[4-[2-(N-triphenylmethyltetrazol-5-yl)-3-thienyl]phenyl]methyl]imidazo[4,5-b]pyridine To a solution of 5,7-dimethyl-2-ethylimidazopyridine, Example 1, Step C, (61 mg, 0.35 mmol) in dry DMF (1.5 ml) was added NAH, 60% in oil dispersion, (21 mg, 0.54 mmol) under N₂. The reaction was allowed to stir for 30 min. To this mixture was added a solution of the product of example 3, step E (113 mg crude) in dry DMF (1.5 ml). After 45 min the reaction was quenched with sat'd NH₄Cl solution and the DMF removed. The solvent was replaced by EtOAc and the insoluable salts removed by filtration. The product was purified by flash chromatography on a silica column eluting with a gradient of EtOAc/Hex (1.5:1–2:1). Removal of the solvent afforded 29 mg (14% steps C through F) of the titled compound. Rf=0.49 (2:1/EtOAc:Hex).

¹H NMR (400 MHz, CDCl₃) δ1.22 (t, 3H), 2.58 (s, 3H), 2.64 (s, 3H), 2.70 (q, 2H), 5.41 (s, 2H), 6.89–6.98 (m, 9H), 7.07 (d, 1H), 7.18–7.27 (m, 11H),.7.42 (d, 1H).

Step G: Preparation of 5,7-dimethyl-2-ethyl-3-[[4-[2-(1H-tetrazol-5-yl)-3-thienyl]phenyl]methyl]imidazo[4,5-b]pyridine.

To a solution of the product of Step F (18 mg, 0.028 mmol) in MeOH (1 ml) was added 2N HCl (10 drops). After several hours the solvent was removed and the product triturated with Et$_2$O to afford 15 mg (75%) of the titled compound as a light yellow solid.

$^1$H NMR (400 MHz, CD$_3$OD) δ1.41 (t, 3H), 2.70 (s, 6H), 3.27 (q, 2H), 5.81 (s, 2H), 7.31-7.42 (m, 6H), 7.82 (d, 1H); FAB mass spectrum, m/e 416 (m+1, calcd for C$_{22}$H$_{21}$N$_7$S, 416).

EXAMPLE 22

7-Methyl-2-propyl-3-[[4-[2-(1H-tetrazol-5-yl)-3-thienyl]phenyl]methyl]imidazo[4,5-b]pyridine (Compound 15 of Table VII)

Following the procedures of Example 21, Steps A through G and replacing 5,7-dimethyl-2-ethylimidazo[4,5-b]pyridine with 7-methyl-2-propylimidazo[4,5-b]pyridine the product of Example 2, Step B, the titled compound can be prepared.

EXAMPLE 23

5-Carbomethoxy-2-ethyl-7-methyl-3-[[4-[2-(1H-tetrazol-5-yl)-3-thienyl]phenyl]methyl]imidazo[4,5-b]pyridine (Compound 23 of Table VII)

Following the procedures of Example 21, Steps A through G and replacing 5,7-dimethyl-2-ethylimidazo[4,5-b]pyridine with 2-ethyl-7-methylimidazo[4,5-b]pyridine the product of Example 3, Step G, the titled compound can be prepared.

EXAMPLE 24

5-Carbomethoxy-7-methyl-2-propyl-3-[[4-[2-(1H-tetrazol-5-yl)-3-thienyl]phenyl]methyl]imidazo[4,5-b]pyridine (Compound 24 of Table VII)

Following the procedures of Example 21, Steps A through G and replacing 5,7-dimethyl-2-ethylimidazo[4,5-b]pyridine with 7-methyl-2-propylimidazo[4,5-b]pyridine the titled compound can be prepared.

EXAMPLE 25

5-Carboxy-2-ethyl-7-methyl-3-[[4-[2-(1H-tetrazol-5-yl)-3-thienyl]phenyl]methyl]imidazo[4,5-b]pyridine (Compound 25 of Table VII)

Following the procedures of Example 23, Steps A through G and subsequent hydrolysis of the ester in the final step, the titled compound can be prepared.

EXAMPLE 26

5-Carboxy-7-methyl-2-propyl-3-[[4-[2-(1H-tetrazol-5-yl)-3-thienyl]phenyl]methyl]imidazo[4,5-b]pyridine (Compound 26 of Table VII)

Following the procedures of Example 24, Steps A through G and subsequent hydrolysis of the ester in the final step, the titled compound can be prepared.

EXAMPLE 27

2-Propyl-1-[[4-[2-(1H-tetrazol-5-yl)-3-thienyl]phenyl]methyl]benzimidazole (Compound 11 of Table V)

Following the procedures of Example 21, Steps A through G replacing the heterocycle of Step D with 2-propylbenzimidazole from Step A of Example 7, the titled compound can be prepared.

EXAMPLE 28

2-Butyl-1-[[4-[2-(1H-tetrazol-5-yl)-3-thienyl]phenyl]methyl]benzimidazole (Compound 12 of Table V)

Following the procedures of Example 21, Steps A through G replacing the heterocycle of Step D with 2-butylbenzimidazole from Step A of Example 8, the titled compound can be prepared.

EXAMPLE 29

2-Chloro-6-methyl-8-propyl-9-[[4-[2-(1H-tetrazol-5-yl)-3-thienyl]phenyl]methyl]purine (Compound 21 of Table VI)

Following the procedures of Example 21, Steps A through G and replacing 5,7-dimethyl-2-ethylimidazo[4,5-b]pyridine with 2-chloro-6-methyl-8-propylpurine the product of Example 9, Step A, the titled compound can be prepared.

EXAMPLE 30

2-Dimethylamino-6-methyl-8-propyl-9-[[4-[2-(1H-tetrazol-5-yl)-3-thienyl]phenyl]methyl]purine (Compound 22 of Table VI)

Following the procedures of Example 21, Steps A through G and replacing 5,7-dimethyl-2-ethylimidazo[4,5-b]pyridine with 2-dimethylamino-6-methyl-8-propylpurine the product of Example 10, Step A, the titled compound can be prepared.

EXAMPLE 31

5,7-Dimethyl-2-ethyl-3-[[4-[2-(1H-tetrazol-5-yl)-3-furanyl]phenyl]methyl]imidazo[4,5-b]pyridine (Compound 27 of Table VII)

Step A: Preparation of 2-[(N-triphenylmethyl)tetrazol-5-yl]furan (scheme II-3, compound 3a, Y=O)

To a solution of 2-cyanofuran (3.84 g; 41.3 mmol) in dry toluene (30 mL) was added Me$_3$SnN$_3$ (10 g; 1.2 equiv.). The mixture was stirred at reflux under N$_2$ for 12 hours. The reaction mixture was diluted with CH$_2$Cl$_2$ and washed with 2N HCl soln and H$_2$O. The organic was dried over anhydrous MgSO$_4$ and concentrated in vacuo. The residue was dissolved in CH$_2$Cl$_2$ (20 mL) and NEt$_3$ (11.0 mL; 2 equiv.) and Ph$_3$CCl (10.3 g; 0.9 equiv.) were added. After 1 hour the mixture was diluted with Et$_2$O/EtOAc and washed with 10% citric acid, 1N NaOH and brine. The organic was dried over MgSO$_4$ and concentrated in vacuo. The product was crystallized from hexanes. The title compound was isolated in 35% yield, Rf=0.30 (10:1 hex/EtOAc).

$^1$H NMR (200 MHz, CDCl$_3$) δ6.53 (dd, 1H), 7.08-7.18 (comp, 6H), 7.21-7.40 (comp, 10H), 7.57 (dd, 1H).

Step B: Preparation of 2-trimethylsilyl-5-(N-triphenylmethyltetrazol-5-yl)furan (scheme II-3, compound 3b, Y=O).

A solution of the product of Step A (1.00 g, 2.65 mmol) in dry THF (10 mL) under N$_2$ was cooled to −20° C. with a dry ice/acetone bath. To this was added 1.6M n BuLi solution (2.5 mL, 4.0 mmol). The reaction slowly turned red in color. As the reaction was warmed to −10° C., the color changed to brown and the reaction became cloudy. The reaction was cooled to −50°

C. and TMSCl (0.335 mL, 2.64 mmol) was added by syringe. The reaction was warmed to 0° C. and quenched with sat'd NH₄Cl solution (6 drops). The solvent was replaced by EtOAc and washed with brine, dried over MgSO₄ and filtered. The product was purified by flash chromatography on a silica column eluting with Hex/EtOAc (40:1). Removal of the solvent affored 590 mg (50%) of the titled product as a white solid. Rf=0.32 (15:1/Hex:EtOAc).

¹H NMR (400 MHz, CDCl₃) δ0.29 (s, 9H), 6.69 (d, 1H), 7.04 (d, 1H), 7.12–7.35 (m, 15H).

Step C: Preparation of 2-trimethylsilyl-4-trimethyltin-5-(N-triphenylmethyltetrazol-5-yl)furan (scheme II-3, compound 3c, Y=O).

A solution of the product of Step B (532 mg, 1.18 mmol) in dry THF (5 mL) under N₂ was cooled to −20° C. with a dry ice/acetone bath. To this was added 1.6M nBuLi solution (1.13 mL, 1.81 mmol) by syringe. A light red color developed. The reaction was warmed to −10° C. and allowed to stir at this temperature for 45 min. Because the color faded another 1.13 ml of 1.6M nBuLi was added. The reaction was cooled to −60° C. and a solution of Me₃SnCl (500 mg, 2.5 mmol) in dry THF (1.5 mL) was added by cannula. The reaction was warmed to rt. To the flask was added Et₂O/EtOAc and the solution washed with 1N NaOH, water, and brine, dried over MgSO₄ and filtered. The product was purified by flash chromatography on a silica column eluting with Hex/EtOAc (50:1). Rf=0.54 (10:1/Hex:EtOAc). Removal of the solvent affored 520 mg (72%) of the titled compound as a white solid.

¹H NMR (400 MHz, CDCl₃) δ0.05 (s, 9H), 0.30 (s, 9H), 6.68 (s, 1H), 7.10–7.13 (m, 5H), 7.30–7.32 (m, 10H).

Step D: Preparation of 2-trimethylsilyl-4-(4-(1-methoxycarbonyl)phenyl)-5-(N-triphenylmethyltetrazol-5-yl)furan (scheme II-3, compound 3d, Y=O).

To a concentrated solution of the product of Step C (187 mg, 0.305 mmol) in dry DMF (1.5 mL) was added p-iodomethylbenzoate (160 mg, 0.612 mmol) and Pd(PPh₃)₂Cl₂ (22 mg, 10 mol%). The reaction was heated at 75° C. for several hrs. Because some trityl had been removed by the heat, NEt₃ (0.043 mL, 0.31 mmol) and Ph₃CCl (41 mg, 0.15 mmol) were added. The DMF was replaced by EtOAc and the product was purified by flash chromatography on a silica column eluting with a gradient of Hex/EtOAc (30:1–15:1). Removal of the solvent affored 100 mg (56%) of the titled compound. Rf=0.23 (10:1/Hex:EtOAc).

¹H NMR (400 MHz, CDCl₃) δ0.34 (s, 9H), 3.93 (s, 3H), 6.86 (s, 1H), 7.05–7.07 (m, 6H), 7.24–7.34 (m, 9H), 7.54 (d, 2H), 7.86 (d, 2H).

Step E: Preparation of 3-(4-(1-methanesulfonyloxymethyl)phenyl)-2-(N-triphenylmethyltetrazol-5-yl)furan (scheme II-3, compound 3e, Y=O).

To a solution of the product of Step D (100 mg, 0.172 mmol) in dry THF (2 mL) under N₂ and cooled to 0° C. was added an 1.0M LAH solution (0.520 mL, 0.520 mmol) by syringe. When the gas evolution subsided the ice bath was removed and the reaction warmed to rt. To the reaction was added Et₂O then 1 drop water, 1 drop 5.0N NaOH, and 1 drop water. The insoluable salts precipitated and MgSO₄ was added and the solids removed by filtration. The solvent was removed in vacuo and the crude alcohol, Rf=0.35 (2:1/Hex:EtOAc), was used in the next step without further purification. A solution of the primary alcohol in dry CH₂Cl₂ (1.5 mL) under N₂ was cooled to 0° C. To this solution was added NEt₃ (0.0527 mL, 0.378 mmol), CH₃SO₂Cl (0.0266 mL, 0.344 mmol), and a catalytic amount of 4-dimethylaminopyridine (3 mg, 15 mol%). The reaction was kept at 0° C. After an hour the reaction was warmed to rt and Et₂O/EtOAc was added to the reaction. The solution was washed with 10% citric acid, 1N NaOH and brine, dried over MgSO₄, and filtered. Removal of the solvent afforded 105 mg (96% 2 steps) of the crude titled compound as a bright yellow solid. Rf=0.43 (2:1/Hex:EtOAc). The mesylate was used crude without further purification.

Step F: Preparation of 5,7-dimethyl-2-ethyl-3-[[4-[2-(N-triphenylmethyltetrazol-5-yl)-3-furanyl]phenyl]methyl]imidazo[4,5-b]pyridine To a solution of 5,7-dimethyl-2-ethylimidazo-[4,5-b]pyridine from Example 1, Step C (58 mg, 0.33 mmol) in dry DMF (2 mL) was added NaH, 60% in oil dispersion, (20 mg, 0.51 mmol) under N₂. The reaction was allowed to stir for 30 min. To this mixture was added a solution of the product of Step E (105 mg crude) in dry DMF (1.5 mL). After 40 min the reaction was quenched with sat'd NH₄Cl solution and the DMF removed. The solvent was replaced by EtOAc and the insoluable salts removed by filtration. The product was purified by flash chromatography on a silica column eluting with a gradient of EtOAc/Hex (1:1–2:1). Removal of the solvent affored 27 mg (24% steps D through F) of the titled compound. Rf=0.47 (2:1/EtOAc:Hex).

¹H NMR (400 MHz, CDCl₃) δ1.24 (t, 3H), 2.59 (s, 3H), 2.65 (s, 3H), 2.74 (q, 2H), 5.44 (s, 2H), 6.64 (d, 1H), 6.92 (s, 1H), 6.95 (d, 2H), 7.02–7.04. (m, 5H), 7.19–7.24 (m, 10H), 7.48 (d, 2H), 7.58 (d, 1H).

Step G: Preparation of 5,7-dimethyl-2-ethyl-3-[[4-[2-(1H-tetrazol-5-yl)-3-furanyl]phenyl]methyl]-imidazo[4,5-b]pyridine.

To a solution of the product of example 4, step F (14 mg, 0.02 mmol) in MeOH (0.5 mL) was added 2N HCl (2 drops). After an hour the solvent was removed and the product triturated with Et₂O to afford 8 mg (91%) of the titled compound as a light yellow solid.

¹H NMR (400 MHz, CD₃OD) δ1.40 (t, 3H), 2.68 (s, 3H), 2.69 (s, 3H), 3.26 (q, 2H), 5.80 (s, 2H), 6.90 (d 1H), 7.40 (s, 1H), 7.43 (d, 2H), 7.77 (d, 2H), 7.87 (d, 1H);

FAB mass spectrum, m/e 400 (m+1, calcd for C₂₂H₂₁N₇O, 400).

EXAMPLE 32

7-Methyl-2-propyl-3-[[4-[2-(1H-tetrazol-5-yl)-3-furanyl]phenyl]methyl]imidazo[4,5-b]pyridine (Compounds 28 of Table VII)

Following the procedures of Example 31, Steps A through G and replacing 5,7-dimethyl-2-ethylimidazo[4,5-b]pyridine with 7-methyl-2-propylimidazo[4,5-b]pyridine the product of Example 2, Step B, the titled compound can be prepared.

EXAMPLE 33

5-Carbomethoxy-2-ethyl-7-methyl-3-[[4-[2-(1H-tetrazol-5-yl)-3-furanyl]phenyl]methyl]imidazo[4,5-b]pyridine (Compound 29 of Table VII)

Following the procedures of Example 31, Steps A through G and replacing 5,7-dimethyl-2-ethylimidazo[4,5-b]pyridine with 2-ethyl-7-methylimidazo[4,5-b]pyridine the product of Example 3, Step G, the titled compound can be prepared.

EXAMPLE 34

5-Carbomethoxy-7-methyl-2-propyl-3-[[4-[2-(1H-tetrazol-5-yl)-3-furanyl]phenyl]methyl]imidazo[4,5-b]pyridine (Compound 30 of Table VII)

Following the procedures of Example 31, Steps A through G and replacing 5,7-dimethyl-2-ethylimidazo[4,5-b]pyridine with 7-methyl-2-propylimidazo[4,5-b]pyridine the titled compound can be prepared.

EXAMPLE 35

5-Carboxy-2-ethyl-7-methyl-3-[[4-[2-(1H-tetrazol-5-yl)-3-furanyl]phenyl]methyl]imidazo[4,5-b]pyridine (Compound 31 of Table VII)

Following the procedures of Example 33, Steps A through G and subsequent hydrolysis of the ester in the final step, the titled compound can be prepared.

EXAMPLE 36

5-Carboxy-7-methyl-2-propyl-3-[[4-[2-(1H-tetrazol-5-yl)-3-furanyl]phenyl]methyl]imidazo[4,5-b]pyridine (Compound 32 of Table VII)

Following the procedures of Example 34, Steps A through G and subsequent hydrolysis of the ester in the final step, the titled compound can be prepared.

EXAMPLE 37

2-Propyl-1-[[4-[2-(1H-tetrazol-5-yl)-3-furanyl]phenyl]methyl]benzimidazole (Compound 6 of Table V)

Following the procedures of Example 31, Steps A through G replacing the heterocycle of Step F with 2-propylbenzimidazole from Step A of Example 7, the titled compound can be prepared.

EXAMPLE 38

2-Butyl-1-[[4-[2-(1H-tetrazol-5-yl)-3-furanyl]phenyl]methyl]benzimidazole (Compound 5 of Table V)

Following the procedures of Example 31, Steps A through G replacing the heterocycle of Step F with 2-butylbenzimidazole from Step A of Example 8, the titled compound can be prepared.

EXAMPLE 39

5-Chloro-6-methyl-8-propyl-9-[[4-[2-(1H-tetrazol-5-yl)-3-furanyl]phenyl]methyl]purine (Compounds 23 of Table VI)

Following the procedures of Example 31, Steps A through G and replacing 5,7-dimethyl-2-ethylimidazo[4,5-b]pyridine with 2-chloro-6-methyl-8-propylpurine, the product of Example 9, Step A, the titled compound can be prepared.

EXAMPLE 40

2-Dimethylamino-6-methyl-8-propyl-9-[[4-[2-(1H-tetrazol-5-yl)-3-furanyl]phenyl]methyl]purine (Compound 24 of Table VI)

Following the procedures of Example 31, Steps A through G and replacing 5,7-dimethyl-2-ethylimidazo[4,5-b]pyridine with 2-dimethylamino-6-methyl-8-purine the product of Example 10, Step A, the titled compound can be prepared.

EXAMPLE 41

5,7-Dimethyl-2-ethyl-3-[[4-[2-(N-benzoylsulfonamido)-3-benzothienyl]phenyl]methyl]imidazo[4,5-b]pyridine (Compound 42 of Table VII)

Step A: Preparation of 3-(4-methylphenyl)benzothiophene (scheme II-4, compound 4a, Y=S, where $R^{11}$ and $R^{12}$ are joined to form a phenyl ring).

To a solution of 3-bromobenzothiophene (709 mg, 3.33 mmol) and p-tolytrimethyltin (850 mg, 1.0 equiv) in dry toluene (12 mL) under $N_2$ was added Pd(PPh$_3$)$_4$ (192 mg, 5 mol %). The mixture was stirred at reflux for 12 h. The solvent was removed in vacuo and the residue was partially dissolved in hex/EtOAc (10:1) and filtered through a plug of silica. The solvent was removed to afford 658 mg (88%) of crude titled compound. Rf=0.56 (25:1 hex/EtOAc).

Step B: Preparation of 3-(4-methylphenyl)-2-chlorosulfonylbenzothiophene (scheme II-4, compound 4c, Y=S, where $R^{11}$ and $R^{12}$ are joined to form a phenyl ring).

To a solution of the product of Step A (293 mg, 1.308 mmol) in dry THF (5 mL) cooled to −20° C. under $N_2$ was added 1.6M nBuLi (2.44 mL, 3.0 equiv). The reddish-brown anion was stirred at −20° C. for 50 min then cooled to −70° C. and SO$_2$(g) was bubbled in until the anion color disappeared (ca. 5 min). To the now slightly yellow solution was added N-chlorosuccinamide (350 mg, 2 equiv) and the mixture was stirred for 1 h and warmed to rt by removing the ice bath. The reaction mixture was diluted with Et$_2$O/EtOAc and washed with H$_2$O, 5% NaHCO$_3$ soln, and brine. The organic was dried over anhydrous MgSO$_4$ and concentrated in vacuo to afford crude titled compound. Rf=0.45 (25:1 hex/EtOAc).

Step C: Preparation of 3-(4-methylphenyl)-2-(N-t-butylsulfonamido)benzothiophene (scheme II-4, compound 4d, Y=S, where $R^{11}$ and $R^{12}$ are joined to form a phenyl ring).

To a solution of the entire crude product of Step B in dry CH$_2$Cl$_2$ (5 mL) was added tbutylamine (2 mL). The mixture was stirred for 2 days and then diluted with CH$_2$Cl$_2$ and washed with 1N HCl, H$_2$O and brine. The organic was dried over anhydrous MgSO$_4$ and concentrated in vacuo. The product was purified by flash chromatography by first eluting with hex/EtOAc (6:1) and then with CH$_2$Cl$_2$ to afford 115 mg (25% for step B and C) of the titled compound. Rf=0.23 (6:1 hex/EtOAc).

$^1$H NMR (400 MHz, CDCl$_3$) δ1.04 (s, 9H), 2.44 (s, 3H), 4.01 (s, 1H), 7.33 (d, 2H), 7.36 (m, 1H), 7.43–7.48 (comp m, 3H), 7.55 (dd, 1H), 7.87 (ddd, 1H); FAB mass spectrum, m/e 360 (m+H, calcd for C$_{19}$H$_{21}$NO$_2$S$_2$, 360).

Step D: Preparation of 3-(4-bromomethylphenyl)-2-(N-t-butylsulfonamido)-benzothiophene (scheme II-4, compound 4e, Y=S, where $R^{11}$ and $R^{12}$ are joined to form a phenyl ring).

To a solution of the product of Step C (115 mg, 0.3203 mmol) in dry benzene (5 mL) was added a ctalytic amount of AIBN and N-bromosuccinamide (68 mg, 1.2 equiv). The mixture was stirred at reflux under $N_2$ for 3 h. After cooling to rt the reaction mixture was diluted with $Et_2O$/EtOAc and washed with $H_2O$ and brine. The organic was dried over anhydrous $MgSO_4$ and concentrated in vacuo to afford 147 mg (100%) of the titled compound. Rf=0.18 (6:1 hex/EtOAc). The bromomethyl compound was used crude without further purification.

Step E: Preparation of 5,7-dimethyl-2-ethyl-3-[[4-[2-(N-t-butylsulfonamido)-3-benzothienyl]phenyl]methyl]imidazo[4,5-b]pyridine (scheme II-10, compound 10a).

To a solution of 5,7-dimethyl-2-ethyl-imidazo[4,5-b]pyridine from Example 1, Step C, (112 mg, 0.2557 mmol) in dry DMF (2 mL) was added 80% NaH in oil (28 mg, 1.5 equiv). When $H_2$ evolution ceased a solution of the product of Step D (147 mg, 0.3356 mmol) in DMF (1 mL) was added. The mixture was stirred at rt for 3 h then quenched with satd $NH_4Cl$ soln and concentrated in vacuo. The residue was dissolved in $CH_2Cl_2$ dried over anhydrous $MgSO_4$, filtered and concentrated in vacuo. A small sample of the reaction mixture was purified by flash chromatography eluting with hex/EtOAc (2:1) to provide the titled compound in pure form. Rf=0.23 (1:1 hex/EtOAc).

$^1$H NMR (400 MHz, $CDCl_3$) $\delta$1.01 (s, 9H), 1.35 (t, 3H), 2.59 (s, 3H), 2.64 (s, 3H), 3.98 (s, 1H), 5.54 (s, 2H), 6.92 (s, 1H), 7.29 (d, 2H), 7.34 (t, 1H), 7.42-7.51 (comp m, 4H), 7.85 (d, 1H).

Step F: Preparation of 5,7-dimethyl-2-ethyl-3-[[4-[2-(sulfonamido)-3-benzothienyl]phenyl]methyl]imidazo[4,5-b]pyridine (scheme II-10, compound 10b)

A solution of the entire product of Step E in TFA (2 mL) and anisole (2 drops) was stirred for 24 h. The TFA was removed at high vacuum and 56 mg (35% for steps E and F) crude sulfonamide remained. Rf=0.35 (100:5:1 $CH_2Cl_2$/MeOH/$NH_4OH$).

Step G: Preparation of 5,7-dimethyl-2-ethyl-3-[[4-[2-(N-benzoylsulfonamido)-3-benzothienyl]phenyl]methyl]imidazo[4,5-b]pyridine (scheme II-10, compound 10c)

To a solution of the product of Step F (26 mg, 0.0546 mmol) in dry pyridine (0.5 mL) was added a catalytic amount of DMAP and benzoyl chloride (0.063 mL, 10 equiv). After stirring for 3 h the pyridine was removed at high vacuum and the residue was taken up in $CH_2Cl_2$ and washed with 5% citric acid soln and $H_2O$. The organic was dried over anhydrous $MgSO_4$ and concentrated in vacuo. The product was purified by flash chromatography eluting with $CHCl_3$/MeOH/$NH_4OH$ (80:10:1) to provide 13.7 mg (44%) of the titled compound. Rf=0.57 (40:10:1 $CHCl_3$/MeOH/$NH_4OH$).

$^1$H NMR (400 MHz, $CDCl_3$) $\delta$1.25 (t, 3H), 2.40 (s, 3H), 2.59 (s, 3H), 2.73 (q, 2H), 3.05 (bs, 1H), 5.31 (s, 2H), 6.79 (s, 1H), 6.94-7.01 (comp, 4H), 7.16-7.29 (comp, 6H), 7.57 (d, 3H).

EXAMPLE 42

7-Methyl-2-propyl-3-[[4-[2-(N-benzoylsulfonamido)-3-benzothienyl]phenyl]methyl]imidazo[4,5-b]pyridine. (Compound 43 of Table VII)

Following the procedures of Example 41, Steps A through G and replacing 5,7-dimethyl-2-ethylimidazo[4,5-b]pyridine with 7-methyl-2-propylimidazo[4,5-b]pyridine the product of Example 2, Step B, the titled compound can be prepared.

EXAMPLE 43

5-Carbomethoxy-2-ethyl-7-methyl-3-[[4-[2-(N-benzoylsulfonamido)-3-benzothienyl]phenyl]methyl]imidazo[4,5-b]pyridine (Compound 44 of Table VII)

Following the procedures of Example 41, Steps A through G and replacing 5,7-dimethyl-2-ethylimidazo[4,5-b]pyridine with 2-ethyl-7-methylimidazo[4,5-b]pyridine the product of Example 3, Step G, the titled compound can be prepared.

EXAMPLE 44

5-Carbomethoxy-7-methyl-2-propyl-3-[[4-[2-(N-benzoylsulfonamido)-3-benzothienyl]phenyl]methyl]imidazo[4,5-b]pyridine (Compound 45 of Table VII)

Following the procedures of Example 41, Steps A through G and replacing 5,7-dimethyl-2-ethylimidazo[4,5-b]pyridine with 7-methyl-2-propylimidazo[4,5-b]pyridine the titled compound can be prepared.

EXAMPLE 45

5-Carboxy-2-ethyl-7-methyl-3-[[4-[2-(N-benzoylsulfonamido)-3-benzothienyl]phenyl]methyl]imidazo[4,5-b]pyridine (Compound 46 of Table VII)

Following the procedures of Example 43, Steps A through G and subsequent hydrolysis of the ester in the final step, the titled compound can be prepared.

EXAMPLE 46

5-Carboxy-7-methyl-2-propyl-3-[[4-[2-(N-benzoylsulfonamido)-3-benzothienyl]methyl]imidazo[4,5-b]pyridine (Compound 47 of Table VII)

Following the procedures of Example 44, Steps A through G and subsequent hydrolysis of the ester in the final step, the titled compound can be prepared.

EXAMPLE 47

2-Propyl-1-[[4-[2-(N-benzoylsulfonamido)-3-benzothienyl]phenyl]methyl]benzimidazole (Compound 25 of Table V)

Following the procedures of Example 41, Steps A through G replacing the heterocycle of Step E with 2-propylbenzimidazole from Step A of Example 7, the titled compound can be prepared.

EXAMPLE 48

2-Butyl-1-[[4-[2-(N-benzoylsulfonamido)-3-benzothienyl]phenyl]methyl]benzimidazole (Compound 26 of Table V)

Following the procedures of Example 41, Steps A through G replacing the heterocycle of Step E with 2-butylbenzimidazole from Step A of Example 8, the titled compound can be prepared.

EXAMPLE 49

2-Chloro-6-methyl-8-propyl-9-[[4-[2-(N-benzoylsulfonamido)-3-benzothienyl]phenyl]methyl]purine (Compound 25 of Table VI)

Following the procedures of Example 41, Steps A through G and replacing 5,7-dimethyl-2-ethylimidazo[4,5-b]pyridine with 2-chloro-6-methyl-8-propylpurine, the product of Example 9, Step A, the titled compound can be prepared.

EXAMPLE 50

2-Dimethylamino-6-methyl-8-propyl-9-[[4-[2-(N-benzoylsulfonamido)-3-benzothienyl]phenyl]methyl]purine (Compound 26 of Table VI)

Following the procedures of Example 41, Steps A through G and replacing 5,7-dimethyl-2-ethylimidazo[4,5-b]pyridine with 2-dimethylamino-6-methyl-8-propylpurine the product of Example 10, Step A, the titled compound can be prepared.

EXAMPLE 51

5,7-Dimethyl-2-ethyl-3-[[4-[2-(N-benzoylsulfonamido)-3-thienyl]phenyl]methyl]imidazo[4,5-b]pyridine (Compound 12 of Table VII) and 5,7-Dimethyl-2-ethyl-3-[[4-[5-trimethylsilyl-2-(N-benzoylsulfonamido)-3-thienyl]methyl]imidazo[4,5-b]pyridine Step A: Preparation of 3-bromo-2-t-butylsulfonamido-5-trimethylsilylthiophene. (scheme II-5, compound 5a, Y=S)

Part 1: To a solution of 2-thiophenesulfonyl chloride (1.22 g, 6.70 mmol) in dry $CH_2Cl_2$ (25 mL) at rt was added $tBuNH_2$ (1.55 mL, 2.2 equiv). After stirring at rt overnight the mixture was diluted with ether and washed with 1N HCl, a sat'd solution of $NaHCO_3$ and brine. The organic was dried over anhydrous $MgSO_4$ and concentrated in vacuo to provide 1.42 g (97%) of t-butylsufonamido-2-thiophene, Rf=0.50 (2:1 hex/EtOAc).

Part 2: To a solution of t-butylsulfonamido-2-thiophene (500 mg, 2.28 mmol) in dry THF (5 mL) cooled to 0° C. under a nitrogen atmosphere was added 1.6M nBuLi (4 mL, 6.4 mmol). After stirring for 30 min trimethylsilylchloride (0.64 mL, 2.2 equiv) was added via syringe. The mixture was stirred for 10 min then 1.6M nBuLi (1.5 mL, 2.4 mmol) was added. After stirring for 30 min $Br_2$ ((0.26 mL, 1.19 equiv) was added. The mixture was allowed to warm to rt and diluted with ether and washed with 1N NaOH and brine. The organic was dried over anhydrous $MgSO_4$ and concentrated in vacuo. The product was purified by flash chromatography eluting with hex/EtOAc (8:1) to afford 198 mg (26%) of the titled compound, Rf=0.32 (6:1 hex/EtOAc).

$^1$H NMR (200 MHz, $CDCl_3$) d 0.33 (s, 9H), 1.27 (s, 3H), 5.01 (bs, 1H), 7.11 (s, 1H).

Step B: Preparation of 3-p-tolyl-2-t-butylsulfonamido-5-trimethylsilylthiophene. (scheme II-5, compound 5b, Y=S)

To a solution of the product of Step A (176 mg, 0.536 mmol) and p-tolyltrimethyltin (205 mg, 1.5 equiv) in dry DMF (0.8 mL) under nitrogen was added $PdCl_2(PPh_3)_2$ (38 mg, 10 mol %). The mixture was stirred under nitrogen at 80° C. for 6 h. The DMF was removed at high vacuum and the residue was partially dissolved in EtOAc and filtered. The filtrate was concentrated in vacuo and the product was purified by flash chromatography eluting with hex/EtOAc (17.5:1) to afford 116 mg (62%) of the titled compound, Rf=0.31 (10:1 hex/EtOAc).

$^1$H NMR (200 MHz, $CDCl_3$) d 0.35 (s, 9H), 0.98 (s, 9H), 2.39 (s, 3H), 4.11 (bs, 1H), 7.12 (s, 1H), 7.26 (d, 2H), 7.50 (d, 2H).

Step C: Preparation of 3-(4-Bromomethylphenyl)-2-t-butylsulfonamido-5-trimethylsilylthiophene. (scheme II-5, compound 5c, Y=S)

To a solution of the product of Step B (207 mg, 0.542 mmol) in dry $CCl_4$ (3 ml), heated to dissolve the reagent, was added NBS (116 mg, 0.651 mmol) and a catalytic amount of AIBN. The reaction was refluxed (110° C.) for 3 h then cooled to rt and the insoluable succinimide was removed by filtration. The solvent was diluted with $Et_2O$/EtOAc and washed with water (2x) and brine, dried over $MgSO_4$ and filtered. The solvent was removed and the crude titled product (250 mg) dried thoroughly overnight.

Step D: Preparation of 5,7-dimethyl-2-ethyl-3-[[4-[2-(N-tbutylsulfonamido)-3-thienyl]phenyl]methyl]imidazo[4,5-b]pyridine [compound 9b, (scheme II-9) where $X^1—X^2—X^3—X^4$=—CH—CH—S—CZ— and Z=$SO_2$NHtBu] and 5,7-dimethyl-2-ethyl-3-[[4-[5-trimethylsilyl-2-(N-tbutylsulfonamido)-3-thienyl]phenyl]methyl]imidazo[4,5-b]pyridine [compound 9a, (scheme II-9) where $X^1—X^2—X^3—X^4$=—CH—C(TMS)—S—CZ— and Z=$SO_2$NHtBu]

To a solution of 5,7-dimethyl-2-ethylimidazopyridine, the product of Example 1, Step C, (143 mg, 0.815 mmol) in dry DMF (3 ml) under $N_2$ was added NaH (32.5 mg, 0.813 mmol). The reaction was allowed to stir for 30 min. To this was added a solution of the product of example 6, step C (250 mg, 0.542 mmol, crude) in dry DMF (2 ml). After 3 h the reaction was quenched with sat'd $NH_4Cl$ solution. The DMF was replaced with EtOAc, dried over $MgSO_4$ and the insoluable salts removed by filtration. The products were purified by flash chromatography on a silica column using EtOAc/Hex (1:1). 83.5 mg (28% 2 steps) of the major product, (Rf=0.36 (2:1 EtOAc/Hex)) where $X^1—X^2—X^3—X^4$=—CH—C(TMS)—S—CZ— and Z=$SO_2$NHtBu, was isolated and 37.3 mg (14% 2 steps) of the minor product, (rf=0.29 (2:1 EtOAc/Hex)) where $X^1—X^2—X^3—X^4$=—CH—CH—S—CZ— and Z=$SO_2$NHtBu was isolated.

Step E: Preparation of 5,7-Dimethyl-2-ethyl-3-[[4-[2-(N-benzoylsulfonamido)-3-thienyl]phenyl]methyl]imidazo[4,5-b]pyridine (Compound 12 of Table VII) [compound 9b, (scheme II-9) where $X^1—X^2—X^3—X^4$=—CH—CH—S—CZ— and Z=$SO_2$NHCOPh] and 5,7-Dimethyl-2-ethyl-3-[[4-[5-trimethylsilyl-2-(N-benzoylsulfonamido)-3-thienyl]methyl]imidazo[4,5-b]pyridine [compound 9a, (scheme II-9) where $X^1—X^2—X^3—X^4$=—CH—C(TMS)—S—CZ— and Z=$SO_2$NHCOPh]

Part 1: To the dry major product of Step D (83.5 mg, 0.151 mmol) was added anisole (2 drops) and TFA (2 ml) and the reaction was allowed to stir overnight. The next day when the TFA was removed the reaction became a deep red color. The two products, with and without the TMS group present, were free based by eluting through silica column using CHCl₃/MeOH/N-H₄OH (100:10:1). The two products were difficult to separate due to their very similar Rf values. Rf=0.72 and 0.69 (40:10:1 CHCl₃/MeOH/NH₄OH). The mixture was used in the following step.

Part 2: To the mixture obtained in part 1 (0.151 mmol, crude) in dry pyridine (0.5 mL) was added benzoylchloride (0.175 ml, 1.51 mmol) and a catalytic amount of DMAP. The reaction turned cloudy and thick. After 2 h the sides of the flask were rinsed with additional pyridine (1 mL) and the reaction allowed to stir another 30 min. The reaction was concentrated then diluted with CH₂Cl₂ and washed with 10% citric acid (2x) and water, dried over MgSO₄, filtered and the solvent removed. The products were partially purified by flash chromatography on a silica column using CHCl₃/MeOH/NH₄OH (80:10:0.75). This separated the products with and without the TMS group, but there were still impurities present in both products as seen by NMR. The products required further purification by HPLC. For the titled compound 9a, (scheme II-9) where $X^1-X^2-X^3-X^4=-CH-C(TMS)-S-CZ-$ and $Z=SO_2NHCOPh$, purification was accomplished using a C18 Dynamax semipreparative column eluting with 0.1% TFA water/CH₃CN (90:10–10:90 over 30 min) at 5 mL/min. The amount purified yielded 6.8 mg (7% 2 steps) of the titled compound, Rf=0.60 (40:10:1 CHCl₃/MeOH/NH₄OH).

¹H NMR (200 MHz, CD₃OD) d 0.35 (s, 9H), 1.36 (t, 3H), 2.67 (s, 6H), 3.14 (q, 2H), 5.75 (s, 2H), 7.18 (s, 1H), 7.29–7.53 (m, 10H).

FAB mass spectrum, m/e 603 (M+1, calcd for C₃₁H₃₄S₂O₃N₄Si 602).

For the product without the TMS group purification was also accomplished using a C18 Dynamax semipreparative column eluting with 0.1% TFA water/CH₃CN using a stepwise gradient (90:10–47:53 over 10 min, isocratic for another 10 min, 47:53–10:90 over 10 min) at 5 mL/min. The amount purified yielded 7.7 mg (10% 2 steps) of the titled compound without TMS Rf=0.51 (40:10:1 CHCl₃/MeOH/NH₄OH).

¹H NMR (400 MHz, CD₃OD) d 1.37 (t, 3H), 2.68 (s, 6H), 3.14 (q, 2H), 5.76 (s, 2H), 7.10 (d, 1H), 7.31–7.43 (m, 8H), 7.53 (d, 2H), 7.87 (d, 1H); FAB mass spectrum, m/e 531 (M+1, calcd for C₂₈H₂₆S₂O₃N₄, 531).

EXAMPLE 52

7-Methyl-2-propyl-3-[[4-[2-(N-benzoylsulfonamido)-3-thienyl]phenyl]methyl]imidazo[4,5-b]pyridine (Compound 48 of Table VII) and 7-methyl-2-propyl-3-[[4-[2-(N-benzoylsulfonamido)(5-trimethylsilyl)-3-thienyl]phenyl]methyl]imidazo[4,5-b]pyridine Following the procedures of Example 51, Steps A through E and replacing 5,7-dimethyl-2-ethylimidazo[4,5-b]pyridine with 7-methyl-2-propylimidazo[4,5-b]pyridine the product of Example 2, Step B, the titled compound can be prepared.

EXAMPLE 53

5-Carbomethoxy-2-ethyl-7-methyl-3-[[4-[2-(N-benzoylsulfonamido)-3-thienyl]phenyl]methyl]imidazo[4,5-b]pyridine (Compound 44 of Table VII) and 5-Carbomethoxy-2-ethyl-7-methyl-3-[[4-[2-(N-benzoylsulfonamido)(5-trimethylsilyl)-3-thienyl]phenyl]methyl]imidazo[4,5-b]pyridine Following the procedures of Example 51, Steps A through E and replacing 5,7-dimethyl-2-ethylimidazo[4,5-b]pyridine with 2-ethyl-7-methylimidazo[4,5-b]pyridine the product of Example 3, Step G, the titled compound can be prepared.

EXAMPLE 54

5-Carbomethoxy-7-methyl-2-propyl-3-[[4-[2-(N-benzoylsulfonamido)-3-thienyl]phenyl]methyl]imidazo[4,5-b]pyridine (Compound 50 of Table VII) and 5-Carbomethoxy-7-methyl-2-propyl-3-[[4-[2-(N-benzoylsulfonamido)(5-trimethylsilyl)-3-thienyl]phenyl]methyl]imidazo[4,5-b]pyridine Following the procedures of Example 51, Steps A through E and replacing 5,7-dimethyl-2-ethylimidazo[4,5-b]pyridine with 7-methyl-2-propylimidazo[4,5-b]pyridine the titled compound can be prepared.

EXAMPLE 55

5-Carboxy-2-ethyl-7-methyl-3-[[4-[2-(N-benzoylsulfonamido)-3-thienyl]phenyl]methyl]imidazo[4,5-b]pyridine (Compound 13 of Table VII) and 5-Carboxy-2-ethyl-7-methyl-3-[[4-[2-(N-benzoylsulfonamide)(5-trimethylsilyl)-3-thienyl]phenyl]methyl]imidazo[4,5-b]pyridine Following the procedures of Example 53, Steps A through E and subsequent hydrolysis of the ester in the final step, the titled compound can be prepared.

EXAMPLE 56

5-Carboxy-7-methyl-2-propyl-3-[[4-[2-(N-benzoylsulfonamido)-3-thienyl]methyl]imidazo[4,5-b]pyridine (Compound 47 of Table VII) and 5-Carboxy-7-methyl-2-propyl-3-[[4-[2-(N-benzoylsulfonamido)(5-trimethylsilyl)-3-thienyl]phenyl]methyl]imidazo[4,5-b]pyridine Following the procedures of Example 54, Steps A through E and subsequent hydrolysis of the ester in the final step, the titled compound can be prepared.

EXAMPLE 57

2-Propyl-1-[[4-[2-(N-benzoylsulfonamido)-3-thienyl]phenyl]methyl]benzimidazole (Compound 16 of Table V) and 2-Propyl-1-[[4-[2-(N-benzoylsulfonamido)(5-trimethylsilyl)-3-thienyl]phenyl]methyl]benzimidazole Following the procedures of Example 51, Steps A through E replacing the heterocycle of Step E with 2-propylbenzimidazole from Step A of Example 7, the titled compound can be prepared.

EXAMPLE 58

2-Butyl-1-[[4-[2-(N-benzoylsulfonamido)-3-thienyl]-phenyl]methyl]benzimidazole (Compound 17 of Table V) and 2-Butyl-1-[[4-[2-(N-benzoylsulfonamido)(5-trimethylsilyl)-3-thienyl]phenyl]methyl]benzimidazole Following the procedures of Example 51, Steps A through E replacing the heterocycle of Step E with 2-butylbenzimidazole from Step A of Example 8, the titled compound can be prepared.

EXAMPLE 59

2-Chloro-6-methyl-8-propyl-9-[[4-[2-(N-benzoylsulfonamido)-3-thienyl]phenyl]methyl]purine, (Compound 27 of Table VI) and 2-Chloro-6-methyl-8-propyl-9-[[4-[2-(N-benzoylsulfonamido)(5-trimethylsilyl)-3-thienyl]phenyl]methyl]-purine Following the procedures of Example 51, Steps A through E and replacing 5,7-dimethyl-2-ethylimidazo[4,5-b]pyridine with 2-chloro-6-methyl-8-propylpurine, the product of Example 9, Step A, the titled compound can be prepared.

EXAMPLE 60

2-Dimethylamino-6-methyl-8-propyl-9-[[4-[2-(N-benzoylsulfonamido)-3-thienyl]phenyl]methyl]purine and 2-Dimethylamino-6-methyl-8-propyl-9-[[4-[2-(N-benzoylsulfonamido)(5-trimethylsilyl)-3-thienyl]phenyl]methyl]purine (Compound 28 of Table VI)

Following the procedures of Example 51, Steps A through E and replacing 5,7-dimethyl-2-ethylimidazo[4,5-b]pyridine with 2-dimethylamino-6-methyl-8-propylpurine the product of Example 10, Step A, the titled compound can be prepared.

EXAMPLE 61

5,7-Dimethyl-2-ethyl-3-[[4-[3-(N-benzoylsulfonamido)2-thienyl]phenyl]methyl]imidazo[4,5-b]pyridine (Compound 11 of Table VII) [compound 9b, scheme II-9, where
$X^1$—$X^2$—$X^3$—$X^4$=—S—CH—CH—CZ— and Z=SO$_2$NHCOPh]

Step A: Preparation of 2,5-dibromo-3-t-butylsulfonamidothiophene (scheme II-7, compound 7b, Y=S)

To chlorosulfonic acid (4.5 mL) was added 2,5-dibromothiophene (0.505 g, 2.09 mmol) by syringe. On mixing the reaction turned dark orange-brown. After 10 min the reaction was poured very carefully over ice (100 ml). The solution turned bright yellow. The product was extracted from the water layer using EtOAc/Et$_2$O (3x). The combined organic layers were washed with water and brine, dried over MgSO$_4$ and filtered. The solvent was replaced with dry CH$_2$Cl$_2$ (4.5 ml) and t-butylamine (0.659 mL, 6.27 mmol) was added. The reaction was stirred overnight. The next day the reaction was diluted with more CH$_2$Cl$_2$ and washed with 1N HCl (3x), dried over MgSO$_4$ and filtered. The product was purified by flash chromatography on a silica column eluting with Hex/EtOAc (20:1) to afford 470 mg (60%) of the titled compound, Rf=0.16 (10:1 Hex-EtOAc).

$^1$H NMR (400 MHz, CDCl$_3$) δ1.25 (s, 9H), 4.75 (s, 1H), 7.30 (s, 1H).

FAB mass spectrum, m/e 378 (M+1, calcd for C$_4$H$_{11}$S$_2$O$_2$NBr$_2$; 378).

Step B: Preparation of 3-t-butylsulfonamidothiophene (scheme II-7, compound 7c, Y=S)

To a solution of the product of Step A (1.70 g, 4.52 mmol) in 24% by volume glacial acetic acid/water (5 mL) was added Zn dust (1.73 g, 26.6 mmol). The mixture was refluxed (120° C.) overnight. The next day the reaction was cooled, diluted with EtOAc and filtered. Et$_2$O/EtOAc was added and the solution washed with 6N HCl (3x), water, carefully with 5% NaHCO$_3$ (2x) and brine. The solution was dried over MgSO$_4$ and filtered. The solvent was removed to afford 851 mg (86%) of the titled compound, Rf=0.23 (10:1 Hex-/EtOAc).

$^1$H NMR (200 MHz, CDCl$_3$) δ1.25 (s, 9H), 4.42 (s, 1H), 7.31–7.40 (m, 2H), 7.92–7.95 (dd, 1H).

Step C: Preparation of 2-bromo-3-t-butylsulfonamidothiophene (scheme II-7, compound 7d, Y=S)

To a solution of the product of Step B (230 mg, 1.05 mmol) in dry THF (5 mL) cooled to −78° C. in a dry ice/acetone bath under N$_2$ was added 1.6M n-butyllithium (3.28 ml, 5.25 mmol) dropwise. The reaction was warmed to −50° C. then cooled back to −78° C. and Br$_2$ (269 ml, 5.24 mmol) was added. The bath was removed and the reaction was warmed to rt. The reaction was quenched with sat'd NH$_4$Cl solution. The solvent was replaced with Et$_2$O/EtOAc and the reaction solution washed with water, 1N NaOH, and brine. The solution was dried over MgSO$_4$, filtered and the solvent removed to afford 298 mg (95%) of the titled compound, Rf=0.53 (2:1 Hex/EtOAc).

$^1$H NMR (400 MHz, CDCl$_3$) δ1.22 (s, 9H), 4.89 (s, 1H), 7.24 (d, 1H), 7.31 (d, 1H).

Step D: Preparation of 2-p-tolyl-3-t-butylsulfonamidothiophene (scheme II-7, compound 7e, Y=S)

To solution of the product of Step C (4.59 mmol, crude) in dry DMF (1 mL) was added p-tolyltrimethyltin (1.77 g, 6.95 mmol) and a catalytic amount of Pd(PPh$_3$)$_2$Cl$_2$ (325 mg, 0.463 mmol). The reaction was heated at 75°–80° C. for 5 h. The reaction was cooled to rt and the solvent replaced with EtOAc and filtered. The product was purified by flash chromatography on a silica column eluting with a gradient of Hex/EtOAc (25:1–15:1) to afford 1.01 g (71%) of the titled compound, Rf=0.49 (3:1 Hex/EtOAc).

$^1$H NMR (200 MHz, CDCl$_3$) δ0.98 (s, 9H), 2.40 (s, 3H), 4.01 (s, 1H), 7.24 (d, 1H), 7.26 (d, 1H), 7.48 (d, 2H), 7.54 (d, 2H); FAB mass spectrum, m/e 310 (M+1, calcd for C$_{15}$H$_{19}$S$_2$O$_2$N, 310).

Step E: Preparation of 2-(4-bromomethylphenyl)-3-t-butylsulfonamidothiophene (scheme II-7, compound 7f, Y=S)

To a solution of the product of Step D (201 mg, 0.651 mmol) under N$_2$ in dry CCl$_4$ (2.5 mL) was added NBS (130 mg, 0.730 mmol) and a catalytic amount of AIBN. The reaction mixture was brought to reflux (110° C.). After 5 h the reaction was cooled to rt and the insoluble succinimide was removed by filtration. The solvent was replaced with Et$_2$O/EtOAc and washed with water (2x) and brine, dried over MgSO$_4$ and filtered.

The solvent was removed and the crude reaction product dried thoroughly under vacuum.

Step F: Preparation of
5,7-dimethyl-2-ethyl-3-[[4-[3-(N-t-butylsulfonamido)-2-thienyl]phenyl]methyl]imidazo[4,5-b]pyridine
[compound 9b, scheme II-9, where
$X^1$—$X^2$—$X^3$—$X^4$=—S—CH—CH—CZ— and
Z=SO$_2$NHtBu]

To a solution of 5,7-dimethyl-2-ethylimidazopyridine the product of Example 1, Step G, (171 mg, 0.978 mmol) in dry DMF (1 mL) under N$_2$ was added NaH (39.9 mg, 0.998 mmol). The reaction was allowed to stir for 30 min. To this was added a solution of the product of Step E (0.651 mmol, crude) in dry DMF (2 mL). After 5 h the reaction was quenched with sat'd NH$_4$Cl solution. The DMF was replaced with Et$_2$O/EtOAc, dried over MgSO$_4$ and the insoluable salts removed by filtration. The product was purified by flash chromatography on a silica column using a gradient of EtOAc/-Hex (1:1–2:1) to afford 140 mg (45% 2 steps) of the titled product, Rf=0.34 (2:1 EtOAc/Hex).

$^1$H NMR (400 MHz, CDCl$_3$) δ0.93 (s, 9H), 1.32 (t, 3H), 2.57 (s, 3H), 2.63 (s, 3H), 2.79 (q, 2H), 3.94 (s, 1H), 5.48 (s, 2H), 6.90 (s, 1H), 7.18 (d, 2H), 7.25 (d, 1H), 7.45 (d, 1H), 7.57 (d, 2H).

FAB mass spectrum, m/e 483.6 (M+1, calcd for C$_{25}$H$_{30}$S$_2$O$_2$N$_4$, 483).

Step G: Preparation of
5,7-Dimethyl-2-ethyl-3-[[4-[3-(N-benzoylsulfonamido)-2-thienyl]phenyl]methyl]imidazo[4,5-b]pyridine
[compound 9b, scheme II-9, where
$X^1$—$X^2$—$X^3$—$X^4$=—S—CH—CH—CZ— and
Z=SO$_2$NHCOPh Part 1: To dry product of Step f (108 mg, 0.224 mmol) was added anisole (2 drops) and TFA (2 mL) and the reaction was allowed to stir overnight. The next day the TFA was removed and the reaction became a deep red color. The product was purified by flash chromatography on a silica column using CHCl$_3$/MeOH/NH$_4$OH (80:10:1). Removal of the solvent afforded the primary sulfonamide, Rf=0.71 (40:10:1 CHCl$_3$/MeOH/NH$_4$OH).

$^1$H NMR (200 MHz, CD$_3$OD) δ1.28 (t, 3H), 2.57 (s, 3H), 2.61 (s, 3H), 2.87 (q, 2H), 5.60 (s, 2H), 7.02 (s, 1H), 7.16 (d, 2H), 7.44 (d, 2H), 7.55 (d, 2H).

FAB mass spectrum, m/e 427.4 (M+1, calcd for C$_{21}$H$_{22}$S$_2$O$_2$N$_4$, 427).

Part 2: To the product of part 1 (20.9 mg, 0.049 mmol) in dry pyridine (0.5 mL) was added benzoylchloride (0.057 ml, 0.49 mmol) and a catalytic amount of DMAP. The reaction turned cloudy and thick. After 2 h the sides of the flask were rinsed with additional pyridine (1 ml) and the reaction allowed to stir another 15 min. The reaction was diluted with CH$_2$Cl$_2$ and washed with 10% citric acid (3x) and water, dried over MgSO$_4$, filtered and the solvent removed. The product was purified by flash chromatography on a silica column using CHCl$_3$/MeOH/NH$_4$OH (80:10:0.8) to afford 18.2 mg (69%) of the titled compound, Rf=0.36 (40:10:1 CHCl$_3$/MeOH/NH$_4$OH).

$^1$H NMR (400 MHz, CD$_3$OD) δ1.29 (t, 3H), 2.58 (s, 3H), 2.61 (s, 3H), 2.84 (q, 2H), 5.54 (s, 2H), 7.02 (s, 1H), 7.09 (d, 2H), 7.23 (dd, 2H), 7.38 (dd, 2H), 7.55–7.64 (m, 5H).

FAB mass spectrum, m/e 531.5 (M+1, calcd for C$_{28}$H$_{26}$S$_2$O$_3$N$_4$, 531).

EXAMPLE 62

7-Methyl-2-propyl-3-[[4-[3-(N-benzoylsulfonamido)-2-thienyl]phenyl]methyl]imidazo[4,5-b]pyridine (Compound 39 of Table VII)

Following the procedures of Example 61, Steps A through G and replacing 5,7-dimethyl-2-ethylimidazo[4,5-b]pyridine with 7-methyl-2-propylimidazo[4,5-b]pyridine the product of Example 2, Step B, the titled compound can be prepared.

EXAMPLE 63

5-Carbomethoxy-2-ethyl-7-methyl-3-[[4-[3-(N-benzoylsulfonamido)-2-thienyl]phenyl]methyl]imidazo[4,5-b]pyridine (Compound 40 of Table VII)

Following the procedures of Example 61, Steps A through G and replacing 5,7-dimethyl-2-ethylimidazo[4,5-b]pyridine with 2-ethyl-7-methylimidazo[4,5-b]pyridine the product of Example 3, Step G, the titled compound can be prepared.

EXAMPLE 64

5-Carbomethoxy-7-methyl-2-propyl-3-[[4-[3-(N-benzoylsulfonamido)-2-thienyl]phenyl]methyl]imidazo[4,5-b]pyridine (Compound 52 of Table VII)

Following the procedures of Example 61, Steps A through G and replacing 5,7-dimethyl-2-ethylimidazo[4,5-b]pyridine with 7-methyl-2-propylimidazo[4,5-b]pyridine the titled compound can be prepared.

EXAMPLE 65

5-Carboxy-2-ethyl-7-methyl-3-[[4-[3-(N-benzoylsulfonamido)-2-thienyl]phenyl]methyl]imidazo[4,5-b]pyridine (Compound 41 of Table VII)

Following the procedures of Example 63, Steps A through G and subsequent hydrolysis of the ester in the final step, the titled compound can be prepared.

EXAMPLE 66

5-Carboxy-7-methyl-2-propyl-3-[[4-[3-(N-benzoylsulfonamido)-2-thienyl]methyl]imidazo[4,5-b]pyridine (Compound 53 of Table VII)

Following the procedures of Example 64, Steps A through G and subsequent hydrolysis of the ester in the final step, the titled compound can be prepared.

EXAMPLE 67

2-Propyl-1-[[4-[3-(N-benzoylsulfonamido)-2-thienyl]phenyl]methyl]benzimidazole (Compound 19 of Table V)

Following the procedures of Example 61, Steps A through G replacing the heterocycle of Step E with 2-propylbenzimidazole from Step A of Example 7, the titled compound can be prepared.

EXAMPLE 68

2-Butyl-1-[[4-[3-(N-benzoylsulfonamido)-2-thienyl]phenyl]methyl]benzimidazole (Compound 20 of Table V)

Following the procedures of Example 61, Steps A through G replacing the heterocycle of Step E with 2-butylbenzimidazole from Step A of Example 8, the titled compound can be prepared.

EXAMPLE 69

2-Chloro-6-methyl-8-propyl-9-[[4-[3-(N-benzoylsulfonamido)-2-benzothienyl]phenyl]methyl]purine (Compound 29 of Table VI)

Following the procedures of Example 61, Steps A through G and replacing 5,7-dimethyl-2-ethylimidazo[4,5-b]pyridine with 2-chloro-6-methyl-8-propylpurine, the product of Example 9, Step A, the titled compound can be prepared.

EXAMPLE 70

2-Dimethylamino-6-methyl-8-propyl-9-[[4-[3-(N-benzoylsulfonamido)-2-benzothienyl]phenyl]methyl]purine (Compound 30 of Table VI)

Following the procedures of Example 61, Steps A through G and replacing 5,7-dimethyl-2-ethylimidazo[4,5-b]pyridine with 2-dimethylamino-6-methyl-8-propylpurine the product of Example 10, Step A, the titled compound can be prepared.

EXAMPLE 71

A representative procedure for the preparation of compounds of Structure 9a, Scheme II-9, $-X^1-X^2-X^3-X^4-=-CH-CR^{12}-S-CZ-$.

Step 1: Preparation of 2-pentyl-5-(t-butylsulfonamido)thiophene (scheme II-11, compound 11a, $R^{12}=(CH_2)_4CH_3$).

To a solution of 2-(t-butylsulfonamido)thiophene (3.42 g, 15.6 mmol) in anhydrous THF coole to $-78°$ C. under $N_2$ was added 2.5M n-BuLi (15.6 mL, 2.5 equiv). The reaction was warmed to $-20°$ C. over 3.5 h. After stirring at $-20°$ C. for an additional h, iodopentane (2.4 mL, 1.2 equiv) was added. The ice bath was removed and the reaction was stirred at rt overnight. The next day the reaction was quenched with sat'd $NH_4Cl$ solution and the THF was removed in vacuo. The residue was extracted with $Et_2O$/EtOAc and washed with water and brine. The organic was dried over anhydrous $MgSO_4$ and concentrated in vacuo. The product was purified by flash chromatography on a silica column eluting with Hex/EtOAc (15:1). Removal of the solvent afforded 2.72 g (60%) of the titled compound as a yellow oil. $Rf=0.4$ (6:1 Hex/EtOAc). $^1H$ NMR (200 MHz, $CDCl_3$) $\delta 0.91$ (t, 3H), 1.28 (s, 9H), 1.33 (m, 4H), 1.68 (bt, 2H), 2.81 (t, 2H), 4.63 (s, 1H), 6.69 (d, 1H), 7.41 (d, 1H).

The following table lists additional compounds (11a, scheme II-11) prepared using the procedure described above. Any variation from the above procedure is noted in the comment column.

Step 2: Preparation of boronic acid derivative 11b (scheme II-11, compound 11b, $R^{12}=(CH_2)_4CH_3$).

To a solution of 2-pentyl-5-(t-butylsulfonamido)thiophene product of Step 1 (2.50 g, 8.65 mmol) in anhydrous THF (15 mL) cooled to $-78°$ C. was added 2.5M n-BuLi (8.7 mL, 2.5 equiv). The mixture was allowed to warm to rt over 4 h and stirred for an additional 30 min. The mixture was cooled back to $-60°$ C. and triisopropyl borate (3.0 mL, 1.5 equiv) was added. The ice bath was removed and the mixture was stirred overnight at rt. The next day the reaction was quenched with 2N HCl (3 mL) and the resulting mixture was stirred for 30 min. The THF was removed under reduced pressure and the residue was taken up into EtOAc. The organic was washed with $H_2O$ and brine and dried over $MgSO_4$. Removal of the solvent afforded 3.2 g (crude) of the titled compound as a thick yellow oil.

Step 3: Preparation of 4-[(4-hydroxymethyl)phenyl]-2-pentyl-5-(t-butylsulfonamido)thiophene (scheme II-11, compound 11c, $R^{12}=(CH_2)_4CH_3$).

To a solution of the product from step B (3.2 g, crude) in toluene (60 mL) and 1N NaOH (17 ml) was added 4-bromobenzyl alcohol (4.85 g, 3 equiv) in EtOH (15 mL). To this mixture was added $Pd(PPh_3)_4$ (300 mg, 3 mol %). The reaction was stirred at reflux under $N_2$ for 4 h. The mixture was cooled to rt and extracted with $Et_2O$/EtOAc. The organic was washed with $H_2O$ and brine, dried over anhydrous $MgSO_4$ and concentrated in vacuo. The product was purified by flash chromatography on a silica column eluting with Hex/EtOAc (2:1). Removal of the solvent afforded 1.97 g (58%) of the titled compound as a slightly yellow solid. $Rf=0.24$ (2:1 Hex/EtOAc). $^1H$ NMR (200 MHz, $CDCl_3$) $\delta 0.91$ (t, 3H), 1.01 (s, 9H), 1.35 (m, 4H), 1.67 (bm, 3H), 2.82 (t, 2H), 4.13 (s, 1H), 4.75 (s, 2H), 6.77 (s, 1H), 7.44 (d, 2H), 7.60 (d, 2H).

Step 4: Preparation of 4-[(4-bromomethyl)phenyl]-2-pentyl-5-(t-butylsulfonamido)thiophene (scheme II-11, compound 11d, $R^{12}=(CH_2)_4CH_3$).

To a solution of the product of step 3 (493 mg, 1.25 mmol) in anhydrous $CCl_4$ (4 mL) and $CH_2Cl_2$ (4 mL) was added $PBr_3$ (0.078 mL, 0.66 equiv). After stirring at rt for 1 h the solvent was removed under reduced pressure and the residue was stripped down from $CCl_4$ several times to remove any residual HBr. The product was purified by flash chromatography on a silica column eluting with Hex/EtOAc (2:1). Removal of the

| | Compounds 11a, Scheme II-11 | | | |
|---|---|---|---|---|
| $R^{12}$ | $R^{12}X$ | % Yield | RF (solvent) | Comments |
| $CH_3$ | $ICH_3$ | 49 | 0.44 (3:1 Hex/EtOAc) | *, white solid, † |
| $CH_2CH_3$ | $ICH_2CH_3$ | 84 | 0.47 (3:1 Hex/EtOAc) | *, oil |
| $(CH_2)_2CH_3$ | $I(CH_2)_2CH_3$ | 65 | 0.52 (2:1 Hex/EtOac) | *, oil |
| $(CH_2)_3CH_3$ | $I(CH_2)_3CH_3$ | 62 | 0.32 (6:1 Hex/EtOAc) | *, yellow oil, @ |
| $CH_2CH(CH_3)_2$ | $ICH_2CH(CH_3)_2$ | 44 | 0.37 (6:1 Hex/EtOAc) | *, yellow oil, # |
| $(CH_2)_4CH_3$ | $I(CH_2)_4CH_3$ | 60 | 0.40 (6:1 Hex/EtOac) | *, yellow oil |
| $CH_2Ph$ | $BrCH_2Ph$ | ~70 | 0.49 (3:1 Hex/EtOAc) | taken on crude |
| $Si(CH_3)_3$ | $ClSi(CH_3)_3$ | 60 | 0.36 (6:1 Hex/EtOAc) | *, solid, @ |

*The high field NMR spectrum and FAB mass spectrum are consistant with the structure assigned.
Yield is based on recovered starting material.
@ A 1.5 M LDA solution was substituted for N-BuLi.
† MPLC purification was necessary.

solvent afforded 473 mg (83%) of the titled compound as a slightly yellow solid. Rf=0.72 (2:1 Hex/EtOAc).

$^1$H NMR (200 MHz, CDCl$_3$) δ0.90 (t, 3H), 0.99 (s, 9H), 1.35 (m, 4H), 1.71 (m, 2H), 2.81 (t, 2H), 4.05 (s, 1H), 4.52 (s, 2H), 6.77 (s, 1H), 7.45 (d, 2H), 7.59 (d, 2H).

The following table lists additional compounds (11d, scheme II-11) prepared using the procedure described above. Any variation from the above procedure is noted in the comment column.

| R$^{12}$ | Compounds 11d, Scheme II-11 | | |
|---|---|---|---|
| | Pd Coupling Yield | Rf (solvent) | Comments |
| CH$_3$ | 27 | 0.67 (2:1 Hex/EtOAc) | *, #, white solid |
| CH$_2$CH$_3$ | 23 | 0.70 (2:1 Hex/EtOAc) | taken on crude |
| (CH$_2$)$_2$CH$_3$ | 52 | 0.44 (1:1 Hex/EtOAc) | *, yellowish solid |
| (CH$_2$)$_3$CH$_3$ | 30 | 0.73 (2:1 Hex/EtOAc) | *, yellowish solid |
| CH$_2$CH(CH$_3$)$_2$ | 28 | 0.25 (2:1 Hex/EtOAc 2x's) | *, yellowish solid |
| (CH$_2$)$_4$CH$_3$ | 58 | 0.40 (6:1 Hex/EtOAc) | *, yellowish solid |
| CH$_2$Ph | 25 | 0.54 (3:1 Hex/EtOAc) | *, #, white solid |
| Si(CH$_3$)$_3$ | 36 | 0.45 (6:1 Hex/EtOac) | *, @, white solid |

*The high field NMR spectrum and FAB mass spectrum are consistant with the structrue assigned.
The palladium catalyzed coupling was done using anhydrous DMF as solvent with NEt$_3$ as base. 4-bromotoluene was substituted for 4-bromobenzyl alcohol in the palladium coupling (step B) and NBS bromination was used to prepare the corresponding bromide.

Step 5: Preparation of 5,7-dimethyl-2-ethyl-3-[[4-[5-propyl-2-(t-butylsulfonamido)-3-thienyl]phenyl]methyl]imidazo[4,5-b]pyridine (scheme II-9, compound 9a, X$^1$—X$^2$—X$^3$—X$^4$=—CH=CR$^{12}$— S—CZ= and R$^{12}$=(CH$_2$)$_2$CH$_3$).

To a solution of 5,7-dimethyl-2-ethylimidazopyridine (425.4 mg, 2.43 mmol) in anhydrous DMF (6 mL) under N$_2$ was added a 60% NaH dispersion (108 mg, 1.1 equiv). The mixture was stirred at rt for 1 h. To this mixture was added a solution of compound 11d (R$^{12}$=n-propyl) (703 mg, 1.63 mmol) in anhydrous DMF (4 mL). After stirring several hours at rt under N$_2$, the reaction was quenched with a sat'd solution of NH$_4$Cl. The DMF was removed under reduced pressure and theresidue was extracted into EtOAc. The organic was washed with brine and dried over anhydrous MgSO$_4$. The product was purified by flash chromatography on a silica column eluting with Hex/EtOAc (1:1). Removal of the solvent afforded 609 mg (72%) of the titled compound as a slightly yellow solid. Rf=0.27 (1:1 Hex/EtOAc).

$^1$H NMR (400 MHz, CDCl$_3$) δ0.93 (s, 9H), 0.96 (t, 3H), 1.32 (t, 3H), 1.71 (m, 2H), 2.57 (s, 3H), 2.64 (s, 3H), 2.75 (t, 2H), 2.81 (q, 2H), 4.01 (s, 1H), 5.49 (s, 2H), 6.70 (s, 1H), 6.92 (s, 1H), 7.17 (d, 2H), 7.51 (d, 2H).

The following compounds were prepared using the alkylation procedure described above. The spectral data is provided below:

Compound 9a, scheme II-9, X$^1$—X$^2$—X$^3$—X$^4$=—CH=CR$^{12}$—S—CZ=, R$^{12}$=CH$_3$:

$^1$H NMR (200 MHz, CDCl$_3$) δ0.95 (s, 9H), 1.32 (t, 3H), 2.49 (s, 3H), 2.58 (s, 3H), 2.64 (s, 3H), 2.81 (q, 2H), 4.01 (s, 1H), 5.49 (s, 2H), 6.71 (s, 1H), 6.91 (s, 1H), 7.18 (d, 2H), 7.52 (d, 2H).

Compound 9a, scheme II-9, X$^1$—X$^2$—X$^3$—X$^4$=—CH=CR$^{12}$—S—CZ=, R$^{12}$=CH$_2$CH$_3$:

$^1$H NMR (200 MHz, CDCl$_3$) δ0.95 (s, 9H), 1.34 (m, 6H), 2.57 (s, 3H), 2.60 (s, 3H), 2.88 (m, 4H), 4.00 (s, 1H), 5.51 (s, 2H), 6.71 (s, 1H), 6.89 (s, 1H), 7.13 (d, 2H), 7.48 (d, 2H).

Compound 9a, scheme II-9, X$^1$—X$^2$—X$^3$—X$^4$=—CH=CR$^{12}$—S—CZ=, R$^{12}$=(CH$_2$)$_3$CH$_3$:

$^1$H NMR (200 MHz, CDCl$_3$) δ0.93 (t, 3H), 0.96 (s, 9H), 1.38 (m, 5H), 1.69 (m, 2H), 2.60 (s, 3H), 2.66 (s, 3H), 2.80 (m, 4H), 4.01 (s, 1H), 5.52 (s, 2H), 6.71 (s, 1H), 6.95 (s, 1H), 7.20 (d, 2H), 7.54 (d, 2H).

Compound 9a, scheme II-9, X$^1$—X$^2$—X$^3$—X$^4$=—CH=CR$^{12}$—S—CZ=, R$^{12}$=CH$_2$CH(CH$_3$)$_2$:

$^1$H NMR (200 MHz, CD$_3$OD) δ0.94 (s, 12H), 0.98 (s, 3H), 1.29 (t, 3H), 1.88 (m, 1H), 2.57 (s, 3H), 2.60 (s, 3H), 2.69 (d, 2H), 2.87 (q, 2H), 5.58 (s, 2H), 6.83 (s, 1H), 7.02 (s, 1H), 7.17 (d, 2H), 7.55 (d, 2H).

Compound 9a, scheme II-9, X$^1$—X$^2$—X$^3$—X$^4$=—CH=CR$^{12}$—S—CZ=, R$^{12}$=(CH$_2$)$_4$CH$_3$:

$^1$H NMR (400 MHz, CDCl$_3$) δ0.87 (bt, 3H), 0.93 (s, 9H), 1.34 (m, 7H), 1.68 (m, 2H), 2.57 (s, 3H), 2.64 (s, 3H), 2.77 (m, 4H), 3.99 (s, 1H), 5.48 (s, 2H), 6.70 (s, 1H), 6.92 (s, 1H), 7.18 (d, 2H), 7.52 (d, 2H).

Compound 9a, scheme II-9, X$^1$—X$^2$—X$^3$—X$^4$=—CH=CR$^{12}$—S—CZ=, R$^{12}$=CH$_2$Ph:

$^1$H NMR (400 MHz, CD$_3$OD) δ0.92 (s, 9H), 1.29 (t, 3H), 2.57 (s, 3H), 2.60 (s, 3H), 2.84 (q, 2H), 4.15 (s, 2H), 5.57 (s, 2H), 6.87 (s, 1H), 7.02 (s, 1H), 7.17 (d, 2H), 7.21–7.30 (comp m, 5H), 7.54 (d, 2H).

Compound 9a, scheme II-9, X$^1$—X$^2$—X$^3$—X$^4$=—CH=CR$^{12}$—S—CZ=, R$^{12}$=Si(CH$_3$)$_3$:

$^1$H NMR (400 MHz, CDCl$_3$) δ0.30 (s, 9H), 0.93 (s, 9H), 1.32 (t, 3H), 2.57 (s, 3H), 2.63 (s, 3H), 2.80 (q, 2H), 4.02 (s, 1H), 5.47 (s, 2H), 6.90 (s, 1H), 7.05 (s, 1H), 7.17 (d, 2H), 7.51 (d, 2H).

Compound 9a, scheme II-9, X$^1$—X$^2$—X$^3$—X$^4$=—CH=CR$^{12}$—S—CZ=, R$^{12}$=CH$_2$N(CH$_2$CH$_2$)$_2$O:

$^1$H NMR (400 MHz, CDCl$_3$) δ0.93 (s, 9H), 1.31 (t, 3H), 2.55 (bt, 4H), 2.57 (s, 3H), 2.62 (s, 3H), 2.76 (q, 2H), 3.66 (s, 2H), 3.71 (t, 4H), 3.99 (s, 1H), 5.47 (s, 2H), 6.83 (s, 1H), 6.89 (s, 1H), 7.18 (d, 2H), 7.51 (d, 2H).

EXAMPLE 72

5,7-Dimethyl-2-ethyl-3-[[4-[2-(N-benzoylsulfonamido)-5-(2-methylpropyl)-3-thienyl]phenyl]methyl]imidazo[4,5-b]pyridine (Compound 54 of Table VII)

Step A: Preparation of 5,7-dimethyl-2-ethyl-3-[[4-[2-(sulfonamido)-5-(2-methylpropyl)-3-thienyl]-phenyl]methyl]imidazo[4,5-b]pyridine.

To a mixture of the compound of Example 71, Step 5, 9a (X$^1$—X$^2$—X$^3$—X$^4$=—CH=CR$^{12}$—S—CZ= and R$^{12}$=CH$_2$CH(CH$_3$)$_2$) (189 mg, 0.352 mmol) and anisole (2 drops) was added TFA (2 mL). After stirring for 2.5 days the solvent was removed under reduced pressure. The residue was taken up in EtOAc and washed with sat'd Na$_2$CO$_3$ solution, H$_2$O and brine. The organic was dried over anhydrous MgSO$_4$ and concentrated in vacuo to afford 190 mg (100%) of the titled product.

Rf=0.34 (20:1 CHCl$_3$/MeOH). This product was used in subsequent reactions without further purification.

Step B: Preparation of 5,7-Dimethyl-2-ethyl-3-[[4-[2-(N-benzoylsulfonamido)-5-(2-methylpropyl)-3-thienyl]phenyl]methyl-]imidazo[4,5-b]pyridine (Compound 54 of Table VII).

To a solution of 1,1'-carbonyldiimidazole (51.6 mg, 0.32 mmol) in anhydrous THF (2 mL) was added benzoic acid (42 mg, 0.34 mmol). The mixture was stirred under N$_2$ at 50° C. for 2.25 h. To this mixture was added a solution of the product of step A (76.3 mg, 0.158 mmol) and DBU (0.047 mL) in anhydrous DMF (1.5 mL). The reaction was stirred at 50° C. under N$_2$ for 2.75 h. To the reaction was added MeOH (0.25 mL) and the mixture was stirred for 2 h. The reaction was concentrated under reduced pressure and the residue was taken up in EtOAc. The organic was washed with a 10% citric acid solution, H$_2$O and brine, dried over anhydrous MgSO$_4$ and concetrated in vacuo. The product was purified by flash chromatography eluting with CH$_2$Cl$_2$/MeOH/NH$_4$OH (80:10:1). Removal of the solvent afforded 76.6 mg (83%) of the titled compound as a white solid. Rf=0.26 (20:1 CHCl$_3$/MeOH).

$^1$H NMR (400 MHz, CD$_3$OD) δ0.96 (d, 6H), 1.29 (t, 3H), 1.88 (m, 1H), 2.57 (s, 3H), 2.61 (s, 3H), 2.66 (d, 2H), 2.72 (q, 2H), 5.51 (s, 2H), 6.78 (s, 1H), 7.01 (s, 1H), 7.08 (d, 2H), 7.22 (t, 2H), 7.39 (t, 1H), 7.60 (d, 2H), 7.62 (d, 2H).

EXAMPLE 73

5,7-Dimethyl-2-ethyl-3-[[4-[2-(N-butyloxycarbonylsulfonamido)-5-propyl-3-thienyl]phenyl]methyl-]imidazo[4,5-b]pyridine (Compound 121 of Table VII)

Step A: Preparation of 5,7-dimethyl-2-ethyl-3-[[4-[2-(sulfonamido)-5-propyl-3-thienyl]phenyl]methyl]imidazo]4,5-b]pyridine.

To a mixture of the compound of Example 71, Step 5, 9a (X$^1$—X$^2$—X$^3$—X$^4$=—CH=CR$^{12}$—S—CZ= and R$^{12}$=CH$_2$CH$_2$CH$_3$) (578 mg, 1.10 mmol) and anisole (5 drops) was added TFA (5 mL). After 2 days the reaction was concentrated under reduced pressure. The residue was taken up in EtOAc and washed with sat'd Na$_2$CO$_3$ solution, H$_2$O and brine. The organic was dried over anhydrous MgSO$_4$ and concentrated in vacuo to afford 499 mg (97%) of the titled product. Rf=0.34 (20:1 CHCl$_3$/MeOH). This product was used in subsequent reactions without further purification.

Step B: Preparation of 5,7-Dimethyl-2-ethyl-3-[[4-[2-(N-butyloxycarbonylsulfonamido)-5-propyl-3-thienyl]phenyl]methyl-]imidazo[4,5-b]pyridine (Compound 121 of Table VII).

To a solution of the product of step A (56 mg, 0.12 mmol) in anhydrous pyridine (1 mL) was added a catalytic amount of 4-pyrrolidinopyridine and butyl chlorformate (0.152 mL, 10 equiv). After stirring overnight at rt, MeOH (0.5 mL) was added and the mixture was stirred for an additional 30 min. The solvent was removed under reduced pressure and the residue was taken up in EtOAc. The organic was washed with a 10% citric acid solution, H$_2$O and brine, dried over anhydrous MgSO$_4$ and concetrated in vacuo. The product was purified by flash chromatography eluting with CH$_2$Cl$_2$/MeOH/NH$_4$OH (80:10:1). Removal of the solvent afforded 55.4 mg (81%) of the titled compound as a white solid. Rf=0.57 (40:10:1 CH$_2$Cl$_2$/MeOH/NH$_4$OH).

$^1$H NMR (400 MHz, CD$_3$OD) δ0.83 (t, 3H), 1.00 (t, 3H), 1.21 (m, 2H), 1.30 (t, 3H), 1.41 (m, 2H), 1.71 (m, 2H), 2.58 (s, 3H), 2.61 (s, 3H), 2.79 (t, 2H)m 2.87 (q, 2H), 3.85 (t, 2H), 5.58 (s, 2H), 6.81 (s, 1H), 7.02 (s, 1H), 7.12 (d, 2H), 7.52 (d, 2H).

The synthesis of Examples 74 through 110, prepared from compounds 9a (X$^1$—X$^2$—X$^3$—X$^4$ = —CH=CR$^{12}$—S—CZ=), is outlined in the following table:

| EXAMPLE | Compound & Table | R$^{12}$ of 9a | R$^{14}$CO$_2$H/R$^{14}$COCl | Method |
|---|---|---|---|---|
| 74 | 2 Table VII | CH$_3$ | PhCH$_2$COCl | # |
| 75 | 112, Table VII | CH$_3$ | (Ph)$_2$CHCOCl | # |
| 76 | 114, Table VII | CH$_2$CH$_3$ | EtOCH$_2$CO$_2$H | * |
| 77 | 113, Table VII | CH$_2$CH$_3$ | (Ph)$_2$CHCOCl | # |
| 78 | 155, Table VII | (CH$_2$)$_2$CH$_3$ | (Ph)$_2$CHCOCl | # |
| 79 | 118, Table VII | (CH$_2$)$_2$CH$_3$ | n-BuOCH$_2$CO$_2$H | * |
| 80 | 129, Table VII | (CH$_2$)$_2$CH$_3$ | N—CH$_3$-2-carboxypyrrole | * |
| 81 | 130, Table VII | (CH$_2$)$_2$CH$_3$ | (CH$_3$)$_2$CHCH$_2$OCOCl | # |
| 82 | 120, Table VII | (CH$_2$)$_3$CH$_3$ | CycPen(CH$_2$)$_2$COCl | # |
| 83 | 134, Table VII | (CH$_2$)$_3$CH$_3$ | BocNH(CH$_2$)$_5$CO$_2$H | * |
| 84 | 135, Table VII | (CH$_2$)$_3$CH$_3$ | H$_2$N(CH$_2$)$_5$CO$_2$H | @ |
| 85 | 115, Table VII | (CH$_2$)$_3$CH$_3$ | EtOCH$_2$CO$_2$H | * |
| 86 | 149, Table VII | (CH$_2$)$_3$CH$_3$ | CH$_3$(CH$_2$)$_3$OCOCl | # |
| 87 | 125, Table VII | CH$_2$CH(CH$_3$)$_2$ | EtOCH$_2$CO$_2$H | * |
| 88 | 136, Table VII | CH$_2$CH(CH$_3$)$_2$ | BocNH(CH$_2$)$_5$CO$_2$H | * |
| 89 | 137, Table VII | CH$_2$CH(CH$_3$)$_2$ | H$_2$N(CH$_2$)$_5$CO$_2$H | @ |
| 90 | 150, Table VII | CH$_2$CH(CH$_3$)$_2$ | CH$_3$(CH$_2$)$_3$OCOCl | # |
| 91 | 124, Table VII | CH$_2$CH(CH$_3$)$_2$ | n-BuOCH$_2$CO$_2$H | * |
| 92 | 138, Table VII | (CH$_2$)$_4$CH$_3$ | BocNH(CH$_2$)$_5$CO$_2$H | * |
| 93 | 139, Table VII | (CH$_2$)$_4$CH$_3$ | H$_2$N(CH$_2$)$_5$CO$_2$H | @ |
| 94 | 126, Table VII | (CH$_2$)$_4$CH$_3$ | EtOCH$_2$CO$_2$H | * |
| 95 | 152, Table VII | (CH$_2$)$_4$CH$_3$ | CH$_3$(CH$_2$)$_3$OCOCl | # |
| 96 | 127, Table VII | (CH$_2$)$_4$CH$_3$ | n-BuOCH$_2$CO$_2$H | * |
| 97 | 128, Table VII | (CH$_2$)$_4$CH$_3$ | N—CH$_3$-2-carboxypyrrole | * |
| 98 | 145, Table VII | CH$_2$Ph | CycPropylCO$_2$H | * |
| 99 | 85, Table VII | CH$_2$N(CH$_2$CH$_2$)$_2$O | (Ph)$_2$CHCOCl | # |
| 100 | 131, Table VII | CH$_2$CH(CH$_3$)$_2$ | CH$_3$O(CH$_2$)$_2$OCOCl | # |
| 101 | 103, Table VII | (CH$_2$)$_2$CH$_3$ | CH$_3$O(CH$_2$)$_2$CO$_2$H | * |
| 102 | 157, Table VII | (CH$_2$)$_2$CH$_3$ | EtOCH$_2$CO$_2$H | * |

-continued

The synthesis of Examples 74 through 110, prepared from compounds 9a
($X^1$—$X^2$—$X^3$—$X^4$ = —CH=$CR^{12}$—S—CZ=),
is outlined in the following table:

| EXAMPLE | Compound & Table | $R^{12}$ of 9a | $R^{14}CO_2H/R^{14}COCl$ | Method |
|---|---|---|---|---|
| 103 | 141, Table VII | $(CH_2)_2CH_3$ | $CH_3(CH_2)_4CO_2H$ | * |
| 104 | 77, Table VII | $CH_3$ | PhCOCl | # |
| 105 | 78, Table VII | $CH_2CH_3$ | PhCOCl | # |
| 106 | 79, Table VII | $(CH_2)_2CH_3$ | $PhCO_2H$ | * |
| 107 | 80, Table VII | $(CH_2)_2CH_3$ | $PhCO_2H$ | * |
| 108 | 82, Table VII | $(CH_2)_4CH_3$ | $PhCO_2H$ | * |
| 109 | 83, Table VII | $CH_2Ph$ | PhCOCl | # |
| 110 | 84, Table VII | $CH_2N(CH_2CH_2)_2O$ | PhCOCl | # |

The antagonist was prepared using the procedure used in Example 72.
*The antagonist was prepared using the procedure used in Example 71.
@ The antagonist was prepared by treatment of the previous Example with TFA in the presence of anisole for 12 hours.

The compounds shown in Tables V–VII can be prepared using the procedures described above:

TABLE V

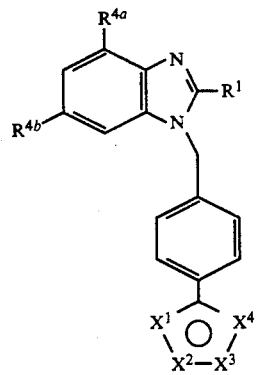

| # | EX # | $R^1$ | $R^{4a}$ | $R^{4b}$ | —$X^1$—$X^2$—$X^3$—$X^4$— | $R^{12}$ | Z |
|---|---|---|---|---|---|---|---|
| 1 | 7 | n-propyl | H | H | —CH—S—CH—CZ— | | 1H-tetrazol-5-yl |
| 2 | 8 | n-butyl | H | H | —CH—S—CH—CZ— | | 1H-tetrazol-5-yl |
| 3 | 17 | n-propyl | H | H | —CH—S—C(Br)—CZ— | | 1H-tetrazol-5-yl |
| 4 | 18 | n-butyl | H | H | —CH—S—C(Br)—CZ— | | 1H-tetrazol-5-yl |
| 5 | 38 | n-butyl | H | H | —CH—CH—O—CZ— | | 1H-tetrazol-5-yl |
| 6 | 37 | n-propyl | H | H | —CH—CH—O—CZ— | | 1H-tetrazol-5-yl |
| 7 | | n-butyl | H | H | —CH—S—CH—CZ— | | $SO_2NHCOPh$ |
| 8 | | n-butyl | H | H | —CH—S—CH—CZ— | | $CO_2H$ |
| 9 | | ethyl | H | H | —CH—S—CH—CZ— | | 1H-tetrazol-5-yl |
| 10 | | ethyl | H | H | —CH—S—CH—CZ— | | $SO_2NHCOPh$ |
| 11 | 27 | n-propyl | H | H | —CH—CH—S—CZ— | | 1H-tetrazol-5-yl |
| 12 | 28 | n-butyl | H | H | —CH—CH—S—CZ— | | 1H-tetrazol-5-yl |
| 13 | | n-butyl | $CH_3$ | H | —CH—S—CH—CZ— | | $SO_2NHCOPh$ |
| 14 | | n-butyl | $CH_3$ | $CH_3$ | —CH—S—CH—CZ— | | $SO_2NHCOPh$ |
| 15 | | ethyl | $CH_3$ | H | —CH—S—CH—CZ— | | $SO_2NHCOPh$ |
| 16 | 57 | n-propyl | H | H | —CH—CH—S—CZ— | | $SO_2NHCOPh$ |
| 17 | 58 | n-butyl | H | H | —CH—CH—S—CZ— | | $SO_2NHCOPh$ |
| 18 | | ethyl | $CH_3$ | $CO_2H$ | —CH—S—CH—CZ— | | $SO_2NHCOPh$ |
| 19 | 67 | n-propyl | H | H | —S—CH—CH—CZ— | | $SO_2NHCOPh$ |
| 20 | 68 | n-butyl | H | H | —S—CH—CH—CZ— | | $SO_2NHCOPh$ |
| 21 | | ethyl | $CH_3$ | $CH_3$ | —CH—S—C($SO_2NHCOPh$)CZ | | $SO_2NHCOPh$ |
| 22 | | ethyl | $CH_3$ | $CH_3$ | —CH—S—CH—CZ— | | 1H-tetrazol-5-yl |
| 23 | | ethyl | $CH_3$ | $CH_3$ | =C—C=S—CZ— / HC   CH / HC=CH | | 1H-tetrazol-5-yl |
| 24 | | ethyl | $CH_3$ | $CH_3$ | =C—C=S—CZ— / HC   CH / HC=CH | | $SO_2NHCOPh$ |
| 25 | 47 | n-propyl | H | H | =C—C=S—CZ— / HC   CH / HC=CH | | $SO_2NHCOPh$ |

TABLE V-continued

| # | EX # | R¹ | R⁴ᵃ | R⁴ᵇ | —X¹—X²—X³—X⁴— | R¹² | Z |
|---|---|---|---|---|---|---|---|
| 26 | 48 | n-butyl | H | H | —C—C—S—CZ— with HC=CH-HC=CH fused | | SO₂NHCOPh |
| 27 | | n-butyl | Me | H | —CH—CR¹²—S—CZ— | nPr | 1H-tetrazol-5-yl |
| 28 | | n-butyl | Me | H | —CH—CR¹²—S—CZ— | iBu | 1H-tetrazol-5-yl |
| 29 | | n-butyl | Me | H | —CH—CR¹²—S—CZ— | nPr | SO₂NHCOPh |
| 30 | | n-butyl | Me | H | —CH—CR¹²—S—CZ— | iBu | SO₂NHCOPh |
| 31 | | n-butyl | Me | H | —CH—CR¹²—S—CZ— | nPn | SO₂NHCOPh |
| 32 | | ethyl | Me | H | —CH—CR¹²—S—CZ— | nPr | 1H-tetrazol-5-yl |
| 33 | | ethyl | Me | H | —CH—CR¹²—S—CZ— | iBu | 1H-tetrazol-5-yl |
| 34 | | ethyl | Me | H | —CH—CR¹²—S—CZ— | nPn | 1H-tetrazol-5-yl |
| 35 | | ethyl | Me | H | —CH—CR¹²—S—CZ— | Bn | 1H-tetrazol-5-yl |
| 36 | | ethyl | Me | H | —CH—CR¹²—S—CZ— | nPr | SO₂NHCOPh |
| 37 | | ethyl | Me | H | —CH—CR¹²—S—CZ— | iBu | SO₂NHCOPh |
| 38 | | ethyl | Me | H | —CH—CR¹²—S—CZ— | nPn | SO₂NHCOPh |
| 39 | | ethyl | Me | H | —CH—CR¹²—S—CZ— | Bn | SO₂NHCOPh |
| 40 | | n-butyl | Me | Me | —CH—CR¹²—S—CZ— | nPr | 1H-tetrazol-5-yl |
| 41 | | n-butyl | Me | Me | —CH—CR¹²—S—CZ— | nBu | 1H-tetrazol-5-yl |
| 42 | | n-butyl | Me | Me | —CH—CR¹²—S—CZ— | iBu | 1H-tetrazol-5-yl |
| 43 | | n-butyl | Me | Me | —CH—CR¹²—S—CZ— | nPn | 1H-tetrazol-5-yl |
| 44 | | n-butyl | Me | Me | —CH—CR¹²—S—CZ— | nPr | SO₂NHCOPh |
| 45 | | n-butyl | Me | Me | —CH—CR¹²—S—CZ— | iBu | SO₂NHCOPh |
| 46 | | n-butyl | Me | Me | —CH—CR¹²—S—CZ— | nPn | SO₂NHCOPh |
| 47 | | ethyl | Me | Me | —CH—CR¹²—S—CZ— | nPr | 1H-tetrazol-5-yl |
| 48 | | ethyl | Me | Me | —CH—CR¹²—S—CZ— | iBu | 1H-tetrazol-5-yl |
| 49 | | ethyl | Me | Me | —CH—CR¹²—S—CZ— | nPn | 1H-tetrazol-5-yl |
| 50 | | ethyl | Me | Me | —CH—CR¹²—S—CZ— | Me | SO₂NHCOPh |
| 51 | | ethyl | Me | Me | —CH—CR¹²—S—CZ— | Et | SO₂NHCOPh |
| 52 | | ethyl | Me | Me | —CH—CR¹²—S—CZ— | nPr | SO₂NHCOPh |
| 53 | | ethyl | Me | Me | —CH—CR¹²—S—CZ— | nBu | SO₂NHCOPh |
| 54 | | ethyl | Me | Me | —CH—CR¹²—S—CZ— | iBu | SO₂NHCOPh |
| 55 | | ethyl | Me | Me | —CH—CR¹²—S—CZ— | nPn | SO₂NHCOPh |
| 56 | | ethyl | Me | Me | —CH—CR¹²—S—CZ— | Bn | SO₂NHCOPh |
| 57 | | ethyl | Me | Me | —CH—CR¹²—S—CZ— | CH₂N(CH₂CH₂)₂O | SO₂NHCOPh |
| 58 | | ethyl | Me | Me | —CH—CR¹²—S—CZ— | CH₂N(CH₂CH₂)₂O | SO₂NHCOCH(Ph)₂ |
| 59 | | n-butyl | Me | CON(Me)₂ | —CH—CR¹²—S—CZ— | nPr | 1H-tetrazol-5-yl |
| 60 | | n-butyl | Me | CON(Me)₂ | —CH—CR¹²—S—CZ— | iBu | 1H-tetrazol-5-yl |
| 61 | | n-butyl | Me | CON(Me)₂ | —CH—CR¹²—S—CZ— | nPr | SO₂NHCOPh |
| 62 | | ethyl | Me | CON(Me)₂ | —CH—CR¹²—S—CZ— | nPr | 1H-tetrazol-5-yl |
| 63 | | ethyl | Me | CON(Me)₂ | —CH—CR¹²—S—CZ— | nBu | 1H-tetrazol-5-yl |
| 64 | | ethyl | Me | CON(Me)₂ | —CH—CR¹²—S—CZ— | iBu | 1H-tetrazol-5-yl |
| 65 | | ethyl | Me | CON(Me)₂ | —CH—CR¹²—S—CZ— | nPn | 1H-tetrazol-5-yl |
| 66 | | ethyl | Me | CON(Me)₂ | —CH—CR¹²—S—CZ— | nBu | SO₂NHCOPh |
| 67 | | ethyl | Me | CON(Me)₂ | —CH—CR¹²—S—CZ— | iBu | SO₂NHCOPh |
| 68 | | ethyl | Me | CON(Me)₂ | —CH—CR¹²—S—CZ— | Bn | SO₂NHCOPh |
| 69 | | n-butyl | Me | CH₂OH | —CH—CR¹²—S—CZ— | nPr | 1H-tetrazol-5-yl |
| 70 | | n-butyl | Me | CH₂OH | —CH—CR¹²—S—CZ— | iBu | 1H-tetrazol-5-yl |
| 71 | | n-butyl | Me | CH₂OH | —CH—CR¹²—S—CZ— | nPr | SO₂NHCOPh |
| 72 | | n-butyl | Me | CH₂OH | —CH—CR¹²—S—CZ— | nPn | SO₂NHCOPh |
| 73 | | ethyl | Me | CH₂OH | —CH—CR¹²—S—CZ— | nBu | 1H-tetrazol-5-yl |
| 74 | | ethyl | Me | CH₂OH | —CH—CR¹²—S—CZ— | iBu | 1H-tetrazol-5-yl |
| 75 | | ethyl | Me | CH₂OH | —CH—CR¹²—S—CZ— | nPn | 1H-tetrazol-5-yl |
| 76 | | ethyl | Me | Me | —CH—CR¹²—S—CZ— | nPr | SO₂NHCO(CH₂)₂OMe |
| 77 | | ethyl | Me | CH₂OH | —CH—CR¹²—S—CZ— | nBu | SO₂NHCOPh |
| 78 | | ethyl | Me | CH₂OH | —CH—CR¹²—S—CZ— | iBu | SO₂NHCOPh |
| 79 | | ethyl | Me | CH₂OH | —CH—CR¹²—S—CZ— | nPn | SO₂NHCOPh |
| 80 | | ethyl | Me | CO₂H | —CH—CR¹²—S—CZ— | nPr | SO₂NHCOPh |
| 81 | | propyl | Me | CO₂H | —CH—CR¹²—S—CZ— | nPr | SO₂NHCOPh |
| 82 | | propyl | Me | CO₂H | —CH—CR¹²—S—CZ— | iBu | SO₂NHCOPh |

TABLE V-continued

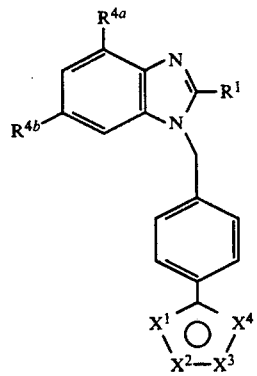

| # | EX # | R¹ | R⁴ᵃ | R⁴ᵇ | —X¹—X²—X³—X⁴— | R¹² | Z |
|---|---|---|---|---|---|---|---|
| 83 | | propyl | Me | CO₂H | —CH=CR¹²—S—CZ— | nPn | SO₂NHCOPh |
| 84 | | ethyl | Me | Me | —CH=CR¹²—S—CZ— | Me | SO₂NHCOCH₂Ph |
| 85 | | ethyl | Me | Me | —CH=CR¹²—S—CZ— | Me | SO₂NHCOCH(Ph)₂ |
| 86 | | ethyl | Me | Me | —CH=CR¹²—S—CZ— | Et | SO₂NHCOCH(Ph)₂ |
| 87 | | ethyl | Me | Me | —CH=CR¹²—S—CZ— | Et | SO₂NHCOCH₂OEt |
| 88 | | ethyl | Me | Me | —CH=CR¹²—S—CZ— | nBu | SO₂NHCOCH₂OEt |
| 89 | | propyl | Me | CO₂H | —CH=CR¹²—S—CZ— | nPn | SO₂NHCOCH₂OBu |
| 90 | | ethyl | Me | Me | —CH=CR¹²—S—CZ— | nPr | SO₂NHCOOPentyl |
| 91 | | ethyl | Me | Me | —CH=CR¹²—S—CZ— | nPr | SO₂NHCOCH₂OBu |
| 92 | | ethyl | Me | Me | —CH=CR¹²—S—CZ— | nPr | SO₂NHCOCH₂OEt |
| 93 | | ethyl | Me | Me | —CH=CR¹²—S—CZ— | nPr | SO₂NHCO(CH₂)₂CycPen |
| 94 | | ethyl | Me | CH₂OH | —CH=CR¹²—S—CZ— | nPr | SO₂NHCOCH₂OEt |
| 95 | | ethyl | Me | CH₂OH | —CH=CR¹²—S—CZ— | iBu | SO₂NHCOCH₂OBu |
| 96 | | ethyl | Me | CO₂H | —CH=CR¹²—S—CZ— | iBu | SO₂NHCOCH₂OBu |
| 97 | | ethyl | Me | Me | —CH=CR¹²—S—CZ— | iBu | SO₂NHCOCH₂OBu |
| 98 | | ethyl | Me | Me | —CH=CR¹²—S—CZ— | iBu | SO₂NHCOCH₂OEt |
| 99 | | ethyl | Me | Me | —CH=CR¹²—S—CZ— | nPn | SO₂NHCOCH₂OEt |
| 100 | | ethyl | Me | Me | —CH=CR¹²—S—CZ— | nPn | SO₂NHCOCH₂OBu |
| 101 | | ethyl | Me | Me | —CH=CR¹²—S—CZ— | nPn | SO₂NHCO₂-N-methylpyrrole |
| 102 | | ethyl | Me | Me | —CH=CR¹²—S—CZ— | nPr | SO₂NHCO₂-N-methylpyrrole |
| 103 | | ethyl | Me | Me | —CH=CR¹²—S—CZ— | nPr | SO₂NHCOOCH₂CH(Me)₂ |
| 104 | | ethyl | Me | Me | —CH=CR¹²—S—CZ— | iBu | SO₂NHCOO(CH₂)₂OMe |
| 105 | | ethyl | Me | Me | —CH=CR¹²—S—CZ— | nPr | SO₂NHCOO(CH₂)₂OMe |
| 106 | | ethyl | Me | Me | —CH=CR¹²—S—CZ— | nBu | SO₂NHCOO(CH₂)₂OMe |
| 107 | | ethyl | Me | Me | —CH=CR¹²—S—CZ— | nBu | SO₂NHCO(CH₂)₅NHBoc |
| 108 | | ethyl | Me | Me | —CH=CR¹²—S—CZ— | nBu | SO₂NHCO(CH₂)₅NH₂ |
| 109 | | ethyl | Me | Me | —CH=CR¹²—S—CZ— | iBu | SO₂NHCO(CH₂)₅NHBoc |
| 110 | | ethyl | Me | Me | —CH=CR¹²—S—CZ— | iBu | SO₂NHCO(CH₂)₅NH₂ |
| 111 | | ethyl | Me | Me | —CH=CR¹²—S—CZ— | nPn | SO₂NHCO(CH₂)₅NHBoc |
| 112 | | ethyl | Me | Me | —CH=CR¹²—S—CZ— | nPn | SO₂NHCO(CH₂)₅NH₂ |
| 113 | | ethyl | Me | Me | —CH=CR¹²—S—CZ— | nPn | SO₂NHCO(CH₂)₄CH₃ |
| 114 | | ethyl | Me | Me | —CH=CR¹²—S—CZ— | nPr | SO₂NHCO(CH₂)₄CH₃ |
| 115 | | ethyl | Me | Me | —CH=CR¹²—S—CZ— | nBu | SO₂NHCO(CH₂)₄CH₃ |
| 116 | | ethyl | Me | Me | —CH=CR¹²—S—CZ— | iBu | SO₂NHCO(CH₂)₄CH₃ |
| 117 | | ethyl | Me | Me | —CH=CR¹²—S—CZ— | nPr | SO₂NHCOcyPr |
| 118 | | ethyl | Me | Me | —CH=CR¹²—S—CZ— | Bn | SO₂NHCOcyPr |
| 119 | | ethyl | Me | Me | —CH=CR¹²—S—CZ— | iBu | SO₂NHCOO(CH₂)₂OMe |
| 120 | | ethyl | Me | CON(Me)₂ | —CH=CR¹²—S—CZ— | iBu | SO₂NHCOcyPr |
| 121 | | ethyl | Me | Me | —CH=CR¹²—S—CZ— | nPr | SO₂NHCOOBu |
| 122 | | ethyl | Me | Me | —CH=CR¹²—S—CZ— | iBu | SO₂NHCOOBu |
| 123 | | ethyl | Me | Me | —CH=CR¹²—S—CZ— | iBu | SO₂NHCOOBu |
| 124 | | ethyl | Me | CO₂H | —CH=CR¹²—S—CZ— | nPr | SO₂NHCOOBu |
| 125 | | ethyl | Me | Me | —CH=CR¹²—S—CZ— | nPn | SO₂NHCOOBu |
| 126 | | ethyl | Me | CO₂H | —CH=CR¹²—S—CZ— | nPn | SO₂NHCOOBu |
| 127 | | ethyl | Me | Me | —CH=CR¹²—S—CZ— | iBu | SO₂NHCOCH(Ph)₂ |
| 128 | | ethyl | Me | Me | —CH=CR¹²—S—CZ— | nPr | SO₂NHCOCH(Ph)₂ |
| 129 | | ethyl | Me | CON(Me)₂ | —CH=CR¹²—S—CZ— | iBu | SO₂NHCOCH(Ph)₂ |
| 130 | | ethyl | Me | Me | —CH=CR¹²—S—CZ— | nPr | SO₂NHCOCH₂OEt |

TABLE VI

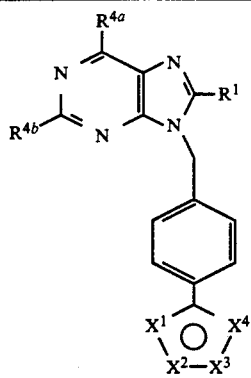

| # | EX # | R¹ | R⁴ᵃ | R⁴ᵇ | —X¹—X²—X³—X⁴— | R¹² | Z |
|---|---|---|---|---|---|---|---|
| 1 | | n-butyl | H | H | —CH—S—CH—CZ— | | 1H-tetrazol-5-yl |
| 2 | | n-butyl | H | H | —CH—S—CH—CZ— | | SO₂NHCOPh |
| 3 | | n-propyl | CH₃ | CH₃ | —CH—S—CH—CZ— | | SO₂NHCOPh |
| 4 | | n-propyl | CH₃ | CO₂H | —CH—S—CH—CZ— | | SO₂NHCOPh |
| 5 | | ethyl | CH₃ | CH₃ | —CH—S—CH—CZ— | | 1H-tetrazol-5-yl |
| 6 | | ethyl | CH₃ | CO₂H | —CH—S—CH—CZ— | | 1H-tetrazol-5-yl |
| 7 | | ethyl | CH₃ | CH₃ | —CH—C(Si(CH₃)₃)—S—CZ— | | SO₂NHCOPh |
| 8 | | n-propyl | CH₃ | CH₃ | =C—C—S—CZ— (fused benzene) | | SO₂NHCOPh |
| 9 | | ethyl | CH₃ | CH₃ | =C—C—S—CZ— (fused benzene) | | SO₂NHCOPh |
| 10 | | ethyl | CH₃ | CH₃ | —CH—CH—S—CZ— | | SO₂NHCOPh |
| 11 | | ethyl | CH₃ | CO₂H | —CH—CH—S—CZ— | | SO₂NHCOPh |
| 12 | | ethyl | CH₃ | CH₃ | —S—CH—CH—CZ— | | 1H-tetrazol-5-yl |
| 13 | | ethyl | CH₃ | CO₂H | —S—CH—CH—CZ— | | 1H-tetrazol-5-yl |
| 14 | | ethyl | CH₃ | CH₃ | —S—CH—CH—CZ— | | SO₂NHCOPh |
| 15 | | ethyl | CH₃ | CO₂H | —S—CH—CH—CZ— | | SO₂NHCOPh |
| 16 | | ethyl | CH₃ | CH₃ | —CH—S—C(SO₂NHCOPh)—CZ— | | H |
| 17 | EX 9 | n-propyl | CH₃ | Cl | —CH—S—CH—CZ— | | 1H-tetrazol-5-yl |
| 18 | 10 | n-propyl | CH₃ | N(CH₃)₂ | —CH—S—CH—CZ— | | 1H-tetrazol-5-yl |
| 19 | 19 | n-propyl | CH₃ | Cl | —CH—S—C(Br)—CZ— | | 1H-tetrazol-5-yl |
| 20 | 20 | n-propyl | CH₃ | N(CH₃)₂ | —CH—S—C(Br)—CZ— | | 1H-tetrazol-5-yl |
| 21 | 29 | n-propyl | CH₃ | Cl | —CH—CH—S—CZ— | | 1H-tetrazol-5-yl |
| 22 | 30 | n-propyl | CH₃ | N(CH₃)₂ | —CH—CH—S—CZ— | | 1H-tetrazol-5-yl |
| 23 | 39 | n-propyl | CH₃ | Cl | —CH—CH—O—CZ— | | 1H-tetrazol-5-yl |
| 24 | 40 | n-propyl | CH₃ | N(CH₃)₂ | —CH—CH—O—CZ— | | 1H-tetrazol-5-yl |
| 25 | 49 | n-propyl | CH₃ | Cl | =C—C—S—CZ— (fused benzene) | | SO₂NHCOPh |
| 26 | 50 | n-propyl | CH₃ | N(CH₃)₂ | =C—C—S—CZ— (fused benzene) | | SO₂NHCOPh |
| 27 | 59 | n-propyl | CH₃ | Cl | —CH—CH—S—CZ— | | SO₂NHCOPh |
| 28 | 60 | n-propyl | CH₃ | N(CH₃)₂ | —CH—CH—S—CZ— | | SO₂NHCOPh |
| 29 | 69 | n-propyl | CH₃ | Cl | —S—CH—CH—CZ— | | SO₂NHCOPh |
| 30 | 70 | n-propyl | CH₃ | N(CH₃)₂ | —S—CH—CH—CZ— | | SO₂NHCOPh |
| 31 | | n-butyl | Me | H | —CH—CR¹²—S—CZ— | nPr | 1H-tetrazol-5-yl |
| 32 | | n-butyl | Me | H | —CH—CR¹²—S—CZ— | iBu | 1H-tetrazol-5-yl |
| 33 | | n-butyl | Me | H | —CH—CR¹²—S—CZ— | nPr | SO₂NHCOPh |
| 34 | | n-butyl | Me | H | —CH—CR¹²—S—CZ— | iBu | SO₂NHCOPh |
| 35 | | n-butyl | Me | H | —CH—CR¹²—S—CZ— | nPn | SO₂NHCOPh |
| 36 | | ethyl | Me | H | —CH—CR¹²—S—CZ— | nPr | 1H-tetrazol-5-yl |
| 37 | | ethyl | Me | H | —CH—CR¹²—S—CZ— | iBu | 1H-tetrazol-5-yl |
| 38 | | ethyl | Me | H | —CH—CR¹²—S—CZ— | nPn | 1H-tetrazol-5-yl |
| 39 | | ethyl | Me | H | —CH—CR¹²—S—CZ— | Bn | 1H-tetrazol-5-yl |
| 40 | | ethyl | Me | H | —CH—CR¹²—S—CZ— | nPr | SO₂NHCOPh |

TABLE VI-continued

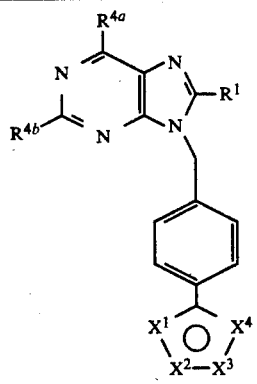

| # | EX # | R¹ | R⁴ᵃ | R⁴ᵇ | —X¹—X²—X³—X⁴— | R¹² | Z |
|---|---|---|---|---|---|---|---|
| 41 | | ethyl | Me | H | —CH—CR¹²—S—CZ— | iBu | SO₂NHCOPh |
| 42 | | ethyl | Me | H | —CH—CR¹²—S—CZ— | nPn | SO₂NHCOPh |
| 43 | | ethyl | Me | H | —CH—CR¹²—S—CZ— | Bn | SO₂NHCOPh |
| 44 | | n-butyl | Me | Me | —CH—CR¹²—S—CZ— | nPr | 1H-tetrazol-5-yl |
| 45 | | n-butyl | Me | Me | —CH—CR¹²—S—CZ— | nBu | 1H-tetrazol-5-yl |
| 46 | | n-butyl | Me | Me | —CH—CR¹²—S—CZ— | iBu | 1H-tetrazol-5-yl |
| 47 | | n-butyl | Me | Me | —CH—CR¹²—S—CZ— | nPn | 1H-tetrazol-5-yl |
| 48 | | n-butyl | Me | Me | —CH—CR¹²—S—CZ— | nPr | SO₂NHCOPh |
| 49 | | n-butyl | Me | Me | —CH—CR¹²—S—CZ— | iBu | SO₂NHCOPh |
| 50 | | n-butyl | Me | Me | —CH—CR¹²—S—CZ— | nPn | SO₂NHCOPh |
| 51 | | ethyl | Me | Me | —CH—CR¹²—S—CZ— | nPr | 1H-tetrazol-5-yl |
| 52 | | ethyl | Me | Me | —CH—CR¹²—S—CZ— | iBu | 1H-tetrazol-5-yl |
| 53 | | ethyl | Me | Me | —CH—CR¹²—S—CZ— | nPn | 1H-tetrazol-5-yl |
| 54 | | ethyl | Me | Me | —CH—CR¹²—S—CZ— | Me | SO₂NHCOPh |
| 55 | | ethyl | Me | Me | —CH—CR¹²—S—CZ— | Et | SO₂NHCOPh |
| 56 | | ethyl | Me | Me | —CH—CR¹²—S—CZ— | nPr | SO₂NHCOPh |
| 57 | | ethyl | Me | Me | —CH—CR¹²—S—CZ— | nBu | SO₂NHCOPh |
| 58 | | ethyl | Me | Me | —CH—CR¹²—S—CZ— | iBu | SO₂NHCOPh |
| 59 | | ethyl | Me | Me | —CH—CR¹²—S—CZ— | nPn | SO₂NHCOPh |
| 60 | | ethyl | Me | Me | —CH—CR¹²—S—CZ— | Bn | SO₂NHCOPh |
| 61 | | ethyl | Me | Me | —CH—CR¹²—S—CZ— | CH₂N(CH₂CH₂)₂O | SO₂NHCOPh |
| 62 | | ethyl | Me | Me | —CH—CR¹²—S—CZ— | CH₂N(CH₂CH₂)₂O | SO₂NHCOCH(Ph)₂ |
| 63 | | n-butyl | Me | CON(Me)₂ | —CH—CR¹²—S—CZ— | nPr | 1H-tetrazol-5-yl |
| 64 | | n-butyl | Me | CON(Me)₂ | —CH—CR¹²—S—CZ— | iBu | 1H-tetrazol-5-yl |
| 65 | | n-butyl | Me | CON(Me)₂ | —CH—CR¹²—S—CZ— | nPr | SO₂NHCOPh |
| 66 | | ethyl | Me | CON(Me)₂ | —CH—CR¹²—S—CZ— | nPr | 1H-tetrazol-5-yl |
| 67 | | ethyl | Me | CON(Me)₂ | —CH—CR¹²—S—CZ— | nBu | 1H-tetrazol-5-yl |
| 68 | | ethyl | Me | CON(Me)₂ | —CH—CR¹²—S—CZ— | iBu | 1H-tetrazol-5-yl |
| 69 | | ethyl | Me | CON(Me)₂ | —CH—CR¹²—S—CZ— | nPn | 1H-tetrazol-5-yl |
| 70 | | ethyl | Me | CON(Me)₂ | —CH—CR¹²—S—CZ— | nBu | SO₂NHCOPh |
| 71 | | ethyl | Me | CON(Me)₂ | —CH—CR¹²—S—CZ— | iBu | SO₂NHCOPh |
| 72 | | ethyl | Me | CON(Me)₂ | —CH—CR¹²—S—CZ— | Bn | SO₂NHCOPh |
| 73 | | n-butyl | Me | CH₂OH | —CH—CR¹²—S—CZ— | nPr | 1H-tetrazol-5-yl |
| 74 | | n-butyl | Me | CH₂OH | —CH—CR¹²—S—CZ— | iBu | 1H-tetrazol-5-yl |
| 75 | | n-butyl | Me | CH₂OH | —CH—CR¹²—S—CZ— | nPr | SO₂NHCOPh |
| 76 | | n-butyl | Me | CH₂OH | —CH—CR¹²—S—CZ— | nPn | SO₂NHCOPh |
| 77 | | ethyl | Me | CH₂OH | —CH—CR¹²—S—CZ— | nBu | 1H-tetrazol-5-yl |
| 78 | | ethyl | Me | CH₂OH | —CH—CR¹²—S—CZ— | iBu | 1H-tetrazol-5-yl |
| 79 | | ethyl | Me | CH₂OH | —CH—CR¹²—S—CZ— | nPn | 1H-tetrazol-5-yl |
| 80 | | ethyl | Me | Me | —CH—CR¹²—S—CZ— | nPr | SO₂NHCO(CH₂)₂OMe |
| 81 | | ethyl | Me | CH₂OH | —CH—CR¹²—S—CZ— | nBu | SO₂NHCOPh |
| 82 | | ethyl | Me | CH₂OH | —CH—CR¹²—S—CZ— | iBu | SO₂NHCOPh |
| 83 | | ethyl | Me | CH₂OH | —CH—CR¹²—S—CZ— | nPn | SO₂NHCOPh |
| 84 | | ethyl | Me | CO₂H | —CH—CR¹²—S—CZ— | nPr | SO₂NHCOPh |
| 85 | | propyl | Me | CO₂H | —CH—CR¹²—S—CZ— | nPr | SO₂NHCOPh |
| 86 | | propyl | Me | CO₂H | —CH—CR¹²—S—CZ— | iBu | SO₂NHCOPh |
| 87 | | propyl | Me | CO₂H | —CH—CR¹²—S—CZ— | nPn | SO₂NHCOPh |
| 88 | | ethyl | Me | Me | —CH—CR¹²—S—CZ— | Me | SO₂NHCOCH₂Ph |
| 89 | | ethyl | Me | Me | —CH—CR¹²—S—CZ— | Me | SO₂NHCOCH(Ph)₂ |
| 90 | | ethyl | Me | Me | —CH—CR¹²—S—CZ— | Et | SO₂NHCOCH(Ph)₂ |
| 91 | | ethyl | Me | Me | —CH—CR¹²—S—CZ— | Et | SO₂NHCOCH₂OEt |
| 92 | | ethyl | Me | Me | —CH—CR¹²—S—CZ— | nBu | SO₂NHCOCH₂OEt |
| 93 | | propyl | Me | CO₂H | —CH—CR¹²—S—CZ— | nPn | SO₂NHCOCH₂OBu |
| 94 | | ethyl | Me | Me | —CH—CR¹²—S—CZ— | nPr | SO₂NHCOOPentyl |
| 95 | | ethyl | Me | Me | —CH—CR¹²—S—CZ— | nPr | SO₂NHCOCH₂OBu |
| 96 | | ethyl | Me | Me | —CH—CR¹²—S—CZ— | nPr | SO₂NHCOCH₂OEt |
| 97 | | ethyl | Me | Me | —CH—CR¹²—S—CZ— | nPr | SO₂NHCO(CH₂)₂CycPen |
| 98 | | ethyl | Me | CH₂OH | —CH—CR¹²—S—CZ— | nPr | SO₂NHCOCH₂OEt |
| 99 | | ethyl | Me | CH₂OH | —CH—CR¹²—S—CZ— | iBu | SO₂NHCOCH₂OBu |
| 100 | | ethyl | Me | CO₂H | —CH—CR¹²—S—CZ— | iBu | SO₂NHCOCH₂OBu |
| 101 | | ethyl | Me | Me | —CH—CR¹²—S—CZ— | iBu | SO₂NHCOCH₂OBu |

TABLE VI-continued

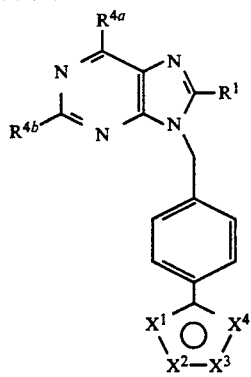

| # | EX # | R¹ | R⁴ᵃ | R⁴ᵇ | —X¹—X²—X³—X⁴— | R¹² | Z |
|---|---|---|---|---|---|---|---|
| 102 | | ethyl | Me | Me | —CH—CR¹²—S—CZ— | iBu | SO₂NHCOCH₂OEt |
| 103 | | ethyl | Me | Me | —CH—CR¹²—S—CZ— | nPn | SO₂NHCOCH₂OEt |
| 104 | | ethyl | Me | Me | —CH—CR¹²—S—CZ— | nPn | SO₂NHCOCH₂OBu |
| 105 | | ethyl | Me | Me | —CH—CR¹²—S—CZ— | nPn | SO₂NHCO₂-N-methylpyrrole |
| 106 | | ethyl | Me | Me | —CH—CR¹²—S—CZ— | nPr | SO₂NHCO₂-N-methylpyrrole |
| 107 | | ethyl | Me | Me | —CH—CR¹²—S—CZ— | nPr | SO₂NHCOOCH₂CH(Me)₂ |
| 108 | | ethyl | Me | Me | —CH—CR¹²—S—CZ— | iBu | SO₂NHCOO(CH₂)₂OMe |
| 109 | | ethyl | Me | Me | —CH—CR¹²—S—CZ— | nPr | SO₂NHCOO(CH₂)₂OMe |
| 110 | | ethyl | Me | Me | —CH—CR¹²—S—CZ— | nBu | SO₂NHCOO(CH₂)₂OMe |
| 111 | | ethyl | Me | Me | —CH—CR¹²—S—CZ— | nBu | SO₂NHCO(CH₂)₅NHBoc |
| 112 | | ethyl | Me | Me | —CH—CR¹²—S—CZ— | nBu | SO₂NHCO(CH₂)₅NH₂ |
| 113 | | ethyl | Me | Me | —CH—CR¹²—S—CZ— | iBu | SO₂NHCO(CH₂)₅NHBoc |
| 114 | | ethyl | Me | Me | —CH—CR¹²—S—CZ— | iBu | SO₂NHCO(CH₂)₅NH₂ |
| 115 | | ethyl | Me | Me | —CH—CR¹²—S—CZ— | nPn | SO₂NHCO(CH₂)₅NHBoc |
| 116 | | ethyl | Me | Me | —CH—CR¹²—S—CZ— | nPn | SO₂NHCO(CH₂)₅NH₂ |
| 117 | | ethyl | Me | Me | —CH—CR¹²—S—CZ— | nPn | SO₂NHCO(CH₂)₄CH₃ |
| 118 | | ethyl | Me | Me | —CH—CR¹²—S—CZ— | nPr | SO₂NHCO(CH₂)₄CH₃ |
| 119 | | ethyl | Me | Me | —CH—CR¹²—S—CZ— | nBu | SO₂NHCO(CH₂)₄CH₃ |
| 120 | | ethyl | Me | Me | —CH—CR¹²—S—CZ— | iBu | SO₂NHCO(CH₂)₄CH₃ |
| 121 | | ethyl | Me | Me | —CH—CR¹²—S—CZ— | nPr | SO₂NHCOcyPr |
| 122 | | ethyl | Me | Me | —CH—CR¹²—S—CZ— | Bn | SO₂NHCOcyPr |
| 123 | | ethyl | Me | Me | —CH—CR¹²—S—CZ— | iBu | SO₂NHCOO(CH₂)₂OMe |
| 124 | | ethyl | Me | CON(Me)₂ | —CH—CR¹²—S—CZ— | iBu | SO₂NHCOcyPr |
| 125 | | ethyl | Me | Me | —CH—CR¹²—S—CZ— | nPr | SO₂NHCOOBu |
| 126 | | ethyl | Me | Me | —CH—CR¹²—S—CZ— | iBu | SO₂NHCOOBu |
| 127 | | ethyl | Me | Me | —CH—CR¹²—S—CZ— | iBu | SO₂NHCOOBu |
| 128 | | ethyl | Me | CO₂H | —CH—CR¹²—S—CZ— | nPr | SO₂NHCOOBu |
| 129 | | ethyl | Me | Me | —CH—CR¹²—S—CZ— | nPn | SO₂NHCOOBu |
| 130 | | ethyl | Me | CO₂H | —CH—CR¹²—S—CZ— | nPn | SO₂NHCOOBu |
| 131 | | ethyl | Me | Me | —CH—CR¹²—S—CZ— | iBu | SO₂NHCOCH(Ph)₂ |
| 132 | | ethyl | Me | Me | —CH—CR¹²—S—CZ— | nPr | SO₂NHCOCH(Ph)₂ |
| 133 | | ethyl | Me | CON(Me)₂ | —CH—CR¹²—S—CZ— | iBu | SO₂NHCOCH(Ph)₂ |
| 134 | | ethyl | Me | Me | —CH—CR¹²—S—CZ— | nPr | SO₂NHCOCH₂OEt |

TABLE VII

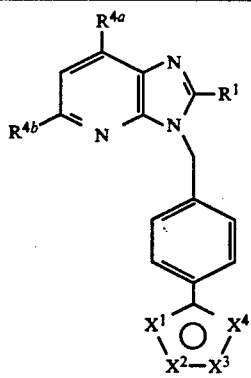

| # | EX # | R¹ | R⁴ᵃ | R⁴ᵇ | —X¹—X²—X³—X⁴— | R¹² | Z |
|---|---|---|---|---|---|---|---|
| 1 | | n-butyl | H | H | —CH—S—CH—CZ— | | 1H-tetrazol-5-yl |
| 2 | 3 | ethyl | CH₃ | CO₂CH₃ | —CH—S—CH—CZ— | | 1H-tetrazol-5-yl |
| 3 | 5 | ethyl | CH₃ | CO₂H | —CH—S—CH—CZ— | | 1H-tetrazol-5-yl |

TABLE VII-continued

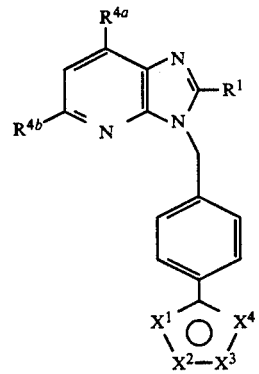

| # | EX # | R¹ | R⁴ᵃ | R⁴ᵇ | —X¹—X²—X³—X⁴— | R¹² | Z |
|---|---|---|---|---|---|---|---|
| 4 | 4 | n-propyl | $CH_3$ | $CO_2CH_3$ | —CH—S—CH—CZ— | | 1H-tetrazol-5-yl |
| 5 | 6 | propyl | $CH_3$ | $CO_2H$ | —CH—S—CH—CZ— | | 1H-tetrazol-5-yl |
| 6 | | n-butyl | $CH_3$ | $CH_3$ | —CH—S—CH—CZ— | | $SO_2NHCOPh$ |
| 7 | 2 | n-propyl | H | $CH_3$ | —CH—S—CH—CZ— | | 1H-tetrazol-5-yl |
| 8 | | ethyl | $CH_3$ | $CH_3$ | —CH—S—CH—CZ— | | $SO_2NHCOPh$ |
| 9 | 1 | ethyl | $CH_3$ | $CH_3$ | —CH—S—CH—CZ— | | 1H-tetrazol-5-yl |
| 10 | | ethyl | $CH_3$ | $CH_3$ | —CH—S—C($SO_2NHCOPh$)—CZ— | | 1H-tetrazol-5-yl |
| 11 | 61 | ethyl | $CH_3$ | $CH_3$ | —S—CH—CH—CZ— | | $SO_2NHCOPh$ |
| 12 | 51 | ethyl | $CH_3$ | $CH_3$ | —CH—CH—S—CZ— | | $SO_2NHCOPh$ |
| 13 | 55 | ethyl | $CH_3$ | $CO_2H$ | —CH—CH—S—CZ— | | $SO_2NHCOPh$ |
| 14 | 21 | ethyl | $CH_3$ | $CH_3$ | —CH—CH—S—CZ— | | 1H-tetrazol-5-yl |
| 15 | 22 | n-propyl | $CH_3$ | H | —CH—CH—S—CZ— | | 1H-tetrazol-5-yl |
| 16 | | ethyl | $CH_3$ | $CO_2H$ | —CH—S—CH—CZ— | | 1H-tetrazol-5-yl |
| 17 | 11 | ethyl | $CH_3$ | $CH_3$ | —CH—S—C(Br)—CZ— | | 1H-tetrazol-5-yl |
| 18 | 12 | propyl | $CH_3$ | H | —CH—S—C(Br)—CZ— | | 1H-tetrazol-5-yl |
| 19 | 13 | ethyl | $CH_3$ | $CO_2CH_3$ | —CH—S—C(Br)—CZ— | | 1H-tetrazol-5-yl |
| 20 | 14 | propyl | $CH_3$ | $CO_2CH_3$ | —CH—S—C(Br)—CZ— | | 1H-tetrazol-5-yl |
| 21 | 15 | ethyl | $CH_3$ | $CO_2H$ | —CH—S—C(Br)—CZ— | | 1H-tetrazol-5-yl |
| 22 | 16 | propyl | $CH_3$ | $CO_2H$ | —CH—S—C(Br)—CZ— | | 1H-tetrazol-5-yl |
| 23 | 23 | ethyl | $CH_3$ | $CO_2CH_3$ | —CH—CH—S—CZ— | | 1H-tetrazol-5-yl |
| 24 | 24 | propyl | $CH_3$ | $CO_2CH_3$ | —CH—CH—S—CZ— | | 1H-tetrazol-5-yl |
| 25 | 25 | ethyl | $CH_3$ | $CO_2H$ | —CH—CH—S—CZ— | | 1H-tetrazol-5-yl |
| 26 | 26 | n-propyl | $CH_3$ | $CO_2H$ | —CH—CH—S—CZ— | | 1H-tetrazol-5-yl |
| 27 | 31 | ethyl | $CH_3$ | $CH_3$ | —CH—CH—O—CZ— | | 1H-tetrazol-5-yl |
| 28 | 32 | n-propyl | $CH_3$ | H | —CH—CH—O—CZ— | | 1H-tetrazol-5-yl |
| 29 | 33 | ethyl | $CH_3$ | $CO_2CH_3$ | —CH—CH—O—CZ— | | 1H-tetrazol-5-yl |
| 30 | 34 | n-propyl | $CH_3$ | $CO_2CH_3$ | —CH—CH—O—CZ— | | 1H-tetrazol-5-yl |
| 31 | 35 | ethyl | $CH_3$ | $CO_2H$ | —CH—CH—O—CZ— | | 1H-tetrazol-5-yl |
| 32 | 36 | n-propyl | $CH_3$ | $CO_2H$ | —CH—CH—O—CZ— | | 1H-tetrazol-5-yl |
| 33 | | ethyl | $CH_3$ | $CH_3$ | —CH—S—CH—CZ— | | 1H-tetrazol-5-yl |
| 34 | | ethyl | $CH_3$ | $CH_3$ | —CH—S—CH—CZ— | | $SO_2NHCOCF_3$ |
| 35 | | ethyl | $CH_3$ | $CH_3$ | —CH—S—CH—CZ— | | $CO_2H$ |
| 36 | | ethyl | $CH_3$ | $CH_3$ | —CH—S—C($SO_2NHCOCF_3$)—CZ— | | H |
| 37 | | ethyl | $CH_3$ | $CH_3$ | —CH—S—C($SO_2NHCOPh$)—CZ— | | H |
| 38 | | ethyl | $CH_3$ | $CH_3$ | —CH—S—C($SO_2NHCO$-4-pyr)—CZ— | | H |
| 39 | 62 | n-propyl | $CH_3$ | H | —S—CH—CH—CZ— | | $SO_2NHCOPh$ |
| 40 | 63 | ethyl | $CH_3$ | $CO_2CH_3$ | —S—CH—CH—CZ— | | $SO_2NHCOPh$ |
| 41 | 65 | ethyl | $CH_3$ | $CO_2H$ | —S—CH—CH—CZ— | | $SO_2NHCOPh$ |
| 42 | 41 | ethyl | $CH_3$ | $CH_3$ | —C—C—S—CZ— (fused benzo) | | $SO_2NHCOPh$ |
| 43 | 42 | n-propyl | $CH_3$ | H | —C—C—S—CZ— (fused benzo) | | $SO_2NHCOPh$ |
| 44 | 43 | ethyl | $CH_3$ | $CO_2CH_3$ | —C—C—S—CZ— (fused benzo) | | $SO_2NHCOPh$ |
| 45 | 44 | n-propyl | $CH_3$ | $CO_2CH_3$ | —C—C—S—CZ— (fused benzo) | | $SO_2NHCOPh$ |

TABLE VII-continued

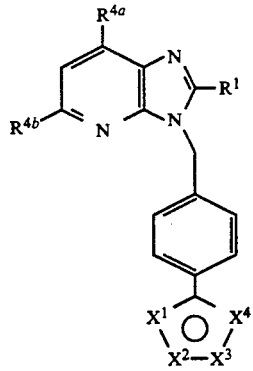

| # | EX # | R¹ | R⁴ᵃ | R⁴ᵇ | —X¹—X²—X³—X⁴— | R¹² | Z |
|---|---|---|---|---|---|---|---|
| 46 | 45 | ethyl | CH₃ | CO₂H | ![benzothiophene-like]  —C=C—S—CZ— / HC=CH—HC=CH | | SO₂NHCOPh |
| 47 | 46 | n-propyl | CH₃ | CO₂H | —C=C—S—CZ— / HC=CH—HC=CH | | SO₂NHCOPh |
| 48 | 52 | n-propyl | CH₃ | H | —CH—CH—S—CZ— | | SO₂NHCOPh |
| 49 | 53 | ethyl | CH₃ | CO₂CH₃ | —CH—CH—S—CZ— | | SO₂NHCOPh |
| 50 | 54 | n-propyl | CH₃ | CO₂CH₃ | —CH—CH—S—CZ— | | SO₂NHCOPh |
| 51 | 56 | n-propyl | CH₃ | CO₂CH₃ | —CH—CH—S—CZ— | | SO₂NHCOPh |
| 52 | 64 | n-propyl | CH₃ | CO₂CH₃ | —S—CH—CH—CZ— | | SO₂NHCOPh |
| 53 | 66 | n-propyl | CH₃ | CO₂H | —S—CH—CH—CZ— | | SO₂NHCOPh |
| 54 | | n-butyl | Me | H | —CH—CR¹²—S—CZ— | nPr | 1H-tetrazol-5-yl |
| 55 | | n-butyl | Me | H | —CH—CR¹²—S—CZ— | iBu | 1H-tetrazol-5-yl |
| 56 | | n-butyl | Me | H | —CH—CR¹²—S—CZ— | nPr | SO₂NHCOPh |
| 57 | | n-butyl | Me | H | —CH—CR¹²—S—CZ— | iBu | SO₂NHCOPh |
| 58 | | n-butyl | Me | H | —CH—CR¹²—S—CZ— | nPn | SO₂NHCOPh |
| 59 | | ethyl | Me | H | —CH—CR¹²—S—CZ— | nPr | 1H-tetrazol-5-yl |
| 60 | | ethyl | Me | H | —CH—CR¹²—S—CZ— | iBu | 1H-tetrazol-5-yl |
| 61 | | ethyl | Me | H | —CH—CR¹²—S—CZ— | nPn | 1H-tetrazol-5-yl |
| 62 | | ethyl | Me | H | —CH—CR¹²—S—CZ— | Bn | 1H-tetrazol-5-yl |
| 63 | | ethyl | Me | H | —CH—CR¹²—S—CZ— | nPr | SO₂NHCOPh |
| 64 | | ethyl | Me | H | —CH—CR¹²—S—CZ— | iBu | SO₂NHCOPh |
| 65 | | ethyl | Me | H | —CH—CR¹²—S—CZ— | nPn | SO₂NHCOPh |
| 66 | | ethyl | Me | H | —CH—CR¹²—S—CZ— | Bn | SO₂NHCOPh |
| 67 | | ethyl | Me | Me | —CH—CR¹²—S—CZ— | Me | 1H-tetrazol-5-yl |
| 68 | | n-butyl | Me | Me | —CH—CR¹²—S—CZ— | nBu | 1H-tetrazol-5-yl |
| 69 | | n-butyl | Me | Me | —CH—CR¹²—S—CZ— | iBu | 1H-tetrazol-5-yl |
| 70 | | n-butyl | Me | Me | —CH—CR¹²—S—CZ— | nPn | 1H-tetrazol-5-yl |
| 71 | | n-butyl | Me | Me | —CH—CR¹²—S—CZ— | nPr | SO₂NHCOPh |
| 72 | | n-butyl | Me | Me | —CH—CR¹²—S—CZ— | iBu | SO₂NHCOPh |
| 73 | | n-butyl | Me | Me | —CH—CR¹²—S—CZ— | nPn | SO₂NHCOPh |
| 74 | | ethyl | Me | Me | —CH—CR¹²—S—CZ— | nPr | 1H-tetrazol-5-yl |
| 75 | | ethyl | Me | Me | —CH—CR¹²—S—CZ— | iBu | 1H-tetrazol-5-yl |
| 76 | | ethyl | Me | Me | —CH—CR¹²—S—CZ— | nPn | 1H-tetrazol-5-yl |
| 77 | 104 | ethyl | Me | Me | —CH—CR¹²—S—CZ— | Me | SO₂NHCOPh |
| 78 | 105 | ethyl | Me | Me | —CH—CR¹²—S—CZ— | Et | SO₂NHCOPh |
| 79 | 106 | ethyl | Me | Me | —CH—CR¹²—S—CZ— | nPr | SO₂NHCOPh |
| 80 | 107 | ethyl | Me | Me | —CH—CR¹²—S—CZ— | nBu | SO₂NHCOPh |
| 81 | 72 | ethyl | Me | Me | —CH—CR¹²—S—CZ— | iBu | SO₂NHCOPh |
| 82 | 108 | ethyl | Me | Me | —CH—CR¹²—S—CZ— | nPn | SO₂NHCOPh |
| 83 | 109 | ethyl | Me | Me | —CH—CR¹²—S—CZ— | Bn | SO₂NHCOPh |
| 84 | 110 | ethyl | Me | Me | —CH—CR¹²—S—CZ— | CH₂N(CH₂CH₂)₂O | SO₂NHCOPh |
| 85 | 99 | ethyl | Me | Me | —CH—CR¹²—S—CZ— | CH₂N(CH₂CH₂)₂O | SO₂NHCOCH(Ph)₂ |
| 86 | | n-butyl | Me | CON(Me)₂ | —CH—CR¹²—S—CZ— | nPr | 1H-tetrazol-5-yl |
| 87 | | n-butyl | Me | CON(Me)₂ | —CH—CR¹²—S—CZ— | iBu | 1H-tetrazol-5-yl |
| 88 | | n-butyl | Me | CON(Me)₂ | —CH—CR¹²—S—CZ— | nPr | SO₂NHCOPh |
| 89 | | ethyl | Me | CON(Me)₂ | —CH—CR¹²—S—CZ— | nPr | 1H-tetrazol-5-yl |
| 90 | | ethyl | Me | CON(Me)₂ | —CH—CR¹²—S—CZ— | nBu | 1H-tetrazol-5-yl |
| 91 | | ethyl | Me | CON(Me)₂ | —CH—CR¹²—S—CZ— | iBu | 1H-tetrazol-5-yl |
| 92 | | ethyl | Me | CON(Me)₂ | —CH—CR¹²—S—CZ— | nPn | 1H-tetrazol-5-yl |
| 93 | | ethyl | Me | CON(Me)₂ | —CH—CR¹²—S—CZ— | nBu | SO₂NHCOPh |
| 94 | | ethyl | Me | CON(Me)₂ | —CH—CR¹²—S—CZ— | iBu | SO₂NHCOPh |
| 95 | | ethyl | Me | CON(Me)₂ | —CH—CR¹²—S—CZ— | Bn | SO₂NHCOPh |

TABLE VII-continued

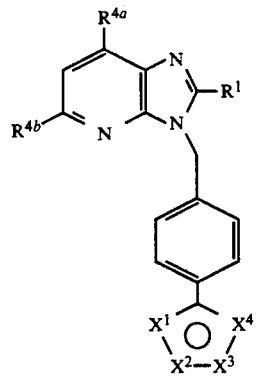

| # | EX # | R¹ | R⁴ᵃ | R⁴ᵇ | —X¹—X²—X³—X⁴— | R¹² | Z |
|---|---|---|---|---|---|---|---|
| 96 | | n-butyl | Me | CH₂OH | —CH—CR¹²—S—CZ— | nPr | 1H-tetrazol-5-yl |
| 97 | | n-butyl | Me | CH₂OH | —CH—CR¹²—S—CZ— | iBu | 1H-tetrazol-5-yl |
| 98 | | n-butyl | Me | CH₂OH | —CH—CR¹²—S—CZ— | nPr | SO₂NHCOPh |
| 99 | | n-butyl | Me | CH₂OH | —CH—CR¹²—S—CZ— | nPn | SO₂NHCOPh |
| 100 | | ethyl | Me | CH₂OH | —CH—CR¹²—S—CZ— | nBu | 1H-tetrazol-5-yl |
| 101 | | ethyl | Me | CH₂OH | —CH—CR¹²—S—CZ— | iBu | 1H-tetrazol-5-yl |
| 102 | | ethyl | Me | CH₂OH | —CH—CR¹²—S—CZ— | nPn | 1H-tetrazol-5-yl |
| 103 | 101 | ethyl | Me | Me | —CH—CR¹²—S—CZ— | nPr | SO₂NHCO(CH₂)₂OMe |
| 104 | | ethyl | Me | CH₂OH | —CH—CR¹²—S—CZ— | nBu | SO₂NHCOPh |
| 105 | | ethyl | Me | CH₂OH | —CH—CR¹²—S—CZ— | iBu | SO₂NHCOPh |
| 106 | | ethyl | Me | CH₂OH | —CH—CR¹²—S—CZ— | nPn | SO₂NHCOPh |
| 107 | | ethyl | Me | CO₂H | —CH—CR¹²—S—CZ— | nPr | SO₂NHCOPh |
| 108 | | propyl | Me | CO₂H | —CH—CR¹²—S—CZ— | nPr | SO₂NHCOPh |
| 109 | | propyl | Me | CO₂H | —CH—CR¹²—S—CZ— | iBu | SO₂NHCOPh |
| 110 | | propyl | Me | CO₂H | —CH—CR¹²—S—CZ— | nPn | SO₂NHCOPh |
| 111 | 74 | ethyl | Me | Me | —CH—CR¹²—S—CZ— | Me | SO₂NHCOCH₂Ph |
| 112 | 75 | ethyl | Me | Me | —CH—CR¹²—S—CZ— | Me | SO₂NHCOCH(Ph)₂ |
| 113 | 77 | ethyl | Me | Me | —CH—CR¹²—S—CZ— | Et | SO₂NHCOCH(Ph)₂ |
| 114 | 76 | ethyl | Me | Me | —CH—CR¹²—S—CZ— | Et | SO₂NHCOCH₂OEt |
| 115 | 85 | ethyl | Me | Me | —CH—CR¹²—S—CZ— | nBu | SO₂NHCOCH₂OEt |
| 116 | | propyl | Me | CO₂H | —CH—CR¹²—S—CZ— | nPn | SO₂NHCOCH₂OBu |
| 117 | | ethyl | Me | Me | —CH—CR¹²—S—CZ— | nPr | SO₂NHCOOCH₂CH(Me)₂ |
| 118 | 79 | ethyl | Me | Me | —CH—CR¹²—S—CZ— | nPr | SO₂NHCOCH₂OBu |
| 119 | | ethyl | Me | Me | —CH—CR¹²—S—CZ— | nPr | SO₂NHCOCH₂OEt |
| 120 | 82 | ethyl | Me | Me | —CH—CR¹²—S—CZ— | nBu | SO₂NHCO(CH₂)₂CycPen |
| 121 | | ethyl | Me | CH₂OH | —CH—CR¹²—S—CZ— | nPr | SO₂NHCOCH₂OEt |
| 122 | | ethyl | Me | CH₂OH | —CH—CR¹²—S—CZ— | iBu | SO₂NHCOCH₂OBu |
| 123 | | ethyl | Me | CO₂H | —CH—CR¹²—S—CZ— | iBu | SO₂NHCOCH₂OBu |
| 124 | 91 | ethyl | Me | Me | —CH—CR¹²—S—CZ— | iBu | SO₂NHCOCH₂OBu |
| 125 | 87 | ethyl | Me | Me | —CH—CR¹²—S—CZ— | iBu | SO₂NHCOCH₂OEt |
| 126 | 94 | ethyl | Me | Me | —CH—CR¹²—S—CZ— | nPn | SO₂NHCOCH₂OEt |
| 127 | 96 | ethyl | Me | Me | —CH—CR¹²—S—CZ— | nPn | SO₂NHCOCH₂OBu |
| 128 | 97 | ethyl | Me | Me | —CH—CR¹²—S—CZ— | nPn | SO₂NHCO₂-N-methylpyrrole |
| 129 | 80 | ethyl | Me | Me | —CH—CR¹²—S—CZ— | nPr | SO₂NHCO₂-N-methylpyrrole |
| 130 | 81 | ethyl | Me | Me | —CH—CR¹²—S—CZ— | nPr | SO₂NHCOOCH₂CH(Me)₂ |
| 131 | 100 | ethyl | Me | Me | —CH—CR¹²—S—CZ— | iBu | SO₂NHCOO(CH₂)₂OMe |
| 132 | | ethyl | Me | Me | —CH—CR¹²—S—CZ— | nPr | SO₂NHCOO(CH₂)₂OMe |
| 133 | | ethyl | Me | Me | —CH—CR¹²—S—CZ— | nBu | SO₂NHCOO(CH₂)₂OMe |
| 134 | 83 | ethyl | Me | Me | —CH—CR¹²—S—CZ— | nBu | SO₂NHCO(CH₂)₅NHBoc |
| 135 | 84 | ethyl | Me | Me | —CH—CR¹²—S—CZ— | nBu | SO₂NHCO(CH₂)₅NH₂ |
| 136 | 88 | ethyl | Me | Me | —CH—CR¹²—S—CZ— | iBu | SO₂NHCO(CH₂)₅NHBoc |
| 137 | 89 | ethyl | Me | Me | —CH—CR¹²—S—CZ— | iBu | SO₂NHCO(CH₂)₅NH₂ |
| 138 | 92 | ethyl | Me | Me | —CH—CR¹²—S—CZ— | nPn | SO₂NHCO(CH₂)₅NHBoc |
| 139 | 93 | ethyl | Me | Me | —CH—CR¹²—S—CZ— | nPn | SO₂NHCO(CH₂)₅NH₂ |
| 140 | | ethyl | Me | Me | —CH—CR¹²—S—CZ— | nPn | SO₂NHCO(CH₂)₄CH₃ |
| 141 | 103 | ethyl | Me | Me | —CH—CR¹²—S—CZ— | nPr | SO₂NHCO(CH₂)₄CH₃ |
| 142 | | ethyl | Me | Me | —CH—CR¹²—S—CZ— | nBu | SO₂NHCO(CH₂)₄CH₃ |
| 143 | | ethyl | Me | Me | —CH—CR¹²—S—CZ— | iBu | SO₂NHCO(CH₂)₄CH₃ |
| 144 | | ethyl | Me | Me | —CH—CR¹²—S—CZ— | nPr | SO₂NHCOcyPr |
| 145 | 98 | ethyl | Me | Me | —CH—CR¹²—S—CZ— | Bn | SO₂NHCOcyPr |
| 146 | | ethyl | Me | Me | —CH—CR¹²—S—CZ— | nPr | SO₂NHCO(CH₂)₂OMe |
| 147 | | ethyl | Me | CON(Me)₂ | —CH—CR¹²—S—CZ— | iBu | SO₂NHCOcyPr |
| 148 | 73 | ethyl | Me | Me | —CH—CR¹²—S—CZ— | nPr | SO₂NHCOOBu |
| 149 | 86 | ethyl | Me | Me | —CH—CR¹²—S—CZ— | nBu | SO₂NHCOOBu |
| 150 | 90 | ethyl | Me | Me | —CH—CR¹²—S—CZ— | iBu | SO₂NHCOOBu |
| 151 | | ethyl | Me | CO₂H | —CH—CR¹²—S—CZ— | nPr | SO₂NHCOOBu |
| 152 | 95 | ethyl | Me | Me | —CH—CR¹²—S—CZ— | nPn | SO₂NHCOOBu |
| 153 | | ethyl | Me | CO₂H | —CH—CR¹²—S—CZ— | nPn | SO₂NHCOOBu |
| 154 | | ethyl | Me | Me | —CH—CR¹²—S—CZ— | iBu | SO₂NHCOCH(Ph)₂ |

TABLE VII-continued

| # | EX # | $R^1$ | $R^{4a}$ | $R^{4b}$ | $-X^1-X^2-X^3-X^4-$ | $R^{12}$ | Z |
|---|---|---|---|---|---|---|---|
| 155 | 78 | ethyl | Me | Me | $-CH-CR^{12}-S-CZ-$ | nPr | $SO_2NHCOCH(Ph)_2$ |
| 156 |  | ethyl | Me | $CON(Me)_2$ | $-CH-CR^{12}-S-CZ-$ | iBu | $SO_2NHCOCH(Ph)_2$ |
| 157 | 102 | ethyl | Me | Me | $-CH-CR^{12}-S-CZ-$ | nPr | $SO_2NHCOCH_2OEt$ |

What is claimed is:

1. A compound of structural formula I:

Formula I or a pharmaceutically acceptable salt thereof wherein:
$R^1$ is:
 (a) $(C_1-C_6)$-alkyl, $(C_2-C_6)$-alkenyl or $(C_2-C_6)$-alkynyl each of which can be unsubstituted or substituted with a substituent selected from the group consisting of:
  i) aryl as defined below in $R^1$(b),
  ii) $(C_3-C_8)$-cycloalkyl,
  iii) Cl, Br, I, F,
  iv) OH,
  v) $NH_2$,
  vi) $NH[(C_1-C_4)\text{-alkyl}]$,
  vii) $N[((C_1-C_4)\text{-alkyl})]_2$,
  viii) $NHSO_2R^2$,
  ix) $CF_3$,
  x) $COOR^2$, or
  xi) $SO_2NHR^{2a}$;
 (b) aryl, wherein aryl is defined as phenyl or naphthyl, unsubstituted or substituted with 1 or 2 substituents selected from the group consisting of:
  i) Cl, Br, I, F,
  ii) $(C_1-C_4)$-alkyl,
  iii) $(C_1-C_4)$-alkoxy,
  iv) $NO_2$,
  v) $CF_3$
  vi) $SO_2NR^{2a}R^{2a}$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl;
 (c) heteroaryl, wherein heteroaryl is defined as a 5- or 6-membered heteroaromatic moiety, which can contain one or two members selected from the group consisting of N, O, S and wherein the heteroaryl is optionally mono- or disubstituted with substituents selected from the group consisting of:
  i) Cl, Br, I, F,
  ii) OH,
  iii) SH,
  iv) $NO_2$,
  v) $(C_1-C_4)$-alkyl,
  vi) $(C_2-C_4)$-alkenyl,
  vii) $(C_2-C_4)$-alkynyl,
  viii) $(C_1-C_4)$-alkoxy, or
  ix) $CF_3$,
 (d) polyfluoro-$(C_1-C_4)$-alkyl, or
 (e) $(C_3-C_8)$-cycloalkyl;
$-A^1-A^2-A^3-A^4-$ is:

(a) $-C(R^4)=C(R^4)-C(R^4)=C(R^4)-$, (b) $-C(R^4)=C(R^4)-C(R^4)=N-$, (c) $-N=C(R^4)-C(R^4)=C(R^4)-$, (d) $-C(R^4)=C(R^4)-N=C(R^4)-$,

-continued

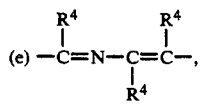(e)

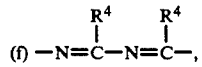(f)

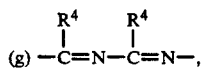(g)

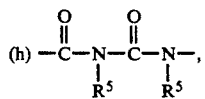(h)

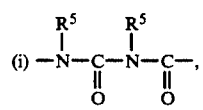(i)

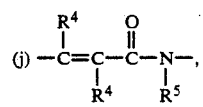(j)

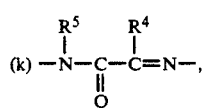(k)

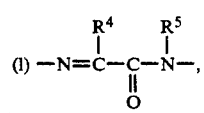(l)

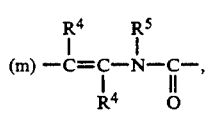(m)

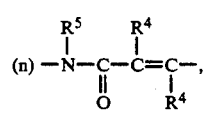(n)

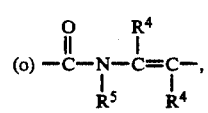(o)

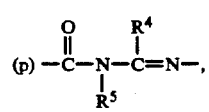(p)

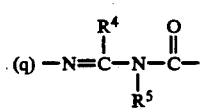(q)

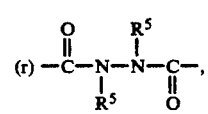(r)

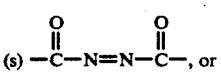(s), or

-continued

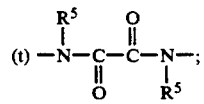(t)

E is:
- (a) a single bond,
- (b) —S(O)$_n$(CH$_2$)$_s$—, or
- (c) —O—;

n is 0 to 2;
s is 0 to 5;
R$^2$ is:
- (a) H, or
- (b) (C$_1$-C$_6$)-alkyl;

R$^{2a}$ is:
- (a) R$^2$,
- (b) CH$_2$-aryl, or
- (c) aryl;

R$^4$ groups are independently:
- (a) H,
- (b) (C$_1$-C$_6$)-alkyl, (C$_2$-C$_6$)-alkenyl, or (C$_2$-C$_6$)-alkynyl, each of which is unsubstituted or substituted with:
  - i) OH,
  - ii) (C$_1$-C$_4$)-alkoxy,
  - iii) CO$_2$R$^2$,
  - iv) OCOR$^2$,
  - v) CONHR$^2$,
  - vi) CON(R$^2$)$_2$,
  - vii) N(R$^2$)C(=O)R$^2$,
  - viii) NH$_2$,
  - ix) (C$_{1-C_4}$)-alkylamino,
  - x) di[(C$_1$-C$_4$)-alkyl]amino,
- (c) —C(=O)-aryl,
- (d) (C$_3$-C$_7$)-cycloalkyl,
- (e) Cl, Br, I, F,
- (f) —OH,
- (g) —OR$^{21}$,
- (h) -(C$_1$-C$_4$)-polyfluoroalkyl,
- (i) —SH,
- (j) —S(O)$_n$-(C$_1$-C$_4$)-alkyl,
- (k) —CO$_2$R$^{2a}$,
- (l) —SO$_3$H,
- (m) —NR$^2$R$^{21}$,
- (n) —NR$^2$C(=O)R$^{21}$,
- (o) —NR$^2$COOR$^{21}$,
- (p) —SO$_2$NR$^2$R$^{2a}$,
- (q) —NO$_2$,
- (r) —NHSO$_2$-(C$_1$-C$_4$)-alkyl,
- (s) —CO$_2$NH$_2$,
- (t) —CONHSO$_2$R$^{14}$,
- (u) 1H-tetrazol-5-yl,
- (v) aryl,
- (w) heteroaryl,
- (x) or morpholinyl, R$^5$ is:
- (a) H, or
- (b) (C$_1$-C$_6$)-alkyl or (C$_2$-C$_6$)-alkenyl, unsubstituted or substituted with:
  - i) hydroxy, or
  - ii) (C$_1$-C$_4$)-alkoxy;

R$^{5a}$ is
- (a) R$^5$, or
- (b) (C$_1$-C$_4$)-acyl;

—X$^1$—X$^2$—X$^3$—X$^4$— is:
- (a) —Y—CR$^{11}$—CR$^{12}$—CZ—, (b) —CR$^{11}$—Y—CR$^{12}$—CZ—,
(c) —CR$^{11}$—CR$^{12}$—Y—CZ—,
(d) —Y—CR$^{11}$—CZ—CR$^{12}$—,
(e) —CR$^{11}$—Y—CZ—CR$^{12}$—, or
(f) —CR$^{11}$—CR$^{12}$—CZ—Y—;

Y is: O, S, SO, or SO$_2$;

R$^9$ and R$^{10}$ are each independently:
(a) H,
(b) Cl, Br, I, F,
(c) NO$_2$,
(d) (C$_1$-C$_6$)-alkyl,
(e) (C$_1$-C$_6$)-acyloxy,
(f) (C$_3$-C$_6$)-cycloalkyl,
(g) (C$_1$-C$_6$)-alkoxy,
(h) —NHSO$_2$R$^{2a}$,
(i) hydroxy-(C$_1$-C$_4$)-alkyl,
(j) (C$_1$-C$_4$)-alkyl-aryl,
(k) S(O)$_n$-(C$_1$-C$_4$)-alkyl,
(n) NR$^{2a}$R$^{2a}$,
(q) CF$_3$,
(r) —SO$_2$NHR$^{2a}$,
(s) furyl,
(t) aryl, wherein aryl is phenyl or naphthyl unsubstituted or substituted with one or two substituents selected from the group consisting of: Cl, Br, I, F, (C$_1$-C$_4$)-alkyl, (C$_1$-C$_4$)-alkoxy, NO$_2$, CF$_3$, (C$_1$-C$_4$)-alkylthio, OH, NH$_2$, —NH[(C$_1$-C$_4$)-alkyl], —N[(C$_1$-C$_4$)-alkyl]$_2$, —CO$_2$H, or —CO$_2$-(C$_1$-C$_4$)-alkyl; or
(u) when R$^9$ and R$^{10}$ are bonded to adjacent carbon atoms, they can be joined to form an aryl ring;

R$^{11}$ and R$^{12}$ are independently:
(a) H,
(b) Cl, Br, I, F,
(c) NO$_2$,
(d) NH$_2$,
(e) NH[(C$_1$-C$_4$)-alkyl],
(f) N[(C$_1$-C$_4$)-alkyl]$_2$,
(g) SO$_2$NHR$^{2a}$,
(h) CF$_3$,
(i) (C$_1$-C$_7$)-alkyl,
(j) (C$_1$-C$_7$)-alkoxy,
(k) (C$_3$-C$_7$)-cycloalkyl,
(l) when R$^{11}$ and R$^{12}$ are bonded to adjacent carbon atoms, they can be joined to form an aryl ring,
(m) O(CH$_2$)$_{n+1}$O(CH$_2$)$_s$CH$_3$,
(n) (CH$_2$)$_{n+1}$O(CH$_2$)$_s$CH$_3$,
(o) (CH$_2$)N(R$^{2a}$)$_2$,
(p) (CH$_2$)$_n$N[CH$_2$CH$_2$]$_2$X,
(q) (CH$_2$)$_n$N[CH$_2$CH$_2$]$_2$CH$_2$,
(r) CH(OR$^{2a}$)[(C$_1$-C$_7$)-alkyl],
(s) CHO,
(t) CO$_2$R$^{2a}$,
(u) CH=CHR$^{2a}$,
(v) CH$_2$CR$^{2a}$=C(R$^{2a}$)$_2$,
(w) (CH$_2$)$_n$NCOR$^{2a}$,
(x) CH(R$^{2a}$)$_2$, or
(y) (C$_1$-C$_4$)-alkyl-aryl;

X is: —O—, —S—, or —NR$^{2a}$—;

Z is:
(a) —CO$_2$R$^{2a}$,
(b) —SO$_3$R$^{13}$,
(c) —NHSO$_2$CF$_3$,
(d) —PO(OR$^{13}$)$_2$,
(e) —SO$_2$NHR$^{14}$,
(f) —CONHOR$^{13}$,

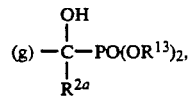

(h) —CN,
(i) —NHSO$_2$R$^{14}$,
(j) —CH$_2$SO$_2$NH-heteroaryl, wherein heteroaryl is an unsubstituted, monosubstituted or disubstituted five or six membered aromatic ring which can optionally contain from 1 to 3 heteroatoms selected from the group consisting of O, N or S and wherein the substituents are members selected from the group consisting of —OH, —SH, -(C$_1$-C$_4$)-alkyl, -(C$_1$-C$_4$)-alkoxy, —CF$_3$, Cl, Br, F, I, —NO$_2$, —CO$_2$H, —CO$_2$-C$_1$-C$_4$-alkyl, —NH$_2$, NH[(C$_1$-C$_4$)-alkyl] and —N[(C$_1$-C$_4$-alkyl]$_2$,
(k) —SO$_2$NH—CO—R$^{14}$,
(l) —CH$_2$SO$_2$NH—CO—R$^{14}$,
(m) —CONH—SO$_2$R$^{14}$,
(n) —CH$_2$CONH—SO$_2$R$^{14}$,
(o) —NHSO$_2$NHCO—R$^{14}$,
(p) —NHCONHSO$_2$—R$^{14}$,

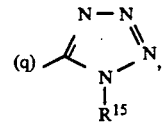

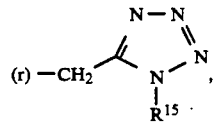

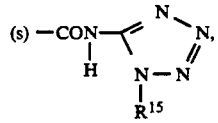

(t) —CONHNHSO$_2$CF$_3$,

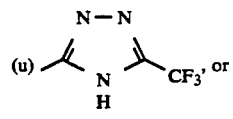

R$^{13}$ is H, or

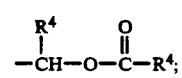

R$^{14}$ is
(a) aryl,
(b) heteroaryl,
(c) (C$_3$-C$_7$)-cycloalkyl, or (d) ($C_1$-$C_7$)-alkyl, unsubstituted or substituted with a substituent selected from the group consisting of: aryl, heteroaryl, —OH, —SH, ($C_1$-$C_4$)-alkyl, —($C_1$-$C_6$)-alkoxy, —S($C_1$-$C_6$)-alkyl, ($C_3$-$C_7$)-cycloalkyl, —$CF_3$, Cl, Br, F, I, —$NO_2$, —$CO_2H$, $CO_2$—($C_1$-$C_4$)-alkyl, —$NH_2$, —N[($C_1$-$C_4$)-alkyl]$_2$, —$PO_3H$ or PO(OH)(O—($C_1$-$C_4$)-alkyl),
(e) ($C_1$-$C_7$)-alkoxy,
(f) $O(CH_2)_{n+1}O(CH_2)_5CH_3$,
(g) $(CH_2)_{n+1}O(CH_2)_5CH_3$,
(h) $CH(R^{2a})_2$,
(i) ($C_1$-$C_6$)-polyfluoroalkyl, or
(j) NH($C_1$-$C_6$)-alkyl;

$R^{15}$ is H, ($C_1$-$C_6$)-alkyl, ($C_2$-$C_4$)-alkenyl, ($C_1$-$C_4$)-alkoxy, or benzyl, wherein the phenyl moiety is unsubstituted or substituted with a substituent selected from the group consisting of: —$NO_2$, —$NH_2$, —OH or —$OCH_3$;

$R^{17}$ is —CN, —$NO_2$, —$CO_2R^{2a}$, or —$CF_3$;

$R^{21}$ is:
(a) H, or
(b) ($C_1$-$C_4$)-alkyl unsubstituted or substituted with:
  i) $NH_2$,
  ii) NH[($C_1$-$C_4$)-alkyl],
  iii) N[($C_1$-$C_4$)-alkyl]$_2$,
  iv) $CO_2H$,
  v) $CO_2$($C_1$-$C_4$)-alkyl,
  vi) OH,
  vii) $SO_3H$,
  viii) $SO_2NH_2$, or
  ix) aryl; or
(c) aryl, with the proviso that when —$A^1$—$A^2$—$A^3$—$A^4$— is —C(Me)=CH—C(Me)=N, E is a single bond, $R^1$ is ethyl —$X^1$—$X^2$—$X^3$—$X^4$— is —CH—$CR^{11}$—S—CZ—, $R^{11}$ is n-butyl, or isobutyl and Z is $SO_2NHCOR^{14}$, then $R^{14}$ cannot be O—n—$C_4H_9$ or $CH_2O$—n—$C_4H_9$.

2. The compound of claim 1 or the pharmaceutically acceptable salt wherein:

$R^1$ is:
(a) ($C_1$-$C_6$)-alkyl, ($C_2$-$C_6$)-alkenyl or ($C_2$-$C_6$)-alkynyl each of which can be unsubstituted or substituted with a substituent selected from the group consisting of:
  i) aryl as defined below in $R^1$(b),
  ii) ($C_3$-$C_8$)-cycloalkyl,
  iii) Cl, Br, I, F,
  iv) OH,
  v) $NH_2$,
  vi) NH[($C_1$-$C_4$)-alkyl],
  vii) N[(($C_1$-$C_4$)-alkyl)]$_2$,
  viii) $NHSO_2R^2$,
  ix) $CF_3$,
  x) $COOR^2$, or
  xi) $SO_2NHR^{2a}$;
(b) aryl, wherein aryl is defined as phenyl or naphthyl, unsubstituted or substituted with 1 or 2 substituents selected from the group consisting of:
  i) Cl, Br, I, F,
  ii) ($C_1$-$C_4$)-alkyl,
  iii) ($C_1$-$C_4$)-alkoxy,
  iv) $NO_2$
  v) $CF_3$
  vi) $SO_2NR^{2a}R^{2a}$,
  vii) ($C_1$-$C_4$)-alkylthio,
  viii) hydroxy,
  ix) amino,
  x) ($C_3$-$C_7$)-cycloalkyl, or
  xi) ($C_3$-$C_{10}$)-alkenyl,
(c) polyfluoro-($C_1$-$C_4$)-alkyl, or
(d) ($C_3$-$C_8$)-cycloalkyl;

—$A^1$—$A^2$—$A^3$—$A^4$— is:

(a) 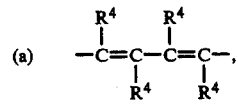

(b) 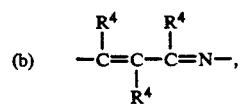

(c) 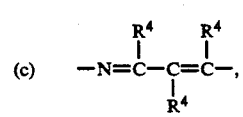

(d) 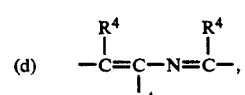

(e) 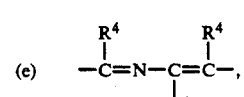

(f) 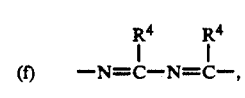

or (g) ;

$R^2$ is:
(a) H, or
(b) ($C_1$-$C_6$)-alkyl;

$R^{2a}$ is:
(a) $R^2$,
(b) $CH_2$-aryl, or
(c) aryl;

$R^4$ groups are independently:
(a) H,
(b) ($C_1$-$C_6$)-alkyl, ($C_2$-$C_6$)-alkenyl, or ($C_2$-$C_6$)-alkynyl, each of which is unsubstituted or substituted with:
  i) OH,
  ii) ($C_1$-$C_4$)-alkoxy,
  iii) $CO_2R^2$,
  iv) $OCOR^2$,
  v) $CONHR^2$,
  vi) $CON(R^2)_2$,
  vii) $N(R^2)C(=O)R^2$,
  viii) $NH_2$,
  ix) ($C_1$-$C_4$)-alkylamino,
  x) di[($C_1$-$C_4$)-alkyl]amino,
(c) ($C_3$-$C_7$)-cycloalkyl,
(d) Cl, Br, I, F,
(e) —$OR^{21}$,
(f) —($C_1$-$C_4$)-polyfluoroalkyl,
(g) —S(O)$_n$—($C_1$-$C_4$)-alkyl,
(h) —$CO_2R^{2a}$, (i) —NR$^2$R$^{21}$,
(j) —NR$^2$C(=O)R$^{21}$,
(k) —NR$^2$COOR$^{21}$,
(l) —SO$_2$NR$^2$R$^{2a}$, or
(m) —NHSO$_2$—(C$_1$-C$_4$)-alkyl;
(n) —CO$_2$NH$_2$,
(o) —CONHSO$_2$R$^{14}$,
(p) -1H-tetrazol-5-yl,
(q) -aryl,
(r) -heteroaryl, wherein heteroaryl is an unsubstituted, monosubstituted or disubstituted five or six membered aromatic ring which can optionally contain from 1 to 3 heteroatoms selected from the group consisting of O, N or S and wherein the substituents are members selected from the group consisting of —OH, —SH, —(C$_1$-C$_4$)-alkyl, —(C$_1$-C$_4$)-alkoxy, —CF$_3$, Cl, Br, F, I, —NO$_2$, —CO$_2$H, —CO$_2$—(C$_1$-C$_4$)-alkyl, —NH$_2$, NH[(C$_1$-C$_4$)-alkyl] and —N[(C$_1$-C$_4$)-alkyl]$_2$,
(s) or -morpholinyl, R$^5$ is:
(a) H, or
(b) (C$_1$-C$_6$)-alkyl or (C$_2$-C$_6$)-alkenyl, unsubstituted or substituted with:
i) hydroxy, or
ii) (C$_1$-C$_4$)-alkoxy;

R$^{5a}$ is
(a) R$^5$, or
(b) (C$_1$-C$_4$)-acyl;

—X$^1$—X$^2$—X$^3$—X$^4$— is:
(a) —Y—CR$^{11}$—CR$^{12}$—CZ—,
(b) —CR$^{11}$—Y—CR$^{12}$—CZ—,
(c) —CR$^{11}$—CR$^{12}$—Y—CZ—,
(d) —Y—CR$^{11}$—CZ—CR$^{12}$—,
(e) —CR$^{11}$—Y—CZ—CR$^{12}$—, or
(f) —CR$^{11}$—CR$^{12}$—CZ—Y—;

Y is: O, or S;

R$^9$ and R$^{10}$ are each independently:
(a) H,
(b) Cl, Br, I, F,
(c) (C$_1$-C$_6$)-alkyl,
(d) (C$_3$-C$_6$)-cycloalkyl,
(e) (C$_1$-C$_6$)-alkoxy,
(f) —NHSO$_2$R$^{2a}$,
(g) S(O)$_n$—(C$_1$-C$_4$)-alkyl,
(h) NR$^{2a}$R$^{2a}$,
(i) CF$_3$,
(j) —SO$_2$NHR$^{2a}$,
(k) when R$^9$ and R$^{10}$ are bonded to adjacent carbon atoms, they can be joined to form an aryl ring;

R$^{11}$ and R$^{12}$ are independently:
(a) H,
(b) Cl, Br, I, F,
(c) NO$_2$,
(d) NH$_2$,
(e) NH[(C$_1$-C$_4$)-alkyl],
(f) N[(C$_1$-C$_4$)-alkyl]$_2$,
(g) SO$_2$NHR$^{2a}$,
(h) CF$_3$,
(i) (C$_1$-C$_6$)-alkyl,
(j) (C$_1$-C$_6$)-alkoxy,
(k) (C$_3$-C$_7$)-cycloalkyl,
(l) when R$^{11}$ and R$^{12}$ are bonded to adjacent carbon atoms, they can be joined to form an aryl ring,
(m) O(CH$_2$)$_{n+1}$O(CH$_2$)$_s$CH$_3$,
(n) (CH$_2$)$_{n+1}$O(CH$_2$)$_s$CH$_3$,
(o) (CH$_2$)N(R$^{2a}$)$_2$,
(p) (CH$_2$)$_n$N[CH$_2$CH$_2$]$_2$X,
(q) (CH$_2$)$_n$N[CH$_2$CH$_2$]$_2$CH$_2$,
(r) CH(OR$^{2a}$)[(C$_1$-C$_7$)-alkyl],
(s) CHO,
(t) CO$_2$R$^{2a}$,
(u) CH=CHR$^{2a}$,
(v) CH$_2$CR$^{2a}$=C(R$^{2a}$)$_2$,
(w) (CH$_2$)$_n$NCOR$^{2a}$,
(x) CH(R$^{2a}$)$_2$, or
(y) (C$_1$-C$_4$)-alkyl-aryl;

Z is:
(a) —CO$_2$R$^{2a}$,
(b) —NHSO$_2$CF$_3$,
(c) —SO$_2$NHR$^{14}$,
(d) —CN,
(e) —NHSO$_2$R$^{14}$,
(f) -1H-tetrazol-5-yl,
(g) —CH$_2$-1H-tetrazol-5-yl,
(h) —CONH- 1H-tetrazol-5-yl, or
(i) —SO$_2$NHCOR$^{14}$;

R$^{21}$:
(a) H, or
(b) (C$_1$-C$_4$)-alkyl unsubstituted or substituted with:
i) NH$_2$,
ii) NH[(C$_1$-C$_4$)-alkyl],
iii) N[(C$_1$-C$_4$)-alkyl]$_2$,
iv) CO$_2$H,
v) CO$_2$(C$_1$-C$_4$)-alkyl,
vi) OH,
vii) SO$_3$H,
viii) SO$_2$NH$_2$, or
ix) aryl; or
(c) aryl.

3. The compound of claim 2 or the pharmaceutically acceptable salt wherein:

R$^1$ is:
(a) (C$_1$-C$_6$)-alkyl or (C$_2$-C$_6$)-alkenyl each of which can be unsubstituted or substituted with a substituent selected from the group consisting of:
i) (C$_3$-C$_8$)-cycloalkyl,
ii) Cl, Br, I, F,
iii) OH,
iv) NH$_2$,
v) NH[(C$_1$-C$_4$)-alkyl],
vi) N[((C$_1$-C$_4$)-alkyl)]$_2$,
vii) CF$_3$, or
viii) COOR$^2$, or
(b) (C$_3$-C$_8$)-cycloalkyl;

—A$^1$—A$^2$—A$^3$—A$^4$— is:

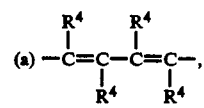

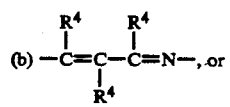

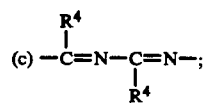

R$^2$ is:
(a) H, or
(b) (C$_1$-C$_6$)-alkyl;

$R^{2a}$ is:
- (a) $R^2$,
- (b) $CH_2$-aryl, or
- (c) aryl;

$R^4$ groups are independently:
- (a) H,
- (b) $(C_1-C_4)$-alkyl, $(C_2-C_6)$-alkenyl, or $(C_2-C_4)$-alkynyl, each of which is unsubstituted or substituted with:
  - i) OH,
  - ii) $(C_1-C_4)$-alkoxy,
  - iii) $CO_2R^2$,
  - iv) $OCOR^2$,
  - v) $CONHR^2$,
  - vi) $CON(R^2)_2$,
  - vii) $N(R^2)C(=O)R^2$,
  - viii) $NH_2$,
  - ix) $(C_1-C_4)$-alkylamino,
  - x) di[$(C_1-C_4)$-alkyl]amino,
- (c) $(C_3-C_7)$-cycloalkyl,
- (d) Cl, Br, I, F,
- (e) $-OR^{21}$,
- (f) $-(C_1-C_4)$-polyfluoroalkyl,
- (g) $-S(O)_n-(C_1-C_4)$-alkyl,
- (h) $-CO_2R^{2a}$,
- (i) $-NR^2R^{21}$,
- (j) $-NR^2C(=O)R^{21}$,
- (k) $-NR^2COOR^{21}$,
- (l) $-SO_2NR^2R^{2a}$, or
- (m) $-NHSO_2-(C_1-C_4)$-alkyl;
- (n) $-CO_2NH_2$,
- (o) $-CONHSO_2R^{14}$,
- (p) -1H-tetrazol-5-yl,
- (q) -aryl,
- (r) -heteroaryl,
- (s) or -morpholinyl, $R^5$ is:
- (a) H, or
- (b) $(C_1-C_6)$-alkyl or $(C_2-C_6)$-alkenyl, unsubstituted or substituted with:
  - i) hydroxy, or
  - ii) $(C_1-C_4)$-alkoxy;

$R^{5a}$ is:
- (a) $R^5$, or
- (b) $(C_1-C_4)$-acyl;

$-X^1-X^2-X^3-X^4-$ is:
- (a) $-Y-CR^{11}=CR^{12}-CZ-$,
- (b) $-CR^{11}=Y-CR^{12}=CZ-$,
- (c) $-CR^{11}=CR^{12}-Y-CZ-$,
- (d) $-Y-CR^{11}=CZ-CR^{12}-$,
- (e) $-CR^{11}=Y-CZ=CR^{12}-$, or
- (f) $-CR^{11}=CR^{12}-CZ-Y-$;

Y is: O or S;
n is: 0 to 2;

$R^{11}$ and $R^{12}$ are independently:
- (a) H,
- (b) Cl, Br, I, F,
- (c) $NH_2$,
- (d) $NH[(C_1-C_4)$-alkyl],
- (e) $NH[(C_1-C_4)$-alkyl]$_2$,
- (f) $SO_2NHR^{2a}$,
- (g) $CF_3$,
- (h) $(C_1-C_6)$-alkyl,
- (i) $(C_1-C_6)$-alkoxy,
- (j) $(C_3-C_7)$-cycloalkyl,
- (k) when $R^{11}$ and $R^{12}$ are bonded to adjacent carbon atoms, they can joined to form a phenyl ring,
- (l) $(CH_2)_n[CH_2CH_2]_2X$, or
- (m) $(C_1-C_4)$-alkyl-aryl;

Z is:
- (a) $-CO_2R^{2a}$,
- (b) $-NHSO_2CF_3$,
- (c) $-SO_2NHR^{14}$,
- (d) -1H-tetrazol-5-yl,
- (e) $-SO_2NHCOR^{14}$, or
- (f) $-NHSO_2R^{14}$;

$R^{21}$ is:
- (a) H, or
- (b) $(C_1-C_4)$-alkyl unsubstituted or substituted with:
  - i) $NH_2$,
  - ii) $NH[(C_1-C_4)$-alkyl],
  - iii) $N[(C_1-C_4)$-alkyl]$_2$,
  - iv) $CO_2H$,
  - v) $CO_2(C_1-C_4)$-alkyl,
  - vi) OH,
  - vii) $SO_3H$,
  - viii) $SO_2NH_2$, or
  - ix) aryl; or
- (c) aryl.

4. The compound of claim 3 or the pharmaceutically acceptable salt of structural formula

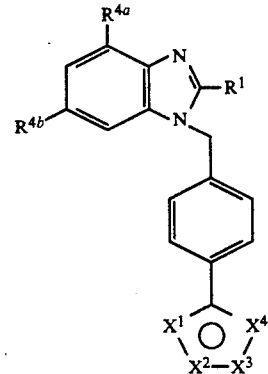

wherein:
$R^1$ is
- (a) $(C_1-C_6)$-alkyl,
- (b) $(C_3-C_8)$-cycloalkyl, or
- (c) $-(C_1-C_4)$-alkyl-$(C_3-C_8)$-cycloalkyl;

$R^{4a}$ is:
- (a) H,
- (b) $(C_1-C_4)$-alkyl,
- (c) $(C_1-C_4)$-polyfluoroalkyl,
- (d) $(C_1-C_3)$-alkoxyl,
- (e) $(C_1-C_3)$-alkylthio,
- (f) $(C_3-C_8)$-cycloalkyl, or
- (g) F, Cl;

$R^{4b}$ is:
- (a) $R^{4a}$,
- (b) $(C_1-C_6)$-alkyl, $(C_2-C_6)$-alkenyl, substituted with a substituent selected from the group consisting of:
  - i) $CO_2R^2$,
  - ii) aryl, or
  - iii) heteroaryl,
- (c) $-OH$,
- (d) $-CO_2R^{2a}$,
- (e) $-NR^2R^{21}$,
- (f) $-CO_2NH_2$,
- (g) $-CONHSO_2R^{14}$,
- (h) 1H-tetrazol-5-yl, (i) aryl,
(k) heteroaryl, or
(l) morpholin-4-yl;

$—X^1—X^2—X^3—X^4—$ is:
(a) $—Y—CR^{11}—CR^{12}—CZ—$,
(b) $—CR^{11}—Y—CR^{12}—CZ—$, or
(c) $—CR^{11}—CR^{12}—Y—CZ—$;

Y is: O, or S;

$R^{11}$ and $R^{12}$ are independently: H, $C_1$-$C_6$-alkyl, $C_1$-$C_6$-alkoxy, ($C_1$-$C_4$)-alkyl-aryl, $O(CH_2)_{n+1}O(CH_2)_sCH_3$, $(CH_2)_{n+1}O(CH_2)_sCH_3$, $(CH_2)_nN[CH_2CH_2]_2X$ or when $R^{11}$ and $R^{12}$ are bonded to adjacent carbon atoms, they can joined to form an phenyl ring;

$R^{14}$ is:
(a) aryl,
(b) heteroaryl,
(c) ($C_3$-$C_7$)-cycloalkyl,
(d) ($C_1$-$C_6$)-alkyl, unsubstituted or substituted with a substituent selected from the group consisting of: aryl, heteroaryl, —OH, —SH, ($C_1$-$C_4$)-alkyl, —($C_1$-$C_6$)-alkoxy, —$S(C_1$-$C_6$)-alkyl, ($C_3$-$C_7$)-cycloalkyl, —$CF_3$, Cl, Br, F, I, —$CO_2H$, $CO_2$—($C_1$-$C_4$)-alkyl, —$NH_2$, —$N[(C_1$-$C_4$)-alkyl]_2$,
(e) ($C_1$-$C_6$)-alkoxy,
(f) $O(CH_2)_{n+1}O(CH_2)_sCH_3$,
(g) $(CH_2)_{n+1}O(CH_2)_sCH_3$,
(h) $CH(R^{2a})_2$,
(i) ($C_1$-$C_6$)-polyfluoroalkyl, or
(j) $NH(C_1$-$C_6$)-alkyl; and Z is:
(a) $CO_2R^2$,
(b) 1H-tetrazol-5-yl,
(c) $CONHSO_2R^{14}$,
(d) $SO_2NHR^{14}$,
(e) $NHSO_2R^{14}$,
(f) $SO_2NHCOR^{14}$, or
(g) $NHSO_2CF_3$.

5. The compound of claim 3 or the pharmaceutically acceptable salt of structural formula

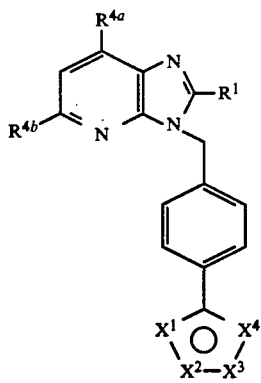

wherein:
$R^1$ is
(a) ($C_1$-$C_6$)-alkyl,
(b) ($C_3$-$C_8$)-cycloalkyl, or
(c) ($C_1$-$C_4$)-alkyl-($C_3$-$C_8$)-cycloalkyl;

$R^{4a}$ is:
(a) H,
(b) ($C_1$-$C_4$)-alkyl,
(c) ($C_1$-$C_4$)-polyfluoroalkyl,
(d) ($C_1$-$C_3$)-alkoxyl,
(e) ($C_1$-$C_3$)-alkylthio,
(f) ($C_3$-$C_8$)-cycloalkyl, or
(g) F, Cl;

$R^{4b}$ is:
(a) $R^{4a}$,
(b) ($C_1$-$C_6$)-alkyl, ($C_2$-$C_6$)-alkenyl, substituted with a substituent selected from the group consisting of:
 i) $CO_2R^2$,
 ii) aryl, or
 iii) heteroaryl,
(c) —OH,
(d) —$CO_2R^{2a}$
(e) —$NR^2R^{21}$,
(f) —$CO_2NH_2$,
(g) —$CONHSO_2R^{14}$,
(h) 1H-tetrazol-5-yl,
(i) aryl,
(j) heteroaryl, or
(k) morpholin-4-yl;

$—X^1—X^2—X^3—X^4—$ is:
(a) $—Y—CR^{11}—CR^{12}—CZ—$,
(b) $—CR^{11}—Y—CR^{12}—CZ—$, or
(c) $—CR^{11}—CR^{12}—Y—CZ—$;

Y is: O, or S;

$R^{11}$ and $R^{12}$ are independently: H, $C_1$-$C_6$-alkyl, $C_1$-$C_6$-alkoxy, ($C_1$-$C_4$)-alkyl-aryl, $O(CH_2)_{n+1}O(CH_2)_sCH_3$, $(CH_2)_{n+1}O(CH_2)_sCH_3$, $(CH_2)_nN[CH_2CH_2]_2O$ or when $R^{11}$ and $R^{12}$ are bonded to adjacent carbon atoms, they can joined to form a phenyl ring;

$R^{14}$ is:
(a) aryl,
(b) heteroaryl,
(c) ($C_3$-$C_7$)-cycloalkyl,
(d) ($C_1$-$C_6$)-alkyl, unsubstituted or substituted with a substituent selected from the group consisting of: aryl, heteroaryl, —OH, —SH, ($C_1$-$C_4$)-alkyl, —($C_1$-$C_6$)-alkoxy, —$S(C_1$-$C_6$)-alkyl, ($C_3$-$C_7$)-cycloalkyl, —$CF_3$, Cl, Br, F, I, —$CO_2H$, $CO_2$—($C_1$-$C_4$)-alkyl, —$NH_2$, —$N[(C_1$-$C_4$)-alkyl]_2$,
(e) ($C_1$-$C_6$)-alkoxy,
(f) $O(CH_2)_{n+1}O(CH_2)_sCH_3$,
(g) $(CH_2)_{n+1}O(CH_2)_sCH_3$,
(h) $CH(R^{2a})_2$,
(i) ($C_1$-$C_6$)-polyfluoroalkyl, or
(j) $NH(C_1$-$C_6$)-alkyl; and Z is:
(a) $CO_2R^2$,
(b) 1H-tetrazol-5-yl,
(c) $CONHSO_2R^{14}$,
(d) $SO_2NHR^{14}$,
(e) $NHSO_2R^{14}$,
(f) $SO_2NHCOR^{14}$, or
(g) $NHSO_2CF_3$.

6. The compound of claim 3 or the pharmaceutically acceptable salt of structural formula

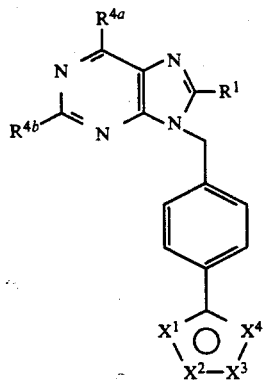

wherein:
R¹ is:
(a) ($C_1$–$C_6$)-alkyl,
(b) ($C_3$–$C_8$)-cycloalkyl, or
(c) ($C_1$–$C_4$)-alkyl-($C_3$–$C_8$)-cycloalkyl;
$R^{4a}$ is:
(a) H,
(b) ($C_1$–$C_4$)-alkyl,
(c) ($C_1$–$C_4$)-polyfluoroalkyl,
(d) ($C_1$–$C_3$)-alkoxyl,
(e) ($C_1$–$C_3$)-alkylthio,
(f) ($C_3$–$C_8$)-cycloalkyl, or
(g) F, Cl;
$R^{4b}$ is:
(a) $R^{4a}$,
(b) ($C_1$–$C_6$)-alkyl, ($C_2$–$C_6$)-alkenyl, substituted with a substituent selected from the group consisting of:
i) $CO_2R^2$,
ii) aryl, or
iii) heteroaryl,
(c) —OH,
(d) —$CO_2R^{2a}$,
(e) —$NR^2R^{21}$,
(f) —$CO_2NH_2$,
(g) —$CONHSO_2R^{14}$,
(h) 1H-tetrazol-5-yl,
(i) aryl,
(j) heteroaryl, or
(k) morpholin-4-yl;
—$X^1$—$X^2$—$X^3$—$X^4$— is:
(a) —Y—$CR^{11}$—$CR^{12}$—CZ—,
(b) —$CR^{11}$—Y—$CR^{12}$—CZ—, or
(c) —$CR^{11}$—$CR^{12}$—Y—CZ—;
Y is: O, or S;
$R^{11}$ and $R^{12}$ are independently: H, $C_1$–$C_6$-alkyl, $C_1$–$C_6$-alkoxy, ($C_1$–$C_4$)-alkyl-aryl, $O(CH_2)_{n+1}O(CH_2)_sCH_3$, $(CH_2)_{n+1}O(CH_2)_sCH_3$, $(CH_2)_nN[CH_2CH_2]_2X$ or when $R^{11}$ and $R^{12}$ are bonded to adjacent carbon atoms, they can joined to form an phenyl ring;
$R^{14}$ is:
(a) aryl,
(b) heteroaryl,
(c) ($C_3$–$C_7$)-cycloalkyl,
(d) ($C_1$–$C_6$)-alkyl, unsubstituted or substituted with a substituent selected from the group consisting of: aryl, heteroaryl, —OH, —SH, ($C_1$–$C_4$)-alkyl, —($C_1$–$C_6$)-alkoxy, —S($C_1$–$C_6$)-alkyl, ($C_3$–$C_7$)-cycloalkyl, —$CF_3$, Cl, Br, F, I, —$CO_2H$, $CO_2$—($C_1$–$C_4$)-alkyl, —$NH_2$, —N[($C_1$–$C_4$)-alkyl]$_2$, (e) ($C_1$–$C_6$)-alkoxy,
(f) $O(CH_2)_{n+1}O(CH_2)_sCH_3$,
(g) $(CH_2)_{n+1}O(CH_2)_sCH_3$,
(h) $CH(R^{2a})_2$,
(i) ($C_1$–$C_6$)-polyfluoroalkyl, or
(j) NH($C_1$–$C_6$)-alkyl; and
Z is:
(a) $CO_2R^2$,
(b) 1H-tetrazol-5-yl,
(c) $CONHSO_2R^{14}$,
(d) $SO_2NHR^{14}$,
(e) $NHSO_2R^{14}$,
(f) $SO_2NHCOR^{14}$, or
(g) $NHSO_2CF_3$.

7. The compound of claim 3 or the pharmaceutically acceptable salt of structural formula

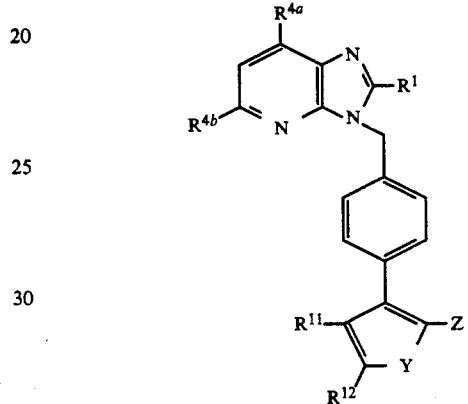

wherein:
R¹ is:
(a) ($C_1$–$C_6$)-alkyl,
(b) ($C_3$–$C_8$)-cycloalkyl, or
(c) ($C_1$–$C_4$)-alkyl-($C_3$–$C_8$)-cycloalkyl;
$R^{4a}$ is:
(a) H,
(b) ($C_1$–$C_4$)-alkyl,
(c) ($C_1$–$C_4$)-polyfluoroalkyl,
(d) ($C_1$–$C_3$)-alkoxyl,
(e) ($C_1$–$C_3$)-alkylthio,
(f) ($C_3$–$C_8$)-cycloalkyl, or
(g) F, Cl;
$R^{4b}$ is:
(a) $R^{4a}$,
(b) ($C_1$–$C_6$)-alkyl, ($C_2$–$C_6$)-alkenyl, substituted with a substituent selected from the group consisting of:
i) $CO_2R^2$,
ii) aryl, or
iii) heteroaryl,
(c) —OH,
(d) —$CO_2R^{2a}$,
(e) —$NR^2R^{21}$,
(f) —$CO_2NH_2$,
(g) —$CONHSO_2R^{14}$,
(h) 1H-tetrazol-5-yl,
(i) aryl,
(k) heteroaryl, or
(l) morpholin-4-yl;
$R^{11}$ is: H or $R^{11}$ and $R^{12}$ can joined to form an phenyl ring;

R[12] is: H, ($C_1$-$C_6$)-alkyl, ($C_1$-$C_6$)-alkoxy, —$CH_2$-aryl, $O(CH_2)_{n+1}O(CH_2)_sCH_3$, $(CH_2)_{n+1}O(CH_2)_sCH_3$, or $CH_2N[CH_2CH_2]_2O$;

Z is:
(a) $CO_2R^2$,
(b) 1H-tetrazol-5-yl,
(c) $CONHSO_2R^{14}$,
(d) $SO_2NHR^{14}$,
(e) $NHSO_2R^{14}$,
(f) $SO_2NHCOR^{14}$, or
(g) $NHSO_2CF_3$; and R[14] is:
(a) ($C_1$-$C_6$)-alkyl,
(b) ($C_1$-$C_6$)-alkoxy,
(c) phenyl,
(d) $CH_2$phenyl,
(e) CH(phenyl)$_2$,

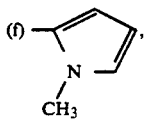

(g) ($C_3$-$C_6$)-cycloalkyl,
(h) ($C_1$-$C_3$)-alkyl-($C_3$-$C_6$)-cycloalkyl,
(i) $(CH_2)_5NH_2$,
(j) $O(CH_2)_{n+1}O(CH_2)_sCH_3$,
(k) $(CH_2)_{n+1}O(CH_2)_sCH_3$,
(l) ($C_1$-$C_4$)-polyfluoroalkyl, or
(m) $NH(C_1$-$C_6$)-alkyl.

8. A compound or its pharmaceutically acceptable salt of structural formula

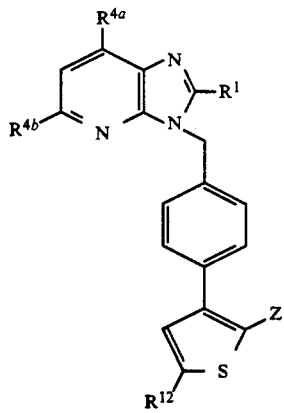

wherein:
R[1] is
(a) ($C_1$-$C_6$)-alkyl,
(b) ($C_3$-$C_8$)-cycloalkyl, or
(c) ($C_1$-$C_4$)-alkyl-($C_3$-$C_8$)-cycloalkyl;
n is: 0, 1 or 2;
s is: 0 to 5;
R[2] is: H or ($C_1$-$C_6$)-alkyl;
R[4a] is:
(a) H,
(b) ($C_1$-$C_4$)-alkyl,
(c) ($C_1$-$C_4$)-polyfluoroalkyl,
(d) ($C_1$-$C_3$)-alkoxyl,
(e) ($C_1$-$C_3$)-alkylthio,
(f) ($C_3$-$C_8$)-cycloalkyl, or
(g) F, Cl;

R[4b] is:
(a) R[4a],
(b) ($C_1$-$C_6$)-alkyl, ($C_2$-$C_6$)-alkenyl, substituted with a substituent selected from the group consisting of:
 i) $CO_2R^2$,
 ii) aryl, or
 iii) heteroaryl,
(c) —OH,
(d) —$CO_2R^{2a}$,
(e) —$NR^2R^{21}$,
(f) —$CO_2NH_2$,
(g) —$CONHSO_2R^{14}$,
(h) 1H-tetrazol-5-yl,
(i) aryl,
(k) heteroaryl, or
(l) morpholin-4-yl;

R[12] is: H, ($C_1$-$C_6$)-alkyl, ($C_1$-$C_6$)-alkoxy, —$CH_2$-phenyl, $O(CH_2)_{n+1}O(CH_2)_sCH_3$, $(CH_2)_{n+1}O(CH_2)_sCH_3$, or $CH_2N[CH_2CH_2]_2O$;

Z is:
(a) $CO_2R^2$,
(b) 1H-tetrazol-5-yl,
(c) $CONHSO_2R^{14}$,
(d) $SO_2NHR^{14}$,
(e) $NHSO_2R^{14}$,
(f) $SO_2NHCOR^{14}$, or
(g) $NHSO_2CF_3$; and R[14] is:
(a) ($C_1$-$C_6$)-alkyl,
(b) ($C_1$-$C_6$)-alkoxy,
(c) phenyl,
(d) $CH_2$phenyl,
(e) CH(phenyl)$_2$,

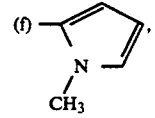

(g) ($C_3$-$C_6$)-cycloalkyl,
(h) ($C_1$-$C_3$)-alkyl-($C_3$-$C_6$)-cycloalkyl,
(i) $(CH_2)_5NH_2$,
(j) $O(CH_2)_{n+1}O(CH_2)_sCH_3$,
(k) $(CH_2)_{n+1}O(CH_2)_sCH_3$,
(l) ($C_1$-$C_4$)-polyfluoroalkyl, or
(m) $NH(C_1$-$C_6$)-alkyl.

9. A compound of structural formula:

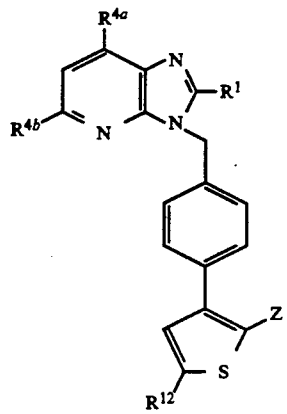

or a pharmaceutically acceptable salt wherein the compound is selected from the table below:

| R¹ | R⁴ᵃ | R⁴ᵇ | R¹² | Z |
|---|---|---|---|---|
| ethyl | CH₃ | CH₃ | H | SO₂NHCOPh |
| ethyl | CH₃ | CO₂H | H | SO₂NHCOPh |
| ethyl | CH₃ | CH₃ | H | 1H-tetrazol-5-yl |
| n-propyl | CH₃ | H | H | 1H-tetrazol-5-yl |
| ethyl | CH₃ | CO₂CH₃ | H | 1H-tetrazol-5-yl |
| propyl | CH₃ | CO₂CH₃ | H | 1H-tetrazol-5-yl |
| ethyl | CH₃ | CO₂H | H | 1H-tetrazol-5-yl |
| n-propyl | CH₃ | CO₂H | H | 1H-tetrazol-5-yl |
| n-propyl | CH₃ | H | H | SO₂NHCOPh |
| ethyl | CH₃ | CO₂CH₃ | H | SO₂NHCOPh |
| n-propyl | CH₃ | CO₂CH₃ | H | SO₂NHCOPh |
| n-propyl | CH₃ | CO₂CH₃ | H | SO₂NHCOPh |
| n-butyl | Me | H | nPr | 1H-tetrazol-5-yl |
| n-butyl | Me | H | iBu | 1H-tetrazol-5-yl |
| n-butyl | Me | H | nPr | SO₂NHCOPh |
| n-butyl | Me | H | iBu | SO₂NHCOPh |
| n-butyl | Me | H | nPn | SO₂NHCOPh |
| ethyl | Me | H | nPr | 1H-tetrazol-5-yl |
| ethyl | Me | H | iBu | 1H-tetrazol-5-yl |
| ethyl | Me | H | nPn | 1H-tetrazol-5-yl |
| ethyl | Me | H | Bn | 1H-tetrazol-5-yl |
| ethyl | Me | H | nPr | SO₂NHCOPh |
| ethyl | Me | H | iBu | SO₂NHCOPh |
| ethyl | Me | H | nPn | SO₂NHCOPh |
| ethyl | Me | H | Bn | SO₂NHCOPh |
| n-butyl | Me | Me | nPr | 1H-tetrazol-5-yl |
| n-butyl | Me | Me | nBu | 1H-tetrazol-5-yl |
| n-butyl | Me | Me | iBu | 1H-tetrazol-5-yl |
| n-butyl | Me | Me | nPn | 1H-tetrazol-5-yl |
| n-butyl | Me | Me | nPr | SO₂NHCOPh |
| n-butyl | Me | Me | iBu | SO₂NHCOPh |
| n-butyl | Me | Me | nPn | SO₂NHCOPh |
| ethyl | Me | Me | nPr | 1H-tetrazol-5-yl |
| ethyl | Me | Me | iBu | 1H-tetrazol-5-yl |
| ethyl | Me | Me | nPn | 1H-tetrazol-5-yl |
| ethyl | Me | Me | Me | SO₂NHCOPh |
| ethyl | Me | Me | Et | SO₂NHCOPh |
| ethyl | Me | Me | nPr | SO₂NHCOPh |
| ethyl | Me | Me | nBu | SO₂NHCOPh |
| ethyl | Me | Me | iBu | SO₂NHCOPh |
| ethyl | Me | Me | nPn | SO₂NHCOPh |
| ethyl | Me | Me | Bn | SO₂NHCOPh |
| ethyl | Me | Me | CH₂N(CH₂CH₂)₂O | SO₂NHCOPh |
| ethyl | Me | Me | CH₂N(CH₂CH₂)₂O | SO₂NHCOCH(Ph)₂ |
| n-butyl | Me | CON(Me)₂ | nPr | 1H-tetrazol-5-yl |
| n-butyl | Me | CON(Me)₂ | iBu | 1H-tetrazol-5-yl |
| n-butyl | Me | CON(Me)₂ | nPr | SO₂NHCOPh |
| ethyl | Me | CON(Me)₂ | nPr | 1H-tetrazol-5-yl |
| ethyl | Me | CON(Me)₂ | nBu | 1H-tetrazol-5-yl |
| ethyl | Me | CON(Me)₂ | iBu | 1H-tetrazol-5-yl |
| ethyl | Me | CON(Me)₂ | nPn | 1H-tetrazol-5-yl |
| ethyl | Me | CON(Me)₂ | nBu | SO₂NHCOPh |
| ethyl | Me | CON(Me)₂ | iBu | SO₂NHCOPh |
| ethyl | Me | CON(Me)₂ | Bn | SO₂NHCOPh |
| n-butyl | Me | CH₂OH | nPr | 1H-tetrazol-5-yl |
| n-butyl | Me | CH₂OH | iBu | 1H-tetrazol-5-yl |
| n-butyl | Me | CH₂OH | nPr | SO₂NHCOPh |
| n-butyl | Me | CH₂OH | nPn | SO₂NHCOPh |
| ethyl | Me | CH₂OH | nBu | 1H-tetrazol-5-yl |
| ethyl | Me | CH₂OH | iBu | 1H-tetrazol-5-yl |
| ethyl | Me | CH₂OH | nPn | 1H-tetrazol-5-yl |
| ethyl | Me | Me | nPr | SO₂NHCO(CH₂)₂OMe |
| ethyl | Me | CH₂OH | nBu | SO₂NHCOPh |
| ethyl | Me | CH₂OH | iBu | SO₂NHCOPh |
| ethyl | Me | CH₂OH | nPn | SO₂NHCOPh |
| ethyl | Me | CO₂H | nPr | SO₂NHCOPh |
| propyl | Me | CO₂H | nPr | SO₂NHCOPh |
| propyl | Me | CO₂H | iBu | SO₂NHCOPh |
| propyl | Me | CO₂H | nPn | SO₂NHCOPh |
| ethyl | Me | Me | Me | SO₂NHCOCH₂Ph |
| ethyl | Me | Me | Me | SO₂NHCOCH(Ph)₂ |
| ethyl | Me | Me | Et | SO₂NHCOCH(Ph)₂ |
| ethyl | Me | Me | Et | SO₂NHCOCH₂OEt |
| ethyl | Me | Me | nBu | SO₂NHCOCH₂OEt |
| propyl | Me | CO₂H | nPn | SO₂NHCOCH₂OBu |
| ethyl | Me | Me | nPr | SO₂NHCOOCH₂CH(Me)₂ |
| ethyl | Me | Me | nPr | SO₂NHCOCH₂OBu |
| ethyl | Me | Me | nPr | SO₂NHCOCH₂OEt |

-continued

| R¹ | R⁴ᵃ | R⁴ᵇ | R¹² | Z |
|---|---|---|---|---|
| ethyl | Me | Me | nBu | SO₂NHCO(CH₂)₂CycPen |
| ethyl | Me | CH₂OH | nPr | SO₂NHCOCH₂OEt |
| ethyl | Me | CH₂OH | iBu | SO₂NHCOCH₂OBu |
| ethyl | Me | CO₂H | iBu | SO₂NHCOCH₂OBu |
| ethyl | Me | Me | iBu | SO₂NHCOCH₂OBu |
| ethyl | Me | Me | iBu | SO₂NHCOCH₂OEt |
| ethyl | Me | Me | nPn | SO₂NHCOCH₂OEt |
| ethyl | Me | Me | nPn | SO₂NHCOCH₂OBu |
| ethyl | Me | Me | nPn | SO₂NHCO₂—N-methylpyrrole |
| ethyl | Me | Me | nPr | SO₂NHCO₂—N-methylpyrrole |
| ethyl | Me | Me | nPr | SO₂NHCOOCH₂CH(Me)₂ |
| ethyl | Me | Me | iBu | SO₂NHCOO(CH₂)₂OMe |
| ethyl | Me | Me | nPr | SO₂NHCOO(CH₂)₂OMe |
| ethyl | Me | Me | nBu | SO₂NHCOO(CH₂)₂OMe |
| ethyl | Me | Me | nBu | SO₂NHCO(CH₂)₅NHBoc |
| ethyl | Me | Me | nBu | SO₂NHCO(CH₂)₅NH₂ |
| ethyl | Me | Me | iBu | SO₂NHCO(CH₂)₅NHBoc |
| ethyl | Me | Me | iBu | SO₂NHCO(CH₂)₅NH₂ |
| ethyl | Me | Me | nPn | SO₂NHCO(CH₂)₅NHBoc |
| ethyl | Me | Me | nPn | SO₂NHCO(CH₂)₅NH₂ |
| ethyl | Me | Me | nPn | SO₂NHCO(CH₂)₄CH₃ |
| ethyl | Me | Me | nPr | SO₂NHCO(CH₂)₄CH₃ |
| ethyl | Me | Me | nBu | SO₂NHCO(CH₂)₄CH₃ |
| ethyl | Me | Me | iBu | SO₂NHCO(CH₂)₄CH₃ |
| ethyl | Me | Me | nPr | SO₂NHCOcyPr |
| ethyl | Me | Me | Bn | SO₂NHCOcyPr |
| ethyl | Me | Me | nPr | SO₂NHCOO(CH₂)₂OMe |
| ethyl | Me | CON(Me)₂ | iBu | SO₂NHCOcyPr |
| ethyl | Me | Me | nPr | SO₂NHCOOBu |
| ethyl | Me | CO₂H | nPr | SO₂NHCOOBu |
| ethyl | Me | Me | nPn | SO₂NHCOOBu |
| ethyl | Me | CO₂H | nPn | SO₂NHCOOBu |
| ethyl | Me | Me | iBu | SO₂NHCOCH(Ph)₂ |
| ethyl | Me | Me | nPr | SO₂NHCOCH(Ph)₂ |
| ethyl | Me | CON(Me)₂ | iBu | SO₂NHCOCH(Ph)₂ |
| ethyl | Me | Me | nPr | SO₂NHCOCH₂OEt |
| ethyl | Me | Me | Me | 1H-tetrazol-5-yl |
| ethyl | Me | Me | Me | SO₂NHCONHBu. |

10. A compound or the pharmaceutically acceptable salt, wherein the compound is selected from the table below:

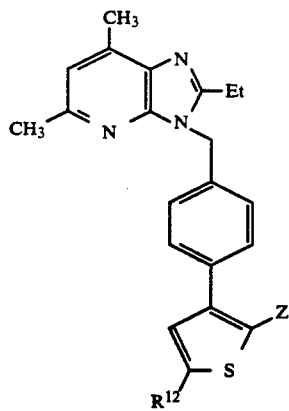

| R¹² | Z |
|---|---|
| Me | 1H-tetrazol-5-yl |
| nPr | 1H-tetrazol-5-yl |
| iBu | 1H-tetrazol-5-yl |
| nPr | SO₂NHCO₂-nBu |
| nPr | SO₂NHCONH-nBu |
| nPr | SO₂NHCO(CH₂)₂-cycPen |
| nPr | SO₂NHCOCH₂OEt |
| nPr | SO₂NHCOCH₂O-nBu |
| nPr | SO₂NHCO(CH₂)₄CH₃ |
| iBu | SO₂NHCO₂-nPn |
| iBu | SO₂NHCONH-nBu |
| iBu | SO₂NHCO(CH₂)₂-cycPen |
| iBu | SO₂NHCOCH₂OEt |
| iBu | SO₂NHCOCH₂O-nBu |
| iBu | SO₂NHCO(CH₂)₄CH₃ |
| nPn | SO₂NHCO₂-nBu |
| nPn | SO₂NHCOCH₂O-nBu. |

11. A pharmaceutical composition useful in the treatment of hypertension which comprises a pharmaceutically acceptable carrier and a therapeutically effective amount of a compound of claim 1.

12. A method of treating hypertension which comprises administering to a patient in need of such treatment a therapeutically effective amount of a compound of claim 1.

13. An ophthalmological formulation for the treatment of ocular hypertension comprising an ophthalmologically acceptable carrier and an effective ocular antihypertensive amount of a compound of claim 1.

14. A method of treating ocular hypertension comprising topical ocular administration to a patient in need of such treatment of an effective ocular antihypertensive amount of a compound of claim 1.

15. A method of treating cognitive dysfunction, anxiety, or depression comprising administering to a patient in need of such treatment, a therapeutically effective amount of a compound of claim 1.

* * * * *